(12) United States Patent
Schnieders et al.

(10) Patent No.: US 9,592,289 B2
(45) Date of Patent: Mar. 14, 2017

(54) STABLE IGG4 BASED BINDING AGENT FORMULATIONS

(71) Applicant: SANOFI, Paris (FR)

(72) Inventors: Julia Schnieders, Frankfurt (DE); Dirk Usener, Frankfurt (DE); Sabrina Ruggeberg, Frankfurt (DE); Ahmed Youssef, Frankfurt (DE); Martina Kirsch, Frankfurt (DE); Annika Hagendorf, Hattersheim (DE)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 13/850,849

(22) Filed: Mar. 26, 2013

(65) Prior Publication Data

US 2014/0004106 A1 Jan. 2, 2014
US 2014/0286933 A9 Sep. 25, 2014

Related U.S. Application Data

(60) Provisional application No. 61/615,539, filed on Mar. 26, 2012.

(30) Foreign Application Priority Data

Feb. 6, 2013 (FR) ...................... 13 51013

(51) Int. Cl.
*A61K 39/395* (2006.01)
*C07K 16/28* (2006.01)

(52) U.S. Cl.
CPC .. *A61K 39/39558* (2013.01); *A61K 39/39591* (2013.01); *C07K 16/2866* (2013.01); *C07K 16/2875* (2013.01); *C07K 2317/21* (2013.01); *C07K 2317/52* (2013.01)

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. |
| 4,179,337 A | 12/1979 | Davis et al. |
| 4,256,746 A | 3/1981 | Miyashita et al. |
| 4,275,149 A | 6/1981 | Litman et al. |
| 4,294,757 A | 10/1981 | Asai |
| 4,301,144 A | 11/1981 | Iwashita et al. |
| 4,307,016 A | 12/1981 | Asai et al. |
| 4,313,946 A | 2/1982 | Powell et al. |
| 4,315,929 A | 2/1982 | Freedman et al. |
| 4,318,980 A | 3/1982 | Boguslaski et al. |
| 4,322,348 A | 3/1982 | Asai et al. |
| 4,331,598 A | 5/1982 | Hasegawa et al. |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,376,110 A | 3/1983 | David |
| 4,424,219 A | 1/1984 | Hashimoto et al. |
| 4,444,887 A | 4/1984 | Hoffmann |
| 4,450,254 A | 5/1984 | Isley et al. |
| 4,496,689 A | 1/1985 | Mitra |
| 4,560,655 A | 12/1985 | Baker |
| 4,640,835 A | 2/1987 | Shimizu et al. |
| 4,657,866 A | 4/1987 | Kumar |
| 4,670,417 A | 6/1987 | Iwasaki et al. |
| 4,676,980 A | 6/1987 | Segal et al. |
| 4,716,111 A | 12/1987 | Osband et al. |
| 4,737,456 A | 4/1988 | Weng et al. |
| 4,767,704 A | 8/1988 | Cleveland et al. |
| 4,791,192 A | 12/1988 | Nakagawa et al. |
| 4,816,397 A | 3/1989 | Boss et al. |
| 4,816,567 A | 3/1989 | Cabilly et al. |
| 4,946,778 A | 8/1990 | Ladner et al. |
| 4,980,286 A | 12/1990 | Morgan et al. |
| 5,122,464 A | 6/1992 | Wilson et al. |
| 5,122,469 A | 6/1992 | Mather et al. |
| 5,223,409 A | 6/1993 | Ladner et al. |
| 5,225,539 A | 7/1993 | Winter |
| 5,314,995 A | 5/1994 | Fell, Jr. et al. |
| 5,413,923 A | 5/1995 | Kucherlapati et al. |
| 5,436,146 A | 7/1995 | Shenk et al. |
| 5,474,981 A | 12/1995 | Leder et al. |

(Continued)

FOREIGN PATENT DOCUMENTS

EP 0239400 9/1987
EP 239400 A2 9/1987

(Continued)

OTHER PUBLICATIONS

Matheus et al. (Pharmaceutical Research, vol. 23, No. 7, Jul. 2006).*
Zheng et al. (International Journal of Pharmaceutics 308 (2006) 46-51).*
IgG sequence alignment, date unknown, 1 page.*
Anti-CXCR5 antibody sequence alignment, 2015, 2 pages.*
Grønborg et al., Molecular & Cellular Proteomics (2002) 1: 517-527.*
Sequence Alignment, 2015, 1 page.*
International Search Report and Written Opinion of the International Searching Authority for Application No. PCT/US2013/033881, dated Sep. 25, 2013 (16 pages).

(Continued)

*Primary Examiner* — Ilia Ouspenski
(74) *Attorney, Agent, or Firm* — McDonnell Boehnen Hulbert & Berghoff LLP

(57) ABSTRACT

The present invention provides stable pharmaceutical antibody formulations, including liquid drug product formulations and lyophilized drug product formulations, comprising an IgG4 binding agent and a citrate buffer, wherein the pH of the formulation is at or below both pH 6 and the pI of the binding agent. The formulations can be used in the treatment of chronic bowel diseases or rheumatoid arthritis.

13 Claims, 23 Drawing Sheets
(19 of 23 Drawing Sheet(s) Filed in Color)

(56) References Cited

U.S. PATENT DOCUMENTS

| | | |
|---|---|---|
| 5,475,092 A | 12/1995 | Chari et al. |
| 5,530,101 A | 6/1996 | Queen |
| 5,534,617 A | 7/1996 | Cunningham et al. |
| 5,545,806 A | 8/1996 | Lonberg et al. |
| 5,565,332 A | 10/1996 | Hoogenboom et al. |
| 5,569,825 A | 10/1996 | Lonberg et al. |
| 5,585,089 A | 12/1996 | Queen et al. |
| 5,585,499 A | 12/1996 | Chari et al. |
| 5,589,205 A | 12/1996 | Ishikawa et al. |
| 5,625,126 A | 4/1997 | Lonberg et al. |
| 5,633,425 A | 5/1997 | Lonberg et al. |
| 5,639,641 A | 6/1997 | Pedersen et al. |
| 5,661,016 A | 8/1997 | Lonberg et al. |
| 5,693,762 A | 12/1997 | Queen et al. |
| 5,698,417 A | 12/1997 | Robinson et al. |
| 5,698,435 A | 12/1997 | Robinson et al. |
| 5,712,163 A | 1/1998 | Parenteau et al. |
| 5,714,352 A | 2/1998 | Jakobovits |
| 5,723,323 A | 3/1998 | Kauffman et al. |
| 5,763,192 A | 6/1998 | Kauffman |
| 5,766,886 A | 6/1998 | Studnicka et al. |
| 5,800,988 A | 9/1998 | Casterman |
| 5,807,715 A | 9/1998 | Morrison et al. |
| 5,814,318 A | 9/1998 | Lonberg et al. |
| 5,814,476 A | 9/1998 | Kauffman |
| 5,817,483 A | 10/1998 | Kauffman |
| 5,821,337 A | 10/1998 | Carter et al. |
| 5,824,514 A | 10/1998 | Kauffman |
| 5,846,545 A | 12/1998 | Chari et al. |
| 5,869,619 A | 2/1999 | Studnicka |
| 5,885,793 A | 3/1999 | Griffiths et al. |
| 5,916,771 A | 6/1999 | Hori et al. |
| 5,939,598 A | 8/1999 | Kucherlapati et al. |
| 5,976,862 A | 11/1999 | Kauffman |
| 6,005,079 A | 12/1999 | Casterman |
| 6,048,728 A | 4/2000 | Inlow et al. |
| 6,180,370 B1 | 1/2001 | Queen |
| 6,184,358 B1 | 2/2001 | Loetscher et al. |
| 6,204,023 B1 | 3/2001 | Robinson et al. |
| 6,277,375 B1 | 8/2001 | Ward |
| 6,333,410 B1 | 12/2001 | Chari et al. |
| 6,514,496 B1 | 2/2003 | Platz et al. |
| 6,632,670 B1 | 10/2003 | Wadsworth et al. |
| 6,632,927 B2 | 10/2003 | Adair et al. |
| 6,642,051 B1 | 11/2003 | Lynch et al. |
| 6,686,175 B1 | 2/2004 | Loetscher et al. |
| 7,241,877 B2 | 7/2007 | Adair et al. |
| 7,244,832 B2 | 7/2007 | Adair et al. |
| 7,262,050 B2 | 8/2007 | Adair et al. |
| 7,288,249 B2 | 10/2007 | Carter et al. |
| 7,405,275 B2 | 7/2008 | Qin et al. |
| 7,407,655 B2 | 8/2008 | Loetscher et al. |
| 8,058,402 B2 | 11/2011 | Granger et al. |
| 8,865,870 B2 | 10/2014 | Youd |
| 2003/0130496 A1 | 7/2003 | Winter et al. |
| 2004/0236078 A1 | 11/2004 | Carter et al. |
| 2005/0276812 A1 | 12/2005 | Ebens et al. |
| 2007/0082365 A1 | 4/2007 | Lipovsek et al. |
| 2008/0181892 A1 | 7/2008 | Ledbetter et al. |
| 2008/0227958 A1 | 9/2008 | Thompson et al. |
| 2010/0061983 A1 | 3/2010 | Loetscher et al. |
| 2013/0315913 A1 | 11/2013 | Zhang |
| 2014/0004106 A1 | 1/2014 | Schnieders |
| 2014/0256918 A1 | 9/2014 | Chu |
| 2014/0377806 A1 | 12/2014 | Youd |

FOREIGN PATENT DOCUMENTS

| | | |
|---|---|---|
| EP | 0332424 | 9/1989 |
| EP | 0338745 | 10/1989 |
| EP | 0396387 | 11/1990 |
| EP | 0413622 | 2/1991 |
| EP | 0439095 | 7/1991 |
| EP | 0519596 | 12/1992 |
| EP | 0592106 | 4/1994 |
| EP | 592106 A1 | 4/1994 |
| EP | 0597101 A1 | 5/1994 |
| RU | 2252786 | 5/2005 |
| WO | 86/05807 | 10/1986 |
| WO | 87/05330 | 9/1987 |
| WO | 89/01036 | 2/1989 |
| WO | 89/09622 | 10/1989 |
| WO | 89/12624 | 12/1989 |
| WO | 91/09967 | 7/1991 |
| WO | 91/10741 | 7/1991 |
| WO | 91/14438 | 10/1991 |
| WO | 92/01047 | 1/1992 |
| WO | 92/06180 | 4/1992 |
| WO | 92/08495 | 5/1992 |
| WO | 92/20316 | 11/1992 |
| WO | 92/22635 | 12/1992 |
| WO | 92/22653 | 12/1992 |
| WO | 93/08829 | 5/1993 |
| WO | 93/14188 | 7/1993 |
| WO | 93/15199 | 8/1993 |
| WO | 93/15200 | 8/1993 |
| WO | 93/16185 | 8/1993 |
| WO | 93/20221 | 10/1993 |
| WO | 93/21232 | 10/1993 |
| WO | 93/21319 | 10/1993 |
| WO | 94/04678 | 3/1994 |
| WO | 94/08598 | 4/1994 |
| WO | 94/12649 | 6/1994 |
| WO | 94/25591 | 11/1994 |
| WO | 96/33735 | 10/1996 |
| WO | 96/34096 | 10/1996 |
| WO | 97/33899 | 9/1997 |
| WO | 97/34631 | 9/1997 |
| WO | 97/34911 | 9/1997 |
| WO | 98/16654 | 4/1998 |
| WO | 98/23289 | 6/1998 |
| WO | 98/24893 | 6/1998 |
| WO | 98/46645 | 10/1998 |
| WO | 98/50433 | 11/1998 |
| WO | 99/23105 | 5/1999 |
| WO | 01/77137 | 10/2001 |
| WO | 0172334 | 10/2001 |
| WO | 03/002607 | 1/2003 |
| WO | 2003/068260 A1 | 8/2003 |
| WO | 2004/015426 | 2/2004 |
| WO | 2004071439 A2 | 8/2004 |
| WO | 2005030793 | 4/2005 |
| WO | 2005/049078 A2 | 6/2005 |
| WO | 2005/117986 | 12/2005 |
| WO | 2006/020935 A2 | 2/2006 |
| WO | 2006/042333 | 4/2006 |
| WO | 2006/044908 A2 | 4/2006 |
| WO | 2007/074880 A1 | 7/2007 |
| WO | 2007/122402 | 11/2007 |
| WO | 2007/124299 A2 | 11/2007 |
| WO | 2007/131676 | 11/2007 |
| WO | 2008/027338 | 3/2008 |
| WO | 2008/071394 A1 | 6/2008 |
| WO | 2008094942 | 8/2008 |
| WO | 2008157409 A1 | 12/2008 |
| WO | 2009/032661 | 3/2009 |
| WO | 2009032661 A1 | 3/2009 |
| WO | WO2009/032661 A1 | 12/2009 |
| WO | 2010103517 | 9/2010 |
| WO | 2012151199 A1 | 11/2012 |
| WO | 2013148350 A2 | 10/2013 |

OTHER PUBLICATIONS

Ishikawa, Tomoyoshi, et al. "Influence of pH on heat-induced aggregation and degradation of therapeutic monoclonal antibodies." Biological & pharmaceutical bulletin 33.8 (2009): 1413-1417.

Krishnan, Sampathkumar,et al. "Development of formulations for therapeutic monoclonal antibodies and Fc fusion proteins." Formulation and Process Development Strategies for Manufacturing Biopharmaceuticals (2010): 383-427.

Li, Yi, Henryk Mach, and Jeffrey T. Blue. "High throughput formulation screening for global aggregation behaviors of three

(56) References Cited

OTHER PUBLICATIONS monoclonal antibodies." Journal of pharmaceutical sciences 100.6 (2011): 2120-2135.
Kolhe, Parag, Elizabeth Amend, and Satish K Singh. "Impact of freezing on pH of buffered solutions and consequences for monoclonal antibody aggregation." Biotechnology progress 26.3 (2010): 727-733.
Karow, Anne R. et al. "Buffer capacity of biologics—from buffer salts to buffering by antibodies." Biotechnology progress 29.2 (2013): 480-492.
Paul, W.E., Fundamental Immunology, 3rd Edition, Raven Press, New York, Chapt. 8, pp. 292-295, 1993.
Rudikoff S. et al., Proc. Natl. Acad. Sci. USA, 79(6):1979-1983, Mar. 1982.
Colman P. M., Research in Immunology, 145:33-36,1994.
PCT/US2013/022280 Response to Written Opinion filed Dec. 19, 2013, 135 pages.
PCT/US2013/022280 Written Opinion of the International Preliminary Examining Authority mailed Mar. 13, 2014, 8 pages.
Clark-Lewis, I. et al., Structure-Function Relationship between the Human Chemokine Receptor CXCR3 and Its Ligands; Journal of Biolgicial Chemistry, vol. 278, No. 1, pp. 289-295, issue of Jan. 3, 2003.
PCT/US2013/022280 International Search Report mailed Sep. 23, 2013, 8 pages.
Rheinwald, vol. 21(A), "Serial cultivation of normal human epidermal keratinocytes," in Methods in Cell Biology, 229-54 (1980).
Riechmann et al., "Reshaping human antibodies for therapy," 332(6162) Nature 323-7 (Mar. 1988).
Rizzo et al., "Validation of a model for the complex of HIV-1 reverse transcriptase with Sustiva through computation of resistance profiles," 122(51) J Am Chem Soc 12898-900 (Dec. 2000).
Robinson et al., "Gene therapy—proceeding from laboratory to clinic," 11(5) Trends in Biotechnology 155 (May 1993).
Roguska et al., "Humanization of murine monoclonal antibodies through variable domain resurfacing," 91(3) Proc Natl Acad Sci USA 969-73 (Feb. 1994).
Roitt A. et al. "Immunology", Moscow, Mir, 110-111 (2000).
Romijn et al., "Identification of the Collagen-binding Site of the von Willebrand Factor A3-domain," 276(13) J Biol Chem 9985-91 (Mar. 2001).
Rosenberg et al., "Vectors for selective expression of cloned DNAs by T7 RNA polymerase," 56(1) Gene 125-35 (1987).
Rosenfeld et al., "Adenovirus-mediated transfer of a recombinant alpha 1-antitrypsin gene to the lung epithelium in vivo," 252(5004) Science 431-4 (Apr. 1991).
Rosenfeld et al., "In vivo transfer of the human cystic fibrosis transmembrane conductance regulator gene to the airway epithelium," 68(1) Cell 143-55 (Jan. 1992).
Rudikoff et al., "Single amino acid substitution altering antigen-binding specificity." 79(6) Proc Natl Acad Sci USA 1979-83 (Mar. 1982).
Ruzheinikov et al., "High-resolution Crystal Structure of the Fab-fragments of a Family of Mouse Catalytic Antibodies with Esterase Activity," 332(2) J Mol Biol 423-35 (Sep. 2003).
Salmons & Günzburg, "Targeting of retroviral vectors for gene therapy," 4(2) Human Gene Therapy 129-41 (Apr. 1993).
Salomonsson et al., "Expression of the B cell-attracting chemokine CXCL13 in the target organ and autoantibody production in ectopic lymphoid tissue in the chronic inflammatory disease Sjögren's syndrome," 55(4) Scand J Immunol 336-42 (Apr. 2002).
Saito et al., "Altered expression of chemokine receptor CXCR5 on T cells of myasthenia gravis patients," 170(1-2) J Neuroimmunol 172-8 (Dec. 2005).
Sanger et al., "DNA sequencing with chain-terminating inhibitors," 74(12) Proc Natl Acad Sci USA 5463-7 (Dec. 1977).
Santerre et al., "Expression of prokaryotic genes for hygromycin B and G418 resistance as dominant-selection markers in mouse L cells," 30(1-3) Gene 147-56 (Oct. 1984).
Saudek et al., "A preliminary trial of the programmable implantable medication system for insulin delivery," 321(9) N Engl J Med 574-9 (Aug. 1989).
Schmutz et al., "Chemokine receptors in the rheumatoid synovium: upregulation of CXCR5," 7(2) Arth Res Ther R217-29 (Dec. 2004).
Schoepfer, "The pRSET family of T7 promoter expression vectors for *Escherichia coli*," 124(1) Gene 83-5 (Feb. 1993).
Scott & Smith, "Searching for peptide ligands with an epitope library," 249(4967) Science 386-90 (Jul. 1990).
Sefton, "Implantable pumps," 14(3) Crit Rev Biomed Eng 201-40 (1987).
Shopes, "A genetically engineered human IgG mutant with enhanced cytolytic activity," 148(9) J Immunol 2918-22 (May 1992).
Short et al., "Complementary combining site contact residue mutations of the anti-digoxin Fab 26-10 permit high affinity wild-type binding," 277(19) J Biol Chem 16365-70 (May 2002).
Sims et al., "A humanized CD18 antibody can block function without cell destruction," 151(4) J Immunol 2296-308 (Aug. 1993).
Sims et al., "Somatic hypermutation and selection of B cells in thymic germinal centers responding to acetylcholine receptor in myasthenia gravis," 167(4) J Immunol 1935-44 (Aug. 2001).
Skerra & Plückthun, "Assembly of a functional immunoglobulin Fv fragment in *Escherichia coli*," 240(4855) Science 1038-41 (May 1988).
Smith, "Filamentous fusion phage: novel expression vectors that display cloned antigens on the virion surface," 228 (4705) Science 1315-7 (Jun. 1985).
Spinetti et al., "The chemokine CXCL13 (BCA-1) inhibits FGF-2 effects on endothelial cells," 289(1) Biochem Biophys Res Commun 19-24 (Nov. 2001).
Spring & Nisonoff et al., "Allotypic markers on Fab fragments of mouse immunoglobulins," 113(2) J Immunol 470-8 (Aug. 1974).
Stanfield et al., "Recurring conformation of the human immunodeficiency virus type 1 gp120 V3 loop," 315(1) Virology 159-73 (Oct. 2003).
Stemple & Anderson, "Isolation of a stem cell for neurons and glia from the mammalian neural crest," 71(6) Cell 973-85 (Dec. 1992).
Stevenson et al., "A chimeric antibody with dual Fc regions (bisFabFc) prepared by manipulations at the IgG hinge," 3(4) Anticancer Drug Des 219-30 (Mar. 1989).
Strong et al., "Three-dimensional structure of murine anti-p-azophenylarsonate Fab 36-71. 1. X-ray crystallography, site-directed mutagenesis, and modeling of the complex with hapten," 30(15) Biochem 3739-45 (Apr. 1991).
Studier, "Use of bacteriophage T7 lysozyme to improve an inducible T7 expression system," 219(1) J Mol Biol 37-44 (May 1991).
Studnicka et al., "Human-engineered monoclonal antibodies retain full specific binding activity by preserving non-CDR complementarity-modulating residues," 7(6) Protein Engineering 805-14 (Jun. 1994).
Sundberg & Mariuzza, "Luxury accommodations: the expanding role of structural plasticity in protein-protein interactions," 8(7) Structure R137-42 (Jul. 2000).
Suresh et al., "Bispecific monoclonal antibodies from hybrid hybridomas," 121 Meth Enzym 210-28 (1986).
Szybalska & Szybalski, "Genetics of human cell lines IV. DNA-mediated heritable transformation of a biochemical trait," 48(12) Proc Natl Acad Sci USA 2026-34 (Dec. 1962).
Tackenberg et al., "Clonal expansions of CD4+ B helper T cells in autoimmune myasthenia gravis," 37(3) Eur J Immunol 849-63 (Mar. 2007).
Takahashi et al., "Human Fas ligand: gene structure, chromosomal location and species specificity," 6(10) Int Immunol 1567-74 (Oct. 1994).
Tamura et al., "Structural correlates of an anticarcinoma antibody: identification of specificity-determining residues (SDRs) and development of a minimally immunogenic antibody variant by retention of SDRs only." 164(3) J Immunol 1432-41 (Feb. 2000).
Taylor et al., "A transgenic mouse that expresses a diversity of human sequence heavy and light chain immunoglobulins," 20(23) Nucleic Acids Res 6287-95 (Dec. 1992).

(56) References Cited

OTHER PUBLICATIONS

Thompson et al., "Affinity maturation of a high-affinity human monoclonal antibody against the third hypervariable loop of human immunodeficiency virus: use of phage display to improve affinity and broaden strain reactivity," 256(1) J Mol Biol 77-88 (Feb. 1996).
Thornton et al., "Protein structure. Prediction of progress at last," 354 (6349) Nature 105-6 (Nov. 1991).
Thorpe & Ross, "The preparation and cytotoxic properties of antibody-toxin conjugates," 62 Immunol Rev 119-58 (1982).
Thorpe, "Antibody Carriers of Cytotoxic Agents in Cancer Therapy: A Review," in Monoclonal Antibodies '84: Biological and Clinical Applications, 475-506 (Pinchera et al. eds., 1985).
Thotakura & Bahl, "Enzymatic deglycosylation of glycoproteins," 138 Meth Enzymol 350-9 (1987).
Tolstoshev, "Gene therapy, concepts, current trials and future directions," 33 Annu Rev Pharmacol Toxicol 573-96 (1993).
Traunecker et al., "Bispecific single chain molecules (Janusins) target cytotoxic lymphocytes on HIV infected cells," 10(12) EMBO J 3655-9 (Dec. 1991).
Ho et al., "Site-directed mutagenesis by overlap extension using the polymerase chain reaction," 77(1) Gene 51-9 (Apr. 1989).
Holland & Holland, "Isolation and identification of yeast messenger ribonucleic acids coding for enolase, glyceraldehyde-3-phosphate dehydrogenase, and phosphoglycerate kinase," 17(23) Biochemistry 4900-7 (Nov. 1978).
Holt et al., "Domain antibodies: proteins for therapy," 21(11) TRENDS in Biotechnology 484-90 (Nov. 2003).
Horton et al., "Gene splicing by overlap extension: tailor-made genes using the polymerase chain reaction," 8(5) BioTechniques 528-35 (May 1990).
Howard et al., "Intracerebral drug delivery in rats with lesion-induced memory deficits," 71(1) J Neurosurg 105-12 (Jul. 1989).
Hudson, "Recombinant antibody constructs in cancer therapy," 11(5) Current Opinion in Immunology 548-57 (Oct. 1999).
Huston et al., "Protein engineering of antibody binding sites: recovery of specific activity in an anti-digoxin single-chain Fv analogue produced in *Escherichia coli*," 85(16) Proc Natl Acad Sci USA 5879-83 (Aug. 1988).
Ishikawa et at., "Aberrant high expression of B lymphocyte chemokine (BLC/CXCL13) by C11b+CD11c+ dendritic cells in murine lupus and preferential chemotaxis of B1 cells towards BLC," 193(12) J Exp Med 1393-402 (Jun. 2001).
Ito et al., "Defective B1 cell homing to the peritoneal cavity and preferential recruitment of B1 cells in the target organs in a murine model for systemic lupus erythematosus," 12(6) J Immunol 3628-34 (Mar. 2004).
Jakobovits et al., "Analysis of homozygous mutant chimeric mice: deletion of the immunoglobulin heavy-chain joining region blocks B-cell development and antibody production," 90(6) Proc Natl Acad Sci USA 2551-5 (Mar. 1993).
Jakobovits et al., "Germ-line transmission and expression of a human-derived yeast artificial chromosome," 362 (6417) Nature 255-8 (Mar. 1993).
James et al., "Antibody multispecificity mediated by conformational diversity," 299(5611) Science 1362-7 (Feb. 2003).
Jespers et al., "Guiding the selection of human antibodies from phage display repertoires to a single epitope of an antigen," 12(9) Biotechnology 899-903 (Sep. 1994).
Jones, "Analysis of polypeptides and proteins," 10(1) Advanced Drug Delivery Reviews 29-90 (Jan. 1993).
Jones et al., "Replacing the complementarity-determining regions in a human antibody with those from a mouse," 321 (6069) Nature 522-5 (May 1986).
Kabat et al., "Sequences of proteins of immunological interest," Fifth Edition, NIH Publication No. 91-3242 (1991) (83 pages).
Kabat & Wu, "Attempts to locate complementarity-determining residues in the variable positions of light and heavy chains," 190 Ann N Y Acad Sci. 382-93 (Dec. 1971).
Karlin & Altschul, "Applications and statistics for multiple high-scoring segments in molecular sequences," 90(12) Proc Natl Acad Sci U S A 5873-7 (Jun. 1993).
Karlin & Altschul, "Methods for assessing the statistical significance of molecular sequence features by using general scoring schemes," 87(6) Proc Natl Acad Sci U S A 2264-8 (Mar. 1990).
Kiem et al., "Retrovirus-mediated gene transduction into canine peripheral blood repopulating cells," 83(6) Blood 1467-73 (Mar. 1994).
Kirschmann et al., "Naturally processed peptides from rheumatoid arthritis associated and non-associated HLA-DR alleles," 155(12) J Immunol 5655-62 (Dec. 1995).
Köhler, "Immunoglobulin chain loss in hybridoma lines," 77(4) Proc Natl Acad Sci USA 2197-9 (Apr. 1980).
Köhler & Milstein, "Continuous cultures of fused cells secreting antibody of predefined specificity." 256(5517) Nature 495-7 (Aug. 1975).
Koller & Smithies, "Inactivating the beta 2-microglobulin locus in mouse embryonic stem cells by homologous recombination," 86(22) Proc Natl Acad Sci USA 8932-5 (Nov. 1989).
Kozarsky & Wilson, "Gene therapy: adenovirus vectors," 3(3) Curr Opin Gen Dev 499-503 (Jun. 1993).
Kozbor & Roder, "The production of monoclonal antibodies from human lymphocytes," 4(3) Immunology Today 72-9 (Mar. 1983).
Kozbor et al., "A human hybrid myeloma for production of human monoclonal antibodies," 133(6) J Immunol 3001-5 (Dec. 1984).
Krumbholz et al., "Chemokines in multiple sclerosis: CXCL12 and CXCL13 up-regulation is differentially linked to CNS immune cell recruitment," 129(1) Brain 200-11 (Jan. 2006).
Kufer et al., "A revival of bispecific antibodies," 22(5) Trends Biotech 238-44 (May 2004).
Kundu et al., "Dynamics of proteins in crystals: comparison of experiment with simple models," 83(2) Biophys J 723-32 (Aug. 2002).
Kunkel, "Rapid and efficient site-specific mutagenesis without phenotypic selection," 82(2) Proc Natl Acad Sci USA 488-92 (Jan. 1985).
Kutemeier et al., "Assembly of humanized antibody genes from synthetic oligonucleotides using a single-round PCR," 17(2) BioTechniques 242-6 (Aug. 1994).
Lamminmaki & Kankare, "Crystal structure of a recombinant anti-estradiol Fab fragment in complex with 17beta—estradiol." 276(39) J Biol Chem 36687-94 (Sep. 2001).
Langer, "New methods in drug delivery," 249(4976) Science 1527-33 (Sep. 1990).
Langer & Peppas, "Chemical and Physical Structure of Polymers as Carriers for Controlled Release of Bioactive Agents: A Review," C23(1) J Macromol Sci Rev Macromol Chem 61-126 (1983).
Lazar et al., "A molecular immunology approach to antibody humanization and functional optimization," 44(8) Mol Immunol 1986-8 (Mar. 2007).
LeFranc et al., "IMGT, the international ImMunoGeneTics information system®," 33(Suppl 1, Database issue) Nucleic Acids Research D593-7 (Jan. 2005).
LeFranc, "IMGT-ONTOLOGY and IMGT databases, tools and Web resources for immunogenetics and immunoinformatics," 40(10) Molec Immunol 647-59 (Jan. 2004).
Legler et al., "B cell-attracting chemokine 1, a human CXC chemokine expressed in lymphoid tissues, selectively attracts B lymphocytes via BLR1/CXCR5," 187(4) J Exp Med 655-60 (Feb. 1998).
Lerner, "How to make a hybridoma," 54(5) Yale J Biology and Medicine 387-402 (Sep. 1981).
Levy et al., "Inhibition of calcification of bioprosthetic heart valves by local controlled-release diphosphonate," 228 (4696) Science 190-2 (Apr. 1985).
Li et al., "Structural basis for inhibition of the epidermal growth factor receptor by cetuximab," 7(4) Cancer Cell 301-11 (Apr. 2005).
Little et al., "Of mice and men: hybridoma and recombinant antibodies" 21(8) Immunology Today 364-70 (Aug. 2000).
Lindmark et al., "Binding of immunoglobulins to protein A and immunoglobulin levels in mammalian sera," 62(1) J Immunol Methods 1-13 (Aug. 1983).

(56) References Cited

OTHER PUBLICATIONS

Lisignoli et al., "Human osteoblasts express functional CXC chemokine receptors 3 and 5: activation by their ligands, CXCL10 and CXCL13, significantly induces alkaline phosphatase and beta-N-acetylhexosaminidase release," 194(1) J Cell Physiol 71-9 (Jan. 2003).
Liu et al., "Characterization of the stability of a fully human monoclonal IgG after prolonged incubation at elevated temperature," 837(1-2) J Chromatog B 35-43 (Jun. 2006).
Loeffler & Behr, "Gene transfer into primary and established mammalian cell lines with lipopolyamine-coated DNA," 217 Meth Enzymol 599-618 (1993).
Lonberg & Huszar, "Human antibodies from transgenic mice," 13(1) Int Rev Immunol 65-93 (1995).
Lopez-Berestein, "Treatment of Systemic Fungal Infections with Liposomal-Amphotericin B," in Liposomes in the Therapy of Infectious Disease and Cancer 317-27 (Lopez-Berestein et al., eds., 1989).
Lowman & Wells, "Affinity maturation of human growth hormone by monovalent phage display," 234(3) J Mol Biol 564-78 (Dec. 1993).
Treat et al., "Liposomes in the Therapy of Infectious Disease and Cancer," 353-65 (Lopez-Berestein et al., eds., 1989).
Urlaub & Chasin, "Isolation of Chinese hamster cell mutants deficient in dihydrofolate reductase activity," 77(7) Proc Natl Acad Sci USA 4216-20 (Jul. 1980).
Vajdos et al., "Comprehensive functional maps of the antigen-binding site of an anti-ErbB2 antibody obtained with shotgun scanning mutagenesis." 320(2) J Mol Biol 415-28 (Jul. 2002).
Vaughan et al., "Human antibodies by design," 16(6) Nature Biotechnology 535-9 (Jun. 1998).
Verhoeyen et al., "Reshaping human antibodies: grafting an antilysozyme activity," 239(4847) Science 1534-6 (Mar. 1988).
Walsh et al., "Gene therapy for human hemoglobinopathies," 204(3) Proc Soc Exp Biol Med 289-300 (Dec. 1993).
Wang et al., "A packaging cell line for propagation of recombinant adenovirus vectors containing two lethal gene-region deletions," 2(10) Gene Therapy 775-83 (Dec. 1995).
Wang et al. "Universal PCR amplification of mouse immunoglobulin gene variable regions: the design of degenerate primers and an assessment of the effect of DNA polymerase 3' to 5' exonuclease activity," 233(1-2) J Immunol Methods 167-77 (Jan. 2000).
Ward et al., "Binding activities of a repertoire of single immunoglobulin variable domains secreted from *Escherichia coli*," 341(6242) Nature 544-6 (Oct. 1989).
Waterhouse et al., "Combinatorial infection and in vivo recombination: a strategy for making large phage antibody repertoires," 21(9) Nucl Acids Res 2265-6 (May 1993).
Webb et al., "Prevention and amelioration of collagen-induced arthritis by blockade of the CD28 co-stimulatory pathway: requirement for both B7-1 and B7-2," 26(10) Eur J Immunol 2320-8 (Oct. 1996).
Wells & Lowman, "Rapid evolution of peptide and protein binding properties in vitro," 2 Curr Opin Struct Biol 597-604 (Aug. 1992).
Wien et al., "Structure of the complex between the Fab fragment of a neutralizing antibody for type 1 poliovirus and its viral epitope," 2(3) Nat Struct Biol 232-43 (Mar. 1995).
Wigler et al., "Transfer of purified herpes virus thymidine kinase gene to cultured mouse cells" 11(1) Cell 223-32 (May 1977).
Wigler et al., "Transformation of mammalian cells with an amplifiable dominant-acting gene," 77(6) Proc Natl Acad Sci USA 3567-70 (Jun. 1980).
Williams et al., "Anti-tumor necrosis factor ameliorates joint disease in murine collagen-induced arthritis," 89(20) Proc Natl Acad Sci USA 97848 (Oct. 1992).
Wilson et al., "The structure of an antigenic determinant in a protein," 37(3) Cell 767-78 (Jul. 1984).
Winter & Milstein, "Man-made antibodies," 349(6307) Nature 293-9 (Jan. 1991).
Wooley et al., "Influence of a recombinant human soluble tumor necrosis factor receptor FC fusion protein on type II collagen-induced arthritis in mice," 151(11) J Immunol 6602-7 (Dec. 1993).
Wu et al., "Humanization of a murine monoclonal antibody by simultaneous optimization of framework and CDR residues." 294(1) J Mol Biol 151-62 (Nov. 1999).
Wu & Wu, "Delivery systems for gene therapy," 3(1) Biotherapy 87-95 (Jan. 1991).
Wu & Wu, "Receptor-mediated in-vitro gene transformation by a soluble DNA carrier system," 262(10) J Biol Chem 4429-32 (Apr. 1987).
Yang et al., "CDR walking mutagenesis for the affinity maturation of a potent human anti-HIV-1 antibody into the picomolar range," 254(3) J Mol Biol 392-403 (Dec. 1995).
Zhu et al., "Probing the antibody-catalyzed water-oxidation pathway at atomic resolution," 101(8) Proc Natl Acad Sci USA 2247-52 (Feb. 2004).
Zhu et al., "The Origin of Enantioselectivity in Aldolase Antibodies: Crystal Structure, Site-directed Mutagenesis, and Computational Analysis," 343(5) J Mol Biol 1269-80 (Nov. 2004).
Zijlstra et al., "Germ-line transmission of a disrupted beta 2-microglobulin gene produced by homologous recombination in embryonic stem cells," 342(6248) Nature 435-8 (Nov. 1989).
Clowes et al., "Long-term biological response of injured rat carotid artery seeded with smooth muscle cells expressing retrovirally introduced human genes," 98(2) J Clin Invest 644-51 (Feb. 1994).
Cockett et al., "High level expression of tissue inhibitor of metalloproteinases in Chinese hamster ovary cells using glutamine synthetase gene amplification," 8(7) Biotechnology 662-7 (Jul. 1990).
Cotten et al., "Receptor-mediated transport of DNA into eukaryotic cells," 217 Meth Enzymol 618-44 (1993).
Colbére-Garapin et al., "A new dominant hybrid selective marker for higher eukaryotic cells," 150(1) J Mol Biol 1-14 (Jul. 1981).
Cole et al., "The EBV-Hybridoma Technique and its Application to Human Lung Cancer," in Monoclonal Antibodies and Cancer Therapy: Proceedings of the Roche-UCLA Symposium, 77-96 (Reisfeld and Sell eds.,1985).
Cote et al., "Generation of human monoclonal antibodies reactive with cellular antigens," 80(7) Proc Natl Acad Sci USA 2026-39 (Apr. 1983).
Creighton, Proteins: Structure and Molecular Properties, W.H. Freeman &Co., New York, pp. 78-87 (1st Edition, 1984).
Crouse et al., "Expression and amplification of engineered mouse dihydrofolate reductase minigenes," 3(2) Mol Cell Biol 257-66 (Feb. 1983).
Cunningham & Wells, "High-resolution epitope mapping of hGH-receptor interactions by alanine-scanning mutagenesis," 244(4908) Science 1081-5 (Jun. 1989).
Cunningham & Wells, "Rational design of receptor-specific variants of human growth hormone," 88(8) Proc Natl Acad Sci USA 3407-11 (Apr. 1991).
Cwirla et al., "Peptides on phage: a vast library of peptides for identifying ligands," 87(16) Proc Natl Acad Sci USA 6378-82 (Aug. 1990).
Davies & Riechmann, "Affinity improvement of single antibody VH domains: residues in all three hypervariable regions affect antigen binding," 2(3) Immunotechnology 169-79 (Sep. 1996).
DePascalis et al., "Grafting of "abbreviated" complementarity-determining regions containing specificity-determining residues essential for ligand contact to engineer a less immunogenic humanized monoclonal antibody." 169(6) J Immunol 3076-84 (Sep. 2002).
Devlin et al., "No excess of homozygosity at loci used for DNA fingerprinting," 249(4975) Science 1416-20 (Sep. 1990).
Di Carlo et al., "Quilty Effect Has the Features of Lymphoid Neogenesis and Shares CXCL13—CXCR5 Pathway With Recurrent Acute Cardiac Rejections," 7(1) Am J Trans 201-10 (Jan. 2007).
Duchosal et al., "Immunization of hu-PBL-SCID mice and the rescue of human monoclonal Fab fragments through combinatorial libraries," 355(6357) Nature 258-62 (Jan. 1992).
During et al., "Controlled release of dopamine from a polymeric brain implant: in vivo characterization," 25(4) Ann Neurol 351-6 (Apr. 1989).

(56) References Cited

OTHER PUBLICATIONS

Edge et al., "Deglycosylation of glycoproteins by trifluoromethanesulfonic acid," 118(1) Anal Biochem 131-7 (Nov. 1981).
Emrich et al., "Transmembrane topology of the lymphocyte-specific G-protein-coupled receptor BLR1: analysis by flow cytometry and immunocytochemistry," 40(3) Cell Mol Biol 413-9 (May 1994).
Fell et al., "Genetic construction and characterization of a fusion protein consisting of a chimeric F(ab') with specificity for carcinomas and human IL-2," 146(7) J Immunol 2446-52 (Apr. 1991).
Fleer et al., "High-level secretion of correctly processed recombinant human interleukin-1 beta in Kluyveromyces lactis," 107(2) Gene 285-95 (Nov. 1991).
Fleury et al., "A complex of influenza hemagglutinin with a neutralizing antibody that binds outside the virus receptor binding site," 6(6) Nat Struct Biol 530-4 (Jun. 1999).
Foecking et al., "Powerful and versatile enhancer-promoter unit for mammalian expression vectors," 45(1) Gene 101-5 (1986).
Forster et al., "A general method for screening mAbs specific for G-protein coupled receptors as exemplified by using epitope tagged BLR1-transfected 293 cells and solid-phase cell ELISA," 196(3) Biochemical Biophysical Research Communications 1496-503 (Nov. 1993).
Freedberg et al., "Flexibility and Function in HIV Protease: Dynamics of the HIV-1 Protease Bound to the Asymmetric Inhibitor Kynostatin 272 (KNI-272)," 120(31) J Am Chem Soc 7916-23 (Jul. 1998).
Furukawa et al., "A role of the third complementarity-determining region in the affinity maturation of an antibody," 276(29) J Biol Chem 27622-8 (Jul. 2001).
Gaffo et al., "Treatment of rheumatoid arthritis," 63(24) Am J Health Syst Pharm 2451-65 (Dec. 2006).
Gallicchio & Levy, "AGBNP: an analytic implicit solvent model suitable for molecular dynamics simulations and high-resolution modeling," 25(4) J Comput Chem 479-99 (Mar. 2004).
Garrard et al., "Fab assembly and enrichment in a monovalent phage display system," 9(12) Biotechnology 1373-7 (Dec. 1991).
Gefter et al. "A simple method for polyethylene glycol-promoted hybridization of mouse myeloma cells," 3(2) Somatic Cell Genet 231-6 (Mar. 1977).
Gentz et al., "Bioassay for trans-activation using purified human immunodeficiency virus tat-encoded protein: trans-activation requires mRNA synthesis," 86(3) Proc Natl Acad Sci USA 821-4 (Feb. 1989).
Gillies et al., "Antibody-targeted interleukin 2 stimulates T-cell killing of autologous tumor cells," 89(4) Proc Natl Acad Sci USA 1428-32 (Feb. 1992).
Gillies et al., "High-level expression of chimeric antibodies using adapted cDNA variable region cassettes," 125(1-2) J Immunol Methods 191-202 (Dec. 1989).
Goding, Chapter 3, "Production of Monoclonal Antibodies," in Monoclonal Antibodies: Principles and Practice, 59-103 (2nd Ed., 1986).
Goeddel et al., "Direct expression in *Escherichia coli* of a DNA sequence coding for human growth hormone," 281 (5732) Nature 544-8 (Oct. 1979).
Goeddel et al., "Synthesis of human fibroblast interferon by *E. coli*," 8(18) Nucl Acids Res 4057-74 (Sep. 1980).
Goldspiel et al., "Human gene therapy," 12(7) Clinical Pharm 488-505 (Jul. 1993).
Gram et al., "In vitro selection and affinity maturation of antibodies from a naive combinatorial immunoglobulin library," 89(8) Proc Natl Acad Sci USA 3576-80 (Apr. 1992).
Greenspan & Bona, "Idiotypes: structure and immunogenicity," 7(5) FASEB J 437-44 (Mar. 1993).
Grossman & Wilson, "Retroviruses: delivery vehicle to the liver," 3(1) Curr Opin Genet Dev 110-4 (Feb. 1993).
Grünberg et al., "Flexibility and conformational entropy in protein-protein binding," 14(12) Structure 683-93 (Apr. 2006).

Guddat et al., "Local and Transmitted Conformational Changes on Complexation of an Anti-sweetener Fab," 236(1) J Mol Biol 247-74 (Feb. 1994).
Guss et al., "Structure of the IgG-binding regions of streptococcal protein G," 5(7) EMBO J 1567-75 (Jul. 1986).
Hakimuddin et al., "A chemical method for deglycosylation of proteins," 259(1) Arch Biochem Biophys 52-7 (Nov. 1987).
Ham & McKeehan, "Media and growth requirements," 58 Meth Enzymol 44-93 (1979).
Harris et al., "Commercial manufacturing scale formulation and analytical characterization of therapeutic recombinant antibodies," 61(3) Drug Dev Res 137-54 (Jul. 2004).
Hawkins et al., "Selection of phage antibodies by binding affinity: Mimicking affinity maturation," 226(3) J Mol Biol 889-96 (Aug. 1992).
Hellström et al., Chapter 15, "Antibodies for Drug Delivery," in Controlled Drug Delivery: Fundamentals and Applications, 623-53 (Robinson & Lee eds., 2nd ed. 1987).
Hinnen et al., "Transformation of yeast," 75(4) Proc Natl Acad Sci USA 1929-33 (Apr. 1978).
Hitzeman et al., "Isolation and characterization of the yeast 3-phosphoglycerokinase gene (PGK) by an immunological screening technique," 255(24) J Biol Chem 12073-80 (Dec. 1980).
Lowman et al., "Selecting high-affinity binding proteins by monovalent phage display," 30(45) Biochemistry 10832-8 (Nov. 1991).
Lowy et al., "Isolation of transforming DNA: cloning the hamster aprt gene," 22(3) Cell 817-23 (Dec. 1980).
Luckow & Summers, "Trends in the development of baculorvirus expression vectors," 6 Nature Biotechnology 47-55 (Jan. 1988).
Ma et al., "Multiple diverse ligands binding at a single protein site: A matter of pre-existing populations," 11(2) Protein Science 184-7 (Feb. 2002).
MacCallum et al., "Antibody-antigen interactions: contact analysis and binding site topography." 262(5) J Mol Biol 732-45 (Oct. 1996).
Mackerell et al., vol. 1, "The Encyclopedia of Computational Chemistry," 271-7 (Schleyer et al., eds. 1998).
Maeda et al., "Production of human alpha-interferon in silkworm using a baculovirus vector," 315(6020) Nature 592-4 (Jun. 1985).
Mader & Keystone, "Optimizing treatment with biologics," 80 J Rheumatol Suppl 16-24 (Nov. 2007).
Marks et al., "X-Ray Structures of D1.3 Fv Mutants," PDB ID; 1A7P, (Accessed Feb. 21, 2012).
Marks et al., "By-passing immunization. Human antibodies from V-gene libraries displayed on phage," 222(3) J Mol Biol 581-97 (Dec. 1991).
Marks et al., "By-passing immunization: building high affinity human antibodies by chain shuffling," 10(7) Biotechnology 779-83 (Jul. 1992).
Mastrangeli et al., "Diversity of airway epithelial cell targets for in vivo recombinant adenovirus-mediated gene transfer," 91(1) J Clin Invest 225-34 (Jan. 1993).
Mazzucchelli et al., "BCA-1 is highly expressed in Helicobacter pylori-induced mucosa-associated lymphoid tissue and gastric lymphoma," 104(10) J Clin Invest R49-54 (Nov. 1999).
McCafferty et al., "Phage antibodies: filamentous phage displaying antibody variable domains," 348(6301) Nature 552-4 (Dec. 1990).
Meijer et al., "The CXCR5 chemokine receptor is expressed by carcinoma cells and promotes growth of colon carcinoma in the liver," 66(19) Cancer Res 9576-82 (Oct. 2006).
Miller et al., vol. 8, "An Insect Baculovirus Host-vector System for High-level Expression of Foreign Genes," Genetic Engineering: Principles and Methods 277-98 (Setlow and Hollaender, eds., 1986).
Milstein & Cuello, "Hybrid hybridomas and their use in immunohistochemistry," 305(5934) Nature 537-40 (Oct. 1983).
Modis et al., "Variable Surface Epitopes in the Crystal Structure of Dengue Virus Type 3 Envelope Glycoprotein," 79 (2) J Virol 1223-31 (Jan. 2005).
Order, "Analysis, Results, and Future Prospective of the Therapeutic Use of Radiolabeled Antibody in Cancer Therapy," in Monoclonal Antibodies for Cancer Detection and Therapy 303-16 (Baldwin and Byers, eds., 1985).
Morgan & Anderson, "Human gene therapy," 62 Ann Rev Biochem 191-217 (1993).

(56) References Cited

OTHER PUBLICATIONS

Morimoto & Inouye, "Single-step purification of F(ab')2 fragments of mouse monoclonal antibodies (immunoglobulins G1) by hydrophobic interaction high performance liquid chromatography using TSKgel Phenyl-5PW ," 24(1-2) J Biochem Biophys Methods 107-17 (Mar. 1992).
Morrison, "Transfectomas provide novel chimeric antibodies," 229(4719) Science 1202-7 (Sep. 1985).
Morrison et al., "Chimeric human antibody molecules: mouse antigen-binding domains with human constant region domains," 81(21) Proc Natl Acad Sci USA 6851-5 (Nov. 1984).
Mulligan & Berg, "Selection for animal cells that express the *Escherichia coli* gene coding for xanthine-guanine phosphoribosyltransferase," 78(4) Proc Natl Acad Sci USA 2072-6 (Apr. 1981).
Mulligan, "The basic science of gene therapy," 260(5110) Science 926-32 (May 1993).
Munson & Rodbard, "Ligand: a versatile computerized approach for characterization of ligand-binding systems," 107(1) Anal Biochem 220-39 (Sep. 1980).
Myers & Miller, "Optimal alignments in linear space," 4(1) Comput Appl Biosci. 11-7 (Mar. 1988).
Naramura et al., "Mechanisms of cellular cytotoxicity mediated by a recombinant antibody-IL2 fusion protein against human melanoma cells," 39(1) Immunol Lett 91-9 (Dec. 1993).
Newman et al., "Modification of the Fc Region of a Primatized IgG Antibody to Human CD4 Retains Its Ability to Modulate CD4 Receptors but Does Not Deplete CD4+ T Cells in Chimpanzees," 98(2) Clin Immunol 164-74 (Feb. 2001).
Nilsson & Karplus, "Empirical energy functions for energy minimization and dynamics of nucleic acids," 7(5) J Comput Chem 591-616 (1986).
Nisonoff, "Idiotypes: concepts and applications," 147(8) J Immunol 2429-38 (Oct. 1991).
Nisonoff et al., "Separation of univalent fragments from the bivalent rabbit antibody molecule by reduction of disulfide bonds," 89 Arch Biochem Biophys 230-44 (Aug. 1960).
Noorchashm et al., "B cell-mediated antigen presentation is required for the pathogenesis of acute cardiac allograft rejection," 177(11) J Immunol 7715-22 (Dec. 2006).
Oi & Morrison, "Chimeric antibodies," 4 BioTechniques 214-21 (1986).
O'Hare et al., "Transformation of mouse fibroblasts to methotrexate resistance by a recombinant plasmid expressing a prokaryotic dihydrofolate reductase," 78(3) Proc Natl Acad Sci USA 1527-31 (Mar. 1981).
Oligino & Dalrymple, "Targeting B cells for the treatment of rheumatoid arthritis," 5(Suppl 4) Arthritis Res Ther S7-11 (Oct. 2003).
Padlan, "A possible procedure for reducing the immunogenicity of antibody variable domains while preserving their ligand-binding properties," 28(4-5) Molecular Immunology 489-98 (Apr. 1991).
Padlan et al., "Structure of an antibody-antigen complex: crystal structure of the HyHEL-10 Fab-lysozyme complex." 86(15) Proc Natl Acad Sci USA 5938-42 (Aug. 1989).
Padlan et al., "Identification of specificity-determining residues in antibodies." 9(1) FASEB J 133-9 (Jan. 1995).
Parham, "On the fragmentation of monoclonal IgG1, IgG2a, and IgG2b from BALB/c mice," 131(6) J Immunol 2895-2902 (Dec. 1983).
Pearson & Lipman "Improved tools for biological sequence comparison," 85(8) Proc Natl Acad Sci USA 2444-8 (Apr. 1988).
Peters et al., "The Immune Epitope Database and Analysis Resource: from vision to blueprint," 3(3) PLoS Biol e91 (Mar. 2005).
Phumyen et al., "Improved binding activity of antibodies against major histocompatibility complex class I chain-related gene A by phage display technology for cancer-targeted therapy." 2012 J Biomed Biotechnol 597647 (Nov. 2012).

Pittelkow & Scott, "New techniques for the in vitro culture of human skin keratinocytes and perspectives on their use for grafting of patients with extensive burns," 61(10) Mayo Clinic Proc 771-7 (Oct. 1986).
Pozharski et al., "Carving a Binding Site: Structural Study of an Anti-Cocaine Antibody" in "Complex with Three Cocaine Analogs," (Accessed Feb. 21, 2012).
Presta et al., "Humanization of an antibody directed against IgE," 151(5) J Immunol 2623-32 (Sep. 1993).
Proudfoot, "Transcriptional interference and termination between duplicated alpha-globin gene constructs suggests a novel mechanism for gene regulation," 322(6079) Nature 562-5 (Aug. 1986).
Qiuping et al., "Selectively frequent expression of CXCR5 enhances resistance to apoptosis in CD8+CD34+ T cells from patients with T-cell-lineage acute lymphocytic leukemia," 24(4) Oncogene 573-84 (Jan. 2005).
Rader et al., "A phage display approach for rapid antibody humanization: designed combinatorial V gene libraries," 95(15) Proc Natl Acad Sci USA 8910-5 (Jul. 1998).
Reddy et al., "Elimination of Fc Receptor-Dependent Effector Functions of a Modified IgG4 Monoclonal Antibody to Human CD4," 164(4) J Immunol 1925-33 (Feb. 2000).
Adem et al., Chapter 16, "Preparation of Second-Generation Phage Libraries", pp. 277-91, Phage Display of Peptides and Proteins, A Laboratory Manual, eds. Kay et al., Academic Press (1996).
Aloisi & Pujol-Borrell, "Lymphoid neogenesis in chronic inflammatory diseases," 6(3) Nat Rev Immunol 205-17 (Mar. 2006).
Altschul et al., "Basic local alignment search tool," 215(3) J Mol Biol. 403-10 (1990).
Altschul et al., "Gapped BLAST and PSI-BLAST: a new generation of protein database search programs," 25(17) Nucleic Acids Res. 3389-402 (1997).
Amit et al., "Three-dimensional structure of an antigen-antibody complex at 2.8 A resolution," 233(4765) Science 747-53 (Aug. 1986).
Arnon et al., "Monoclonal Antibodies for Immunotargeting of Drugs in Cancer Therapy" in Monoclonal Antibodies and Cancer Therapy: Proceedings of the Roche-UCLA Symposium, 243-56 (Reisfeld and Sell eds., Jan. 1985).
Angal et al., "A single amino acid substitution abolishes the heterogeneity of chimeric mouse/human (IgG4) antibody," 30(1) Mol Imm 105-8 (Jan. 1993).
Aplin & Wriston, "Preparation, properties, and applications of carbohydrate conjugates of proteins and lipids," 10 (4) CRC Crit Rev Biochem 259-306 (May 1981).
Baddoura et al., "Lymphoid neogenesis in murine cardiac allografts undergoing chronic rejection," 5(3) Am J Trans 510-6 (Mar. 2005).
Banfield et al., "VL:VH domain rotations in engineered antibodies: Crystal structures of the Fab fragments from two murine antitumor antibodies and their engineered human constructs," 29(2) Proteins 161-71 (Oct. 1997).
Barbas et al., "In vitro evolution of a neutralizing human antibody to human immunodeficiency virus type 1 to enhance affinity and broaden strain cross-reactivity," 91(9) Proc Natl Acad Sci USA 3809-13 (Apr. 1994).
Barbas et al., "Assembly of combinatorial antibody libraries on phage surfaces: the gene III site," 88(18) Proc Natl Acad Sci USA 7978-82 (Sep. 1991).
Barone et al., "Association of CXCL13 and CCL21 expression with the progressive organization of lymphoid-like structures in Sjögren's syndrome," 52(6) Arth Rheum 1773-84 (Jun. 2005).
Barth et al., "Algorithms for constrained molecular dynamics," 16(10) J Comp Chem 1192-209 (Oct. 1995).
Barnes & Sato et al., "Methods for growth of cultured cells in serum-free medium," 102(2) Anal Biochem 255-70 (Mar. 1980).
Bentley et al., "Three-dimensional structure of an idiotope—anti-idiotope complex," 348(6298) Nature 254-7 (Nov. 1990).
Berman et al., "The Protein Data Bank," 28(1) Nucleic Acids Research 235-42 (Jan. 2000).
Beuscher IV et al., "Structure and Dynamics of Blue Fluorescent Antibody 19G2 at Blue and Violet Fluorescent Temperatures," pp. 1-2, (Accessed Feb. 21, 2012).

(56) References Cited

OTHER PUBLICATIONS

Birch & Racher, "Antibody production," 58(5-6) Adv Drug Del Rev 671-85 (Aug. 2006).
Bird et al, "Single-chain antigen-binding proteins," 242(4877) Science 423-6 (Oct. 1988).
Bizebard et al., "Refined three-dimensional structure of the Fab fragment of a murine IgG1,Iambda antibody," D50 (Parts) Acta Crystallogr D Biol Crystallogr 768-77 (Sep. 1994).
Bhat et al., "Bound water molecules and conformational stabilization help mediate an antigen-antibody association," 91(3) Proc Natl Acad Sci USA 1089-93 (Feb. 1994).
Blythe & Flower, "Benchmarking B cell epitope prediction: Underperformance of existing methods," 14(1) Protein Science 246-8 (Jan. 2005).
Boder et al., "Directed evolution of antibody fragments with monovalent femtomolar antigen-binding affinity," 97(20) Proc Natl Acad Sci USA 10701-5 (Sep. 2000).
Boerner et al., "Production of antigen-specific human monoclonal antibodies from in vitro-primed human splenocytes," 147(1) J Immunol 86-95 (Jul. 1991).
Bout et al., "Lung gene therapy: in vivo adenovirus-mediated gene transfer to rhesus monkey airway epithelium," 5(1) Human Gene Therapy 3-10 (Jan. 1994).
Brennan et al., "Preparation of bispecific antibodies by chemical recombination of monoclonal immunoglobulin G1 fragments," 229(4708) Science 813 (Jul. 1985).
Brodeur et al., Chapter 4 "Mouse-Human Myeloma Partners for the Production of Heterohybridomas," in Monoclonal Antibody Production Techniques and Applications, 51-63 (LB Schook ed. 1st ed. 1987).
Brooks et al., "CHARMM: A program for macromolecular energy, minimization, and dynamics calculations," 4(2) J Comput Chem 187-217 (1983).
Brown et al., "The Structural Basis of Repertoire Shift in an Immune Response to Phosphocholine," 191(12) J Exp Med 2101-12 (Jun. 2000).
Brüggemann et al., "Designer mice: the production of human antibody repertoires in transgenic animals," 7 The Year in Immunol 33-40 (1993).
Buchwald et al., "Long-term, continuous intravenous heparin administration by an implantable infusion pump in ambulatory patients with recurrent venous thrombosis," 88(4) Surgery 507-16 (Oct. 1980).
Bürkle et al., "Overexpression of the CXCR5 chemokine receptor, and its ligand, CXCL13 in B-cell chronic lymphocytic leukemia," 110(9) Blood 3316-3325 (Nov. 2007).
Cañete et al., "Ectopic lymphoid neogenesis in psoriatic arthritis," 66(6) Ann Rheum Dis 720-6 (Jun. 2007).

Carlsen et al., "B cell attracting chemokine 1 (CXCL13) and its receptor CXCR5 are expressed in normal and aberrant gut associated lymphoid tissue," 51(3) Gut 364-71 (Sep. 2002).
Caron et al., "Engineered humanized dimeric forms of IgG are more effective antibodies," 176(4) J Exp Med 1191-5 (Oct. 1992).
Carter et al., "Humanization of an anti-p185HER2 antibody for human cancer therapy," 89(10) Proc Natl Acad Sci USA 4285-9 (May 1992).
Carter et al., "High level *Escherichia coli* expression and production of a bivalent humanized antibody fragment," 10 (2) Biotechnology 163-7 (Feb. 1992).
Case et al., "The Amber biomolecular simulation programs," 26(16) J Comput Chem 1668-88 (Dec. 2005).
Casset et al. "A peptide mimetic of an anti-CD4 monoclonal antibody by rational design." 307(1) Biochem Biophys Res Commun. 198-205 (Jul. 2003).
Celikel et al., "von Willebrand factor conformation and adhesive function is modulated by an internalized water molecule," 7(10) Nat Struct Biol 881-4 (Oct. 2000).
Celikel et al., "Crystal structure of the von Willebrand factor A1 domain in complex with the function blocking NMC-4 Fab," 5(3) Nat Struct Biol 189-94 (Mar. 1998).
Chang et al., "Phenotypic expression in *E. coli* of a DNA sequence coding for mouse dihydrofolate reductase," 275 (5681) Nature 615-24 (Oct. 1978).
Chardés et al., "Efficient amplification and direct sequencing of mouse variable regions from any immunoglobulin gene family," 452(3) FEBS Letters 386-94 (Jun. 1999).
Chothia & Lesk, "Canonical structures for the hypervariable regions of immunoglobulins," 196(4) J Mol Biol 901-17 (Aug. 1987).
Cieplak et al., "Molecular mechanical models for organic and biological systems going beyond the atom centered two body additive approximation: aqueous solution free energies of methanol and N-methyl acetamide, nucleic acid base, and amide hydrogen bonding and chloroform/water partition coefficients of the nucleic acid bases," 22(10) J Comp Chem 1048-57 (May 2001).
Chen et al., "Selection and analysis of an optimized anti-VEGF antibody: crystal structure of an affinity-matured Fab in complex with antigen." 293(4) J. Mol. Biol. 865-81 (Nov. 1999).
Clackson et al., "Making antibody fragments using phage display libraries," 352(6336) Nature 624-8 (Aug. 1991).
Clark "Antibody humanization: a case of the 'Emperor's new clothes'?" 21(8) Immunol Today 397-402 (Aug. 2000).
Cline, "Perspectives for gene therapy: inserting new genetic information into mammalian cells by physical techniques and viral vectors," 29(1) Pharmacol Ther 69-92 (1985).
U.S. Appl. No. 13/745,377, filed Jan. 18, 2013, Michele Youd.
U.S. Appl. No. 14/158,056, filed Jan. 17, 2014, Ruiyin Chu.
U.S. Appl. No. 14/480,052, filed Sep. 8, 2014, Michele Youd.
U.S. Appl. No. 13/840,260, filed Mar. 15, 2013, Meng Zhang.
U.S. Appl. No. 13/850,849, filed Mar. 26, 2013, Julia Schnieders.

* cited by examiner

SEQUENCE LISTING

<160> NUMBER OF SEQ ID NOS: 29

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic

```
                             peptide

<400> SEQUENCE: 1

Gly Tyr Asn Trp His
1               5

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Ile Thr His Ser Gly Ser Thr Asn Tyr Asn Pro Ser Leu Lys Ser
1               5                   10                  15

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Ile Ala Val Ala Gly Thr Gly Tyr Tyr Gly Met Asp Val
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ala Ser Gln Gly Ile Asn Ser Ala Phe Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Ala Ser Ser Leu Glu Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Gln Phe Asn Ser Tyr Pro Leu Thr
1               5

<210> SEQ ID NO 7
```

```
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7
```

| Gln | Val | Gln | Leu | Gln | Gln | Trp | Gly | Ala | Gly | Leu | Leu | Lys | Pro | Ser | Glu |
|---|---|---|---|---|---|---|---|---|---|---|---|---|---|---|---|
| 1 | | | | 5 | | | | | 10 | | | | | 15 | |

| Thr | Leu | Ser | Leu | Thr | Cys | Ala | Val | Tyr | Gly | Gly | Ser | Phe | Ser | Gly | Tyr |
|---|---|---|---|---|---|---|---|---|---|---|---|---|---|---|---|
| | | | 20 | | | | | 25 | | | | | 30 | | |

| Asn | Trp | His | Trp | Ile | Arg | Gln | Pro | Pro | Gly | Lys | Gly | Leu | Glu | Trp | Ile |
|---|---|---|---|---|---|---|---|---|---|---|---|---|---|---|---|
| | | 35 | | | | | 40 | | | | | 45 | | | |

| Gly | Glu | Ile | Thr | His | Ser | Gly | Ser | Thr | Asn | Tyr | Asn | Pro | Ser | Leu | Lys |
|---|---|---|---|---|---|---|---|---|---|---|---|---|---|---|---|
| | 50 | | | | | 55 | | | | | 60 | | | | |

| Ser | Arg | Val | Thr | Ile | Ser | Val | Asp | Thr | Ser | Lys | Asn | Gln | Phe | Ser | Leu |
|---|---|---|---|---|---|---|---|---|---|---|---|---|---|---|---|
| 65 | | | | | 70 | | | | | 75 | | | | | 80 |

| Lys | Leu | Ser | Ser | Val | Thr | Ala | Ala | Asp | Thr | Ala | Val | Tyr | Tyr | Cys | Val |
|---|---|---|---|---|---|---|---|---|---|---|---|---|---|---|---|
| | | | | 85 | | | | | 90 | | | | | 95 | |

| Arg | Glu | Ile | Ala | Val | Ala | Gly | Thr | Gly | Tyr | Tyr | Gly | Met | Asp | Val | Trp |
|---|---|---|---|---|---|---|---|---|---|---|---|---|---|---|---|
| | | | 100 | | | | | 105 | | | | | 110 | | |

| Gly | Gln | Gly | Thr | Thr | Val | Thr | Val | Ser | Ser | Ala | Ser | Thr | Lys | Gly | Pro |
|---|---|---|---|---|---|---|---|---|---|---|---|---|---|---|---|
| | | 115 | | | | | 120 | | | | | 125 | | | |

| Ser | Val | Phe | Pro | Leu | Ala | Pro | Cys | Ser | Arg | Ser | Thr | Ser | Glu | Ser | Thr |
|---|---|---|---|---|---|---|---|---|---|---|---|---|---|---|---|
| | 130 | | | | | 135 | | | | | 140 | | | | |

| Ala | Ala | Leu | Gly | Cys | Leu | Val | Lys | Asp | Tyr | Phe | Pro | Glu | Pro | Val | Thr |
|---|---|---|---|---|---|---|---|---|---|---|---|---|---|---|---|
| 145 | | | | | 150 | | | | | 155 | | | | | 160 |

| Val | Ser | Trp | Asn | Ser | Gly | Ala | Leu | Thr | Ser | Gly | Val | His | Thr | Phe | Pro |
|---|---|---|---|---|---|---|---|---|---|---|---|---|---|---|---|
| | | | | 165 | | | | | 170 | | | | | 175 | |

| Ala | Val | Leu | Gln | Ser | Ser | Gly | Leu | Tyr | Ser | Leu | Ser | Ser | Val | Val | Thr |
|---|---|---|---|---|---|---|---|---|---|---|---|---|---|---|---|
| | | | | 180 | | | | | 185 | | | | | 190 | |

| Val | Pro | Ser | Ser | Ser | Leu | Gly | Thr | Lys | Thr | Tyr | Thr | Cys | Asn | Val | Asp |
|---|---|---|---|---|---|---|---|---|---|---|---|---|---|---|---|
| | | | 195 | | | | | 200 | | | | | 205 | | |

| His | Lys | Pro | Ser | Asn | Thr | Lys | Val | Asp | Lys | Arg | Val | Glu | Ser | Lys | Tyr |
|---|---|---|---|---|---|---|---|---|---|---|---|---|---|---|---|
| | 210 | | | | | 215 | | | | | 220 | | | | |

| Gly | Pro | Pro | Cys | Pro | Pro | Cys | Pro | Ala | Pro | Glu | Phe | Glu | Gly | Gly | Pro |
|---|---|---|---|---|---|---|---|---|---|---|---|---|---|---|---|
| 225 | | | | | 230 | | | | | 235 | | | | | 240 |

| Ser | Val | Phe | Leu | Phe | Pro | Pro | Lys | Pro | Lys | Asp | Thr | Leu | Met | Ile | Ser |
|---|---|---|---|---|---|---|---|---|---|---|---|---|---|---|---|
| | | | | 245 | | | | | 250 | | | | | 255 | |

| Arg | Thr | Pro | Glu | Val | Thr | Cys | Val | Val | Val | Asp | Val | Ser | Gln | Glu | Asp |
|---|---|---|---|---|---|---|---|---|---|---|---|---|---|---|---|
| | | | 260 | | | | | 265 | | | | | 270 | | |

| Pro | Glu | Val | Gln | Phe | Asn | Trp | Tyr | Val | Asp | Gly | Val | Glu | Val | His | Asn |
|---|---|---|---|---|---|---|---|---|---|---|---|---|---|---|---|
| | | 275 | | | | | 280 | | | | | 285 | | | |

| Ala | Lys | Thr | Lys | Pro | Arg | Glu | Glu | Gln | Phe | Asn | Ser | Thr | Tyr | Arg | Val |
|---|---|---|---|---|---|---|---|---|---|---|---|---|---|---|---|
| | 290 | | | | | 295 | | | | | 300 | | | | |

| Val | Ser | Val | Leu | Thr | Val | Leu | His | Gln | Asp | Trp | Leu | Asn | Gly | Lys | Glu |
|---|---|---|---|---|---|---|---|---|---|---|---|---|---|---|---|
| 305 | | | | | 310 | | | | | 315 | | | | | 320 |

| Tyr | Lys | Cys | Lys | Val | Ser | Asn | Lys | Gly | Leu | Pro | Ser | Ser | Ile | Glu | Lys |
|---|---|---|---|---|---|---|---|---|---|---|---|---|---|---|---|
| | | | | 325 | | | | | 330 | | | | | 335 | |

| Thr | Ile | Ser | Lys | Ala | Lys | Gly | Gln | Pro | Arg | Glu | Pro | Gln | Val | Tyr | Thr |
|---|---|---|---|---|---|---|---|---|---|---|---|---|---|---|---|
| | | | 340 | | | | | 345 | | | | | 350 | | |

| Leu | Pro | Pro | Ser | Gln | Glu | Glu | Met | Thr | Lys | Asn | Gln | Val | Ser | Leu | Thr |
|---|---|---|---|---|---|---|---|---|---|---|---|---|---|---|---|
| | | 355 | | | | | 360 | | | | | 365 | | | |

| Cys | Leu | Val | Lys | Gly | Phe | Tyr | Pro | Ser | Asp | Ile | Ala | Val | Glu | Trp | Glu |
|---|---|---|---|---|---|---|---|---|---|---|---|---|---|---|---|

```
                370                 375                 380
Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

<210> SEQ ID NO 8
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Asn Ser Ala
            20                  25                  30

Phe Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 9
<211> LENGTH: 240
<212> TYPE: PRT
<213> ORGANISM: Homo sapiens

<400> SEQUENCE: 9

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
```

```
                20                  25                  30
Cys Ser Val Ala Arg Val Gly Leu Gly Leu Leu Leu Leu Met Gly
         35                  40                  45

Ala Gly Leu Ala Val Gln Gly Trp Phe Leu Leu Gln Leu His Trp Arg
 50                  55                  60

Leu Gly Glu Met Val Thr Arg Leu Pro Asp Pro Ala Gly Ser Trp
 65                  70                  75                  80

Glu Gln Leu Thr Gln Glu Arg Ser His Glu Val Asn Pro Ala Ala
                 85                  90                  95

His Leu Thr Gly Ala Asn Ser Ser Leu Thr Gly Ser Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
        195                 200                 205

Leu Glu Ala Gly Glu Glu Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240

<210> SEQ ID NO 10
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Lys His Leu Trp Phe Phe Leu Leu Leu Val Ala Ala Pro Arg Trp
 1               5                  10                  15

Val Leu Ser Gln Val Gln Leu Gln Gln Trp Gly Ala Gly Leu Leu Lys
                20                  25                  30

Pro Ser Glu Thr Leu Ser Leu Thr Cys Ala Val Tyr Gly Gly Ser Phe
            35                  40                  45

Ser Gly Tyr Asn Trp His Trp Ile Arg Gln Pro Pro Gly Lys Gly Leu
 50                  55                  60

Glu Trp Ile Gly Glu Ile Thr His Ser Gly Ser Thr Asn Tyr Asn Pro
65                  70                  75                  80

Ser Leu Lys Ser Arg Val Thr Ile Ser Val Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Val Arg Glu Ile Ala Val Ala Gly Thr Gly Tyr Tyr Gly Met
        115                 120                 125

Asp Val Trp Gly Gln Gly Thr Thr Val Thr Val Ser Ser Ala Ser Thr
    130                 135                 140
```

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Lys Thr Tyr Thr Cys
    210                 215                 220

Asn Val Asp His Lys Pro Ser Asn Thr Lys Val Asp Lys Arg Val Glu
225                 230                 235                 240

Ser Lys Tyr Gly Pro Pro Cys Pro Pro Cys Pro Ala Pro Glu Phe Glu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

Gln Glu Asp Pro Glu Val Gln Phe Asn Trp Tyr Val Asp Gly Val Glu
    290                 295                 300

Val His Asn Ala Lys Thr Lys Pro Arg Glu Glu Gln Phe Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Gly Leu Pro Ser Ser
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Gln Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Arg Leu Thr
            420                 425                 430

Val Asp Lys Ser Arg Trp Gln Glu Gly Asn Val Phe Ser Cys Ser Val
        435                 440                 445

Met His Glu Ala Leu His Asn His Tyr Thr Gln Lys Ser Leu Ser Leu
    450                 455                 460

Ser Leu Gly
465

<210> SEQ ID NO 11
<211> LENGTH: 1404
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1401)

<400> SEQUENCE: 11 atg aag cac ctg tgg ttc ttt ctg ctg ctg gtg gcc gct cct aga tgg       48
Met Lys His Leu Trp Phe Phe Leu Leu Leu Val Ala Ala Pro Arg Trp

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| 1   |     |     |     | 5   |     |     |     |     | 10  |     |     |     |     | 15  |     |      |
| gtg | ctg | tcc | cag | gtg | cag | ctg | cag | cag | tgg | ggc | gct | ggc | ctg | ctg | aag | 96   |
| Val | Leu | Ser | Gln | Val | Gln | Leu | Gln | Gln | Trp | Gly | Ala | Gly | Leu | Leu | Lys |      |
|     |     |     | 20  |     |     |     |     | 25  |     |     |     |     | 30  |     |     |      |
| cct | tcc | gag | aca | ctg | tcc | ctg | acc | tgc | gcc | gtg | tac | ggc | ggc | tcc | ttc | 144  |
| Pro | Ser | Glu | Thr | Leu | Ser | Leu | Thr | Cys | Ala | Val | Tyr | Gly | Gly | Ser | Phe |      |
|     |     | 35  |     |     |     |     | 40  |     |     |     |     | 45  |     |     |     |      |
| tcc | ggc | tac | aac | tgg | cac | tgg | atc | agg | cag | cct | ccc | ggc | aag | ggc | ctg | 192  |
| Ser | Gly | Tyr | Asn | Trp | His | Trp | Ile | Arg | Gln | Pro | Pro | Gly | Lys | Gly | Leu |      |
|     | 50  |     |     |     |     | 55  |     |     |     |     | 60  |     |     |     |     |      |
| gaa | tgg | atc | ggc | gag | atc | acc | cac | tcc | ggc | tcc | acc | aac | tac | aac | cct | 240  |
| Glu | Trp | Ile | Gly | Glu | Ile | Thr | His | Ser | Gly | Ser | Thr | Asn | Tyr | Asn | Pro |      |
| 65  |     |     |     |     | 70  |     |     |     |     | 75  |     |     |     |     | 80  |      |
| agc | ctg | aag | tcc | aga | gtg | acc | atc | tcc | gtg | gac | acc | tcc | aag | aac | cag | 288  |
| Ser | Leu | Lys | Ser | Arg | Val | Thr | Ile | Ser | Val | Asp | Thr | Ser | Lys | Asn | Gln |      |
|     |     |     |     | 85  |     |     |     |     | 90  |     |     |     |     | 95  |     |      |
| ttc | tcc | ctg | aag | ctg | tcc | tct | gtg | acc | gcc | gct | gac | acc | gcc | gtg | tac | 336  |
| Phe | Ser | Leu | Lys | Leu | Ser | Ser | Val | Thr | Ala | Ala | Asp | Thr | Ala | Val | Tyr |      |
|     |     |     | 100 |     |     |     |     | 105 |     |     |     |     | 110 |     |     |      |
| tac | tgt | gtg | cgg | gag | atc | gcc | gtg | gct | ggc | acc | ggc | tac | tac | ggc | atg | 384  |
| Tyr | Cys | Val | Arg | Glu | Ile | Ala | Val | Ala | Gly | Thr | Gly | Tyr | Tyr | Gly | Met |      |
|     |     | 115 |     |     |     |     | 120 |     |     |     |     | 125 |     |     |     |      |
| gat | gtg | tgg | ggc | cag | ggc | acc | acc | gtg | acc | gtg | tcc | agc | gct | tct | acc | 432  |
| Asp | Val | Trp | Gly | Gln | Gly | Thr | Thr | Val | Thr | Val | Ser | Ser | Ala | Ser | Thr |      |
|     | 130 |     |     |     |     | 135 |     |     |     |     | 140 |     |     |     |     |      |
| aag | ggc | cct | tcc | gtg | ttc | cct | ctg | gcc | cct | tgc | tcc | cgg | tcc | acc | tcc | 480  |
| Lys | Gly | Pro | Ser | Val | Phe | Pro | Leu | Ala | Pro | Cys | Ser | Arg | Ser | Thr | Ser |      |
| 145 |     |     |     | 150 |     |     |     |     | 155 |     |     |     |     | 160 |     |      |
| gag | tcc | acc | gcc | gct | ctg | ggc | tgc | ctg | gtg | aag | gac | tac | ttc | cct | gag | 528  |
| Glu | Ser | Thr | Ala | Ala | Leu | Gly | Cys | Leu | Val | Lys | Asp | Tyr | Phe | Pro | Glu |      |
|     |     |     |     | 165 |     |     |     |     | 170 |     |     |     |     | 175 |     |      |
| cct | gtg | acc | gtg | tcc | tgg | aac | tct | ggc | gcc | ctg | acc | tcc | ggc | gtg | cac | 576  |
| Pro | Val | Thr | Val | Ser | Trp | Asn | Ser | Gly | Ala | Leu | Thr | Ser | Gly | Val | His |      |
|     |     |     | 180 |     |     |     |     | 185 |     |     |     |     | 190 |     |     |      |
| acc | ttc | cct | gcc | gtg | ctg | cag | tcc | tcc | ggc | ctg | tac | tcc | ctg | tcc | tcc | 624  |
| Thr | Phe | Pro | Ala | Val | Leu | Gln | Ser | Ser | Gly | Leu | Tyr | Ser | Leu | Ser | Ser |      |
|     |     | 195 |     |     |     |     | 200 |     |     |     |     | 205 |     |     |     |      |
| gtg | gtg | acc | gtg | cct | tcc | tcc | tcc | ctg | ggc | acc | aag | acc | tac | acc | tgt | 672  |
| Val | Val | Thr | Val | Pro | Ser | Ser | Ser | Leu | Gly | Thr | Lys | Thr | Tyr | Thr | Cys |      |
|     | 210 |     |     |     |     | 215 |     |     |     |     | 220 |     |     |     |     |      |
| aac | gtg | gac | cac | aag | cct | tcc | aac | acc | aag | gtg | gac | aag | cgg | gtg | gag | 720  |
| Asn | Val | Asp | His | Lys | Pro | Ser | Asn | Thr | Lys | Val | Asp | Lys | Arg | Val | Glu |      |
| 225 |     |     |     |     | 230 |     |     |     |     | 235 |     |     |     |     | 240 |      |
| tcc | aag | tac | ggc | cct | cct | tgc | cct | ccc | tgc | cct | gcc | cct | gag | ttc | gag | 768  |
| Ser | Lys | Tyr | Gly | Pro | Pro | Cys | Pro | Pro | Cys | Pro | Ala | Pro | Glu | Phe | Glu |      |
|     |     |     |     | 245 |     |     |     |     | 250 |     |     |     |     | 255 |     |      |
| ggc | gga | cct | agc | gtg | ttc | ctg | ttc | cct | cct | aag | cct | aag | gac | acc | ctg | 816  |
| Gly | Gly | Pro | Ser | Val | Phe | Leu | Phe | Pro | Pro | Lys | Pro | Lys | Asp | Thr | Leu |      |
|     |     |     | 260 |     |     |     |     | 265 |     |     |     |     | 270 |     |     |      |
| atg | atc | tcc | cgg | acc | cct | gag | gtg | acc | tgt | gtg | gtg | gtg | gac | gtg | tcc | 864  |
| Met | Ile | Ser | Arg | Thr | Pro | Glu | Val | Thr | Cys | Val | Val | Val | Asp | Val | Ser |      |
|     |     | 275 |     |     |     |     | 280 |     |     |     |     | 285 |     |     |     |      |
| cag | gag | gac | cct | gag | gtc | cag | ttc | aac | tgg | tac | gtg | gac | ggc | gtg | gag | 912  |
| Gln | Glu | Asp | Pro | Glu | Val | Gln | Phe | Asn | Trp | Tyr | Val | Asp | Gly | Val | Glu |      |
|     | 290 |     |     |     |     | 295 |     |     |     |     | 300 |     |     |     |     |      |
| gtg | cac | aac | gcc | aag | acc | aag | cct | cgg | gag | gag | cag | ttc | aat | tcc | acc | 960  |
| Val | His | Asn | Ala | Lys | Thr | Lys | Pro | Arg | Glu | Glu | Gln | Phe | Asn | Ser | Thr |      |
| 305 |     |     |     |     | 310 |     |     |     |     | 315 |     |     |     |     | 320 |      |
| tac | cgg | gtg | gtg | tct | gtg | ctg | acc | gtg | ctg | cac | cag | gac | tgg | ctg | aac | 1008 |

```
                Tyr Arg Val Val Ser Val Leu Thr Val Leu His Gln Asp Trp Leu Asn
                                325                 330                 335 ggc aaa gaa tac aag tgt aag gtc tcc aac aag ggc ctg ccc tcc tcc          1056
Gly Lys Glu Tyr Lys Cys Lys Val Ser Asn Lys Gly Leu Pro Ser Ser
            340                 345                 350 atc gag aaa acc atc tcc aag gcc aag ggc cag cct agg gag cct cag          1104
Ile Glu Lys Thr Ile Ser Lys Ala Lys Gly Gln Pro Arg Glu Pro Gln
        355                 360                 365 gtg tac acc ctg cct cct agc cag gaa gag atg acc aag aac cag gtg          1152
Val Tyr Thr Leu Pro Pro Ser Gln Glu Glu Met Thr Lys Asn Gln Val
    370                 375                 380 tcc ctg acc tgt ctg gtg aag ggc ttc tac cct tcc gac atc gcc gtg          1200
Ser Leu Thr Cys Leu Val Lys Gly Phe Tyr Pro Ser Asp Ile Ala Val
385                 390                 395                 400 gag tgg gag tcc aac ggc cag cct gag aac aac tac aag acc acc cct          1248
Glu Trp Glu Ser Asn Gly Gln Pro Glu Asn Asn Tyr Lys Thr Thr Pro
                405                 410                 415 cct gtg ctg gac tcc gac ggc tcc ttc ttc ctg tac tcc agg ctg acc          1296
Pro Val Leu Asp Ser Asp Gly Ser Phe Phe Leu Tyr Ser Arg Leu Thr
            420                 425                 430 gtg gac aag tcc cgg tgg cag gag ggc aac gtc ttt tcc tgc tcc gtg          1344
Val Asp Lys Ser Arg Trp Gln Glu Gly Asn Val Phe Ser Cys Ser Val
        435                 440                 445 atg cac gag gcc ctg cac aac cac tac acc cag aag tcc ctg tcc ctg          1392
Met His Glu Ala Leu His Asn His Tyr Thr Gln Lys Ser Leu Ser Leu
    450                 455                 460 tct ctg ggc tga                                                           1404
Ser Leu Gly
465

<210> SEQ ID NO 12
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Asp Met Arg Val Pro Ala Gln Leu Leu Gly Leu Leu Leu Leu Trp
1               5                   10                  15

Leu Pro Gly Ala Arg Cys Ala Ile Gln Leu Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Asn Ser Ala Phe Ala Trp Tyr Gln Gln Lys Pro Gly Lys
    50                  55                  60

Ala Pro Lys Leu Leu Ile Tyr Asp Ala Ser Ser Leu Glu Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Phe Asn Ser Tyr Pro Leu Thr Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160
```

```
                Phe Tyr Pro Arg Glu Ala Lys Val Gln Trp Lys Val Asp Asn Ala Leu
                                165                 170                 175

Gln Ser Gly Asn Ser Gln Glu Ser Val Thr Glu Gln Asp Ser Lys Asp
                            180                 185                 190

Ser Thr Tyr Ser Leu Ser Ser Thr Leu Thr Leu Ser Lys Ala Asp Tyr
                        195                 200                 205

Glu Lys His Lys Val Tyr Ala Cys Glu Val Thr His Gln Gly Leu Ser
                    210                 215                 220

Ser Pro Val Thr Lys Ser Phe Asn Arg Gly Glu Cys
                225                 230                 235

<210> SEQ ID NO 13
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(708)

<400> SEQUENCE: 13 atg gac atg aga gtg cct gct cag ctg ctg gga ctg ctg ctg ctg tgg        48
Met Asp Met Arg Val Pro Ala Gln Leu Leu Gly Leu Leu Leu Leu Trp
1               5                   10                  15 ctg cct ggc gct aga tgc gcc atc cag ctg acc cag tcc ccc tcc tct        96
Leu Pro Gly Ala Arg Cys Ala Ile Gln Leu Thr Gln Ser Pro Ser Ser
            20                  25                  30 ctg tcc gcc tcc gtg ggc gac aga gtg acc atc acc tgt cgg gcc tcc       144
Leu Ser Ala Ser Val Gly Asp Arg Val Thr Ile Thr Cys Arg Ala Ser
        35                  40                  45 cag ggc atc aac tcc gcc ttc gcc tgg tat cag cag aag cct ggc aag       192
Gln Gly Ile Asn Ser Ala Phe Ala Trp Tyr Gln Gln Lys Pro Gly Lys
    50                  55                  60 gcc cct aag ctg ctg atc tac gac gcc tcc tcc ctg gaa tcc ggc gtg       240
Ala Pro Lys Leu Leu Ile Tyr Asp Ala Ser Ser Leu Glu Ser Gly Val
65                  70                  75                  80 ccc tcc aga ttt tcc ggc tcc ggc tct ggc acc gac ttc acc ctg acc       288
Pro Ser Arg Phe Ser Gly Ser Gly Ser Gly Thr Asp Phe Thr Leu Thr
                85                  90                  95 atc tcc agc ctg cag cct gag gac ttc gcc acc tac tac tgc cag cag       336
Ile Ser Ser Leu Gln Pro Glu Asp Phe Ala Thr Tyr Tyr Cys Gln Gln
            100                 105                 110 ttc aac tcc tac cct ctg acc ttc ggc gga ggc acc aag gtg gag atc       384
Phe Asn Ser Tyr Pro Leu Thr Phe Gly Gly Gly Thr Lys Val Glu Ile
        115                 120                 125 aag cgt acg gtg gct gca cca tct gtc ttc atc ttc ccg cca tct gat       432
Lys Arg Thr Val Ala Ala Pro Ser Val Phe Ile Phe Pro Pro Ser Asp
    130                 135                 140 gag cag ttg aaa tct gga act gcc tct gtt gtg tgc ctg ctg aat aac       480
Glu Gln Leu Lys Ser Gly Thr Ala Ser Val Val Cys Leu Leu Asn Asn
145                 150                 155                 160 ttc tat ccc aga gag gcc aaa gta cag tgg aag gtg gat aac gcc ctc       528
Phe Tyr Pro Arg Glu Ala Lys Val Gln Trp Lys Val Asp Asn Ala Leu
                165                 170                 175 caa tcg ggt aac tcc cag gag agt gtc aca gag cag gac agc aag gac       576
Gln Ser Gly Asn Ser Gln Glu Ser Val Thr Glu Gln Asp Ser Lys Asp
            180                 185                 190 agc acc tac agc ctc agc agc acc ctg acg ctg agc aaa gca gac tac       624
```

```
Ser Thr Tyr Ser Leu Ser Ser Thr Leu Thr Leu Ser Lys Ala Asp Tyr
        195                 200                 205 gag aaa cac aaa gtc tac gcc tgc gaa gtc acc cat cag ggc ctg agc    672
Glu Lys His Lys Val Tyr Ala Cys Glu Val Thr His Gln Gly Leu Ser
    210                 215                 220 tcg ccc gtc aca aag agc ttc aac agg gga gag tgt tag                711
Ser Pro Val Thr Lys Ser Phe Asn Arg Gly Glu Cys
225                 230                 235

<210> SEQ ID NO 14
<211> LENGTH: 372
<212> TYPE: PRT
<213> ORGANISM: Homo sapiens

<400> SEQUENCE: 14

Met Asn Tyr Pro Leu Thr Leu Glu Met Asp Leu Glu Asn Leu Glu Asp
1               5                   10                  15

Leu Phe Trp Glu Leu Asp Arg Leu Asp Asn Tyr Asn Asp Thr Ser Leu
            20                  25                  30

Val Glu Asn His Leu Cys Pro Ala Thr Glu Gly Pro Leu Met Ala Ser
        35                  40                  45

Phe Lys Ala Val Phe Val Pro Val Ala Tyr Ser Leu Ile Phe Leu Leu
    50                  55                  60

Gly Val Ile Gly Asn Val Leu Val Leu Val Ile Leu Glu Arg His Arg
65                  70                  75                  80

Gln Thr Arg Ser Ser Thr Glu Thr Phe Leu Phe His Leu Ala Val Ala
                85                  90                  95

Asp Leu Leu Leu Val Phe Ile Leu Pro Phe Ala Val Ala Glu Gly Ser
            100                 105                 110

Val Gly Trp Val Leu Gly Thr Phe Leu Cys Lys Thr Val Ile Ala Leu
        115                 120                 125

His Lys Val Asn Phe Tyr Cys Ser Ser Leu Leu Leu Ala Cys Ile Ala
    130                 135                 140

Val Asp Arg Tyr Leu Ala Ile Val His Ala Val His Ala Tyr Arg His
145                 150                 155                 160

Arg Arg Leu Leu Ser Ile His Ile Thr Cys Gly Thr Ile Trp Leu Val
                165                 170                 175

Gly Phe Leu Leu Ala Leu Pro Glu Ile Leu Phe Ala Lys Val Ser Gln
            180                 185                 190

Gly His His Asn Asn Ser Leu Pro Arg Cys Thr Phe Ser Gln Glu Asn
        195                 200                 205

Gln Ala Glu Thr His Ala Trp Phe Thr Ser Arg Phe Leu Tyr His Val
    210                 215                 220

Ala Gly Phe Leu Leu Pro Met Leu Val Met Gly Trp Cys Tyr Val Gly
225                 230                 235                 240

Val Val His Arg Leu Arg Gln Ala Gln Arg Arg Pro Gln Arg Gln Lys
                245                 250                 255

Ala Val Arg Val Ala Ile Leu Val Thr Ser Ile Phe Phe Leu Cys Trp
            260                 265                 270

Ser Pro Tyr His Ile Val Ile Phe Leu Asp Thr Leu Ala Arg Leu Lys
        275                 280                 285

Ala Val Asp Asn Thr Cys Lys Leu Asn Gly Ser Leu Pro Val Ala Ile
    290                 295                 300

Thr Met Cys Glu Phe Leu Gly Leu Ala His Cys Cys Leu Asn Pro Met
305                 310                 315                 320
```

```
Leu Tyr Thr Phe Ala Gly Val Lys Phe Arg Ser Asp Leu Ser Arg Leu
            325                 330                 335

Leu Thr Lys Leu Gly Cys Thr Gly Pro Ala Ser Leu Cys Gln Leu Phe
            340                 345                 350

Pro Ser Trp Arg Arg Ser Ser Leu Ser Glu Ser Glu Asn Ala Thr Ser
            355                 360                 365

Leu Thr Thr Phe
    370

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Phe Ser Leu Ile Asp Tyr Gly Val Asn
1               5                   10

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Val Ile Trp Gly Asp Gly Thr Thr Tyr
1               5

<210> SEQ ID NO 17
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ile Val Tyr
1

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Ser Ser Lys Ser Leu Leu His Ser Ser Gly Lys Thr Tyr Leu Tyr
1               5                   10                  15

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19
```

```
Arg Leu Ser Ser Leu Ala
1               5
```

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Met Gln His Leu Glu Tyr Pro Tyr Thr
1               5
```

<210> SEQ ID NO 21
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Gln Val Gln Leu Lys Glu Ser Gly Pro Gly Leu Val Ala Pro Ser Glu
1               5                   10                  15

Ser Leu Ser Ile Thr Cys Thr Val Ser Gly Phe Ser Leu Ile Asp Tyr
            20                  25                  30

Gly Val Asn Trp Ile Arg Gln Pro Pro Gly Lys Gly Leu Glu Trp Leu
        35                  40                  45

Gly Val Ile Trp Gly Asp Gly Thr Thr Tyr Tyr Asn Pro Ser Leu Lys
    50                  55                  60

Ser Arg Leu Ser Ile Ser Lys Asp Asn Ser Lys Ser Gln Val Phe Leu
65                  70                  75                  80

Lys Val Thr Ser Leu Thr Thr Asp Asp Thr Ala Met Tyr Tyr Cys Ala
                85                  90                  95

Arg Ile Val Tyr Trp Gly Gln Gly Thr Leu Val Thr Val Ser Ala
            100                 105                 110
```

<210> SEQ ID NO 22
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Asp Ile Val Met Thr Gln Ala Ala Pro Ser Val Ala Val Thr Pro Gly
1               5                   10                  15

Ala Ser Val Ser Ile Ser Cys Arg Ser Ser Lys Ser Leu Leu His Ser
            20                  25                  30

Ser Gly Lys Thr Tyr Leu Tyr Trp Phe Leu Gln Arg Pro Gly Gln Ser
        35                  40                  45

Pro Gln Leu Leu Ile Tyr Arg Leu Ser Ser Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
```

<210> SEQ ID NO 23
<211> LENGTH: 326
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325
```

<210> SEQ ID NO 24
<211> LENGTH: 107

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 25
<211> LENGTH: 437
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Lys Glu Ser Gly Pro Gly Leu Val Ala Pro Ser Glu
1               5                   10                  15

Ser Leu Ser Ile Thr Cys Thr Val Ser Gly Phe Ser Leu Ile Asp Tyr
            20                  25                  30

Gly Val Asn Trp Ile Arg Gln Pro Pro Gly Lys Gly Leu Glu Trp Leu
        35                  40                  45

Gly Val Ile Trp Gly Asp Gly Thr Thr Tyr Tyr Asn Pro Ser Leu Lys
    50                  55                  60

Ser Arg Leu Ser Ile Ser Lys Asp Asn Ser Lys Ser Gln Val Phe Leu
65                  70                  75                  80

Lys Val Thr Ser Leu Thr Thr Asp Asp Thr Ala Met Tyr Tyr Cys Ala
                85                  90                  95

Arg Ile Val Tyr Trp Gly Gln Gly Thr Leu Val Thr Val Ser Ala Ala
            100                 105                 110

Ser Thr Lys Gly Pro Ser Val Phe Pro Leu Ala Pro Cys Ser Arg Ser
        115                 120                 125

Thr Ser Glu Ser Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Lys Thr Tyr
            180                 185                 190

Thr Cys Asn Val Asp His Lys Pro Ser Asn Thr Lys Val Asp Lys Arg
        195                 200                 205
```

```
Val Glu Ser Lys Tyr Gly Pro Pro Cys Pro Pro Cys Pro Ala Pro Glu
    210                 215                 220

Phe Glu Gly Gly Pro Ser Val Phe Leu Phe Pro Pro Lys Pro Lys Asp
225                 230                 235                 240

Thr Leu Met Ile Ser Arg Thr Pro Glu Val Thr Cys Val Val Val Asp
                245                 250                 255

Val Ser Gln Glu Asp Pro Glu Val Gln Phe Asn Trp Tyr Val Asp Gly
            260                 265                 270

Val Glu Val His Asn Ala Lys Thr Lys Pro Arg Glu Glu Gln Phe Asn
        275                 280                 285

Ser Thr Tyr Arg Val Val Ser Val Leu Thr Val Leu His Gln Asp Trp
    290                 295                 300

Leu Asn Gly Lys Glu Tyr Lys Cys Lys Val Ser Asn Lys Gly Leu Pro
305                 310                 315                 320

Ser Ser Ile Glu Lys Thr Ile Ser Lys Ala Lys Gly Gln Pro Arg Glu
                325                 330                 335

Pro Gln Val Tyr Thr Leu Pro Pro Ser Gln Glu Glu Met Thr Lys Asn
            340                 345                 350

Gln Val Ser Leu Thr Cys Leu Val Lys Gly Phe Tyr Pro Ser Asp Ile
        355                 360                 365

Ala Val Glu Trp Glu Ser Asn Gly Gln Pro Glu Asn Asn Tyr Lys Thr
    370                 375                 380

Thr Pro Pro Val Leu Asp Ser Asp Gly Ser Phe Phe Leu Tyr Ser Arg
385                 390                 395                 400

Leu Thr Val Asp Lys Ser Arg Trp Gln Glu Gly Asn Val Phe Ser Cys
                405                 410                 415

Ser Val Met His Glu Ala Leu His Asn His Tyr Thr Gln Lys Ser Leu
            420                 425                 430

Ser Leu Ser Leu Gly
            435

<210> SEQ ID NO 26
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Ile Val Met Thr Gln Ala Ala Pro Ser Val Ala Val Thr Pro Gly
1               5                   10                  15

Ala Ser Val Ser Ile Ser Cys Arg Ser Ser Lys Ser Leu Leu His Ser
            20                  25                  30

Ser Gly Lys Thr Tyr Leu Tyr Trp Phe Leu Gln Arg Pro Gly Gln Ser
        35                  40                  45

Pro Gln Leu Leu Ile Tyr Arg Leu Ser Ser Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125
```

```
Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215

<210> SEQ ID NO 27
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Met Gly Trp Ser Cys Ile Ile Leu Phe Leu Val Ala Thr Ala Thr Gly
1               5                   10                  15

Val His Ser

<210> SEQ ID NO 28
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Gly Trp Ser Cys Ile Ile Leu Phe Leu Val Ala Thr Ala Thr Gly
1               5                   10                  15

Val His Ser Gln Val Gln Leu Lys Glu Ser Gly Pro Gly Leu Val Ala
            20                  25                  30

Pro Ser Glu Ser Leu Ser Ile Thr Cys Thr Val Ser Gly Phe Ser Leu
        35                  40                  45

Ile Asp Tyr Gly Val Asn Trp Ile Arg Gln Pro Pro Gly Lys Gly Leu
    50                  55                  60

Glu Trp Leu Gly Val Ile Trp Gly Asp Gly Thr Thr Tyr Asn Pro
65                  70                  75                  80

Ser Leu Lys Ser Arg Leu Ser Ile Ser Lys Asp Asn Ser Lys Ser Gln
                85                  90                  95

Val Phe Leu Lys Val Thr Ser Leu Thr Thr Asp Asp Thr Ala Met Tyr
            100                 105                 110

Tyr Cys Ala Arg Ile Val Tyr Trp Gly Gln Gly Thr Leu Val Thr Val
        115                 120                 125

Ser Ala Ala Ser Thr Lys Gly Pro Ser Val Phe Pro Leu Ala Pro Cys
    130                 135                 140

Ser Arg Ser Thr Ser Glu Ser Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175
```

```
Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Lys Thr Tyr Thr Cys Asn Val Asp His Lys Pro Ser Asn Thr Lys Val
    210                 215                 220

Asp Lys Arg Val Glu Ser Lys Tyr Gly Pro Pro Cys Pro Pro Cys Pro
225                 230                 235                 240

Ala Pro Glu Phe Glu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser Gln Glu Asp Pro Glu Val Gln Phe Asn Trp Tyr
        275                 280                 285

Val Asp Gly Val Glu Val His Asn Ala Lys Thr Lys Pro Arg Glu Glu
    290                 295                 300

Gln Phe Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Gly Leu Pro Ser Ser Ile Glu Lys Thr Ile Ser Lys Ala Lys Gly Gln
            340                 345                 350

Pro Arg Glu Pro Gln Val Tyr Thr Leu Pro Pro Ser Gln Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Arg Leu Thr Val Asp Lys Ser Arg Trp Gln Glu Gly Asn Val
            420                 425                 430

Phe Ser Cys Ser Val Met His Glu Ala Leu His Asn His Tyr Thr Gln
        435                 440                 445

Lys Ser Leu Ser Leu Ser Leu Gly
    450                 455

<210> SEQ ID NO 29
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Gly Trp Ser Cys Ile Ile Leu Phe Leu Val Ala Thr Ala Thr Gly
1               5                   10                  15

Val His Ser Asp Ile Val Met Thr Gln Ala Ala Pro Ser Val Ala Val
            20                  25                  30

Thr Pro Gly Ala Ser Val Ser Ile Ser Cys Arg Ser Ser Lys Ser Leu
        35                  40                  45

Leu His Ser Ser Gly Lys Thr Tyr Leu Tyr Trp Phe Leu Gln Arg Pro
    50                  55                  60

Gly Gln Ser Pro Gln Leu Leu Ile Tyr Arg Leu Ser Ser Leu Ala Ser
65                  70                  75                  80
```

```
Gly Val Pro Asp Arg Phe Ser Gly Ser Gly Thr Ala Phe Thr
            85                  90              95

Leu Arg Ile Ser Arg Val Glu Ala Glu Asp Val Gly Val Tyr Tyr Cys
            100             105                 110

Met Gln His Leu Glu Tyr Pro Tyr Thr Phe Gly Gly Gly Thr Lys Leu
        115                 120                 125

Glu Ile Lys Arg Thr Val Ala Ala Pro Ser Val Phe Ile Phe Pro Pro
        130                 135             140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
        210                 215                 220

Leu Ser Ser Pro Val Thr Lys Ser Phe Asn Arg Gly Glu Cys
225                 230                 235
```

STABLE IGG4 BASED BINDING AGENT FORMULATIONS

CROSS-REFERENCE TO RELATED APPLICATIONS

This application claims priority to U.S. Provisional Application Ser. No. 61/615,539, filed Mar. 26, 2012, which is incorporated herein by reference in its entirety. This application also claims the benefit of foreign priority to French Patent Application Serial No. 1351013 filed Feb. 6, 2013, which is incorporated herein by reference in its entirety.

BACKGROUND OF THE INVENTION

The human LIGHT antigen is one potential cytokine target that has been implicated in the processes of chronic inflammatory autoimmune disease. As a member of the TNF superfamily (TNFSF) of ligands, LIGHT is also known as TNFSF14 or CD258. LIGHT is expressed on the surface of T cells upon activation in a tightly regulated manner. However, LIGHT is also present at detectable levels constitutively on the surface of immature dendritic cells and on T cells and natural killer (NK) cells of the gut. LIGHT mediates its biologic effects by binding three TNF superfamily receptors, including the lymphotoxin β receptor (LTβR), the herpes virus entry mediator (HVEM), and decoy receptor 3 (DcR3). LIGHT-expressing lymphocytes can induce IBD-like symptoms in humans, and increases of LIGHT expression have been observed in patients with active Crohn's disease and other inflammatory disorders such as Graft-vs.-Host Disease.

CXCR5, also known as Burkitt lymphoma receptor (BLR1), CD185, MDR15, and MGC117347, is a G protein-coupled receptor that is a member of the CXC chemokine receptor family. The unprocessed CXCR5 precursor is 372 amino acids in length with a molecular weight of 42 $K_D$. CXCR5 has a role in B cell migration and localization within particular anatomic compartments. Knockout mice lack peripheral lymph nodes, have fewer Peyer's patches and have decreased B cell levels. CXCL13, also known as BLC, is a ligand for CXCR5. CXCL13 is a B cell chemoattractant.

Anti-LIGHT binding agents and anti-CXCR5 binding agents are each therapeutically relevant, and a need exists to formulate each of these binding agents into drug products that may be administered to subjects, particularly human subjects, for the treatment of inflammatory diseases.

In order to develop a pharmaceutical formulation containing an anti-LIGHT binding agent or an anti-CXCR5 binding agent suitable for intravenous or subcutaneous administration, the binding agent must be concentrated to about 20 mg/mL or greater, usually about 100-150 mg/mL, and even up to 250 mg/mL. Many complications can arise at such high concentrations, including an increase in viscosity, a shift of pH, a change of the color of the solution, and the formation of visible and sub-visible particles.

The formulation of these binding agents is further complicated by the fact that these agents are highly prone to aggregation at such high concentrations.

The formulation of IgG4 antibodies is even further complicated by the fact that IgG4 antibodies tend to form half-molecules at high concentrations in solution. However, IgG4 antibodies are of therapeutic interest because they have reduced effector function.

SUMMARY OF THE INVENTION

To meet these and other needs, provided herein are highly stable IgG4 binding agent formulations. Highly stable IgG4 binding agent formulations have surprisingly been found in the form of liquids and lyophilized powders that comprise an IgG4 binding agent and a citrate buffer, wherein the pH of the formulation is at or below both about pH 6 and the isoelectric point (pI) of the binding agent. These formulations improve upon conventional formulations, which often lead to dimerization of the binding agent, such as an antibody, upon increasing the concentration of the binding agent, such as an antibody, in the formulation. In particular, the formulations of the invention reduce the amount of unwanted byproducts, including aggregates, half-molecules, degradation products, low molecular weight proteins (LM-WPs), high molecular weight proteins (HMWPs), and rearrangements of acid, basic, and neutral isoforms of the binding agent, such as an antibody, component in the formulation.

In certain aspects, the invention provides a stable formulation comprising: a binding agent comprising at least a portion of a Fc region of an IgG4 antibody; and about 5 to about 50 mM citrate as a buffering agent; wherein the pH of the formulation is at or below both about pH 6 and the pI of the binding agent. In certain embodiments of the invention, the binding agent is an antibody.

In certain embodiments of the invention, the binding agent or antibody binds to lymphotoxin-like, exhibits inducible expression and competes with herpes virus glycoprotein D for herpes virus entry mediator, a receptor expressed on lymphocytes (LIGHT). In specific embodiments of the invention, the anti-LIGHT binding agent or antibody comprises a heavy chain variable region and a light chain variable region, the heavy chain variable region comprising complementary determining regions (CDRs) comprising the amino acid sequences of SEQ ID NOS: 1, 2, and 3, and the light chain variable region comprising CDRs comprising the amino acid sequences of SEQ ID NOS: 4, 5, and 6. In other specific embodiments of the invention, the antibody is a fully human IgG4 anti-LIGHT antibody comprising a heavy chain comprising the amino acid sequence of SEQ ID NO: 7 and a light chain comprising the amino acid sequence of SEQ ID NO: 8.

In certain embodiments of the invention, the binding agent or antibody binds to C-X-C chemokine receptor type 5 (CXCR5). In specific embodiments of the invention, the anti-CXCR5 binding agent or antibody comprises a heavy chain variable region and a light chain variable region, the heavy chain variable region comprising complementary determining regions (CDRs) comprising the amino acid sequences of SEQ ID NOS: 15, 16, and 17, and the light chain variable region comprising CDRs comprising the amino acid sequences of SEQ ID NOS: 18, 19, and 20. In other specific embodiments of the invention, the antibody is a humanized IgG4 anti-CXCR5 antibody comprising a heavy chain comprising the amino acid sequence of SEQ ID NO: 25 and a light chain comprising the amino acid sequence of SEQ ID NO: 26.

In certain embodiments of the invention, the antibody concentration is from about 5 to about 280 mg/mL. In certain specific embodiments of the invention, the antibody concentration is about 150 mg/mL. In other specific embodiments of the invention, the antibody concentration is about 50 mg/mL. In further specific embodiments of the invention, the antibody concentration is about 20 mg/mL. In yet further specific embodiments of the invention, the antibody concentration is about 100 mg/mL.

In certain embodiments of the invention, the citrate concentration is from about 5 to about 15 mM. In some embodiments of the invention, the citrate concentration is about 10 mM. In some embodiments of the invention, the citrate buffer is sodium citrate dihydrate.

In certain embodiments of the invention, the pH of the formulation is from about pH 5 and about pH 6. In specific embodiments of the invention, the pH of the formulation is selected from the group consisting of about pH 5.0, about pH 5.5, and about pH 6.0.

In certain specific embodiment of the invention, the pI of the binding agent or antibody is from about 6.8 and about 7.2. In alternative specific embodiments of the invention, the pI of the binding agent or antibody is from about 7.6 and about 8.4.

In certain specific embodiments of the invention, the formulation further comprises a surfactant. In certain specific embodiments of the invention, the concentration of surfactant is between about 0.001% and about 0.1% w/v. In certain embodiments of the invention, the surfactant is a polysorbate. In certain specific embodiments of the invention, the polysorbate is polysorbate 20. In some specific embodiments of the invention, the concentration of polysorbate 20 is about 0.005% w/v. In alternative specific embodiments of the invention, the concentration of polysorbate 20 is about 0.01% w/v. In further alternative specific embodiments of the invention, the concentration of polysorbate 20 is about 0.02% w/v.

In certain embodiments of the invention, the formulation further comprises a tonicity agent. In certain specific embodiments of the invention, the concentration of tonicity agent is between about 0.1% and about 10% w/v. In certain specific embodiments of the invention, the tonicity agent is a saccharide. In some specific embodiments of the invention, the saccharide is mannitol. In other specific embodiments of the invention, the concentration of mannitol is between about 1% and about 10% w/v. In yet other specific embodiments of the invention, the concentration of mannitol is about 4%. In alternative specific embodiments of the invention, the saccharide is sucrose. In some specific embodiments of the invention, the concentration of sucrose is between about 1% and about 10% w/v. In some specific embodiments of the invention, the concentration of sucrose is about 5% w/v. In alternative specific embodiments of the invention, the concentration of sucrose is about 6% w/v. In yet other specific embodiments of the invention, the concentration of sucrose is about 4.5% w/v. In further specific alternative embodiments of the invention, the tonicity agent is sodium chloride. In some specific embodiments of the invention, the concentration of sodium chloride is between about 0.01% and about 1%. In some specific embodiments of the invention, the concentration of sodium chloride is about 0.2%. In other specific embodiments of the invention, the tonicity agent is a combination of sucrose and sodium chloride. In specific embodiments of the invention, the concentration of sucrose is between about 1% and about 10% w/v. In other specific embodiments of the invention, the concentration of sodium chloride is between about 0.01% and about 1%. In alternative specific embodiments of the invention, the concentration of sucrose is about 6% w/v and the concentration of sodium chloride is about 0.2%. In yet further alternative specific embodiments of the invention, the concentration of sucrose is about 4.5% w/v and the concentration of sodium chloride is about 0.2%.

In certain embodiments of the invention, the formulation further comprises an amino acid. In certain specific embodiments of the invention, the amino acid concentration is between about 0.1% and about 5% w/v. In certain specific embodiments of the invention, the amino acid is proline or arginine. In specific embodiments of the invention, the proline or arginine concentration is between about 1% and about 2% w/v. In other specific embodiments of the invention, the proline concentration is about 1.5% w/v. In alternative specific embodiments of the invention, the arginine concentration is about 1% w/v.

In certain embodiments of the invention, the formulation is a liquid formulation. In other specific embodiments of the invention, the formulation is a lyophilized formulation.

In certain embodiments of the invention, the formulation is stable for at least 6 months at +5° C. In alternative embodiments of the invention, the formulation is stable for at least 9 months at +5° C.

In certain embodiments of the invention, the formulation exhibits a reduced amount of at least one byproduct selected from the group consisting of aggregates, half-molecules, degradation products, low molecular weight proteins, high molecular weight proteins, and and rearrangements of acidic/basic/neutral isoforms of the antibody as compared to either a reference anti-LIGHT formulation comprising an anti-LIGHT antibody in phosphate buffered saline at pH 7.3 or a reference anti-CXCR5 formulation comprising an anti-LIGHT antibody in phosphate buffered saline at pH 7.3.

In certain specific embodiments of the invention, the invention provides a stable liquid antibody formulation suitable for subcutaneous administration, the formulation comprising:

a) about 150 mg/mL of a fully human IgG4 anti-LIGHT (lymphotoxin-like, exhibits inducible expression and competes with HSV glycoprotein D for HVEM, a receptor expressed by T lymphocytes) antibody comprising a heavy chain comprising the amino acid sequence of SEQ ID NO: 7 and a light chain comprising the amino acid sequence of SEQ ID NO: 8;

b) about 10 mM citrate buffer;

c) about 0.005% polysorbate 20; and d) about 4% mannitol;

wherein the pH of the formulation is about pH 5.5.

In other specific embodiments of the invention, the invention provides a stable liquid antibody formulation suitable for intravenous administration, the formulation comprising:

a) about 50 mg/mL of a fully human IgG4 anti-LIGHT (lymphotoxin-like, exhibits inducible expression and competes with HSV glycoprotein D for HVEM, a receptor expressed by T lymphocytes) antibody comprising a heavy chain comprising the amino acid sequence of SEQ ID NO: 7 and a light chain comprising the amino acid sequence of SEQ ID NO: 8;

b) about 10 mM citrate buffer; and c) about 0.01% polysorbate 20;

wherein the pH of the formulation is about pH 5.5.

In yet other specific embodiments of the invention, the invention provides a stable lyophilized antibody formulation suitable for intravenous administration, the formulation comprising:

a) about 50 mg/mL of a fully human IgG4 anti-LIGHT (lymphotoxin-like, exhibits inducible expression and competes with HSV glycoprotein D for HVEM, a receptor expressed by T lymphocytes) antibody comprising a heavy chain comprising the amino acid sequence of SEQ ID NO: 7 and a light chain comprising the amino acid sequence of SEQ ID NO: 8;

b) about 10 mM citrate buffer;

c) about 0.01% polysorbate 20;

d) about 5% sucrose; and e) about 1.5% proline;

wherein the pH of the formulation is about pH 5.5.

In alternative specific embodiments of the invention, the invention provides a stable antibody formulation comprising:
a) about 20 mg/mL of a humanized IgG4 anti-CXCR5 (C-X-C chemokine receptor type 5) antibody comprising a heavy chain comprising the amino acid sequence of SEQ ID NO: 25 and a light chain comprising the amino acid sequence of SEQ ID NO: 26;
b) about 10 mM citrate buffer;
c) about 0.02% polysorbate 20;
d) about 6% sucrose; and
e) about 0.2% sodium chloride;
wherein the pH of the formulation is about pH 6.0.

In further alternative specific embodiments of the invention, the invention provides a stable antibody formulation comprising:
a) about 100 mg/mL of a humanized IgG4 anti-CXCR5 (C-X-C chemokine receptor type 5) antibody comprising a heavy chain comprising the amino acid sequence of SEQ ID NO: 25 and a light chain comprising the amino acid sequence of SEQ ID NO: 26;
b) about 10 mM citrate buffer;
c) about 0.01% polysorbate 20;
d) about 4.5% sucrose;
e) about 0.2% sodium chloride; and
f) about 1% arginine;
wherein the pH of the formulation is about pH 6.0.

In certain embodiments of the invention, the invention provides a kit comprising a container comprising: 1) the formulation of any one of the previous claims, and 2) a label or instructions for the administration and use of the formulation. In certain embodiments of the invention, the label comprises one or more of the following: instructions for the administration of the formulation, instructions for use of the formulation, instructions concerning the storage conditions of the formulation, information concerning lot and batch number of the formulation and/or kit, information concerning the composition of the formulation, safety information, information concerning possible adverse reactions, secondary effects, and/or side effects in connection with the administration of the formulation, or information concerning possible indications and/or contra-indications of the formulation.

In certain embodiments of the invention, the invention provides a pre-filled device or pre-filled container, such as a syringe, cartridge, vial, ampoule, or autoinjector comprising the formulation of the invention. In certain other embodiments, the invention provides a kit comprising such pre-filled syringe, cartridge, vial, ampoule, or autoinjector.

In certain embodiments, the invention provides a method for treating an inflammatory bowel disease comprising administering to a subject in need thereof a formulation of the invention.

In other certain embodiments, the invention provides a method for treating rheumatoid arthritis comprising administering to a subject in need thereof a formulation of the invention.

In certain embodiments, the invention provides a formulation for use in a method of diagnosis or treatment of the human or animal body. In specific embodiments, the formulation is used in the treatment of inflammatory bowel disease. In alternative embodiments, the formulation is used in the treatment of rheumatoid arthritis.

In certain embodiments of the invention, the invention provides a method for preparing a formulation of the invention comprising mixing the components of the formulation and adjusting the pH, wherein the preparation is performed under sterile conditions or the formulation is sterilized after the mixing of the components and the pH adjustment or both.

In certain specific embodiments of the invention, the invention provides a method for preparing a stable antibody formulation comprising: a) providing an anti-LIGHT binding agent; b) resuspending the anti-LIGHT binding agent in about 5 to about 50 mM citrate buffer; and c) adjusting the pH of the formulation to about pH 5.0 to about pH 6.0.

BRIEF DESCRIPTION OF THE FIGURES

The patent or application file contains at least one drawing executed in color. Copies of this patent or patent application publication with color drawing(s) will be provided by the Office upon request and payment of the necessary fee.

As shown in FIG. 4, SEC detected high molecular weight proteins (HMWP), e.g., di-/oligomers (RRT0.8) or aggregates, and low molecular weight proteins (LMWPs) or degradation products. The first batch of Reference Lot batch had a purity of 97% monomer content.

As shown in FIG. 5, rearrangements of acidic, neutral, and basic isoforms occurred during stability studies. The first batch of Reference Lot had a distribution of acidic/neutral/basic isoforms of 42.3/55.6/1.9%.

As shown in FIG. 6, the three domains of the antibody unfold at 68° C., 75° C., and 78° C.

DETAILED DESCRIPTION

A. Definitions

Figure 1:
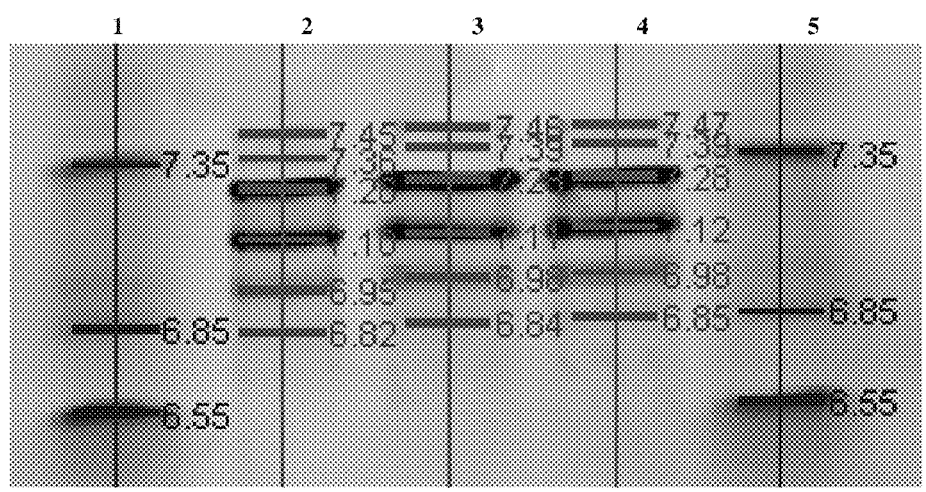
FIG. 1 is a picture of a gel showing the results of denatured isoelectric focusing experiments that were used to determine the isoelectric point (pI) of the fully human IgG4 anti-LIGHT antibody comprising a heavy chain comprising the amino acid sequence of SEQ ID NO: 7 and a light chain comprising the amino acid sequence of SEQ ID NO: 8 formulated in phosphate buffered saline at pH 7.3 at a concentration of 5.5 mg/mL (the "Original Formulation", "PBS Formulation", or "Reference Lot"). Lanes 1 & 5: IEF Calibration Kit High Range pI 5-10.5; lanes 2 & 4: a first batch of Reference Lot; lanes 3 & 4: a second batch of Reference Lot. The pI values are indicated by numbers.

Unless defined otherwise, all technical and scientific terms used herein have the same meaning as is commonly understood by one of ordinary skill in the art.

It is noted here that as used in this specification and the appended claims, the singular forms "a", "an", and "the" also include plural reference, unless the context clearly dictates otherwise.

The term "about" or "approximately" means within 10%, such as within 5% (or 1% or less) of a given value or range.

The terms "administer" or "administration" refers to the act of injecting or otherwise physically delivering a substance as it exists outside the body (e.g., a formulation of the invention) into a patient, such as by mucosal, intradermal, intravenous, subcutaneous, intramuscular delivery and/or any other method of physical delivery described herein or known in the art. When a disease, or a symptom thereof, is being treated, administration of the substance typically occurs after the onset of the disease or symptoms thereof. When a disease or its symptoms are being prevented, administration of the substance typically occurs before the onset of the disease or symptoms thereof.

In the context of a polypeptide, the term "analog" refers to a polypeptide that possesses a similar or identical function as a LIGHT or CXCR5 polypeptide, a fragment of a LIGHT or CXCR5 polypeptide, a LIGHT or CXCR5 epitope, or an anti-LIGHT or anti-CXCR5 antibody, but does not necessarily comprise a similar or identical amino acid sequence of a LIGHT or CXCR5 polypeptide, a fragment of a LIGHT or CXCR5 polypeptide, a LIGHT or CXCR5 epitope, or an anti-LIGHT or anti-CXCR5 antibody, or possess a similar or identical structure of a LIGHT or CXCR5 polypeptide, a fragment of a LIGHT or CXCR5 polypeptide, a LIGHT or CXCR5 epitope, or an anti-LIGHT or anti-CXCR5 antibody. A polypeptide that has a similar amino acid sequence refers to a polypeptide that satisfies at least one of the following: (a) a polypeptide having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of a LIGHT or CXCR5 polypeptide (e.g., SEQ ID NO: 9 or SEQ ID NO: 14, respectively), a fragment of a LIGHT or CXCR5 polypeptide, a LIGHT or CXCR5 epitope, or an anti-LIGHT or anti-CXCR5 antibody described herein; (b) a polypeptide encoded by a nucleotide sequence that hybridizes under stringent conditions to a nucleotide sequence encoding a LIGHT or CXCR5 polypeptide, a fragment of a LIGHT or CXCR5 polypeptide, a LIGHT or CXCR5 epitope, or an anti-LIGHT or anti-CXCR5 antibody (or VH or VL region thereof) described herein of at least 5 amino acid residues, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, or at least 150 amino acid residues (see, e.g., Sambrook et al. (2001) Molecular Cloning: A Laboratory Manual, Cold Spring Harbor Laboratory Press, Cold Spring Harbor, N.Y.; Maniatis et al. (1982) Molecular Cloning: A Laboratory Manual, Cold Spring Harbor Press, Cold Spring Harbor, N.Y.); and (c) a polypeptide encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical to the nucleotide sequence encoding a LIGHT or CXCR5 polypeptide, a fragment of a LIGHT or CXCR5 polypeptide, a LIGHT or CXCR5 epitope, or an anti-LIGHT or anti-CXCR5 antibody (or VH or VL region thereof) described herein. A polypeptide with similar structure to a LIGHT or CXCR5 polypeptide, a fragment of a LIGHT or CXCR5 polypeptide, a LIGHT or CXCR5 epitope, or an anti-LIGHT or anti-CXCR5 antibody refers to a polypeptide that has a similar secondary, tertiary or quaternary structure of a LIGHT or CXCR5 polypeptide, a fragment of a LIGHT or CXCR5 polypeptide, a LIGHT or CXCR5 epitope, or a LIGHT or CXCR5 antibody. The structure of a polypeptide can determined by methods known to those skilled in the art, including but not limited to, X-ray crystallography, nuclear magnetic resonance, and crystallographic electron microscopy.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions X 100%). In one embodiment, the two sequences are the same length.

The determination of percent identity between two sequences (e.g., amino acid sequences or nucleic acid sequences) can also be accomplished using a mathematical algorithm. A non-limiting example of a mathematical algorithm utilized for the comparison of two sequences is the algorithm of Karlin and Altschul, 1990, Proc. Natl. Acad. Sci. U.S.A. 87:2264 2268, modified as in Karlin and Altschul, 1993, Proc. Natl. Acad. Sci. U.S.A. 90:5873 5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to nucleic acid molecules of interest. BLAST protein searches can be performed with the XBLAST program parameters set, e.g., to score 50, wordlength=3 to obtain amino acid sequences homologous to a protein molecule of interest. To obtain gapped alignments for comparison purposes, Gapped BLAST can be utilized as described in Altschul et al., 1997, Nucleic Acids Res. 25:3389 3402. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web at ncbi dot nlm dot nih dot gov). Another non limiting example of a mathematical algorithm utilized for the comparison of sequences is the algorithm of Myers and Miller, 1988, CABIOS 4:11 17. Such an algorithm is incorporated in the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

An "antagonist" or "inhibitor" refers to a molecule capable of inhibiting one or more biological activities of a target molecule. Antagonists may interfere with the binding of a receptor to a ligand and vice versa, by incapacitating or killing cells activated by a ligand, and/or by interfering with receptor or ligand activation (e.g., tyrosine kinase activation) or signal transduction after ligand binding to a receptor. The antagonist may completely block receptor-ligand interactions or may substantially reduce such interactions. All such points of intervention by an antagonist shall be considered equivalent for purposes of the instant invention.

For example, an "antagonist" or "inhibitor" of LIGHT refers to a molecule that is capable of inhibiting or otherwise decreasing one or more of the biological activities of LIGHT, such as in a cell expressing LIGHT or in a cell expressing a LIGHT ligand, such as a LIGHT receptor. For example, in certain embodiments, antibodies of the invention are antagonist antibodies that inhibit or otherwise decrease secretion of CCL20, IL-8, and/or RANTES from a cell having a cell surface-expressed LIGHT receptor (e.g., HVEM, LTβR and/or DcR3) when said antibody is contacted with said cell. In some embodiments, an antagonist of LIGHT (e.g., an antagonistic antibody of the invention) may, for example, act by inhibiting or otherwise decreasing the activation and/or cell signaling pathways of the cell expressing a LIGHT receptor, thereby inhibiting a LIGHT-mediated biological activity of the cell relative to the LIGHT-mediated biological activity in the absence of antagonist. In certain embodiments of the invention, the anti-LIGHT antibodies are fully human, antagonistic anti-LIGHT antibodies, such as fully human, monoclonal, antagonistic anti-LIGHT antibodies.

For example, an "antagonist" or "inhibitor" of CXCR5 refers to a molecule capable of inhibiting one or more biological activities, such as signaling, by CXCR5. Thus, included within the scope of the invention are antagonists (e.g., neutralizing antibodies) that bind to CXCR5, CXCL13 or other ligands of CXCR5, or a complex of CXCR5 and a ligand thereof, such as CXCL13; amino acid sequence variants or derivatives of CXCR5 or CXCL13 which antagonize the interaction between CXCR5 and a ligand, such as CXCL13; soluble CXCR5, optionally fused to a heterologous molecule such as an immunoglobulin region (e.g., an immunoadhesin); a complex comprising CXCR5 in association with another receptor or biological molecule; synthetic or native sequence peptides which bind to CXCR5; and so on.

The terms "antibody", "immunoglobulin", or "Ig" may be used interchangeably herein. The term antibody includes, but is not limited to, synthetic antibodies, monoclonal antibodies, recombinantly produced antibodies, multispecific antibodies (including bi-specific antibodies), human antibodies, humanized antibodies, chimeric antibodies, intrabodies, single-chain Fvs (scFv) (e.g., including monospecific, bispecific, etc.), camelized antibodies, Fab fragments, F(ab') fragments, disulfide-linked Fvs (sdFv), anti-idiotypic (anti-Id) antibodies, and epitope-binding fragments of any of the above. In particular, antibodies include immunoglobulin molecules and immunologically active portions of immunoglobulin molecules, i.e., antigen binding domains or molecules that contain an antigen-binding site that specifically binds to a LIGHT antigen (e.g., one or more complementarity determining regions (CDRs) of an anti-LIGHT antibody) or CXCR5 antigen (e.g., one or more complementarity determining regions (CDRs) of an anti-CXCR5 antibody). The anti-LIGHT or anti-CXCR5 antibodies can be of any type (e.g., IgG, IgE, IgM, IgD, IgA and IgY), any class (e.g., IgG1, IgG2, IgG3, IgG4, IgA1 and IgA2), or any subclass (e.g., IgG2a and IgG2b) of immunoglobulin molecule. In some embodiments, the anti-LIGHT antibodies are fully human, such as fully human monoclonal anti-LIGHT antibodies. In certain embodiments, the anti-LIGHT antibodies are IgG antibodies, human IgG4 antibodies. Alternatively, in some embodiments, the anti-CXCR5 antibodies are humanized, such as humanized monoclonal anti-CXCR5 antibodies. In certain embodiments, the anti-CXCR5 antibodies are IgG antibodies, humanized IgG4 antibodies.

As used herein, the term "anti-LIGHT antibody" means an antibody or polypeptide derived therefrom (a derivative) that binds specifically to human LIGHT as defined herein, including, but not limited to, molecules that inhibit or substantially reduce the binding of LIGHT to its ligands or inhibit LIGHT activity.

As used herein, the term "anti-CXCR5 antibody" means an antibody or polypeptide derived therefrom (a derivative) that binds specifically to human CXCR5 as defined herein, including, but not limited to, molecules that inhibit or substantially reduce the binding of CXCR5 to its ligands or inhibit CXCR5 activity.

The term "B cell activity" means higher than normal B cell levels, which can be local, or evidence of a biological manifestation or function of a B cell, such as antibody expression, Bruton's tyrosine kinase presence or activity, expression or presence of CD19, expression or presence of B cell activating factor and so on.

The term "binding agent" means any molecule, such as an antibody, a siRNA, a nucleic acid, an aptamer, a protein, or a small molecule organic compound, that binds or specifically binds to LIGHT or CXCR5, or a variant or a fragment thereof.

The term "by-product" includes undesired products, which detract or diminish the proportion of therapeutic/prophylactic binding agent, such as an antibody, in a given formulation. For example, typical by-products include aggregates of the antibody, fragments of the antibody, e.g. produced by degradation of the antibody by deamidation or hydrolysis, or mixtures thereof. Typically, aggregates are complexes that have a molecular weight greater than the monomer antibody. Antibody degradation products may include, for example, fragments of the antibody, for example, brought about by deamidation or hydrolysis. Typically, degradation products are complexes that have a molecular weight less than the monomer antibody. In the case of an IgG antibody, such degradation products are less than about 150 kD.

The terms "composition" and "formulation" are intended to encompass a product containing the specified ingredients (e.g., an anti-LIGHT antibody or an anti-CXCR5 antibody) in, optionally, the specified amounts, as well as any product that results, directly or indirectly, from the combination of the specified ingredients in, optionally, the specified amounts.

The terms "constant region" or "constant domain" refer to a carboxy terminal portion of the light and heavy chain which is not directly involved in binding of the antibody to antigen but exhibits various effector functions, such as interaction with the Fc receptor. The terms refer to the portion of an immunoglobulin molecule having a more conserved amino acid sequence relative to the other portion of the immunoglobulin, the variable domain, which contains the antigen binding site. The constant domain contains the CH1, CH2 and CH3 domains of the heavy chain and the CHL domain of the light chain.

The term "CXCR5" relates to the naturally occurring, known molecule found on lymphocytes, particularly B cells, and particularly naïve B cells; to such a molecule isolated from such cells; to such a molecule manufactured recombinantly using known materials and means, and using a nucleic acid encoding a CXCR5; as well as to portions of CXCR5, such as the extracellular (EC) domain, that retain the characteristics and properties relevant to the practice of the instant invention, such as CXCL13 binding. A soluble CXCR5 molecule can consist essentially of the EC domain of CXCR5, which includes, generally, about the first sixty amino acids of the molecule, that is, the amino terminal portion of CXCR5.

CXCR5 is a non-promiscuous receptor. CXCL13 is a ligand of CXCR5 and is expressed constitutively on stromal cells, such as follicular dendritic cells, and in lymphoid tissues. CXCL13 specifically attracts B cells and a small subset of T cells called B helper follicular T cells, TFH. This may not be unexpected given the many interactions between T cell and B cell populations in the immune system. Moreover, activated T cells induce or upregulate CXCR5 expression. Infiltration of lymphocytes into tertiary, ectopic germinal centers (GCs) has been found to correlate well with increased disease severity and tolerance breakdown in certain disorders that present with such atypical lymph node-like structures. Using in vivo murine models, such as CXCR5−/− and CXCL13−/− mice, the absence of either the receptor or the ligand results in an altered GC fine architecture due to altered T and B cell localization, and possibly interaction. These mice are also protected against developing severe collagen-induced arthritis (CIA). As CXCR5 is selectively expressed on mature B cells, which are linked to the pathogenesis of RA, blocking this receptor will modulate the arthritogenic response in affected individuals. Rheumatoid arthritis treatment with biologics (i.e., anti-TNFα and anti-CD20 antibodies, Rituximab) has shown to be clinically effective; in particular, patients on B cell-directed therapy have shown long-lasting improvements in clinical signs and symptoms. Selective targeting of CXCR5, which is only expressed on mature B cells and B helper T cells, will not affect B cell development or immunocompromise the patient. Unlike Rituximab, the instant anti-CXCR5 antibody is a neutralizing antibody that does not mediate cell cytotoxicity.

A "CXCR5 disease" is a malady, disorder, disease, condition, abnormality and so on, that is characterized by or caused by overexpression or increased levels of CXCL13 or other CXCR5 ligand, increased levels of B cells, increased levels of B cell activity, increased levels of CXCR5, or improper metabolism and activity of CXCR5.

The term "epitope" refers to a localized region on the surface of an antigen, such as a LIGHT or CXCR5 polypeptide, or LIGHT or CXCR5 polypeptide fragment, that is capable of being bound to one or more antigen binding regions of a binding agent, such as an antibody, and that has antigenic or immunogenic activity in an animal, such a mammal, such as in a human, that is capable of eliciting an immune response. An epitope having immunogenic activity is a portion of a polypeptide that elicits an antibody response in an animal. An epitope having antigenic activity is a portion of a polypeptide to which an antibody specifically binds, as determined by any method well known in the art, for example, such as an immunoassay. Antigenic epitopes need not necessarily be immunogenic. Epitopes usually consist of chemically active surface groupings of molecules, such as amino acids or sugar side chains, and have specific three dimensional structural characteristics, as well as specific charge characteristics. A region of a polypeptide contributing to an epitope may be contiguous amino acids of the polypeptide or the epitope may come together from two or more non-contiguous regions of the polypeptide. The epitope may or may not be a three-dimensional surface feature of the antigen. In certain embodiments, a LIGHT or CXCR5 epitope is a three-dimensional surface feature of a LIGHT or CXCR5 polypeptide (e.g., in a trimeric form of a LIGHT polypeptide). In other embodiments, a LIGHT epitope is a linear feature of a LIGHT or CXCR5 polypeptide (e.g., in a trimeric form or monomeric form of the LIGHT polypeptide). Anti-LIGHT or anti-CXCR5 antibodies may specifically bind to an epitope of the monomeric (denatured) form of LIGHT or CXCR5, an epitope of the trimeric (native) form of LIGHT or CXCR5, or both the monomeric (denatured) form and the trimeric (native) form of LIGHT or CXCR5. In specific embodiments, the anti-LIGHT antibodies specifically bind to an epitope of the trimeric form of LIGHT but do not specifically bind the monomeric form of LIGHT.

The term "excipients" refers to inert substances that are commonly used as a diluent, vehicle, preservative, binder, stabilizing agent, etc. for drugs and includes, but is not limited to, proteins (e.g., serum albumin, etc.), amino acids (e.g., aspartic acid, glutamic acid, lysine, arginine, glycine, histidine, etc.), fatty acids and phospholipids (e.g., alkyl sulfonates, caprylate, etc.), surfactants (e.g., SDS, polysorbate, nonionic surfactant, etc.), saccharides (e.g., sucrose, maltose, trehalose, etc.) and polyols (e.g., mannitol, sorbitol, etc.). See, also, Remington's Pharmaceutical Sciences (1990) Mack Publishing Co., Easton, Pa., which is hereby incorporated by reference in its entirety.

In the context of a peptide or polypeptide, the term "fragment" refers to a peptide or polypeptide that comprises less than the full length amino acid sequence. Such a fragment may arise, for example, from a truncation at the amino terminus, a truncation at the carboxy terminus, and/or an internal deletion of a residue(s) from the amino acid sequence. Fragments may, for example, result from alternative RNA splicing or from in vivo protease activity. In certain embodiments, hLIGHT or hCXCR5 fragments include polypeptides comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least contiguous 100 amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of a LIGHT or CXCR5 polypeptide or an antibody that specifically binds to a LIGHT or CXCR5 polypeptide. In a specific embodiment, a fragment of a LIGHT or CXCR5 polypeptide or an antibody that specifically binds to a LIGHT or CXCR5 antigen retains at least 1, at least 2, or at least 3 functions of the polypeptide or antibody.

The terms "fully human antibody" or "human antibody" are used interchangeably herein and refer to an antibody that comprises a human variable region and, possibly a human constant region. In specific embodiments, the terms refer to an antibody that comprises a variable region and constant region of human origin. "Fully human" anti-LIGHT antibodies, in certain embodiments, can also encompass antibodies that bind LIGHT polypeptides and are encoded by nucleic acid sequences that are naturally occurring somatic variants of a human germline immunoglobulin nucleic acid sequence. In a specific embodiment, the anti-LIGHT antibodies are fully human antibodies. The term "fully human antibody" includes antibodies having variable and constant regions corresponding to human germline immunoglobulin sequences as described by Kabat et al. (See Kabat et al. (1991) Sequences of Proteins of Immunological Interest, Fifth Edition, U.S. Department of Health and Human Services, NIH Publication No. 91-3242). Methods of producing fully human antibodies are known in the art.

The phrase "recombinant human antibody" includes human antibodies that are prepared, expressed, created, or isolated by recombinant means, such as antibodies expressed using a recombinant expression vector transfected into a host cell, antibodies isolated from a recombinant, combinatorial human antibody library, antibodies isolated from an animal (e.g., a mouse or cow) that is transgenic and/or transchromosomal for human immunoglobulin genes (see, e.g., Taylor, L. D. et al. (1992) Nucl. Acids Res. 20:6287-6295) or antibodies prepared, expressed, created, or isolated by any other means that involves splicing of human immunoglobulin gene sequences to other DNA sequences. Such recombinant human antibodies can have variable and constant regions derived from human germline immunoglobulin sequences (See Kabat, E. A. et al. (1991) Sequences of Proteins of Immunological Interest, Fifth Edition, U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

An "IgG4 binding agent" or a "binding agent comprising at least a portion of an IgG4 Fc region" both refer to binding agents described herein that include at least a fragment of IgG4 Fc. In certain embodiments, the fragment comprises 10, 20, 30, 40, 50, 100, 110, 120, 130, 140, 150, 160, 170, 180, 190, 200, 210 or 220 amino acids of the IgG4 Fc region. In other embodiments, the fragment includes 10-50, 50-100, 100-150, or 150-200 amino acids of the IgG4 Fc region. In other embodiments, the portion of the IgG4 Fc region can have a certain homology to the IgG4 Fc region. For example, the IgG4 binding agent may include a portion of a protein with greater than 50, 60, 70, 80, 90, 93, 95, 96, 97, 98, 99, or 100% homology to the IgG4 Fc region. Exemplary Fc regions of IgG4 are described throughout the specification.

The term "heavy chain", when used in reference to an antibody, refers to five distinct types, called alpha ($\alpha$), delta ($\Delta$), epsilon ($\epsilon$), gamma ($\gamma$), and mu ($\mu$), based on the amino acid sequence of the heavy chain constant domain. These distinct types of heavy chains are well known in the art and give rise to five classes of antibodies, IgA, IgD, IgE, IgG, and IgM, respectively, including four subclasses of IgG, namely IgG1, IgG1, IgG3, and IgG4. In some embodiments, the heavy chain is a human heavy chain.

"Humanized" forms of non-human (e.g., murine) antibodies are chimeric immunoglobulins, immunoglobulin chains or fragments thereof (such as $F_v$, $F_{ab}$, $F_{ab'}$, $F_{(ab')2}$ or other target-binding subsequences of antibodies) that contain sequences derived from non-human immunoglobulin, as compared to a human antibody. In general, the humanized antibody will comprise substantially all of one, and typically two, variable domains, in which all or substantially all of the CDR regions correspond to those of a non-human immunoglobulin and all or substantially all of the FR regions are those of a human immunoglobulin template sequence. The humanized antibody may also comprise at least a portion of an immunoglobulin constant region ($F_c$), typically that of the human immunoglobulin template chosen. In general, the goal is to have an antibody molecule that is minimally immunogenic in a human. Thus, it is possible that one or more amino acids in one or more CDRs also can be changed to one that is less immunogenic to a human host, without substantially minimizing the specific binding function of the one or more CDRs to CXCR5 or to CXCL13. Alternatively, the FR can be non-human but those amino acids most immunogenic are replaced with ones less immunogenic. Nevertheless, CDR grafting, as discussed above, is not the only way to obtain a humanized antibody. For example, modifying just the CDR regions may be insufficient as it is not uncommon for framework residues to have a role in determining the three-dimensional structure of the CDR loops and the overall affinity of the antibody for its ligand. Hence, any means can be practiced so that the non-human parent antibody molecule is modified to be one that is less immunogenic to a human, and global sequence identity with a human antibody is not always a necessity. So, humanization also can be achieved, for example, by the mere substitution of just a few residues, particularly those which are exposed on the antibody molecule and not buried within the molecule, and hence, not readily accessible to the host immune system. Such a method is taught herein with respect to substituting "mobile" or "flexible" residues on the antibody molecule, the goal being to reduce or dampen the immunogenicity of the resultant molecule without comprising the specificity of the antibody for its epitope or determinant. See, for example, Studnicka et al., Prot Eng 7(6) 805-814, 1994; Mol Imm 44:1986-1988, 2007; Sims et al., J Immunol 151:2296 (1993); Chothia et al., J Mol Biol 196:901 (1987); Carter et al., Proc Natl Acad Sci USA 89:4285 (1992); Presta et al., J Immunol 151:2623 (1993), WO 2006/042333 and U.S. Pat. No. 5,869,619.

An "isolated" or "purified" binding agent, such as an antibody, is substantially free of cellular material or other contaminating proteins from the cell or tissue source from which the binding agent is derived, or substantially free of chemical precursors or other chemicals when chemically synthesized. For example, the language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, or 5% (by dry weight) of heterologous protein (also referred to herein as a "contaminating protein"). When the antibody is recombinantly produced, it is also desirable to be substantially free of culture medium, i.e., culture medium represents less than about 20%, 10%, or 5% of the volume of the protein preparation. When the antibody is produced by chemical synthesis, in some embodiments it is substantially free of chemical precursors or other chemicals, i.e., it is separated from chemical precursors or other chemicals that are involved in the synthesis of the protein. Accordingly, such preparations of the antibody have less than about 30%, 20%, 10%, 5% (by dry weight) of chemical precursors or compounds other than the antibody of interest. In some embodiments, anti-LIGHT or anti-CXCR5 antibodies are isolated or purified.

The term "human LIGHT," "hLIGHT" or "hLIGHT polypeptide" and similar terms refer to the polypeptides ("polypeptides," "peptides" and "proteins" are used interchangeably herein) comprising the amino acid sequence of SEQ ID NO: 9 and related polypeptides, including SNP variants thereof. Related polypeptides include allelic variants (e.g., SNP variants); splice variants; fragments; derivatives; substitution, deletion, and insertion variants; fusion polypeptides; and interspecies homologs, in some embodiments, which retain LIGHT activity and/or are sufficient to generate an anti-LIGHT immune response. Also encompassed are soluble forms of LIGHT that are sufficient to generate an anti-LIGHT immunological response. As those skilled in the art will appreciate, an anti-LIGHT binding agent, such as an antibody, can bind to a LIGHT polypeptide, polypeptide fragment, antigen, and/or epitope, as an epitope is part of the larger antigen, which is part of the larger polypeptide fragment, which, in turn, is part of the larger polypeptide. hLIGHT can exist in a trimeric (native) or monomeric (denatured) form.

The term "human CXCR5," "hCXCR5" or "hCXCR5 polypeptide" and similar terms refer to the polypeptides ("polypeptides," "peptides" and "proteins" are used interchangeably herein) comprising the amino acid sequence of SEQ ID NO: 14 and related polypeptides, including SNP variants thereof. Related polypeptides include allelic variants (e.g., SNP variants); splice variants; fragments; derivatives; substitution, deletion, and insertion variants; fusion polypeptides; and interspecies homologs, in some embodiments, which retain CXCR5 activity and/or are sufficient to generate an anti-CXCR5 immune response. Also encompassed are soluble forms of CXCR5 that are sufficient to generate an anti-CXCR5 immunological response. As those skilled in the art will appreciate, an anti-CXCR5 binding agent, such as an antibody, can bind to a CXCR5 polypeptide, polypeptide fragment, antigen, and/or epitope, as an epitope is part of the larger antigen, which is part of the larger polypeptide fragment, which, in turn, is part of the larger polypeptide.

The term "Kabat numbering," and like terms are recognized in the art and refer to a system of numbering amino acid residues that are more variable (i.e. hypervariable) than other amino acid residues in the heavy and light chain variable regions of an antibody, or an antigen binding portion thereof (Kabat et al. (1971) Ann. NY Acad. Sci. 190:382-391 and, Kabat et al. (1991) Sequences of Proteins of Immunological Interest, Fifth Edition, U.S. Department of Health and Human Services, NIH Publication No. 91-3242). For the heavy chain variable region, the hypervariable region typically ranges from amino acid positions 31 to 35 for CDR1, amino acid positions 50 to 65 for CDR2, and amino acid positions 95 to 102 for CDR3. For the light chain variable region, the hypervariable region typically ranges from amino acid positions 24 to 34 for CDR1, amino acid positions 50 to 56 for CDR2, and amino acid positions 89 to 97 for CDR3.

The term "light chain" when used in reference to an antibody refers to two distinct types, called kappa (κ) of lambda (λ) based on the amino acid sequence of the constant domains. Light chain amino acid sequences are well known in the art. In some embodiments, the light chain is a human light chain.

The terms "manage", "managing", and "management" refer to the beneficial effects that a subject derives from a therapy (e.g., a prophylactic or therapeutic agent), which does not result in a cure of the infection. In certain embodiments, a subject is administered one or more therapies (e.g., prophylactic or therapeutic agents, such as a formulation of the invention) to "manage" a LIGHT-mediated disease (e.g., chronic bowel disease, IBD, Crohn's disease, ulcerative colitis, or GVHD) or CXCR5-mediated disease (e.g., rheumatoid arthritis), one or more symptoms thereof, so as to prevent the progression or worsening of the disease.

The term "monoclonal antibody" refers to an antibody obtained from a population of homogenous or substantially homogeneous antibodies, and each monoclonal antibody will typically recognize a single epitope on the antigen. In some embodiments, a "monoclonal antibody" is an antibody produced by a single hybridoma or other cell. The term "monoclonal" is not limited to any particular method for making the antibody. For example, monoclonal antibodies may be made by the hybridoma method as described in Kohler et al.; Nature, 256:495 (1975) or may be isolated from phage libraries. Other methods for the preparation of clonal cell lines and of monoclonal antibodies expressed thereby are well known in the art (see, for example, Chapter 11 in: Short Protocols in Molecular Biology, (2002) 5th Ed.; Ausubel et al., eds., John Wiley and Sons, New York).

The term "pharmaceutically acceptable" means being approved by a regulatory agency of the Federal or a state government, or listed in the U.S. Pharmacopeia, European Pharmacopeia or other generally recognized Pharmacopeia for use in animals, and more particularly in humans.

By "pharmaceutically acceptable excipient" is meant any inert substance that is combined with an active molecule, such as a monoclonal antibody, for preparing an agreeable or convenient dosage form. The "pharmaceutically acceptable excipient" is an excipient that is non-toxic to recipients at the dosages and concentrations employed, and is compatible with other ingredients of the formulation comprising the monoclonal antibody.

The terms "prevent", "preventing", and "prevention" refer to the total or partial inhibition of the development, recurrence, onset or spread of a LIGHT-mediated or CXCR5-mediated disease and/or symptom related thereto, resulting from the administration of a therapy or combination of therapies provided herein (e.g., a combination of prophylactic or therapeutic agents, such as a formulation of the invention).

The term "prophylactic agent" refers to any agent that can totally or partially inhibit the development, recurrence, onset or spread of a LIGHT-mediated or CXCR5-mediated disease and/or symptom related thereto in a subject. In certain embodiments, the term "prophylactic agent" refers to a formulation of the invention. In certain other embodiments, the term "prophylactic agent" refers to an agent other than a formulation of the invention. In some embodiments, a prophylactic agent is an agent that is known to be useful to or has been or is currently being used to prevent a LIGHT-mediated or CXCR5-mediated disease and/or a symptom related thereto, or impede the onset, development, progression and/or severity of a LIGHT-mediated or CXCR5-mediated disease and/or a symptom related thereto. In specific embodiments, the prophylactic agent is a fully human anti-LIGHT antibody, such as a fully human anti-LIGHT monoclonal antibody, or a humanized anti-CXCR5 antibody, such as a humanized anti-CXCR5 monoclonal antibody.

The term "LIGHT antigen" refers to that portion of a LIGHT polypeptide to which a binding agent, such as an antibody, specifically binds. A LIGHT antigen also refers to an analog or derivative of a LIGHT polypeptide or fragment thereof to which a binding agent, such as an antibody, specifically binds. In some embodiments, a LIGHT antigen is a monomeric LIGHT antigen or a trimeric LIGHT antigen. A region of a LIGHT polypeptide contributing to an epitope may be contiguous amino acids of the polypeptide, or the epitope may come together from two or more non-contiguous regions of the polypeptide. The epitope may or may not be a three-dimensional surface feature of the antigen. A localized region on the surface of a LIGHT antigen that is capable of eliciting an immune response is a LIGHT epitope. The epitope may or may not be a three-dimensional surface feature of the antigen.

The term "CXCR5 antigen" refers to that portion of a CXCR5 polypeptide to which a binding agent, such as an antibody, specifically binds. A CXCR5 antigen also refers to an analog or derivative of a CXCR5 polypeptide or fragment thereof to which a binding agent, such as an antibody, specifically binds. A region of a CXCR5 polypeptide contributing to an epitope may be contiguous amino acids of the polypeptide, or the epitope may come together from two or more non-contiguous regions of the polypeptide. The epitope may or may not be a three-dimensional surface feature of the antigen. A localized region on the surface of a CXCR5 antigen that is capable of eliciting an immune response is a CXCR5 epitope. The epitope may or may not be a three-dimensional surface feature of the antigen.

The terms "LIGHT-mediated disease" and "LIGHT-mediated disorder" are used interchangeably and refer to any disease that is completely or partially caused by or is the result of LIGHT. In certain embodiments, LIGHT is aberrantly (e.g., highly) expressed on the surface of a cell. In some embodiments, LIGHT may be aberrantly upregulated on a particular cell type. In other embodiments, normal, aberrant, or excessive cell signaling is caused by binding of LIGHT to a LIGHT ligand. In certain embodiments, the LIGHT ligand is a LIGHT receptor (e.g., HVEM, LTβR, or DCR3), for example, that is expressed on the surface of a cell, such as a colonic epithelial cell. In certain embodiments, the LIGHT-mediated disease is a chronic bowel disease, an inflammatory bowel disease (IBD), such as Crohn's disease (CD) or ulcerative colitis (UC). In other embodiments, the LIGHT-mediated disease is graft-versus-host disease (GVHD).

The terms "CXCR5-mediated disease" and "CXCR5-mediated disorder" are used interchangeably and refer to any disease that is completely or partially caused by or is the result of CXCR5. In certain embodiments, CXCR5 is aberrantly (e.g., highly) expressed on the surface of a cell. In some embodiments, CXCR5 may be aberrantly upregulated on a particular cell type. In other embodiments, normal, aberrant, or excessive cell signaling is caused by binding of CXCR5 to a CXCR5 ligand. In certain embodiments, the CXCR5 ligand is CXCL13. In certain embodiments, the CXCR5-mediated disease is rheumatoid arthritis (RA).

The term "saccharide" refers to a class of molecules that are derivatives of polyhydric alcohols. Saccharides are commonly referred to as carbohydrates and may contain different amounts of sugar (saccharide) units, e.g., monosaccharides, disaccharides, and polysaccharides.

The terms "specifically binds" or "specifically binding" mean specifically binding to an antigen or a fragment thereof and not specifically binding to other antigens. For example, an antibody that specifically binds to an antigen may bind to other peptides or polypeptides with lower affinity, as determined by, e.g., radioimmunoassays (RIA), enzyme-linked immunosorbent assays (ELISA), BIACORE, or other assays known in the art. Antibodies or variants or fragments thereof that specifically bind to an antigen may be cross-reactive with related antigens. In some embodiments, antibodies or variants or fragments thereof that specifically bind to an antigen do not cross-react with other antigens. An antibody or a variant or a fragment thereof that specifically binds to a LIGHT or CXCR5 antigen can be identified, for example, by immunoassays, BIAcore, or other techniques known to those of skill in the art. Typically a specific or selective reaction will be at least twice background signal or noise, and more typically more than 10 times background. See, e.g., Paul, ed., 1989, Fundamental Immunology Second Edition, Raven Press, New York at pages 332-336 for a discussion regarding antibody specificity.

A "stable" or "stabilized" formulation is one in which the binding agent, such as an antibody, therein essentially retains its physical stability, identity, integrity, and/or chemical stability, identity, integrity, and/or biological activity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10:29-90 (1993), for example. Stability can be measured at a selected temperature and other storage conditions for a selected time period. The stability may be determined by at least one of the methods selected from the group consisting of visual inspection, SDS-PAGE, IEF, HPSEC, RFFIT, and kappa/lambda ELISA. For example, an antibody "retains its physical stability" in a pharmaceutical formulation, if it shows no signs of aggregation, precipitation, and/or denaturation upon visual examination of color and/or clarity, or as measured by UV light scattering, SDS-PAGE, or by (high pressure) size exclusion chromatography (HPSEC). In some embodiments, when using the formulations of the invention, 5% or less, typically 4% or less, typically 3% or less, more typically 2% or less, and particularly 1% or less of the antibodies forms aggregates, as measured by HPSEC or any other suitable method for measuring aggregation formation. For example, an antibody is considered stable in a particular formulation if the antibody monomer has a purity of about 90%, typically about 95%, in particular about 98% after a certain predetermined period of time under certain storage conditions in a particular formulation. Chemical stability can be assessed by detecting and quantifying chemically altered forms of the protein. Chemical alteration may involve size modification (e.g., clipping), which can be evaluated using (HP)SEC, SDS-PAGE, and/or matrix-assisted laser desorption ionization/time-of-flight mass spectrometry (MALDI/TOF MS), for example. Other types of chemical alteration include charge alteration (e.g., occurring as a result of deamidation), which can be evaluated by ion-exchange chromatography, for example. An antibody "retains its biological activity" in a pharmaceutical formulation at a given time, if the biological activity of the antibody at a given time is at least about 90% (within the errors of the assay) of the biological activity exhibited at the time the pharmaceutical formulation was prepared, as determined in an antigen binding assay or virus neutralizing assay, for example.

The terms "subject" and "patient" are used interchangeably. As used herein, a subject is typically a mammal, such as a non-primate (e.g., cows, pigs, horses, cats, dogs, rats, etc.) or a primate (e.g., monkey and human), and in some embodiments a human. In one embodiment, the subject is a mammal, such as a human, having a LIGHT-mediated or CXCR5-mediated disease. In another embodiment, the subject is a mammal, such as a human, at risk of developing a LIGHT-mediated or CXCR5-mediated disease.

The term "therapeutically effective amount" refers to the amount of a therapy (e.g., a formulation of the invention) that is sufficient to reduce and/or ameliorate the severity and/or duration of a given disease and/or a symptom related thereto. This term also encompasses an amount necessary for the reduction or amelioration of the advancement or progression of a given disease, reduction or amelioration of the recurrence, development or onset of a given disease, and/or to improve or enhance the prophylactic or therapeutic effect(s) of another therapy (e.g., a therapy other than a formulation of the invention). In some embodiments, the therapeutically effective amount of an antibody of the invention is from about 0.1 mg/kg (mg of antibody per kg weight of the subject) to about 100 mg/kg. In certain embodiments, a therapeutically effective amount of an antibody provided therein is about 0.1 mg/kg, about 0.5 mg/kg, about 1 mg/kg, 3 mg/kg, 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg about 90 mg/kg or about 100 mg/kg (or a range therein). In some embodiments, "therapeutically effective amount" as used herein also refers to the amount of an antibody of the invention to achieve a specified result (e.g., inhibition of a LIGHT biological activity of a cell, such as inhibition of secretion of CCL20, IL-8, or RANTES from the cell; or inhibition of a CXCR5 biological activity of a cell, such as binding to CXCL13).

The term "therapeutic agent" refers to any agent that can be used in the treatment, management or amelioration of a LIGHT-mediated or CXCR5-mediated disease and/or a symptom related thereto. In certain embodiments, the term "therapeutic agent" refers to a formulation of the invention. In certain other embodiments, the term "therapeutic agent" refers to an agent other than a formulation of the invention. In some embodiments, a therapeutic agent is an agent that is known to be useful for, or has been or is currently being used for the treatment, management or amelioration of a LIGHT-mediated or CXCR5-mediated disease or one or more symptoms related thereto.

The term "therapy" refers to any protocol, method, and/or agent that can be used in the prevention, management, treatment, and/or amelioration of a LIGHT-mediated disease (e.g., IBD or GVHD) or CXCR5-mediated disease (e.g., rheumatoid arthritis). In certain embodiments, the terms "therapies" and "therapy" refer to a biological therapy, supportive therapy, and/or other therapies useful in the prevention, management, treatment, and/or amelioration of a LIGHT-mediated or CXCR5-mediated disease known to one of skill in the art, such as medical personnel.

The terms "treat", "treatment", and "treating" refer to the reduction or amelioration of the progression, severity, and/or duration of a LIGHT-mediated disease (e.g., chronic bowel disease, IBD, or GVHD) or CXCR5-mediated disease (e.g., rheumatoid arthritis) resulting from the administration of one or more therapies (including, but not limited to, the administration of one or more prophylactic or therapeutic agents, such as a formulation of the invention). In specific embodiments for LIGHT, such terms refer to the reduction or inhibition of the binding of LIGHT to HVEM, the reduction or inhibition of the binding of LIGHT to LTβR, the reduction or inhibition of the binding of LIGHT to DcR3, the reduction or inhibition of the production or secretion of CCL20 from a cell expressing a LIGHT receptor of a subject, the reduction or inhibition of the production or secretion of IL-8 from a cell expressing a LIGHT receptor of a subject, the reduction or inhibition of the production or secretion of RANTES from a cell expressing a LIGHT receptor of a subject, and/or the inhibition or reduction of one or more symptoms associated with a LIGHT-mediated disease, such as a chronic bowel disease, IBD, or GVHD. In specific embodiments for CXCR5, such terms refer to the reduction or inhibition of the binding of CXCR5 to CXCL13, and/or the inhibition or reduction of one or more symptoms associated with a CXCR5-mediated disease, such as rheumatoid arthritis.

The terms "variable region" or "variable domain" refer to a portion of the light and heavy chains, typically about the amino-terminal 120 to 130 amino acids in the heavy chain and about 100 to 110 amino acids in the light chain, which differ extensively in sequence among antibodies and are used in the binding and specificity of each particular antibody for its particular antigen. The variability in sequence is concentrated in those regions called complementarity determining regions (CDRs), while the more highly conserved regions in the variable domain are called framework regions (FR). The CDRs of the light and heavy chains are primarily responsible for the interaction of the antibody with antigen. Numbering of amino acid positions is according to the EU Index, as in Kabat et al. (1991) Sequences of proteins of immunological interest. (U.S. Department of Health and Human Services, Washington, D.C.) $5^{th}$ ed. ("Kabat et al."). In some embodiments, the variable region is a human variable region.

B. Formulations and Formulation Components

As stated previously, the formulations of the invention have surprisingly been found in the form of liquids and lyophilized powders that comprise an IgG4 binding agent and a citrate buffer, wherein the pH of the formulation is at or below both about pH 6 and the isoelectric point (pI) of the binding agent. The formulations of the invention provide significant improvements over conventional IgG4 binding agent formulations (e.g., phosphate buffered saline (PBS) formulations), which form unwanted byproducts upon increasing the concentration of the binding agent in the formulation. In particular, the formulations of the invention have a reduced amount of aggregates, half-molecules, degradation products, low molecular weight proteins (LMWPs), high molecular weight proteins (HMWPs), and rearrangements of acid, basic, and neutral isoforms of the binding agent in the formulations.

i. Anti-LIGHT Binding Agents, and Variants and Fragments Thereof

In certain embodiments, the formulations of the invention include an anti-LIGHT binding agent. The binding agents may be any molecule, such as an antibody, a siRNA, a nucleic acid, an aptamer, a protein, or a small molecule organic compound, that binds or specifically binds to LIGHT, or a variant or a fragment thereof. In some embodiments, the binding agent is an anti-LIGHT antibody, or a variant thereof, or an antigen binding fragment thereof. Anti-LIGHT antibodies specifically bind to a LIGHT (lymphotoxin-like, exhibits inducible expression and competes with HSV glycoprotein D for HVEM, a receptor expressed by T lymphocytes) protein, polypeptide fragment, or epitope. The LIGHT molecule may be from any species. In some embodiments, the LIGHT molecule is from a human, known herein as "hLIGHT". hLIGHT has the following amino acid sequence, which is identified as SEQ ID NO: 9:

```
                                                  (SEQ ID NO: 9)
  1    MEESVVRPSV  FVVDGQTDIP  FTRLGRSHRR  QSCSVARVGL
       GLLLLLMGAG

51    LAVQGWFLLQ  LHWRLGEMVT  RLPDGPAGSW  EQLTQERRSH
       EVNPAAHLTG

101    ANSSLTGSGG  PLLWETQLGL  AFLRGLSYHD  GALVVTKAGY
       YYIYSKVQLG

150    GVGCPLGLAS  TITHGLYKRT  PRYPEELELL  VSQQSPCGRA
       TSSSRVWWDS

200    SFLGGVVHLE  AGEEVVVRVL  DERLVRLRDG  TRSYFGAFMV
```

In certain exemplary embodiments, the anti-LIGHT antibody is a humanized antibody, a fully human antibody, or a variant thereof or an antigen-binding fragment thereof. In some embodiments, anti-LIGHT antibodies prevent binding of LIGHT with its receptors and inhibit LIGHT biological activity (e.g., the LIGHT-mediated production or secretion of CCL20, IL-8, or RANTES from cells expressing a LIGHT ligand, such as a LIGHT receptor (e.g., HVEM, LTβR, and/or DcR3).

In certain specific embodiments, the anti-LIGHT antibody comprises a heavy chain variable region (VH) comprising the amino acid sequence of any one or more of the following complementary determining regions (CDRs):

```
HCDR1 -       GYNWH;              (SEQ ID NO: 1)

HCDR2 -       EITHSGSTNYNPSLKS;   (SEQ ID NO: 2)
or

HCDR3 -       EIAVAGTGYYGMDV.     (SEQ ID NO: 3)
```

In other specific embodiments, the anti-LIGHT antibody comprises a light chain variable region (VL) comprising the amino acid sequence of any one or more of the following complementary determining regions (CDRs):

```
LCDR1 -       RASQGINSAFA;        (SEQ ID NO: 4)

LCDR2 -       DASSLES;            (SEQ ID NO: 5)
or

LCDR3 -       QQFNSYPLT.          (SEQ ID NO: 6)
```

In one specific embodiment, the anti-LIGHT antibody comprises a heavy chain variable region (VH) comprising the amino acid sequences of SEQ ID NOs: 1, 2, and 3.

In another specific embodiment, the anti-LIGHT antibody comprises a light chain variable region (VL) comprising the amino acid sequences of SEQ ID NOs: 4, 5, and 6.

In more specific embodiments, the anti-LIGHT antibody comprises a heavy chain variable region comprising the amino acid sequences of SEQ ID NOs: 1, 2, and 3; and a light chain variable region comprising the amino acid sequences of SEQ ID NOs: 4, 5, and 6.

In specific embodiments, the anti-LIGHT antibody comprises a heavy chain comprising the amino acid sequence of SEQ ID NO: 7:

```
  1    QVQLQQWGAG  LLKPSETLSL  TCAVYGGSFS  GYNWHWIRQP  PGKGLEWIGE   (SEQ ID NO: 7)

51    ITHSGSTNYN  PSLKSRVTIS  VDTSKNQFSL  KLSSVTAADT  AVYYCVREIA

101    VAGTGYYGMD  VWGQGTTVTV  SSASTKGPSV  FPLAPCSRST  SESTAALGCL

151    VKDYFPEPVT  VSWNSGALTS  GVHTFPAVLQ  SSGLYSLSSV  VTVPSSSLGT

201    KTYTCNVDHK  PSNTKVDKRV  ESKYGPPCPP  CPAPEFEGGP  SVFLFPPKPK

251    DTLMISRTPE  VTCVVVDVSQ  EDPEVQFNWY  VDGVEVHNAK  TKPREEQFNS

301    TYRVVSVLTV  LHQDWLNGKE  YKCKVSNKGL  PSSIEKTISK  AKGQPREPQV

351    YTLPPSQEEM  TKNQVSLTCL  VKGFYPSDIA  VEWESNGQPE  NNYKTTPPVL

401    DSDGSFFLYS  RLTVDKSRWQ  EGNVFSCSVM  HEALHNHYTQ  KSLSLSLG
```

Positions 1-122: variable region of the heavy chain (VH). The CDRs (complementary determining regions, according to Kabat definition) are underlined.

Positions 123-448: constant region of human IgG4 (SwissProt IGHG4_HUMAN with the two mutations S241P and L248E, according to Kabat numbering).

In other specific embodiments, the anti-LIGHT antibody comprises a light chain comprising the amino acid sequence of SEQ ID NO: 8:

```
  1    AIQLTQSPSS  LSASVGDRVT  ITCRASQGIN  SAFAWYQQKP  GKAPKLLIYD   (SEQ ID NO: 8)

51    ASSLESGVPS  RFSGSGSGTD  FTLTISSLQP  EDFATYYCQQ  FNSYPLTFGG
```

```
101 GTKVEIKRTV AAPSVFIFPP SDEQLKSGTA SVVCLLNNFY PREAKVQWKV

151 DNALQSGNSQ ESVTEQDSKD STYSLSSTLT LSKADYEKHK VYACEVTHQG

201 LSSPVTKSFN RGEC
```

Positions 1-107: variable region of the light chain (VL). The CDRs (complementary determining regions, according to Kabat definition) are underlined.
Positions 108-214: constant region of human Cκ.

In further embodiments, the anti-LIGHT antibody comprises a heavy chain comprising the amino acid sequence of SEQ ID NO: 7, and a light chain comprising the amino acid sequence of SEQ ID NO: 8.

In certain embodiments, the anti-LIGHT antibody comprises a heavy chain derived from the amino acid sequence of SEQ ID NO: 10, which may be encoded by the nucleic acid sequence of SEQ ID NO: 11.

```
          M  K  H  L  W  F  F  L  L  L  V  A  A  P  R  W  V  L  S  Q  V  Q  L  Q  Q  W  G  •
    1   ATGAAGCACCTGTGGTTCTTTCTGCTGCTGGTGGCCGCTCCTAGATGGGTGCTGTCCCAGGTGCAGCTGCAGCAGTGGGG

• A  G  L  L  K  P  S  E  T  L  S  L  T  C  A  V  Y  G  G  S  F  S  G  Y  N  W  H  •
   81   CGCTGGCCTGCTGAAGCCTTCCGAGACACTGTCCCTGACCTGCGCCGTGTACGGCGGCTCCTTCTCCGGCTACAACTGGC

• W  I  R  Q  P  P  G  K  G  L  E  W  I  G  E  I  T  H  S  G  S  T  N  Y  N  P
  161   ACTGGATCAGGCAGCCTCCCGGCAAGGGCCTGGAATGGATCGGCGAGATCACCCACTCCGGCTCCACCAACTACAACCCT

S  L  K  S  R  V  T  I  S  V  D  T  S  K  N  Q  F  S  L  K  L  S  S  V  T  A  A  •
  241   AGCCTGAAGTCCAGAGTGACCATCTCCGTGGACACCTCCAAGAACCAGTTCTCCCTGAAGCTGTCCTCTGTGACCGCCGC

• D  T  A  V  Y  Y  C  V  R  E  I  A  V  A  G  T  G  Y  Y  G  M  D  V  W  G  Q  G  •
  321   TGACACCGCCGTGTACTACTGTGTGCGGGAGATCGCCGTGGCTGGCACCGGCTACTACGGCATGGATGTGGGGCCAGG

• T  T  V  T  V  S  S  A  S  T  K  G  P  S  V  F  P  L  A  P  C  S  R  S  T  S
  401   GCACCACCGTGACCGTGTCCAGCGCTTCTACCAAGGGCCCTTCCGTGTTCCCTCTGGCCCCTTGCTCCCGGTCCACCTCC

E  S  T  A  A  L  G  C  L  V  K  D  Y  F  P  E  P  V  T  V  S  W  N  S  G  A  L  •
  481   GAGTCCACCGCCGCTCTGGGCTGCCTGGTGAAGGACTACTTCCCTGAGCCTGTGACCGTGTCCTGGAACTCTGGCGCCCT

• T  S  G  V  H  T  F  P  A  V  L  Q  S  S  G  L  Y  S  L  S  S  V  V  T  V  P  S  •
  561   GACCTCCGGCGTGCACACCTTCCCTGCCGTGCTGCAGTCCTCCGGCCTGTACTCCCTGTCCTCCGTGGTGACCGTGCCTT

• S  S  L  G  T  K  T  Y  T  C  N  V  D  H  K  P  S  N  T  K  V  D  K  R  V  E
  641   CCTCCTCCCTGGGCACCAAGACCTACACCTGTAACGTGGACCACAAGCCTTCCAACACCAAGGTGGACAAGCGGGTGGAG

S  K  Y  G  P  P  C  P  P  C  P  A  P  E  F  E  G  G  P  S  V  F  L  F  P  P  K  •
  721   TCCAAGTACGGCCCTCCTTGCCCTCCCTGCCCTGCCCCTGAGTTCGAGGGCGGACCTAGCGTGTTCCTGTTCCCTCCTAA

• P  K  D  T  L  M  I  S  R  T  P  E  V  T  C  V  V  V  D  V  S  Q  E  D  P  E  V  •
  801   GCCTAAGGACACCCTGATGATCTCCCGGACCCCTGAGGTGACCTGTGTGGTGGTGGACGTGTCCCAGGAGGACCCTGAGG

• Q  F  N  W  Y  V  D  G  V  E  V  H  N  A  K  T  K  P  R  E  E  Q  F  N  S  T
  881   TCCAGTTCAACTGGTACGTGGACGGCGTGGAGGTGCACAACGCCAAGACCAAGCCTCGGGAGGAGCAGTTCAATTCCACC

Y  R  V  V  S  V  L  T  V  L  H  Q  D  W  L  N  G  K  E  Y  K  C  K  V  S  N  K  •
  961   TACCGGGTGGTGTCTGTGCTGACCGTGCTGCACCAGGACTGGCTGAACGGCAAAGAATACAAGTGTAAGGTCTCCAACAA

• G  L  P  S  S  I  E  K  T  I  S  K  A  K  G  Q  P  R  E  P  Q  V  Y  T  L  P  P  •
 1041   GGGCCTGCCCTCCTCCATCGAGAAAACCATCTCCAAGGCCAAGGGCCAGCCTAGGGAGCCTCAGGTGTACACCCTGCCTC

• S  Q  E  E  M  T  K  N  Q  V  S  L  T  C  L  V  K  G  F  Y  P  S  D  I  A  V
 1121   CTAGCCAGGAAGAGATGACCAAGAACCAGGTGTCCCTGACCTGTCTGGTGAAGGGCTTCTACCCTTCCGACATCGCCGTG

E  W  E  S  N  G  Q  P  E  N  N  Y  K  T  T  P  P  V  L  D  S  D  G  S  F  F  L  •
 1201   GAGTGGGAGTCCAACGGCCAGCCTGAGAACAACTACAAGACCACCCCTCCTGTGCTGGACTCCGACGGCTCCTTCTTCCT

• Y  S  R  L  T  V  D  K  S  R  W  Q  E  G  N  V  F  S  C  S  V  M  H  E  A  L  H  •
 1281   GTACTCCAGGCTGACCGTGGACAAGTCCCGGTGGCAGGAGGGCAACGTCTTTTCCTGCTCCGTGATGCACGAGGCCCTGC

• N  H  Y  T  Q  K  S  L  S  L  S  L  G  *   (SEQ ID NO: 10)
 1361   ACAACCACTACACCCAGAAGTCCCTGTCCCTGTCTCTGGGCTGA (SEQ ID NO: 11)
```

Amino acids 1-19: signal peptide
Amino acids 20-141: 124F19k2 variable region (VH)
Amino acids 142-end: hIgG4 PE constant region
Nucleic acids 1-57: nucleic acids encoding the signal peptide
Nucleic acids 58-423: nucleic acids encoding the 124F19k2 variable region (VH)
Nucleic acids 424-end: nucleic acids encoding the hIgG4 PE constant region In alternative specific embodiments, the anti-LIGHT antibody comprises a light chain derived from the amino acid sequence of SEQ ID NO: 12, which may be encoded by the nucleic acid sequence of SEQ ID NO: 13.

antibody is a fully human IgG4 anti-LIGHT antibody comprising a heavy chain variable region and a light chain variable region, the heavy chain variable region comprising 3 complementary determining regions (CDRs) comprising the amino acid sequences of SEQ ID NOs: 1, 2, and 3, and the light chain variable region comprising 3 CDRs comprising the amino acid sequences of SEQ ID NOs: 4, 5, and 6. Identification, isolation, preparation, and characterization of anti-LIGHT antibodies, including the anti-LIGHT antibody comprising a heavy chain amino acid sequence comprising SEQ ID NO: 7 and a light chain amino acid sequence comprising SEQ ID NO: 8, have been described in detail in

```
      M  D  M  R  V  P  A  Q  L  L  G  L  L  L  L  W  L  P  G  A  R  C  A  I  Q  L  T  •
  1   ATGGACATGAGAGTGCCTGCTCAGCTGCTGGGACTGCTGCTGCTGTGGCTGCCTGGCGCTAGATGCGCCATCCAGCTGAC

• Q  S  P  S  S  L  S  A  S  V  G  D  R  V  T  I  T  C  R  A  S  Q  G  I  N  S  A  •
 81   CCAGTCCCCCTCCTCTCTGTCCGCCTCCGTGGGCGACAGAGTGACCATCACCTGTCGGGCCTCCCAGGGCATCAACTCCG

• F  A  W  Y  Q  Q  K  P  G  K  A  P  K  L  L  I  Y  D  A  S  S  L  E  S  G  V
161   CCTTCGCCTGGTATCAGCAGAAGCCTGGCAAGGCCCCTAAGCTGCTGATCTACGACGCCTCCTCCCTGGAATCCGGCGTG

P  S  R  F  S  G  S  G  S  G  T  D  F  T  L  T  I  S  S  L  Q  P  E  D  F  A  T  •
241   CCCTCCAGATTTTCCGGCTCCGGCTCTGGCACCGACTTCACCCTGACCATCTCCAGCCTGCAGCCTGAGGACTTCGCCAC

• Y  Y  C  Q  Q  F  N  S  Y  P  L  T  F  G  G  G  T  K  V  E  I  K  R  T  V  A  A  •
321   CTACTACTGCCAGCAGTTCAACTCCTACCCTCTGACCTTCGGCGGAGGCACCAAGGTGGAGATCAAGCGTACGGTGGCTG

• P  S  V  F  I  F  P  P  S  D  E  Q  L  K  S  G  T  A  S  V  V  C  L  L  N  N
401   CACCATCTGTCTTCATCTTCCCGCCATCTGATGAGCAGTTGAAATCTGGAACTGCCTCTGTTGTGCCTGCTGAATAAC

F  Y  P  R  E  A  K  V  Q  W  K  V  D  N  A  L  Q  S  G  N  S  Q  E  S  V  T  E  •
481   TTCTATCCCAGAGAGGCCAAAGTACAGTGGAAGGTGGATAACGCCCTCCAATCGGGTAACTCCCAGGAGAGTGTCACAGA

• Q  D  S  K  D  S  T  Y  S  L  S  S  T  L  T  L  S  K  A  D  Y  E  K  H  K  V  Y  •
561   GCAGGACAGCAAGGACAGCACCTACAGCCTCAGCAGCACCCTGACGCTGAGCAAAGCAGACTACGAGAAACACAAAGTCT

• A  C  E  V  T  H  Q  G  L  S  S  P  V  T  K  S  F  N  R  G  E     C  *    (SEQ ID NO: 12)
641   ACGCCTGCGAAGTCACCCATCAGGGCCTGAGCTCGCCCGTCACAAAGAGCTTCAACAGGGGAGAGTGTTAG (SEQ ID NO: 13)
```

Amino acids 1-22: signal peptide
Amino acids 23-129: 124F19k2 variable region (VL)
Amino acids 130-end: hKappa constant region
Nucleic acids 1-66: nucleic acids encoding the signal peptide
Nucleic acids 67-387: nucleic acids encoding the 124F19k2 variable region (VL)
Nucleic acids 388-end: nucleic acids encoding the hKappa constant region In an embodiment of the invention, the anti-LIGHT antibody is a fully human antibody. Examples of fully human antibody isotypes include IgA, IgD, IgE, IgG, and IgM. In some embodiments, the anti-LIGHT antibody is an IgG antibody. There are four forms of IgG. In some embodiments, the anti-LIGHT antibody is an IgG4 antibody. In some embodiments of the invention, the anti-LIGHT antibody is a fully human IgG4 antibody.

In some embodiments, the anti-LIGHT antibody further comprises a constant region, e.g., a human IgG constant region. In some embodiments, the constant region is a human IgG4 constant region. In additional embodiments, the constant region is a modified human IgG4 constant region. In other embodiments, the constant region is a human Cκ constant region.

In some embodiments of the invention, the anti-LIGHT antibody is a fully human IgG4 anti-LIGHT antibody comprising a heavy chain comprising the amino acid sequence of SEQ ID NO: 7 and a light chain comprising the amino acid sequence of SEQ ID NO: 8 (the "Lead LIGHT Antibody"). In alternative embodiments of the invention, the anti-LIGHT U.S. Pat. No. 8,058,402, corresponding to PCT Publication WO 2008/027338, which are incorporated herein by reference.

Certain embodiments of formulations of the invention also include variants of anti-LIGHT binding agents, such as antibodies. Specifically, the formulations of the invention may include variants of the anti-LIGHT antibody that is a fully human IgG4 anti-LIGHT antibody comprising a heavy chain comprising the amino acid sequence of SEQ ID NO: 7 and a light chain comprising the amino acid sequence of SEQ ID NO: 8. Variants of anti-LIGHT antibodies may have similar physicochemical properties based on their high similarity, and therefore are also included within the scope of the invention. Variants are defined as antibodies with an amino acid sequence that is at least 95%, at least 97%, for instance at least 98% or 99% homologous to an anti-LIGHT antibody, and capable of competing for binding to a LIGHT polypeptide, a LIGHT polypeptide fragment, or a LIGHT epitope. In some embodiments, the variants will ameliorate, neutralize, or otherwise inhibit LIGHT biological activity (e.g., the LIGHT-mediated production or secretion of CCL20, IL-8, or RANTES from cells expressing a LIGHT ligand, such as a LIGHT receptor (e.g., HVEM, LTβR, and/or DcR3). Determining competition for binding to the target can be done by routine methods known to the skilled person in the art. In some embodiments, the variants are human antibodies, and, in some embodiments, are IgG4 molecules. In some embodiments, a variant is at least 95%, 96%, 97%, 98%, or 99% identical in amino acid sequence with the Lead Antibody. The term "variant" refers to an antibody that comprises an amino acid sequence that is altered by one or more amino acids compared to the amino acid sequences of the anti-LIGHT antibody. The variant may have conservative sequence modifications, including amino acid substitutions, modifications, additions, and deletions.

Examples of modifications include, but are not limited to, glycosylation, acetylation, pegylation, phosphorylation, amidation, derivatization by known protecting/blocking groups, proteolytic cleavage, and linkage to a cellular ligand or other protein. Amino acid modifications can be introduced by standard techniques known in the art, such as site-directed mutagenesis, molecular cloning, oligonucleotide-directed mutagenesis, and random PCR-mediated mutagenesis in the nucleic acid encoding the antibodies. Conservative amino acid substitutions include the ones in which the amino acid residue is replaced with an amino acid residue having similar structural or chemical properties. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine, tryptophan), nonpolar side chains (e.g., glycine, alanine, valine, leucine, isoleucine, proline, phenylalanine, methionine), beta-branched side chains (e.g., threonine, valine, isoleucine), and aromatic side chains (e.g., tyrosine, phenylalanine, tryptophan). It will be clear to the skilled artisan that classifications of amino acid residue families other than the one used above can also be employed. Furthermore, a variant may have non-conservative amino acid substitutions, e.g., replacement of an amino acid with an amino acid residue having different structural or chemical properties. Similar minor variations may also include amino acid deletions or insertions, or both. Guidance in determining which amino acid residues may be substituted, modified, inserted, or deleted without abolishing immunological activity may be found using computer programs well known in the art. Computer algorithms, such as, inter alia, Gap or Bestfit, which are known to a person skilled in the art, can be used to optimally align amino acid sequences to be compared and to define similar or identical amino acid residues. Variants may have the same or different, either higher or lower, binding affinities compared to an anti-LIGHT antibody, but are still capable of specifically binding to LIGHT, and may have the same, higher or lower, biological activity as the anti-LIGHT antibody.

Embodiments of the invention also include antigen binding fragments of the anti-LIGHT binding agents, such as antibodies. The term "antigen binding domain," "antigen binding region," "antigen binding fragment," and similar terms refer to that portion of an antibody which comprises the amino acid residues that interact with an antigen and confer on the binding agent its specificity and affinity for the antigen (e.g., the complementary determining regions (CDR)). The antigen binding region can be derived from any animal species, such as rodents (e.g., rabbit, rat or hamster) and humans. In some embodiments, the antigen binding region will be of human origin. Non-limiting examples of antigen binding fragments include: Fab fragments, F(ab')2 fragments, Fd fragments, Fv fragments, single chain Fv (scFv) molecules, dAb fragments, and minimal recognition units consisting of the amino acid residues that mimic the hypervariable region of the antibody.

In some embodiments of the invention, the anti-LIGHT binding agents (or a variant thereof or an antigen binding fragment thereof) will ameliorate, neutralize, or otherwise inhibit LIGHT biological activity in vivo (e.g., the LIGHT-mediated production or secretion of CCL20, IL-8, or RANTES from a cell expressing a LIGHT receptor, e.g., HVEM, LTβR, and/or DcR3).

In some embodiments of the invention, the anti-LIGHT binding agents (or a variant thereof or an antigen binding fragment thereof) are antagonist binding agents that ameliorate, neutralize, or otherwise inhibit LIGHT biological activity in vivo (e.g., the LIGHT-mediated production or secretion of CCL20, IL-8, or RANTES from cells expressing a LIGHT ligand, such as a LIGHT receptor, (e.g., HVEM, LTβR, and/or DcR3).

In some embodiments, the anti-LIGHT binding agent (or a variant thereof or an antigen binding fragment thereof) is present in the formulations in an amount from about 5 mg/mL to about 280 mg/mL, e.g., about 5 mg/mL to about 200 mg/mL, about 50 mg/mL to about 250 mg/mL, about 100 mg/mL to about 250 mg/mL, about 50 mg/mL to about 200 mg/mL, and about 100 mg/mL to about 200 mg/mL. For example, the anti-LIGHT binding agent may be present in the formulation in an amount of about 5 mg/mL, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, about 100 mg/mL, about 105 mg/mL, about 110 mg/mL, about 115 mg/mL, about 120 mg/mL, about 125 mg/mL, about 130 mg/mL, about 135 mg/mL, about 140 mg/mL, about 145 mg/mL, about 150 mg/mL, about 155 mg/mL, about 160 mg/mL, about 165 mg/mL, about 170 mg/mL, about 175 mg/mL, about 180 mg/mL, about 185 mg/mL, about 190 mg/mL, about 195 mg/mL, about 200 mg/mL, about 205 mg/mL, about 210 mg/mL, about 215 mg/mL, about 220 mg/mL, about 225 mg/mL, about 230 mg/mL, about 235 mg/mL, about 240 mg/mL, about 245 mg/mL, about 250 mg/mL, about 255 mg/mL, about 260 mg/mL, about 265 mg/mL, about 270 mg/mL, about 275 mg/mL, or about 280 mg/mL.

In alternative embodiments, the anti-LIGHT binding agent may be present in the formulation in an amount from about 5 to about 25 mg/mL, from about 26 to about 50 mg/mL, from about 51 to about 75 mg/mL, from about 76 to about 100 mg/mL, from about 101 to about 125 mg/mL, from about 126 to about 150 mg/mL, from about 151 to about 175 mg/mL, from about 176 to about 200 mg/mL, from about 201 mg/mL to about 225 mg/mL, from about 226 mg/mL to about 250 mg/mL, from about 251 to about 280 mg/mL, from about 5 to about 10 mg/mL, from about 40 to about 60 mg/mL, from about 75 to about 85 mg/mL, or from about 140 to about 160 mg/mL.

In certain exemplary embodiments, the anti-LIGHT binding agent is present in the formulation in an amount from about 50 mg/mL to about 170 mg, about 100 mg/mL to about 160 mg/mL, for example about 150 mg/mL. Alternatively, the anti-LIGHT binding agent is present in an amount of about 50 mg/mL. In another exemplary embodiment, a fully human IgG4 anti-LIGHT antibody comprising a heavy chain comprising the amino acid sequence of SEQ ID NO: 7 and a light chain comprising the amino acid sequence of SEQ ID NO: 8 is present in the formulation in an amount of about 150 mg/mL.

ii. Anti-CXCR5 Binding Agents, and Variants and Fragments Thereof

In certain embodiments, the formulations of the invention include an anti-CXCR5 binding agent. The binding agents may be any molecule, such as an antibody, a siRNA, a nucleic acid, an aptamer, a protein, or a small molecule organic compound, that binds or specifically binds to CXCR5, or a variant or a fragment thereof. In some embodiments, the binding agent is an anti-CXCR5 antibody, or a variant thereof, or an antigen binding fragment thereof. Anti-CXCR5 antibodies specifically bind to a CXCL13 (also known as BLC) protein, polypeptide fragment, or epitope. The CXCR5 molecule may be from any species. In some embodiments, the CXCR5 molecule is from a human, known herein as "hCXCR5". hCXCR5 has the following amino acid sequence, which is identified as SEQ ID NO: 14:

```
                                          (SEQ ID NO: 14)
MNYPLTLEMD  LENLEDLFWE  LDRLDNYNDT  SLVENHLCPA

TEGPLMASFK  AVFVPVAYSL  IFLLGVIGNV  LVLVILERHR

QTRSSTETFL  FHLAVADLLL  VFILPFAVAE  GSVGWVLGTF

LCKTVIALHK  VNFYCSSLLL  ACIAVDRYLA  IVHAVHAYRH

RRLLSIHITC  GTIWLVGFLL  ALPEILFAKV  SQGHHNNSLP

RCTFSQENQA  ETHAWFTSRF  LYHVAGFLLP  MLVMGWCYVG

VVHRLRQAQR  RPQRQKAVRV  AILVTSIFFL  CWSPYHIVIF

LDTLARLKAV  DNTCKLNGSL  PVAITMCEFL  GLAHCCLNPM

LYTFAGVKFR  SDLSRLLTKL  GCTGPASLCQ  LFPSWRRSSL

SESENATSLT  TF.
```

In certain exemplary embodiments, the anti-CXCR5 antibody is a humanized antibody, a fully human antibody, or a variant thereof or an antigen-binding fragment thereof. In some embodiments, anti-CXCR5 antibodies prevent binding of CXCR5 with its ligands and inhibit CXCR5 biological activity (e.g., the binding of CXCR5 to CXCL13).

In certain specific embodiments, the anti-CXCR5 antibody comprises a heavy chain variable region (VH) comprising the amino acid sequence of any one or more of the following complementary determining regions (CDRs):

```
    HCDR1 - GFSLIDYGVN;       (SEQ ID NO: 15)

HCDR2 - VIWGDGTTY;        (SEQ ID NO: 16)
    or

HCDR3 - IVY.              (SEQ ID NO: 17)
```

In other specific embodiments, the anti-CXCR5 antibody comprises a light chain variable region (VL) comprising the amino acid sequence of any one or more of the following complementary determining regions (CDRs):

```
    LCDR1 - RSSKSLLHSSGKTYLY;  (SEQ ID NO: 18)

LCDR2 - RLSSLA;            (SEQ ID NO: 19)
    or

LCDR3 - MQHLEYPYT.         (SEQ ID NO: 20)
```

In one specific embodiment, the anti-CXCR5 antibody comprises a heavy chain variable region (VH) comprising the amino acid sequences of SEQ ID NOs: 15, 16, and 17.

In another specific embodiment, the anti-CXCR5 antibody comprises a light chain variable region (VL) comprising the amino acid sequences of SEQ ID NOs: 18, 19, and 20.

In more specific embodiments, the anti-CXCR5 antibody comprises a heavy chain variable region comprising the amino acid sequences of SEQ ID NOs: 15, 16, and 17; and a light chain variable region comprising the amino acid sequences of SEQ ID NOs: 18, 19, and 20.

In a specific embodiment, the anti-CXCR5 antibody comprises a heavy chain variable region comprising the amino acid sequence of SEQ ID NO: 21:

```
                                          (SEQ ID NO: 21)
QVQLKESGPG  LVAPSESLSI  TCTVSGFSLI  DYGVNWIRQP

PGKGLEWLGV  IWGDGTTYYN  PSLKSRLSIS  KDNSKSQVFL

KVTSLTTDDT  AMYYCARIVY  WGQGTLVTVS  A.
```

In another specific embodiment, the anti-CXCR5 antibody comprises a light chain variable region comprising the amino acid sequence of SEQ ID NO: 22:

```
                                          (SEQ ID NO: 22)
DIVMTQAAPS  VAVTPGASVS  ISCRSSKSLL  HSSGKTYLYW

FLQRPGQSPQ  LLIYRLSSLA  SGVPDRFSGS  GSGTAFTLRI

SRVEAEDVGV  YYCMQHLEYP  YTFGGGTKLE  IK.
```

In more specific embodiments, the anti-CXCR5 antibody comprises a heavy chain variable region comprising the amino acid sequence of SEQ ID NO: 21; and a light chain variable region comprising the amino acid sequence of SEQ ID NO: 22.

In some embodiments, the anti-CXCR5 antibody further comprises a constant region, e.g., a human IgG constant region. In some embodiments, the constant region is a human IgG4 constant region. In additional embodiments, the constant region is a modified human IgG4 constant region. In some embodiments, the human IgG4 constant region has the following modifications: S241P (shown below in SEQ ID NO: 23 in bold), L248E (shown below in SEQ ID NO: 23 in bold), and the lack of a terminal lysine in order to avoid heterogeneity. In some embodiments, the IgG4 constant region comprises the amino acid sequence of SEQ ID NO: 23:

```
                                          (SEQ ID NO: 23)
ASTKGPSVFP  LAPCSRSTSE  STAALGCLVK  DYFPEPVTVS

WNSGALTSGV  HTFPAVLQSS  GLYSLSSVVT  VPSSSLGTKT

YTCNVDHKPS  NTKVDKRVES  KYGPPCPPCP  APEFEGGPSV

FLFPPKPKDT  LMISRTPEVT  CVVVDVSQED  PEVQFNWYVD

GVEVHNAKTK  PREEQFNSTY  RVVSVLTVLH  QDWLNGKEYK

CKVSNKGLPS  SIEKTISKAK  GQPREPQVYT  LPPSQEEMTK

NQVSLTCLVK  GFYPSDIAVE  WESNGQPENN  YKTTPPVLDS

DGSFFLYSRL  TVDKSRWQEG  NVFSCSVMHE  ALHNHYTQKS

LSLSLG.
```

In other embodiments, the constant region is a human Cκ constant region. In some embodiments, the Cκ constant region comprises the amino acid sequence of SEQ ID NO: 24:

```
                                                (SEQ ID NO: 24)
RTVAAPSVFI FPPSDEQLKS GTASVVCLLN NFYPREAKVQ

WKVDNALQSG NSQESVTEQD SKDSTYSLSS TLTLSKADYE

KHKVYACEVT HQGLSSPVTK SFNRGEC.
```

In specific embodiments, the anti-CXCR5 antibody comprises a heavy chain comprising the amino acid sequence of SEQ ID NO: 25:

```
                                                (SEQ ID NO: 25)
QVQLKESGPG LVAPSESLSI TCTVSGFSLI DYGVNWIRQP

PGKGLEWLGV IWGDGTTYYN PSLKSRLSIS KDNSKSQVFL

KVTSLTTDDT AMYYCARIVY WGQGTLVTVS AASTKGPSVF

PLAPCSRSTS ESTAALGCLV KDYFPEPVTV SWNSGALTSG

VHTFPAVLQS SGLYSLSSVV TVPSSSLGTK TYTCNVDHKP

SNTKVDKRVE SKYGPPCPPC PAPEFEGGPS VFLFPPKPKD

TLMISRTPEV TCVVVDVSQE DPEVQFNWYV DGVEVHNAKT

KPREEQFNST YRVVSVLTVL HQDWLNGKEY KCKVSNKGLP

SSIEKTISKA KGQPREPQVY TLPPSQEEMT KNQVSLTCLV

KGFYPSDIAV EWESNGQPEN NYKTTPPVLD SDGSFFLYSR

LTVDKSRWQE GNVFSCSVMH EALHNHYTQK SLSLSLG.
```

Positions 1-111: variable region of the heavy chain (VH). The CDRs (complementarity determining regions, according to Kabat definition) are underlined.
Positions 112-432: constant region of human IgG4 (SwissProt IGHG4_HUMAN, including the following modifications: S241P, L248E, and the lack of a terminal lysine in order to avoid heterogeneity).

In other specific embodiments, the anti-CXCR5 antibody comprises a light chain comprising the amino acid sequence of SEQ ID NO: 26:

```
                                                (SEQ ID NO: 26)
DIVMTQAAPS VAVTPGASVS ISCRSSKSLL HSSGKTYLYW

FLQRPGQSPQ LLIYRLSSLA SGVPDRFSGS GSGTAFTLRI

SRVEAEDVGV YYCMQHLEYP YTFGGGTKLE IKRTVAAPSV

FIFPPSDEQL KSGTASVVCL LNNFYPREAK VQWKVDNALQ

SGNSQESVTE QDSKDSTYSL SSTLTLSKAD YEKHKVYACE

VTHQGLSSPV TKSFNRGEC.
```

Positions 1-112: variable region of the light chain (VL). The CDRs (complementarity determining regions, according to Kabat definition) are underlined.
Positions 113-182: constant region of human Cκ.

In further embodiments, the anti-CXCR5 antibody comprises a heavy chain comprising the amino acid sequence of SEQ ID NO: 25, and a light chain comprising the amino acid sequence of SEQ ID NO: 26.

In some embodiments, the anti-CXCR5 antibody further comprises a leader sequence. The leader sequence, in some embodiments, comprises an amino acid sequence from 1-30 amino acids in length, such as 25-25 amino acids, and typically 19 amino acids. The heavy chain, light chain, or both the heavy and light chain may comprise a leader sequence. In some embodiments, the leader sequence comprises the amino acid sequence of SEQ ID NO: 16 : MGWSCIILFLVATATGVHS (SEQ ID NO: 27).

In specific embodiments, the anti-CXCR5 antibody comprises a heavy chain derived from the amino acid sequence of SEQ ID NO: 28:

```
                                                (SEQ ID NO: 28)
MGWSCIILFL VATATGVHSQ VQLKESGPGL VAPSESLSIT

CTVSGFSLID YGVNWIRQPP GKGLEWLGVI WGDGTTYYNP

SLKSRLSISK DNSKSQVFLK VTSLTTDDTA MYYCARIVYW

GQGTLVTVSA ASTKGPSVFP LAPCSRSTSE STAALGCLVK

DYFPEPVTVS WNSGALTSGV HTFPAVLQSS GLYSLSSVVT

VPSSSLGTKT YTCNVDHKPS NTKVDKRVES KYGPPCPPCP

APEFEGGPSV FLFPPKPKDT LMISRTPEVT CVVVDVSQED

PEVQFNWYVD GVEVHNAKTK PREEQFNSTY RVVSVLTVLH

QDWLNGKEYK CKVSNKGLPS SIEKTISKAK GQPREPQVYT

LPPSQEEMTK NQVSLTCLVK GFYPSDIAVE WESNGQPENN

YKTTPPVLDS DGSFFLYSRL TVDKSRWQEG NVFSCSVMHE

ALHNHYTQKS LSLSLG.
```

Positions 1-19: leader sequence
Positions 20-130: variable region of the heavy chain (VH). The CDRs (complementarity determining regions, according to Kabat definition) are underlined.
Positions 131-456: constant region of human IgG4 (SwissProt IGHG4_HUMAN, including the following modifications: S241P, L248E, and the lack of a terminal lysine in order to avoid heterogeneity).

In other specific embodiments, the anti-CXCR5 antibody comprises a light chain derived from the amino acid sequence of SEQ ID NO: 29:

```
                                                (SEQ ID NO: 29)
MGWSCIILFL VATATGVHSD IVMTQAAPSV AVTPGASVSI

SCRSSKSLLH SSGKTYLYWF LQRPGQSPQL LIYRLSSLAS

GVPDRFSGSG SGTAFTLRIS RVEAEDVGVY YCMQHLEYPY

TFGGGTKLEI KRTVAAPSVF IFPPSDEQLK SGTASVVCLL

NNFYPREAKV QWKVDNALQS GNSQESVTEQ DSKDSTYSLS

STLTLSKADY EKHKVYACEV THQGLSSPVT KSFNRGEC.
```

Positions 1-19: leader sequence
Positions 20-131: variable region of the light chain (VL). The CDRs (complementarity determining regions, according to Kabat definition) are underlined.
Positions 132-238: constant region of human Cκ.

In further embodiments, the anti-CXCR5 antibody comprises a heavy chain comprising the amino acid sequence of SEQ ID NO: 28, and a light chain comprising the amino acid sequence of SEQ ID NO: 29.

In some embodiments of the invention, the anti-CXCR5 antibody is a humanized or a fully human antibody. Examples of humanized and fully human antibody isotypes include IgA, IgD, IgE, IgG, and IgM. In some embodiments, the anti-CXCR5 antibody is an IgG antibody. There are four forms of IgG. In some embodiments, the anti-CXCR5 antibody is an IgG4 antibody. In some embodiments of the invention, the anti-CXCR5 antibody is a humanized IgG4 antibody.

In some embodiments of the invention, the anti-CXCR5 antibody is a humanized IgG4 anti-CXCR5 antibody comprising a heavy chain comprising the amino acid sequence of SEQ ID NO: 25 and a light chain comprising the amino acid sequence of SEQ ID NO: 26 (the "Lead CXCR5 Antibody"). In alternative embodiments of the invention, the anti-CXCR5 antibody is a humanized IgG4 anti-CXCR5 antibody comprising a heavy chain variable region and a light chain variable region, the heavy chain variable region comprising 3 complementary determining regions (CDRs) comprising the amino acid sequences of SEQ ID NOs: 15, 16, and 17, and the light chain variable region comprising 3 CDRs comprising the amino acid sequences of SEQ ID NOs: 18, 19, and 20. Identification, isolation, preparation, and characterization of anti-CXCR5 antibodies, including the anti-CXCR5 antibody comprising a heavy chain amino acid sequence comprising SEQ ID NO: 25 and a light chain amino acid sequence comprising SEQ ID NO: 26, have been described in detail in PCT Publication WO 2009/032661, which are incorporated herein by reference.

Certain embodiments of formulations of the invention also include variants of anti-CXCR5 binding agents, such as antibodies. Specifically, the formulations of the invention may include variants of the anti-CXCR5 antibody that is a humanized IgG4 anti-CXCR5 antibody comprising a heavy chain comprising the amino acid sequence of SEQ ID NO: 25 and a light chain comprising the amino acid sequence of SEQ ID NO: 26. Variants of anti-CXCR5 antibodies may have similar physicochemical properties based on their high similarity, and therefore are also included within the scope of the invention. Variants are defined as antibodies with an amino acid sequence that is at least 95%, at least 97%, for instance at least 98% or 99% homologous to an anti-CXCR5 antibody, and capable of competing for binding to a CXCR5 polypeptide, a CXCR5 polypeptide fragment, or a CXCR5 epitope. In some embodiments, the variants will ameliorate, neutralize, or otherwise inhibit CXCR5 biological activity (e.g., the binding of CXCL13 to CXCR5). Determining competition for binding to the target can be done by routine methods known to the skilled person in the art. In some embodiments, the variants are human antibodies, and, in some embodiments, are IgG4 molecules. In some embodiments, a variant is at least 95%, 96%, 97%, 98%, or 99% identical in amino acid sequence with the Lead Antibody. The term "variant" refers to an antibody that comprises an amino acid sequence that is altered by one or more amino acids compared to the amino acid sequences of the anti-CXCR5 antibody. The variant may have conservative sequence modifications, including amino acid substitutions, modifications, additions, and deletions.

Examples of modifications include, but are not limited to, glycosylation, acetylation, pegylation, phosphorylation, amidation, derivatization by known protecting/blocking groups, proteolytic cleavage, and linkage to a cellular ligand or other protein. Amino acid modifications can be introduced by standard techniques known in the art, such as site-directed mutagenesis, molecular cloning, oligonucleotide-directed mutagenesis, and random PCR-mediated mutagenesis in the nucleic acid encoding the antibodies. Conservative amino acid substitutions include the ones in which the amino acid residue is replaced with an amino acid residue having similar structural or chemical properties. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine, tryptophan), nonpolar side chains (e.g., glycine, alanine, valine, leucine, isoleucine, proline, phenylalanine, methionine), beta-branched side chains (e.g., threonine, valine, isoleucine), and aromatic side chains (e.g., tyrosine, phenylalanine, tryptophan). It will be clear to the skilled artisan that classifications of amino acid residue families other than the one used above can also be employed. Furthermore, a variant may have non-conservative amino acid substitutions, e.g., replacement of an amino acid with an amino acid residue having different structural or chemical properties. Similar minor variations may also include amino acid deletions or insertions, or both. Guidance in determining which amino acid residues may be substituted, modified, inserted, or deleted without abolishing immunological activity may be found using computer programs well known in the art. Computer algorithms, such as, inter alia, Gap or Bestfit, which are known to a person skilled in the art, can be used to optimally align amino acid sequences to be compared and to define similar or identical amino acid residues. Variants may have the same or different, either higher or lower, binding affinities compared to an anti-CXCR5 antibody, but are still capable of specifically binding to CXCR5, and may have the same, higher or lower, biological activity as the anti-CXCR5 antibody.

Embodiments of the invention also include antigen binding fragments of the anti-CXCR5 binding agents, such as antibodies. The term "antigen binding domain," "antigen binding region," "antigen binding fragment," and similar terms refer to that portion of an antibody which comprises the amino acid residues that interact with an antigen and confer on the binding agent its specificity and affinity for the antigen (e.g., the complementary determining regions (CDR)). The antigen binding region can be derived from any animal species, such as rodents (e.g., rabbit, rat or hamster) and humans. In some embodiments, the antigen binding region will be of human origin. Non-limiting examples of antigen binding fragments include: Fab fragments, F(ab')2 fragments, Fd fragments, Fv fragments, single chain Fv (scFv) molecules, dAb fragments, and minimal recognition units consisting of the amino acid residues that mimic the hypervariable region of the antibody.

In some embodiments of the invention, the anti-CXCR5 binding agents (or a variant thereof or an antigen binding fragment thereof) will ameliorate, neutralize, or otherwise inhibit CXCR5 biological activity in vivo (e.g., the binding of CXCL13 to CXCR5).

In some embodiments of the invention, the anti-CXCR5 binding agents (or a variant thereof or an antigen binding fragment thereof) are antagonist binding agents that ameliorate, neutralize, or otherwise inhibit CXCR5 biological activity in vivo (e.g., the binding of CXCL13 to CXCR5).

In some embodiments, the anti-CXCR5 binding agent (or a variant thereof or an antigen binding fragment thereof) is present in the formulations in an amount from about 5 mg/mL to about 280 mg/mL, e.g., about 5 mg/mL to about 200 mg/mL, about 5 mg/mL to about 125 mg/mL, about 5 mg/mL to about 75 mg/mL, about 5 mg/mL to about 50 mg/mL, and about 5 mg/mL to about 25 mg/mL. For example, the anti-CXCR5 binding agent may be present in the formulation in an amount of about 5 mg/mL, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, about 100 mg/mL, about 105 mg/mL, about 110 mg/mL, about 115 mg/mL, about 120 mg/mL, about 125 mg/mL, about 130 mg/mL, about 135 mg/mL, about 140 mg/mL, about 145 mg/mL, about 150 mg/mL, about 155 mg/mL, about 160 mg/mL, about 165 mg/mL, about 170 mg/mL, about 175 mg/mL, about 180 mg/mL, about 185 mg/mL, about 190 mg/mL, about 195 mg/mL, about 200 mg/mL, about 205 mg/mL, about 210 mg/mL, about 215 mg/mL, about 220 mg/mL, about 225 mg/mL, about 230 mg/mL, about 235 mg/mL, about 240 mg/mL, about 245 mg/mL, about 250 mg/mL, about 255 mg/mL, about 260 mg/mL, about 265 mg/mL, about 270 mg/mL, about 275 mg/mL, or about 280 mg/mL.

In alternative embodiments, the anti-CXCR5 binding agent may be present in the formulation in an amount from about 5 to about 25 mg/mL, from about 26 to about 50 mg/mL, from about 51 to about 75 mg/mL, from about 76 to about 100 mg/mL, from about 101 to about 125 mg/mL, from about 126 to about 150 mg/mL, from about 151 to about 175 mg/mL, from about 176 to about 200 mg/mL, from about 201 mg/mL to about 225 mg/mL, from about 226 mg/mL to about 250 mg/mL, from about 251 to about 280 mg/mL, from about 5 to about 25 mg/mL, from about 40 to about 60 mg/mL, from about 75 to about 85 mg/mL, or from about 90 to about 110 mg/mL.

In certain exemplary embodiments, the anti-CXCR5 binding agent is present in the formulation in an amount of about 20 mg/mL. Alternatively, the anti-CXCR5 binding agent is present in an amount of about 100 mg/mL. In another exemplary embodiment, a humanized IgG4 anti-CXCR5 antibody comprising a heavy chain comprising the amino acid sequence of SEQ ID NO: 25 and a light chain comprising the amino acid sequence of SEQ ID NO: 26 is present in the formulation in an amount of about 20 mg/mL or 100 mg/mL.

iii. Buffering Agents

The formulations of the invention comprise a citrate buffer as a buffering agent. A buffering agent maintains a physiologically suitable pH. In addition, a buffering agent enhances isotonicity and chemical stability of the formulation. In some embodiments, the citrate buffer is present in the formulations at a concentration from about 0.5 mM to about 50 mM, e.g., about 5 mM to about 15 mM. For example, the citrate buffer may be present in the formulation at a concentration about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, about 30 mM, about 31 mM, about 32 mM, about 33 mM, about 34 mM, about 35 mM, about 36 mM, about 37 mM, about 38 mM, about 39 mM, about 40 mM, about 41 mM, about 42 mM, about 43 mM, about 44 mM, about 45 mM, about 46 mM, about 47 mM, about 48 mM, about 49 mM, and about 50 mM. In some embodiments, the citrate buffer is present in the formulation at a concentration from about 7 mM to about 13 mM, such as from about 9 mM to about 11 mM. In some embodiments, the citrate buffer is present at a concentration of about 10 mM.

In certain embodiments, the formulations of the invention have a pH at or below pH 6. In some embodiments, the pH of the formulations ranges from about 5.0 to about 6.0. For example, the pH of the formulations may be about 5.0, about 5.1, about 5.2, about 5.3, about 5.4, about 5.5, about 5.6, about 5.7, about 5.8, about 5.9, and about 6.0. In some embodiments, the pH of the formulations may range from about 5.5 to about 6.0. In some embodiments, the pH is either about 5.5 or about 6.0. The pH of the formulation may be measured by any means known to those of skill in the art. A means for measuring pH is using a pH meter with a micro-electrode. The pH of the formulation may be adjusted using any means known in the art. Exemplary chemicals for altering the pH of the formulations are hydrochloric acid (HCl) and sodium hydroxide (NaOH).

Figure 11:
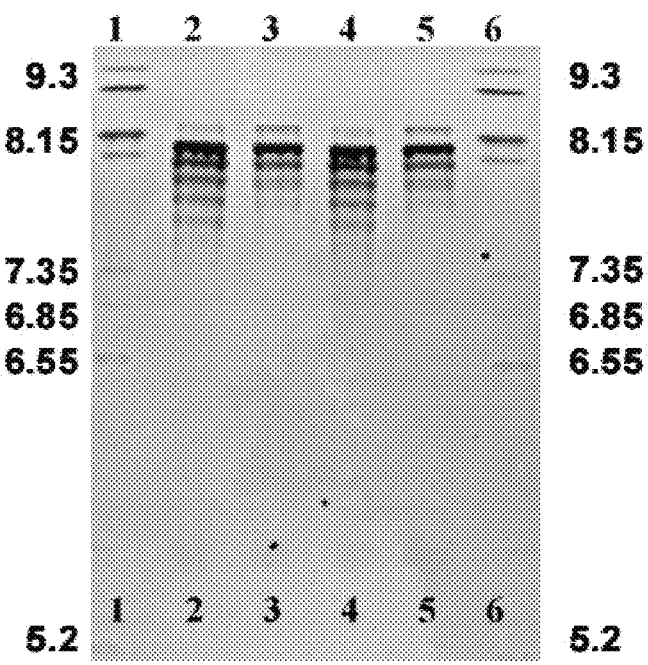
FIG. 11 is a picture of a gel showing the results of isoelectric focusing to determine the pI (isoelectric point) of the Lead CXCR5 Antibody. Lanes 1,6: IEF Calibration High Range pI Kit; Lanes 2,4: Reference Standard Lead Antibody LP08031; and Lanes 3,5: Lead Antibody Drug Substance, RSN0151.

In certain embodiments, the formulations of the invention have a pH at or below the isoelectric point (pI) of the binding agent, such as an antibody. The isoelectric point is the pH at which a particular molecule or surface carries no net electrical charge. The pI of an anti-LIGHT or an anti-CXCR5 binding agent may be determined by any means known to those of skill in the art. In some embodiments, the pI of an anti-LIGHT or anti-CXCR5 antibody is determined by denatured isoelectric focusing. As shown in FIG. 1, the pI of a fully human IgG4 anti-LIGHT antibody comprising a heavy chain comprising the amino acid sequence of SEQ ID NO: 7 and a light chain comprising the amino acid sequence of SEQ ID NO: 8 is 6.8-7.2. As shown in FIG. 11, the pI of a humanized IgG4 anti-CXCR5 antibody comprising a heavy chain comprising the amino acid sequence of SEQ ID NO: 25 and a light chain comprising the amino acid sequence of SEQ ID NO: 26 is 7.6-8.4.

iv. Surfactants

The formulations of the invention may, optionally, further comprise a surfactant, which is also known as a stabilizing agent. Surfactants/stabilizing agents are chemical compounds that interact and stabilize biological molecules and/or general pharmaceutical excipients in a formulation. In certain embodiments, surfactants may be used in conjunction with lower temperature storage. Surfactants generally protect the binding agent from air/solution interface induced stresses and solution/surface induced stresses, which may otherwise result in protein aggregation. Surfactants may include, but are not limited to, polysorbates, glycerin, dicarboxylic acids, oxalic acid, succinic acid, fumaric acids, phthalic acids, and combinations thereof. Those skilled in the art are aware that other surfactants, e.g. non-ionic or ionic detergents, can be used as long as they are pharmaceutically acceptable, i.e. suitable for administration to subjects. The surfactant is, in some embodiments, a polysorbate. Examples of polysorbates include polysorbate 20, polysorbate 40, polysorbate 60, polysorbate 65, and polysorbate 80.

In exemplary embodiments, the surfactant is present in the formulations in an amount from about 0.001% to about 0.1% (w/v). For example, the surfactant may be present in the formulations in an amount of about 0.001% (w/v), about 0.002% (w/v), about 0.003% (w/v), about 0.004% (w/v), about 0.005% (w/v), about 0.006% (w/v), about 0.007% (w/v), about 0.008% (w/v), about 0.009% (w/v), about 0.01% (w/v), about 0.02% (w/v), about 0.03% (w/v), about 0.04% (w/v), about 0.05% (w/v), about 0.06% (w/v), about 0.07% (w/v), about 0.08% (w/v), about 0.09% (w/v), and about 0.1% (w/v). In particular embodiments, the surfactant is present in the formulations from about 0.003% to about 0.05% (w/v), about 0.004% to about 0.025% (w/v), or about 0.005% to about 0.02% (w/v), e.g. about 0.005% (w/v). For example, polysorbate 20 may be present in an amount from about 0.001% to about 0.1% (w/v), about 0.002% to about 0.01% (w/v), about 0.003% to about 0.008% (w/v), and about 0.004% to about 0.006% (w/v), e.g., about 0.005% (w/v). In alternative embodiments, polysorbate 20 is present in an amount from about 0.001% to about 0.1% (w/v), about 0.005% to about 0.05% (w/v), and about 0.0075% to about 0.025% (w/v), e.g., about 0.01% (w/v). In further alternative embodiments, polysorbate 20 is present in an amount from about 0.001% to about 0.1% (w/v), about 0.005% to about 0.05% (w/v), and about 0.01% to about 0.03% (w/v), e.g., about 0.02% (w/v).

v. Tonicity Agents

The formulations of the invention may, optionally, further comprise a tonicity agent. Typically, tonicity agents are used to adjust or maintain the osmolality of the formulations in order to bring it closer to the osmotic pressure of body fluids, such as blood or plasma. Tonicity agents may also maintain the binding agent levels in a formulation. In part, the tonicity agent contributes to preserving the level, ratio, or proportion of the therapeutically active binding agent present in the formulation. As used herein, the term "tonicity" refers to the behavior of biologic components in a fluid environment or solution. Isotonic solutions possess the same osmotic pressure as blood plasma, and can be intravenously infused into a subject without changing the osmotic pressure of the subject's blood plasma. Indeed, in certain embodiments of the invention, the tonicity agent is present in an amount sufficient to render the formulation suitable for intravenous infusion. Often, the tonicity agent serves as a bulking agent or a stabilizing agent as well. As such, the tonicity agent may allow the binding agent to overcome various stresses, such as freezing and shear. Tonicity agents may include, but are not limited to, saccharides, sugars, glycerol, sorbitol, mannitol, sodium chloride, potassium chloride, magnesium chloride, and other inorganic salts. Those skilled in the art are aware that other tonicity agents can be used as long as they are pharmaceutically acceptable, i.e. suitable for administration to subjects.

In certain embodiments, the tonicity agent is present in the formulations in an amount from about 0.1% to 10% (w/v). For example, the tonicity agent may be present in the formulation in an amount of about 0.1% (w/v), about 0.2% (w/v), about 0.3% (w/v), about 0.4% (w/v), about 0.5% (w/v), about 0.6% (w/v), about 0.7% (w/v), about 0.8% (w/v), about 0.9% (w/v), about 1% (w/v), about 2% (w/v), about 3% (w/v), about 4% (w/v), about 4.5% (w/v), about 5% (w/v), about 5.5% (w/v), about 6% (w/v), about 7% (w/v), about 8% (w/v), about 9% (w/v), and about 10% (w/v). Alternatively, the tonicity agent may be present in the formulation in an amount from about 2% to about 8% (w/v), from about 3% to about 7% (w/v), and from about 4% to about 6% (w/v). In further alternative embodiments, the tonicity agent may be present in the formulation in an amount from about 0.1% to about 1%, from about 0.1% to about 0.5%, from about 0.1 to about 0.3%, and about 0.2%.

In certain exemplary embodiments, the tonicity agent is a saccharide. Examples of saccharides include glucose, sucrose (which is also known as saccharose), maltose, trehalose, dextrose, xylitol, fructose and mannitol. For example, mannitol may be present in an amount of about 1% to about 10% (w/v), about 2% to about 8% (w/v), or about 3% to about 5% (w/v), e.g., about 4% (w/v). Alternatively, sucrose (which is also known as saccharose) may be present in an amount of about 1% to about 10% (w/v), about 3% to about 8% (w/v), or about 4% to about 6% (w/v), e.g., about 4.5, 5, 5.5, or 6% (w/v).

In certain other exemplary embodiments, the tonicity agent is sodium chloride. For example, sodium chloride may be present in an amount of about 0.1% (w/v), about 0.2% (w/v), about 0.3% (w/v), about 0.4% (w/v), about 0.5% (w/v), about 0.6% (w/v), about 0.7% (w/v), about 0.8% (w/v), about 0.9% (w/v), and about 1% (w/v). Alternatively, sodium chloride may be present in the formulation in an amount from about 0.1% to about 1%, from about 0.1% to about 0.5%, from about 0.1 to about 0.3%, and about 0.2%.

In further exemplary embodiments, the formulations may comprise one or more tonicity agents. For example, the formulations may comprise one or more of the above tonicity agents in the above concentrations. In certain specific embodiments, the formulations may comprise sucrose and sodium chloride, wherein each of the sucrose and sodium chloride concentrations is between about 0.1% to about 10% (w/v). In some embodiments, the sucrose concentration is about 6% and the sodium chloride concentration is about 0.2%. Alternatively, the sucrose concentration is about 4.5% and the sodium chloride concentration is about 0.2%.

In certain embodiments of the invention, the osmolality of the formulations range from about 200 mOsm/kg to about 350 mOsm/kg, about 270 mOsm/kg to about 330 mOsm/kg, about 280 mOsm/kg to about 320 mOsm/kg, or about 290 mOsm/kg to about 310 mOsm/kg, e.g., about 300 mOsm/kg. In other words, the formulations of the invention are, in some embodiments, substantially isotonic, i.e. having substantially the same osmotic pressure as human blood. Osmolality can be measured by any means known to those of skill in the art, such as using vapor pressure or ice-freezing type osmometers. The osmolality of the formulations of the invention can, for instance, be regulated by the one or more tonicity agents described herein.

vi. Amino Acids

The formulations of the invention may, optionally, further comprise an amino acid. Examples of amino acids include, but are not limited to, glycine, alanine, aspartic acid, lysine, serine, tyrosine, cysteine, glutamine, methionine, arginine, and proline. In exemplary embodiments, the amino acid is present in the formulations in an amount from about 0.1% to 5% (w/v). For example, the amino acid may be present in the formulation in an amount of about 0.1% (w/v), about 0.2% (w/v), about 0.3% (w/v), about 0.4% (w/v), about 0.5% (w/v), about 0.6% (w/v), about 0.7% (w/v), about 0.8% (w/v), about 0.9% (w/v), about 1.0% (w/v), about 1.1% (w/v), about 1.2% (w/v), about 1.3% (w/v), about 1.4% (w/v), about 1.5% (w/v), about 1.6% (w/v), about 1.7% (w/v), about 1.8% (w/v), about 1.9% (w/v), about 2.0% (w/v), about 3% (w/v), about 4% (w/v), and about 5% (w/v). Alternatively, the amino acid is present in the formulation in an amount from about 1.3% to about 1.8% (w/v), or about 1.4% to about 1.6% (w/v), e.g., about 1.5% (w/v). In further alternative embodiments, the amino acid is present in the formulation in an amount from about 0.5% to about 1.5% (w/v), or about 0.8% to about 1.2% (w/v), e.g., about 1.0% (w/v). An exemplary amino acid is proline or arginine. For example, proline may be present in the formulation in an amount from about 1% to about 2%, (w/v) about 1.3% to about 1.8% (w/v), about 1.4% to about 1.6% (w/v), e.g., about 1.5% (w/v). Alternatively, arginine may be present in the formulation in an amount from about 0.5% to about 1.5% (w/v), or about 0.8% to about 1.2% (w/v), e.g., about 1.0% (w/v).

vii. Other Excipients

Furthermore, the formulations of the invention may comprise other excipients including, but not limited to, water for injection, diluents, solubilizing agents, soothing agents, additional buffers, inorganic or organic salts, antioxidants, or the like. In some embodiments, however, the formulations of the invention comprise no other excipients, except those described above. Other pharmaceutically acceptable carriers, excipients, or stabilizers, such as those described in Remington's Pharmaceutical Sciences $16^{th}$ edition, Osol, A.

Ed. (1980) may be included in the formulation provided that they do not adversely affect the desired characteristics of the formulation. In a particular embodiment, the formulation is substantially free of preservatives, although, in alternative embodiments, preservatives may be added as necessary. For example, cryoprotectants or lyoprotectants may be included in lyophilized formulations.

viii. Liquid or Lyophilized Formulations

The formulations of the invention may either be liquid formulations or lyophilized formulations. In some embodiments, the formulations are liquid formulations. In some embodiments, the liquid formulations are ready for injection. Alternatively, the formulations may be lyophilized powders. In some embodiments, the lyophilized powders are ready to be combined with a solvent just prior to administration.

ix. Exemplary Formulations

In one exemplary embodiment of the invention, the invention provides a stable liquid antibody formulation suitable for subcutaneous administration, the formulation comprising:

a) greater than about 80 mg/ml, e.g., about 150 mg/ml, of a fully human IgG4 anti-LIGHT (lymphotoxin-like, exhibits inducible expression and competes with HSV glycoprotein D for HVEM, a receptor expressed by T lymphocytes) antibody comprising a heavy chain comprising the amino acid sequence of SEQ ID NO: 7 and a light chain comprising the amino acid sequence of SEQ ID NO: 8;

b) about 10 mM citrate buffer;
c) about 0.005% (w/v) polysorbate 20; and
d) about 4% (w/v) mannitol;
wherein the pH of the formulation is about pH 5.5

In certain exemplary embodiments, this formulation may be manufactured by:

a) dissolving about 10 mM sodium citrate dihydrate in water for injection and adjusting the pH of the buffered solution to about pH 5.5, e.g., using either hydrochloric acid or sodium hydroxide;

b) adding greater than about 80 mg/ml, e.g., about 150 mg/ml, of a fully human IgG4 anti-LIGHT (lymphotoxin-like, exhibits inducible expression and competes with HSV glycoprotein D for HVEM, a receptor expressed by T lymphocytes) antibody comprising a heavy chain comprising the amino acid sequence of SEQ ID NO: 7 and a light chain comprising the amino acid sequence of SEQ ID NO: 8, about 4% (w/v) mannitol, and 0.005% (w/v) polysorbate 20 to the buffered solution from step a) while stirring in a vessel made of inert material until completely dissolved, and then adjusting the pH of the resulting formulation to about pH 5.5 using either hydrochloric acid or sodium hydroxide, and then adding buffered solution from step a) to adjust the final weight of the resulting formulation;

c) filtering the formulation from step b) under aseptic conditions using a sterilized, compatible membrane filter having a nominal pore size of 0.2 μM, and then sterilizing the formulation by filtration under aseptic conditions into sterilized containers made out of inert material using a sterilized, compatible membrane filter having a nominal pore size of 0.2 μM;

d) filling the formulation from step c) under aseptic conditions into sterilized vials that are closed with stoppers and flip-off caps with a flange; and, optionally, e) inspecting the containers from step d) for coarse contaminants, intact sealing, and visible particles.

In another exemplary embodiment of the invention, the invention provides a stable liquid antibody formulation suitable for intravenous administration, the formulation comprising:

a) about 5 to about 80 mg/mL, e.g., about 50 mg/mL, of a fully human IgG4 anti-LIGHT (lymphotoxin-like, exhibits inducible expression and competes with HSV glycoprotein D for HVEM, a receptor expressed by T lymphocytes) antibody comprising a heavy chain comprising the amino acid sequence of SEQ ID NO: 7 and a light chain comprising the amino acid sequence of SEQ ID NO: 8;

b) about 10 mM citrate buffer; and
c) about 0.01% (w/v) polysorbate 20;
wherein the pH of the formulation is about pH 5.5.

In an alternative exemplary embodiment of the invention, the invention provides a stable lyophilized antibody formulation suitable for intravenous administration, the formulation comprising:

a) about 5 to about 80 mg/mL, e.g., about 50 mg/mL, of a fully human IgG4 anti-LIGHT (lymphotoxin-like, exhibits inducible expression and competes with HSV glycoprotein D for HVEM, a receptor expressed by T lymphocytes) antibody comprising a heavy chain comprising the amino acid sequence of SEQ ID NO: 7 and a light chain comprising the amino acid sequence of SEQ ID NO: 8;

b) about 10 mM citrate buffer;
c) about 0.01% (w/v) polysorbate 20;
d) about 5% (w/v) sucrose; and
e) about 1.5% (w/v) proline;
wherein the pH of the formulation is about pH 5.5.

In an exemplary embodiment of the invention, the invention provides a stable antibody formulation comprising:

a) about 20 mg/mL of a humanized IgG4 anti-CXCR5 (C-X-C chemokine receptor type 5) antibody comprising a heavy chain comprising the amino acid sequence of SEQ ID NO: 25 and a light chain comprising the amino acid sequence of SEQ ID NO: 26;

b) about 10 mM citrate buffer;
c) about 0.02% polysorbate 20;
d) about 6% sucrose; and
e) about 0.2% sodium chloride;
wherein the pH of the formulation is about pH 6.0.

In an alternative exemplary embodiment of the invention, the invention provides a stable antibody formulation comprising:

a) about 100 mg/mL of a humanized IgG4 anti-CXCR5 (C-X-C chemokine receptor type 5) antibody comprising a heavy chain comprising the amino acid sequence of SEQ ID NO: 25 and a light chain comprising the amino acid sequence of SEQ ID NO: 26;

b) about 10 mM citrate buffer;
c) about 0.01% polysorbate 20;
d) about 4.5% sucrose;
e) about 0.2% sodium chloride; and
f) about 1% arginine;
wherein the pH of the formulation is about pH 6.0.

x. Stability

The formulations of the invention are stable at 5° C. for at least about 1, 2, 3, 4, 5, 6, 7, 8, 9, 10, 11 or 12 months or more, and typically at least about 12, 18 or 24 months or more. In exemplary embodiments, they are stable at 5° C. for at least about 6 months or more. In other exemplary embodiments, they are stable at 5° C. for at least about 9 months. In further exemplary embodiments, they are stable at 5° C. for at least about 1 year or more, and typically about 2 years.

C. Modes of Administration

In certain embodiments of the invention, the formulations are suitable for administration parenterally, intravenously, intramuscularly, intradermally, subcutaneously, or a combination thereof. The formulations of the invention are suitable for delivery by a variety of techniques.

In some embodiments of the invention, the formulation is administered intravenously. For example, it is desirable that formulations containing 80 mg/mL of IgG4 binding agent, such as an antibody, or less administered intravenously. Therefore, the formulations are typically sterile. Methods for making formulations sterile are well known in the art and include, for example, filtration through sterile filtration membranes or autoclaving the ingredients of the formulation, with the exception of the antibodies, at about 120° C. for about 30 minutes. For example, the invention provides a stable liquid antibody formulation suitable for intravenous administration, the formulation comprising: a) about 5 to about 80 mg/mL, e.g., about 50 mg/mL, of a fully human IgG4 anti-LIGHT (lymphotoxin-like, exhibits inducible expression and competes with HSV glycoprotein D for HVEM, a receptor expressed by T lymphocytes) antibody comprising a heavy chain comprising the amino acid sequence of SEQ ID NO: 7 and a light chain comprising the amino acid sequence of SEQ ID NO: 8; b) about 10 mM citrate buffer; and c) about 0.01% (w/v) polysorbate 20; wherein the pH of the formulation is about pH 5.5. Alternatively, the invention provides a stable antibody formulation comprising: a) about 20 mg/mL of a humanized IgG4 anti-CXCR5 (C-X-C chemokine receptor type 5) antibody comprising a heavy chain comprising the amino acid sequence of SEQ ID NO: 25 and a light chain comprising the amino acid sequence of SEQ ID NO: 26; b) about 10 mM citrate buffer; c) about 0.02% polysorbate 20; d) about 6% sucrose; and e) about 0.2% sodium chloride; wherein the pH of the formulation is about pH 6.0.

In some embodiments of the invention, the formulation is administered subcutaneously. For example, it is desirable that formulations containing more than 80 mg/mL of IgG4 binding agent, such as an antibody, are administered subcutaneously. In a specific embodiment, it is desirable to administer subcutaneously to subjects a stable liquid antibody formulation comprising: a) about 150 mg/mL of a fully human IgG4 anti-LIGHT (lymphotoxin-like, exhibits inducible expression and competes with HSV glycoprotein D for HVEM, a receptor expressed by T lymphocytes) antibody comprising a heavy chain comprising the amino acid sequence of SEQ ID NO: 7 and a light chain comprising the amino acid sequence of SEQ ID NO: 8; b) about 10 mM citrate buffer; c) about 0.005% (w/v) polysorbate 20; d) about 4% (w/v) mannitol; and wherein the pH of the formulation is about pH 5.5. Alternatively, the invention provides a stable antibody formulation comprising: a) about 100 mg/mL of a humanized IgG4 anti-CXCR5 (C-X-C chemokine receptor type 5) antibody comprising a heavy chain comprising the amino acid sequence of SEQ ID NO: 25 and a light chain comprising the amino acid sequence of SEQ ID NO: 26; b) about 10 mM citrate buffer; c) about 0.01% polysorbate 20; d) about 4.5% sucrose; e) about 0.2% sodium chloride; and f) about 1% arginine; wherein the pH of the formulation is about pH 6.0.

D. Dosages and Dosage Forms

Effective doses of the formulations of the invention vary depending upon many different factors, including means of administration, target site, physiological state of the subject, whether the subject is human or an animal, other medications administered, and whether treatment is prophylactic or therapeutic. Usually, the subject is a human, but non-human mammals including transgenic mammals can also be treated. Treatment dosages may need to be titrated to optimize safety and efficacy.

The formulations of the invention may be administered on multiple occasions. Intervals between single dosages can be daily, weekly, biweekly, monthly or yearly. Intervals can also be irregular. In some methods, the dosage is adjusted to achieve a certain plasma binding agent, such as an antibody, concentration. Dosage and frequency will vary depending on the half-life of the anti-LIGHT or anti-CXCR5 binding agent, such as an antibody, in the subject. In general, human antibodies show the longest half-life, followed by humanized antibodies, chimeric antibodies, and nonhuman antibodies.

In further embodiments, the invention provides a pharmaceutical unit dosage form comprising a therapeutically effective amount of a formulation of the invention for the treatment of one or more diseases in a subject through administration of the dosage form to the subject. In some embodiments, the subject is a human. The human may be an adult or may be an infant. The term "pharmaceutical unit dosage form" refers to a physically discrete unit suitable as unitary dosages for the subjects to be treated, each unit containing a predetermined quantity of active compound calculated to produce the desired therapeutic/prophylactic effect in association with the required citrate buffer and pH.

The unit dosage form may be a container comprising the formulation. Suitable containers include, but are not limited to, sealed ampoules, vials, bottles, syringes, and test tubes. The containers may be formed from a variety of materials, such as glass or plastic, and may have a sterile access port (for example, the container may be a vial having a stopper pierceable by a hypodermic injection needle). In some embodiments, the container is a vial. Generally, the container should maintain the sterility and stability of the formulation.

In specific embodiments, the formulations are packaged in 2 mL vials that are made of clear, colorless type I glass, and closed with a stopper (fluoropolymer-coated bromobutyl) sealed with flip-of caps with flange (polypropylene). The vials are, in some embodiments, filled with 1.2 mL of the formulations so that the vial has an overfill volume of about 0.2 mL per vial, and an extractable volume of 1.0 mL. For example, this means that the dosage strength of anti-LIGHT antibody (e.g., 150 mg/mL) will be contained within 1 mL of solution.

In specific embodiment, the formulations are secondarily packaged in a container, such as a cardboard box, that protects the vials from light.

E. Methods of Treatment

Further provided herein are methods for treating a LIGHT-mediated disease or disorder, the methods comprising administering a formulation of the invention to a subject. The invention further relates to a formulation of the invention for use in a herein-described method for treating a LIGHT-mediated disease or disorder. In certain embodiments, the LIGHT-mediated disease is a chronic bowel disease, or an inflammatory bowel disease (IBD), such as Crohn's disease (CD) or ulcerative colitis (UC). In other embodiments, the LIGHT mediated disease is graft-versus-host disease (GVHD).

Also provided herein are methods for treating a CXCR5-mediated disease or disorder, the methods comprising administering a formulation of the invention to a subject. The invention further relates to a formulation of the invention for use in a herein-described method for treating a CXCR-5 mediated disease or disorder. In certain embodiments, the anti-CXCR5 binding agent is used for reduction of signs and symptoms, inhibition of progression of structural damage, induction of a major clinical response, and prevention of disability in adult patients with moderately to severely active Rheumatoid Arthritis (RA) who have had inadequate response to one or more Disease-Modifying Anti-Rheumatic Drugs (DMARDs), such as methotrexate (MTX), or TNFα antagonists. The anti-CXCR5 binding agent may be used in combination with DMARDs or anti-TNFα agonists.

In certain embodiments, the formulations of the invention can be administered in combination with one or more therapies (e.g., therapies that are not the formulations of the invention that are currently administered to prevent, treat, manage, and/or ameliorate a LIGHT-mediated disease or a CXCR5-mediated disease. The use of the term "in combination" does not restrict the order in which therapies are administered to a subject. A first therapy can be administered before (e.g., 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks), concurrently, or after (e.g., 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks) the administration of a second therapy to a subject that had, has, or is susceptible to a LIGHT-mediated disease or a CXCR5-mediated disease. Any additional therapy can be administered in any order with the other additional therapies. Non-limiting examples of therapies that can be administered in combination with an antibody of the invention include approved anti-inflammatory agents listed in the U.S. Pharmacopoeia and/or Physician's Desk Reference.

F. Kits

Certain embodiments of the invention include a kit comprising a formulation of the invention. The kit may further comprise one or more containers comprising pharmaceutically acceptable excipients, and include other materials desirable from a commercial and user standpoint, including filters, needles and syringes. Associated with the kits can be instructions customarily included in commercial packages of therapeutic, prophylactic or diagnostic products, that contain information about, for example, the indications, usage, dosage, manufacture, administration, contra-indications, and/or warnings concerning the use of such therapeutic, prophylactic or diagnostic products. The kit can also be associated with a label that can be any kind of data carrier (e.g., a leaflet, sticker, chip, print or bar code) comprising information. In certain embodiments, the instructions etc. as listed above can be comprised in or on the label. The kit can further comprise a device for administration of the formulation, and particularly a device that contains the formulation, i.e., a pre-filled device such as, but not limited to, a pre-filled syringe or a pre-filled autoinjector. The kit can also comprise a container comprising the formulation, i.e., a pre-filled container, such as a pre-filled vial, cartouche, sachet, or ampoule.

G. Combination of Different Embodiments

In the context of the present invention, any of the herein described embodiments can be combined with one or more of the other herein described embodiments unless explicitly stated to the contrary. Particularly, any of the herein described binding agents and antibodies and the herein described formulations thereof can be used in combination with any of the kits, pre-filled devices or pre-filled containers, or can be used in the methods of treatment or medical uses as described herein in connection with the respective antibody (e.g., the stable formulations comprising the anti-LIGHT antibodies or anti-CXCR5 antibodies can be combined with any of the herein described kits, containers or devices). Any of the herein described binding agents specifically binding an antigen (e.g., a binding agent specifically binding LIGHT or a binding agent specifically binding CXCR5) can also be used in any of the methods of treatment that are described herein in connection with the respective antibodies (i.e., anti-LIGHT or anti-CXCR5) and vice versa.

EXAMPLES

To help illustrate the invention, the following examples are provided. The examples are not intended to limit the scope of the invention in any way. In general, the practice of the present invention employs, unless otherwise indicated, conventional techniques of pharmaceutical formulation, chemistry, molecular biology, recombinant DNA technology, immunology such as antibody technology, and standard techniques of polypeptide preparation as described, for example, in Sambrook, Fritsch and Maniatis, Molecular Cloning: Cold Spring Harbor Laboratory Press (1989); Antibody Engineering Protocols (Methods in Molecular Biology), volume 51, Ed.: Paul S., Humana Press (1996); Antibody Engineering: A Practical Approach (Practical Approach Series, 169), Eds.: McCafferty J. et al., Humana Press (1996); Antibodies: A Laboratory Manual, Harlow and Lane, Cold Spring Harbor Laboratory Press (1999); and Current Protocols in Molecular Biology, Eds. Ausubel et al., John Wiley & Sons (1992).

Anti-LIGHT

A fully human IgG4 anti-LIGHT antibody comprising a heavy chain comprising the amino acid sequence of SEQ ID NO: 7 and a light chain comprising the amino acid sequence of SEQ ID NO: 8 (the "Lead LIGHT Antibody") was used in Examples 1-9 in order to determine optimal formulation conditions.

Materials

Drug Substance Batch

The Lead Antibody, formulated in phosphate buffered saline (PBS) at a concentration of 5.5 mg/mL and at a pH of 7.3 (the "Original Formulation", "PBS Formulation", or "Reference Lot"), was used in the following examples.

Excipients

Table 1 shows the excipients that were used in the following examples, which were chosen according to their acceptability/suitability for use in parenteral products.

TABLE 1

| Excipients used in this study | | |
|---|---|---|
| Excipients | Art. No./Charge | Supplier |
| Arginine | 1.01587 | Merck |
| Citric acid | 100241 | Merck |
| HCl | 114027 | Merck |
| Sodium acetate | 1.06265 | Merck |
| Sodium chloride | 10158 | Riedel de Haen |
| Sodium hydroxide | 114076 | Merck |
| Sodium citrate | 114196 | Boehringer Ingelheim KG |

TABLE 1-continued

Excipients used in this study

| Excipients | Art. No./Charge | Supplier |
|---|---|---|
| Polysorbate 20 | 139850 | Fluka |
| Trehalose-dihydrat | T9531 | Sigma-Aldrich |

Methods

The following methods were used to manufacture the experimental formulations and the formulations of the invention containing the Lead LIGHT Antibody.

Manufacturing & Composition of Buffers

All buffers were manufactured under stirring to dissolve the respective excipients. pH was adjusted using 0.1 M HCl or 0.1 M NaOH. The general concentration of all buffers was 10 mM.

Manufacturing & Composition of Excipient Stock Solutions

All stock solutions were manufactured under stirring to dissolve the excipients. Concentration was given as weight/weight (w/w).

Sterile Filtration of Samples

All samples, solutions, buffers, etc. were sterile filtered (0.22 µm) using a Sartopore-2 membrane. The samples were filtered into sterilized bottles or vials and closed under aseptic conditions inside a clean-bench to prevent microbiological contamination.

Mechanical Stress Test

Mechanical stress with an agitation speed of 350/minute for 2.5 hours at room temperature was performed using a horizontal laboratory shaker with a 26 mm distance (shaker & incubation hood from Bühler Company). 2R vials were filled with 1 mL solution with a head space of about 2.5 mL. The mechanical stress test was planned and performed during the first pre-formulation studies and during relevant studies for surfactant selection.

Thermal Stress Test

Thermal stress was used as a stress test during all steps of the pre-formulation program. The samples were stored at +40° C. for either 24 hours or 7 days, depending on the study.

Analytical Methods in Formulation Fill and Finish

The following analytical methods were used in the formulation fill and finish in the following examples.

Appearance

Appearance of the antibody solutions were checked visually, and additionally documented by taking a picture with a digital camera.

pH

All pH measurements were performed using a pH-meter with a micro-electrode.

Concentration Using UV

The protein concentrations of all antibody solutions were measured against buffer using a NanoDrop ND1000. Proteins concentrations near or below 5 mg/mL were diluted 1:3, while higher protein concentrations near 20 mg/mL were diluted 1:20, and the absorption was measured at 215 nm and 280 nm.

Dynamic Light Scattering (DLS)

The hydrodynamic diameter of the molecule was measured using laser light scattering. The samples were sterile filtered prior to the analytics if turbidity was observed, thus only soluble aggregates could be detected.

Differential Scanning Calorimetry (DSC)

Aliquots of most pre-formulation samples were examined by DSC using a VPCapillary DSC from Microcal and scanned in the autosampling instrument at 90° C./hour with a filter time of 2 seconds. 400 µl samples were placed into 96-well plates and analyzed for the unfolding temperature Tm.

Osmolarity

Osmolarity was measured using an automated Knaur Osmometer.

Density

Density of the formulations was measured using a falling sphere viscosimeter DMA4500 Anton Paar.

Analytical Methods in Bioanalytics FF

The following analytical methods were used in the bioanalytics fill and finish in the following examples.

Size Exclusion Chromatography (SEC)

Aggregates, as well as degradation products of the Lead Antibody, were quantified using size exclusion GL chromatography. The test was carried out by isocratic HPLC with a SUPERDEX 200 10/300 column.

SDS-PAGE, Reducing and Non-Reducing

Sodium dodecyl sulfate polyacrylamide gel electrophoresis (SDS-PAGE) was used to analyze the molecular integrity (e.g., half molecules) and the purity. This electrophoretic analysis was performed with 4-12% gradient gels under reducing and non-reducing conditions. The proteins were visualized with Coomassie staining after electrophoretic separation.

Weak Cation Exchange (WCX)

Weak cation exchange chromatography was used to monitor the charge heterogeneity of the antibody. The percentages of basic, neutral, and acidic isoforms were reported. The test was carried out by discontinuous high performance liquid chromatography (HPLC) with a ProPac WCX10 column.

Antigen-Enzyme Linked Immunosorbent Assay (Antigen-ELISA)

Antigen-ELISA was performed to determine the functionality of the antibody. The binding properties to native LIGHT protein were monitored in comparison to the current standard of the antibody. This potency was reported as the relative $EC_{50}$.

Isoelectric Focusing (IEF)

IEF was performed. The isoelectric pattern was specific for the Lead Antibody and served as an identification test. Degradation could be seen by a different charge pattern.

Storage

All buffer solutions, excipient solutions, and samples were stored at 5° C. (±3° C.), if not otherwise mentioned.

Summary of all Formulations Prepared & Analyzed

Table 2 below shows a summary of all of the formulations that were prepared and analyzed in the following examples. Each of the formulations contained the Lead LIGHT Antibody at the concentration listed.

TABLE 2

Summary of all formulations prepared and analyzed

| Sample number | Buffer | pH | Concentration | Comment |
|---|---|---|---|---|
| Formulation 1.1 | Citrate 10 mM | 5.0 | 5.5 mg/mL | |
| Formulation 1.2 | Citrate 10 mM | 5.5 | 5.5 mg/mL | |
| Formulation 1.3 | Citrate 10 mM | 6.0 | 5.5 mg/mL | |
| Formulation 2 | PBS | 7.3 | <80 5 mg/mLmg/mL | Very |
| | Citrate 10 mM | 5.0 | | turbid |

TABLE 2-continued

Summary of all formulations prepared and analyzed

| Sample number | Buffer | pH | Concentration | Comment |
|---|---|---|---|---|
| Formulation 3.1 | PS20 0.01% Citrate 10 mM | 5.5 | 5 mg/mL | |
| Formulation 3.2 | PS20 0.01% Citrate 10 mM | 5.5 | 5 mg/mL | |
| Formulation 4 | PS20 0.01% Citrate 10 mM | 5.0 | 80 mg/mL | clear |
| Formulation 5 | PS20 0.01% Citrate 10 mM PS20 0.01% Proline 1.5% | 5.5 | 5 mg/mL | |
| Formulation 6.1 | Sucrose 5% Citrate 10 mM PS20 0.01% | 5.5 | 50 mg/mL | Lyo |
| Formulation 6.2 | Sucrose 5% | | 50 mg/mL | Lyo |
| Formulation 7 | Histidine 10 mM Histidine 10 mM | 5.5 5.5 | 50 mg/mL | |
| Formulation 8 | PS20 0.01% | | 50 mg/mL | |
| Formulation 9 | Citrate 10 mM Citrate 10 mM | 5.5 5.5 | 50 mg/mL | |
| Formulation 10 | PS20 0.01% Citrate 10 mM | 5.5 | 50 mg/mL | |
| Formulation 11 | Sucrose 5% | | 50 mg/mL | lyo |
| Formulation 12 | Citrate 10 mM | 7.0 | 5 mg/mL | μDSC |
| Formulation 13 | PBS | 5.0 | 5 mg/mL | μDSC |

Example 1

Characterization of a Phosphate Buffered Saline (PBS) Formulation and Disadvantages Associated Therewith In this example, the Reference Lot was characterized. As stated in the Materials section above, the Reference Lot contains the Lead LIGHT Antibody formulated in phosphate buffered saline (PBS) at a concentration of 5.5 mg/mL and at a pH of 7.3, and produced in research solutions Vitry (BioSCP).

Isoelectric focusing (IEF) was used to determine the isoelectric point (pI) of the Lead Antibody. The pI of the Lead LIGHT Antibody was theoretically calculated as 6.28, and then measured by denatured isoelectric focusing using standard methods known in the art. As shown in FIG. 1, the main bands show that the pI of the Lead LIGHT Antibody was 6.8-7.2.

Figure 2:
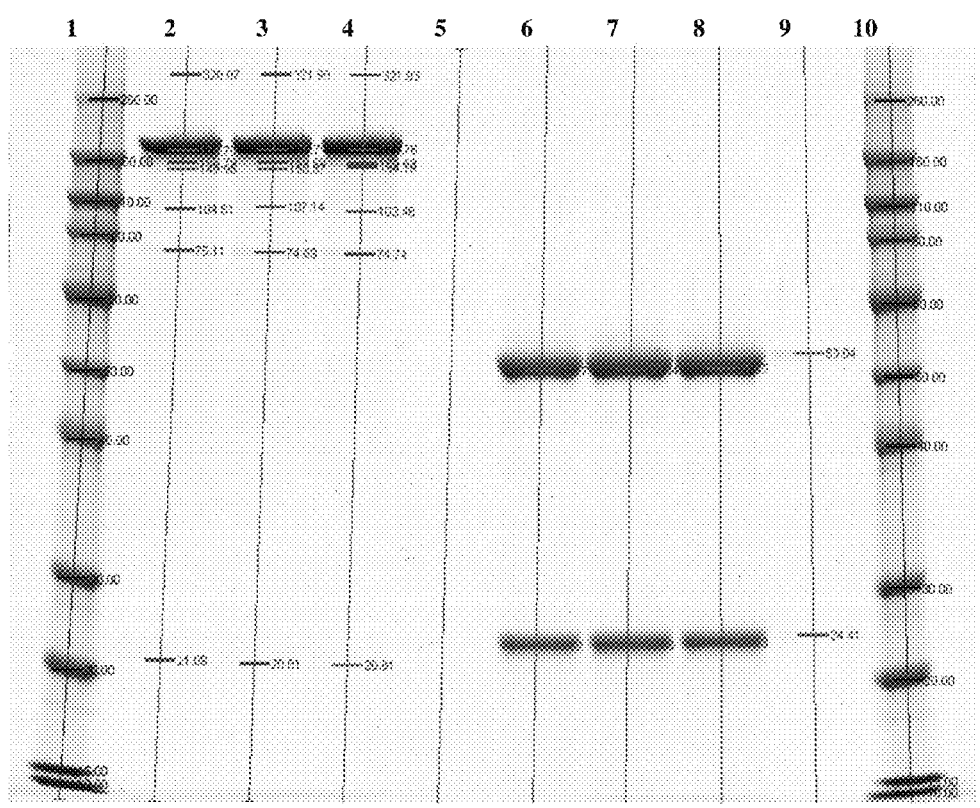
FIG. 2 is a picture of an SDS-PAGE gel that compared different Reference Lot batches under reducing and non-reducing conditions. Lanes 1 & 10: Biorad Precision Plus Protein Standard; lane 5: empty; lane 2: a first batch of Reference Lot under non-reduced conditions; lanes 3 & 4: a second batch of Reference Lot under non-reduced conditions; lane 6: a first batch of Reference Lot under reduced conditions; lanes 7 & 8: a second batch of Reference Lot under reduced conditions; and lane 9: system control. The sizes are indicated by numbers within the rows.
Figure 3:
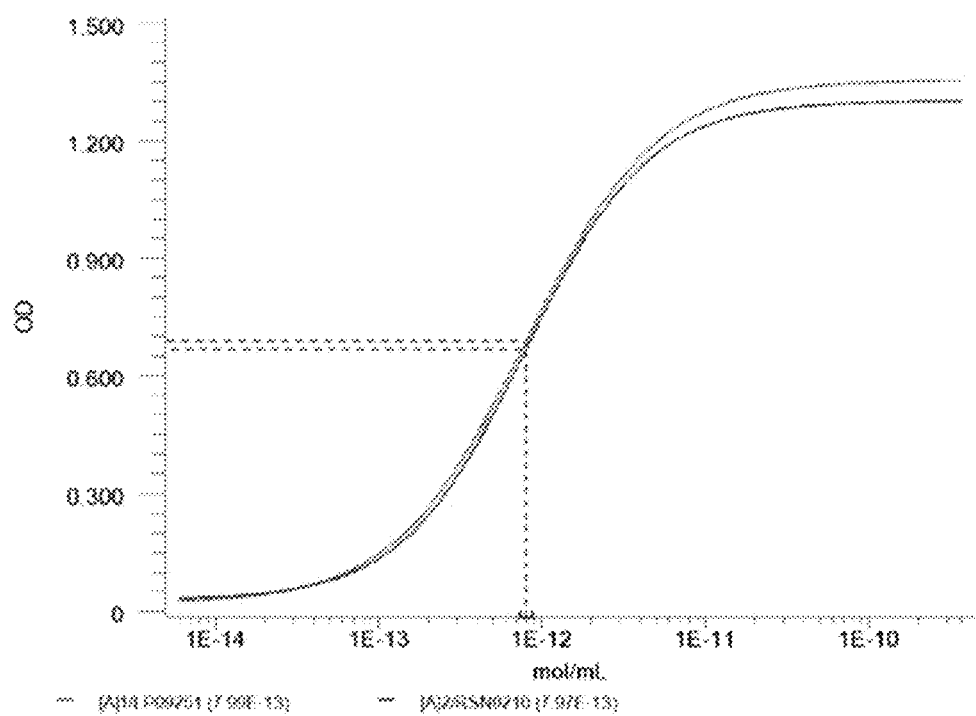
FIG. 3 shows an ELISA graph that was used to determine the antigen binding activity of the first and second batches of Reference Lot.

SDS-PAGE was used to identify the molecular weight of the antibody monomer, potential aggregates, or the presence of half-molecules. FIG. 2 shows an SDS-PAGE gel that compared different Reference Lot batches under reducing and non-reducing conditions. An ELISA was used to determine the antigen binding activity of the Lead LIGHT Antibody. FIG. 3 shows an ELISA graph that was used to determine the antigen binding activity of the first and second batches of Reference Lot.

Figure 4:
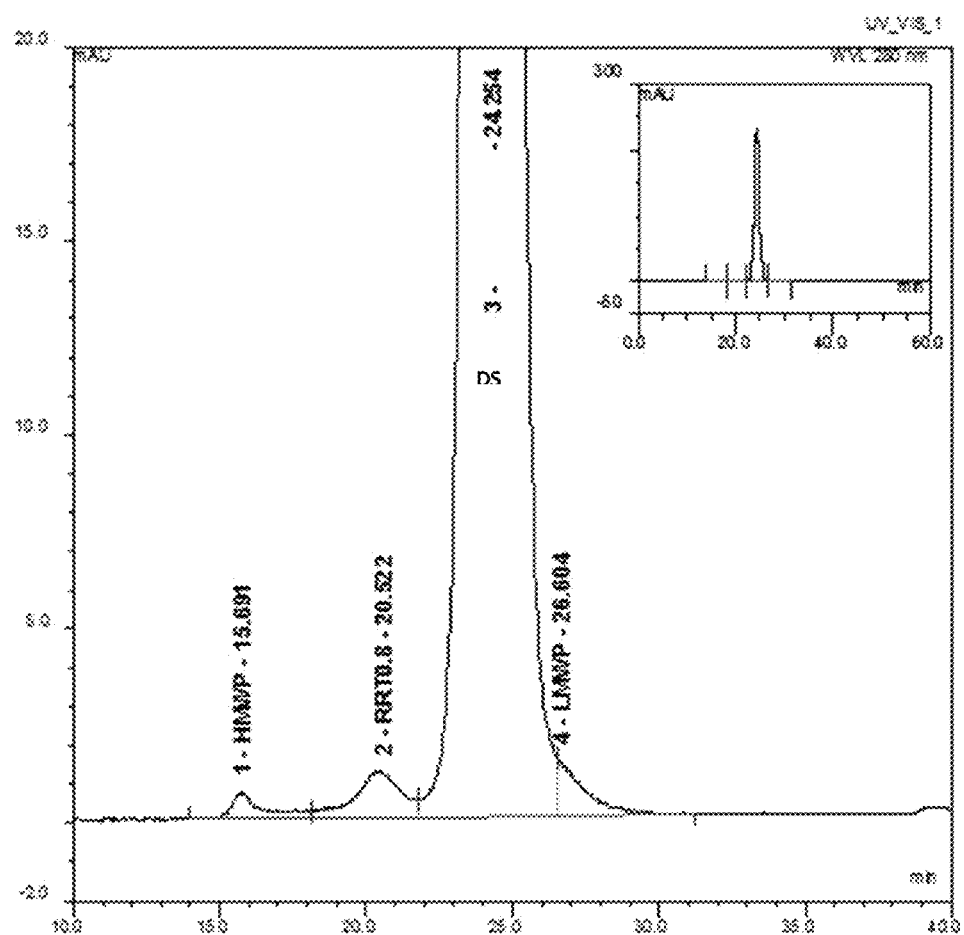
FIG. 4 shows a size exclusion chromatography (SEC) chromatogram of the first batch of Reference Lot.

SEC was used to determine the presence of aggregates, as well as degradation products of the first batch of Reference Lot. As shown in FIG. 4, size exclusion chromatography detected high molecular weight proteins (HMWP), e.g., di-/oligomers (RRT0.8) or aggregates, and low molecular weight proteins (LMWPs) or degradation products. The first batch of Reference Lot had a purity of 97% monomer content.

Figure 5:
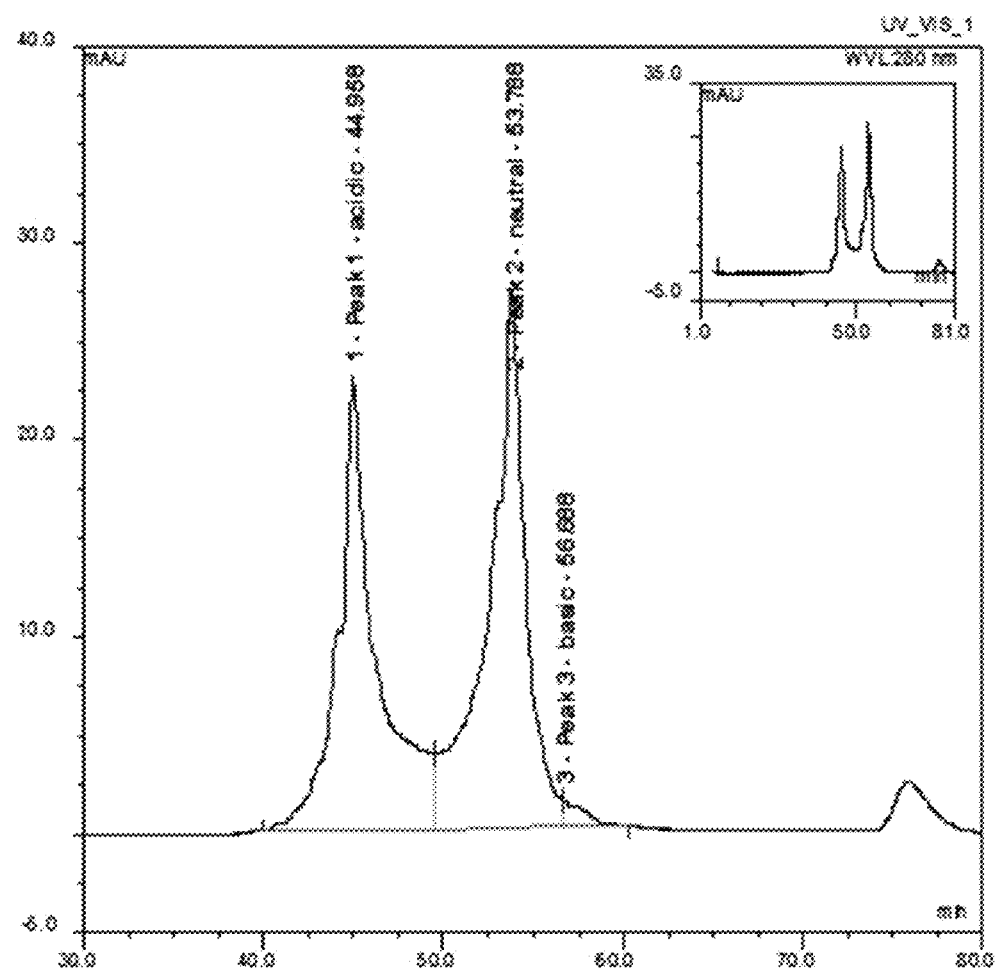
FIG. 5 shows a weak cation exchange chromatogram for the first batch of Reference Lot.

WCX was used to monitor the charge heterogeneity of the first batch of Reference Lot. As shown in FIG. 5, rearrangements of acidic, neutral, and basic isoforms occurred during stability studies. The first batch of Reference Lot had a distribution of acidic/neutral/basic isoforms of 42.3/55.6/1.9%.

Figure 6:
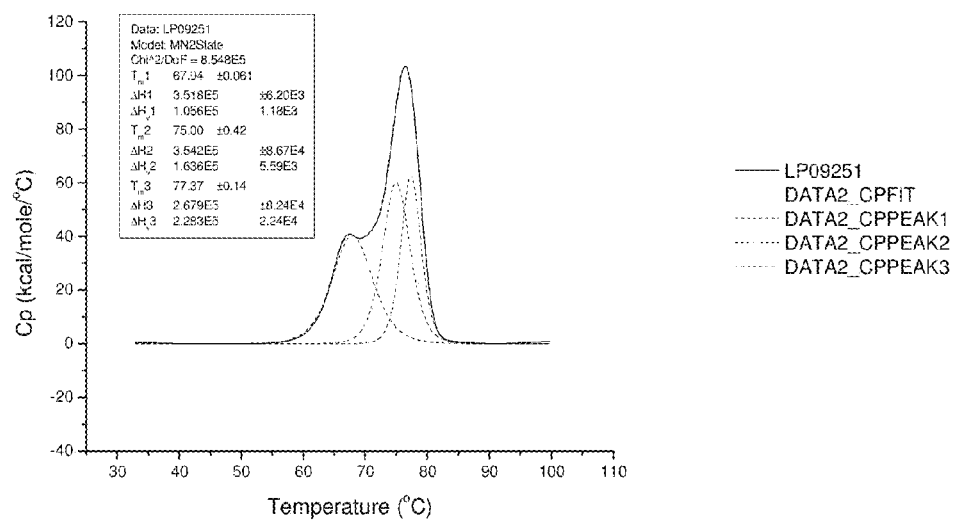
FIG. 6 shows a differential scanning calorimetry thermogram of the first batch of Reference Lot.

DSC was used to analyze the unfolding temperature Tm of the first batch of Reference Lot. As shown in FIG. 6, the three domains of the antibody unfold at 68° C., 75° C., and 78° C.

Figure 7:
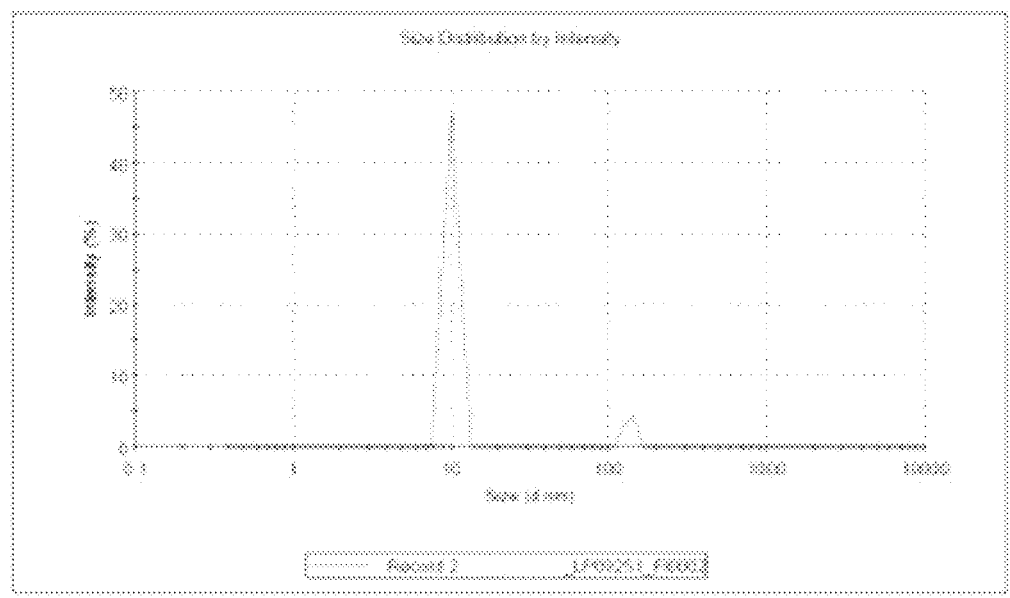
FIG. 7 shows a dynamic light scattering pattern of the first batch of Reference Lot, which was unfiltered. DLS was used to determine the hydrodynamic diameter of the first batch of Reference Lot antibody monomer and potential soluble aggregates.
Figure 8:
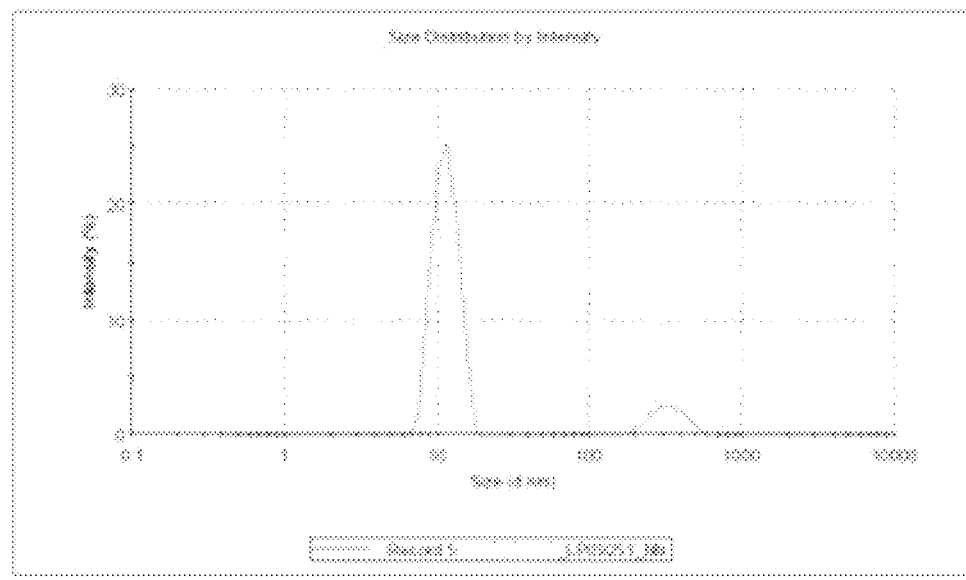
FIG. 8 shows a dynamic light scattering pattern of the first batch of Reference Lot, which was filtered. DLS was used to determine the hydrodynamic diameter of the first batch of Reference Lot antibody monomer and potential soluble aggregates.
Figure 10:
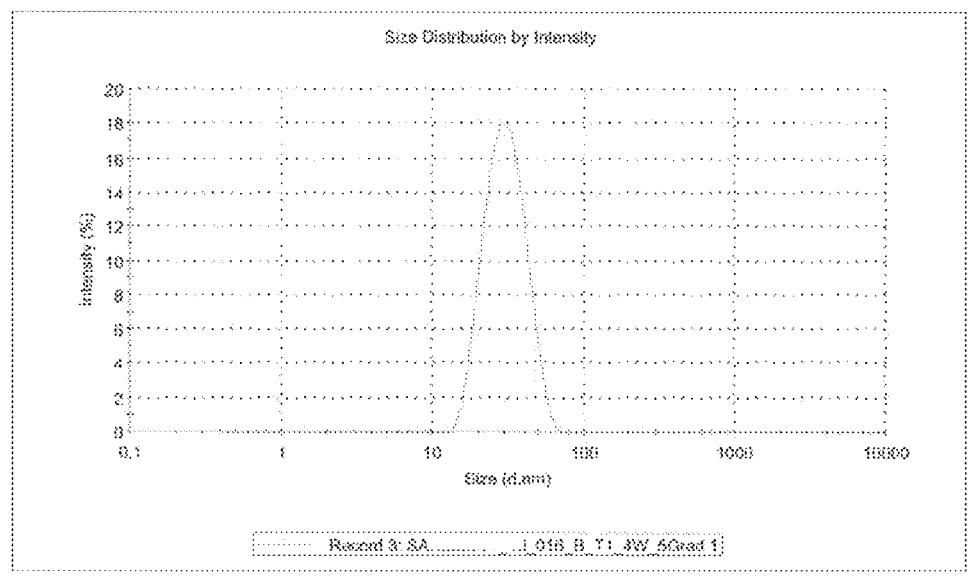
FIG. 10 shows a dynamic light scattering pattern of Formulation 14. DLS was used to determine the hydrodynamic diameter of the antibody monomer and potential soluble aggregates.

DLS was used to determine the hydrodynamic diameter of the antibody monomer and potential soluble aggregates. As shown in FIGS. 7 & 8, a hydrodynamic diameter of about 10 nm was detected, but aggregates were seen in PBS. However, aggregates were not seen in citrate buffer (FIG. 10).

Example 2

Development of Citrate-Buffered Formulations, and Advantages Associated Therewith The original buffer, phosphate buffered saline (PBS) at a pH of 7.3, was, in terms of pH, very close to the isoelectric point (pI) of the Lead Antibody (see Example 1). In addition, the Original Formulation exhibited aggregates; half-molecules; degradation products; low molecular weight proteins (LMWPs); high molecular weight proteins (HMWPs); and rearrangements of acidic, basic, and neutral antibody isoforms (see Example 1). Thus, there was a need for an improved formulation that does not suffer from these disadvantages.

Formulations of the Lead LIGHT Antibody (a fully human IgG4 anti-LIGHT antibody comprising a heavy chain comprising the amino acid sequence of SEQ ID NO: 7 and a light chain comprising the amino acid sequence of SEQ ID NO: 8) containing 10 mM citrate buffer at a pH of 5, 5.5, and 6, with and without polysorbate 20 were tested. Table 3 shows the analytical results of the first batch of Reference Lot, and the various experimental formulations of the Lead LIGHT Antibody formulated into citrate, at a pH of 5.0 and 5.5 and 6.0, with and without polysorbate 20. Aggregates were found in dynamic light scattering (DLS) measurements for the Reference Lot, but not in all other tested formulations. Tm, as measured by differential scanning calorimetry (μDSC), indicated that the higher the pH, the higher the thermodynamic stability could be assumed. But for high antibody concentrated formulations, the pH had to be chosen below the pI of the antibody.

As shown in Table 4, size exclusion chromatography (SEC) data showed a significantly reduced amount of high molecular weight proteins (HMWPs) for the Lead LIGHT Antibody in citrate buffer as compared to the Reference Lot (phosphate buffer at pH 7.3). In contrast, no differences could be detected with SDS-PAGE (Table 5).

TABLE 3

Analytical Results of Formulations

| Sample number | Tm1 [° C.] | Tm2 [° C.] | Tm3 [° C.] | pH | ZAve [nm] | Concentration [mg/mL] | Buffer |
|---|---|---|---|---|---|---|---|
| Reference Lot | 67.94 | 75.00 | 77.37 | 7.3 | 179.85 | 5.5 | PBS |
| Formulation 1.1 | 58.39 | 69.98 | 75.75 | 5.0 | 10.97 | 5.0 | Citrate 10 mM |
| Formulation 1.2 | 62.02 | 72.26 | 76.59 | 5.5 | 10.71 | 5.0 | Citrate 10 mM |
| Formulation 1.3 | 65.46 | 73.74 | 77.02 | 6.0 | 10.81 | 5.0 | Citrate 10 mM |
| Formulation 3.1 | 58.33 | 69.93 | 75.74 | 5.0 | 13.14 | 5.0 | Citrate 10 mM PS20 0.01% |
| Formulation 3.2 | 61.42 | 71.97 | 76.45 | 5.5 | 12.79 | 5.0 | Citrate 10 mM PS20 0.01% | buffer components were optimized for increased concentrations of Lead LIGHT Antibody. Table 6 shows the analytical results of the first batch of high concentration (about 40 mg/ml) antibody formulations: high phosphate buffered saline (PBS) at a pH of 7.3 (Formulation 2) or citrate at a pH of 5.5 with polysorbate 20 (Formulation 4).

TABLE 6

Analytical results of Formulations 2 & 4

| Sample number | Tm1 [° C.] | Tm2 [° C.] | Tm3 [° C.] | pH | ZAve [nm] | Concentration [mg/mL] | Buffer |
|---|---|---|---|---|---|---|---|
| Reference Lot | 67.94 | 75.00 | 77.37 | 7.3 | 10.05 | 5.5 | PBS |
| Formulation 2 | 67.87 | 74.87 | 77.28 | 7.3 | 12.89 | 42.1 | PBS |
| Formulation 4 | 61.55 | 72.00 | 76.48 | 5.5 | 16.71 | 39.97 | Citrate 10 mM PS20 0.01% |

TABLE 4

SEC data of Formulations

| Sample Name | ANTIBODY Area mAU*min | ANTIBODY Rel. Area % | RRT0.8 Area mAU*min | RRT0.8 Rel. Area % | LMWP Area mAU*min | LMWP Rel. Area % | HMWPs Area mAU*min | HMWPs Rel. Area % | Monomer Content [mg/mL] |
|---|---|---|---|---|---|---|---|---|---|
| Ref. Lot | 255.61 | 98.00 | 3.98 | 1.52 | 1.50 | 0.57 | 0.59 | 0.23 | |
| Formulation 3.1 | 223.23 | 98.07 | 3.22 | 1.42 | 1.01 | 0.44 | 0.16 | 0.07 | 45.49 |
| Formulation 3.2 | 257.09 | 98.24 | 3.74 | 1.43 | 0.79 | 0.30 | 0.09 | 0.03 | 48.92 |

TABLE 5

SDS-PAGE data of Formulations

| Sample Name | size kDa | Rel. QTY % | size kDa | Rel. QTY % | size kDa | Rel. QTY % | size kDa | Rel. QTY % | comment |
|---|---|---|---|---|---|---|---|---|---|
| Ref. Lot | 172.5 | 98.4 | 150.1 | 1.4 | 68.4 | 0.2 | | | Additional bands <0.5% |
| Formulation 3.1 | 166.1 | 97.7 | 147.8 | 2 | 71.5 | 0.3 | | | Identical pattern to Ref. Lot |
| Formulation 3.2 | 166.2 | 96.2 | 147.2 | 3.4 | 71.4 | 0.4 | | | Identical pattern to Ref. Lot |

Example 3

Development of High-Concentration Antibody Formulations

In view of the improvements provided by the Citrate-Buffered Antibody Formulation of Example 2, the citrate Slightly reduced monomer content was observed after concentrating the protein solution in citrate buffer. Moreover, dimer concentration was reduced and high molecular weight proteins (HMWPs) could be significantly reduced as well (see Table 7). In contrast, these impurities and byproducts were increased by increasing the concentration in phosphate buffer. No differences could be detected with SDS-PAGE analysis (Table 8).

TABLE 7

SEC data of Formulations 2 & 4

| | SEC Analysis | | | | | | | | |
|---|---|---|---|---|---|---|---|---|---|
| | ANTIBODY | | RRT0.8 | | LMWP | | HMWPs | | |
| Sample Name | Area mAU*min | Rel. Area % | Area mAU*min | Rel. Area % | Area mAU*min | Rel. Area % | Area mAU*min | Rel. Area % | Monomer Gehalt [mg/mL] |
| Ref. Lot | 255.61 | 98.00 | 3.98 | 1.52 | 1.50 | 0.57 | 0.59 | 0.23 | |
| Formulation 2 | 121.42 | 97.39 | 2.13 | 1.71 | 0.98 | 0.79 | 0.15 | 0.12 | 44.08 |
| Formulation 4 | 141.90 | 97.65 | 2.17 | 1.49 | 1.16 | 0.80 | 0.09 | 0.06 | 45.83 |

TABLE 8

SDS-PAGE data of Formulations 2 & 4

| | SDS-PAGE Analysis | | | | | | | | |
|---|---|---|---|---|---|---|---|---|---|
| | Antibody | | Main 2. band | | Half molecules | | Additional bands | | |
| Sample Name | size kDa | Rel. QTY % | size kDa | Rel. QTY % | size kDa | Rel. QTY % | size kDa | Rel. QTY % | comment |
| Ref. Lot | 172.5 | 98.4 | 150.1 | 1.4 | 68.4 | 0.2 | | | Additional bands <0.5% |
| Formulation 2 | 170.6 | 97.9 | 147.6 | 1.9 | 72.2 | 0.2 | | | Identical pattern to Ref. Lot |
| Formulation 4 | 171 | 97.2 | 149 | 2.5 | 70.5 | 0.3 | | | Identical pattern to Ref. Lot |

Example 4

Development of Lyophilized Antibody Formulations

To test the feasibility of lyophilization, different lyophilized experimental formulations were manufactured and subjected to stability analysis. The concentration of the Lead LIGHT Antibody was increased to 50 mg/mL.

Table 9 shows the freeze drying program that was used in this example.

TABLE 9

| Freeze drying program | |
|---|---|
| Lyo program (vacuum) N° | 8 |
| Chamber loading | 5 min/RT/100% |
| Freezing | 2 h/−45° C./100% |
| Main drying I | 30 min/−45° C./30% |

TABLE 9-continued

| Freeze drying program | |
|---|---|
| Lyo program (vacuum) N° | 8 |
| Main drying II | 5 h/−20° C./30% |
| Main drying III | 8 h/+20° C./30% |
| Final drying | 2 h/+20° C./3% |

Table 10 shows the analytical results of the first batch of Reference Lot, and the various experimental lyophilized formulations of the Lead LIGHT Antibody formulated into various combinations of citrate buffer, sucrose, polysorbate 20, and proline.

As shown in Table 11, high molecular weight proteins (HMWPs) could clearly be reduced by using citrate buffer. No differences in dimer content were seen over the time of storage at 40° C. An increase of low molecular weight proteins (LMWPs) after freeze drying was observed. As before, these differences could not be detected with SDS-PAGE analysis (Table 12).

TABLE 10

Analytical data of Formulations 6-6.2 & 11

| Sample number | Tm1 | Tm2 | Tm3 | Time/ Temp. | pH | ZAve [nm] | Concentration | Buffer |
|---|---|---|---|---|---|---|---|---|
| Reference Lot | 67.94 | 75.00 | 77.37 | | 7.3 | 10.05 | 5.5 mg/mL | PBS |
| Formulation 6 | Nd | Nd | Nd | N/A | 5.7 | 17.46 | 57.32 | Citrate 10 mM PS20 0.01% |

TABLE 10-continued

Analytical data of Formulations 6-6.2 & 11

| Sample number | Tm1 | Tm2 | Tm3 | Time/Temp. | pH | ZAve [nm] | Concentration | Buffer |
|---|---|---|---|---|---|---|---|---|
| Formulation 6.1 | 64.30 | 72.61 | 77.02 | T0 | 5.7 | 59.66 | Nd | Citrate 10 mM |
|  |  |  |  | T1/5° C. | 5.7 | 18.85 | Nd | PS20 |
|  |  |  |  | T1/40° C. | 5.7 | 19.12 | Nd | 0.01% |
|  |  |  |  | T2/5° C. | 5.7 | Nd | Nd | Prolin 1.5% |
|  |  |  |  | T2/40° C. | 5.7 | Nd | Nd | Sucrose 5% |
| Formulation 6.2 | 65.45 | 75.08 | 79.37 | T0 | 5.7 | 19.58 | Nd | Citrate 10 mM |
|  |  |  |  | T1/5° C. | 5.7 | 31.34 | Nd | PS20 |
|  |  |  |  | T1/40° C. | 5.7 | 18.1 | Nd | 0.01% |
|  |  |  |  | T2/5° C. | 5.7 | Nd | Nd | Sucrose 5% |
|  |  |  |  | T2/40° C. | 5.7 | Nd | Nd |  |
| Formulation 11 | 68.84 | 75.61 | 77.91 | T0 | 7.0 | 98.60 | 56.49 | PBS |
|  |  |  |  | T1/5° C. | 5.7 | 20.22 | Nd | Sucrose 5% |
|  |  |  |  | T1/40° C. | 5.7 | 22.68 | Nd |  |
|  |  |  |  | T2/5° C. | 5.7 | Nd | Nd |  |
|  |  |  |  | T2/40° C. | 5.7 | Nd | Nd |  |

TABLE 11

SEC data of Formulations 6.1-6.2 & 11

| | | SEC Analysis | | | | | | |
|---|---|---|---|---|---|---|---|---|
| | | ANTIBODY | | RRT0.8 | | LMWP | | HMWPs | |
| Sample Name | Time | Area [mAU*min] | Rel. Area [%] | Area [mAU*min] | Rel. Area [%] | Area [mAU*min] | Rel. Area [%] | Area [mAU*min] | Rel. Area [%] |
| Ref. Lot |  | 255.61 | 98.00 | 3.98 | 1.52 | 1.50 | 0.57 | 0.59 | 0.23 |
| Formulation 6.1 | T0 | 222.94 | 97.43 | 3.89 | 1.70 | 1.91 | 0.83 | 0.09 | 0.04 |
| Formulation 6.1 | T1 5° C. | 369.72 | 97.57 | 6.31 | 1.66 | 2.75 | 0.73 | 0.18 | 0.05 |
| Formulation 6.1 | T1 40° C. | 405.49 | 97.35 | 7.33 | 1.76 | 3.60 | 0.86 | 0.12 | 0.03 |
| Formulation 6.1 | T2 5° C. | 422.46 | 97.59 | 7.01 | 1.62 | 2.74 | 0.63 | 0.68 | 0.16 |
| Formulation 6.1 | T2 40° C. | 289.65 | 97.28 | 5.50 | 1.85 | 2.13 | 0.72 | 0.48 | 0.16 |
| Formulation 6.2 | T0 | 230.06 | 97.61 | 3.93 | 1.67 | 1.64 | 0.70 | 0.07 | 0.03 |
| Formulation 6.2 | T1 5° C. | 407.17 | 97.56 | 6.81 | 1.63 | 3.23 | 0.77 | 0.17 | 0.04 |
| Formulation 6.2 | T1 40° C. | 468.74 | 97.36 | 8.79 | 1.83 | 3.78 | 0.78 | 0.16 | 0.03 |
| Formulation 6.2 | T2 5° C. | 552.31 | 97.64 | 9.80 | 1.73 | 2.96 | 0.52 | 0.61 | 0.11 |
| Formulation 6.2 | T2 40° C. | 249.95 | 96.78 | 5.39 | 2.09 | 2.39 | 0.93 | 0.52 | 0.20 |
| Formulation 11 | T0 | 211.45 | 97.49 | 3.64 | 1.68 | 1.47 | 0.68 | 0.35 | 0.16 |
| Formulation 11 | T1 5° C. | 339.08 | 97.71 | 5.45 | 1.57 | 2.28 | 0.66 | 0.23 | 0.07 |
| Formulation 11 | T1 40° C. | 700.91 | 97.30 | 12.69 | 1.76 | 5.19 | 0.72 | 1.60 | 0.22 |
| Formulation 11 | T2 5° C. | 325.80 | 97.17 | 5.80 | 1.73 | 2.17 | 0.65 | 1.52 | 0.45 |
| Formulation 11 | T2 40° C. | 229.29 | 96.96 | 4.33 | 1.83 | 1.78 | 0.75 | 1.09 | 0.46 |

TABLE 12

SDS-PAGE data of Formulations 6.1-6.2 & 11

| | | SDS-PAGE Analysis | | | | | | |
|---|---|---|---|---|---|---|---|---|
| | | ANTIBODY | | Main 2.Band | | HM | | Additional bands | |
| Sample Name | Sample ID | size | Rel. QTY | size | Rel. QTY | size | Rel. QTY | size | Rel. QTY | comment |
| Ref. Lot |  | 182.9 | 95.6 | 161.2 | 2.3 | 73.8 | 0.5 |  |  |  |
| Formulation 6.1 | T0 | 175.6 | 94.7 | 156.1 | 2.7 | 73.5 | 0.5 |  |  |  |
| Formulation 6.1 | T1 5° C. | 180.2 | 86.9 | 159.9 | 11.4 | 75.9 | 0.1 |  |  |  |
| Formulation 6.1 | T1 40° C. | 179.2 | 90.4 | 158.5 | 7.5 | 76.1 | 0.4 |  |  |  |
| Formulation 6.1 | T2 5° C. | 177.3 | 95.6 | 157.9 | 2.1 | 74.9 | 0.3 |  |  |  |
| Formulation 6.1 | T2 40° C. | 179.8 | 94.7 | 159.8 | 2.9 | 75.4 | 0.3 |  |  |  |
| Formulation 6.2 | T0 | 176.6 | 94.9 | 156.3 | 2.6 | 73.6 | 0.5 |  |  |  |
| Formulation 6.2 | T1 5° C. | 180.2 | 89.8 | 159.3 | 7.9 | 76.3 | 0.4 |  |  |  |
| Formulation 6.2 | T1 40° C. | 182.1 | 88.7 | 160.9 | 9.4 | 76.3 | 0.1 |  |  |  |
| Formulation 6.2 | T2 5° C. | 177.5 | 95.5 | 160.2 | 2.9 | 75.4 | 0.2 |  |  |  |
| Formulation 6.2 | T2 40° C. | 180.9 | 95.5 | 161.5 | 2.4 | 75.7 | 0.3 |  |  |  |

TABLE 12-continued

SDS-PAGE data of Formulations 6.1-6.2 & 11

| | | SDS-PAGE Analysis | | | | | | | |
|---|---|---|---|---|---|---|---|---|---|
| | | ANTIBODY | | Main 2.Band | | HM | | Additional bands | |
| Sample Name | Sample ID | size | Rel. QTY | size | Rel. QTY | size | Rel. QTY | size | Rel. QTY | comment |
| Formulation 11 | T0 | 178.7 | 95.1 | 156.5 | 2.3 | 73.7 | 0.4 | | |
| Formulation 11 | T1 5° C. | 181.0 | 70.0 | 154.7 | 25.7 | 74.5 | 0.3 | | |
| Formulation 11 | T1 40° C. | 181.3 | 66.2 | 154.2 | 28.9 | 74.5 | 0.3 | | |
| Formulation 11 | T2 5° C. | 177.7 | 87.5 | 155.9 | 10.9 | 75.2 | 0.3 | | |
| Formulation 11 | T2 40° C. | 176.8 | 86.2 | 155.2 | 12.0 | 74.5 | 0.3 | | |

Example 5

Accelerated Stability Study

An accelerated stability study was performed with citrate and histidine buffers. Table 13 shows the analytical results of the first batch of Reference Lot, and the various experimental formulations of the Lead LIGHT Antibody formulated into various combinations of citrate buffer or histidine buffer. Notably, the citrate formulation of the invention appeared in all experiments to perform better than histidine. In particular, citrate formulations had a higher monomer content compared to the both the Reference Lot batch and the histidine (Table 13) and the content or low molecular weight proteins (LMWPs) and high molecular weight proteins (HMWPs) were also significantly lower (Table 14). As before, these differences could not be detected with SDS-PAGE analysis (Table 15).

TABLE 13

Analytical data of Formulations 7, 8, 9 & 10

| Sample number | Tm1 [° C.] | Tm2 [° C.] | Tm3 [° C.] | pH | ZAve [nm] | Concentration [mg/mL] | Buffer |
|---|---|---|---|---|---|---|---|
| Ref. Lot | 67.94 | 75.00 | 77.37 | 7.3 | 10.05 | 5.5 | PBS |
| Formulation 7 | 58.95 | 68.51 | 76.20 | 5.5 | 12.97 | 53.65 | Histidine 10 mM |
| Formulation 8 | 58.69 | 68.23 | 76.12 | 5.4 | 13.29 | 58.72 | Histidine 10 mM PS20 0.01% |
| Formulation 9 | 61.67 | 72.01 | 76.53 | 5.6 | 59.26 | 55.01 | Citrate 10 mM |
| Formulation 10 | 62.24 | 72.32 | 76.61 | 5.6 | 17.3 | 55.8 | Citrate 10 mM PS20 0.01% |

TABLE 14

SEC Analysis of Formulations 7 & 8 & 9 & 10

| | | ANTIBODY | | RRT0.8 | | LMWP | | HMWPs | | Monomer |
|---|---|---|---|---|---|---|---|---|---|---|
| Sample Name | Time | Area [mAU*min] | Rel. Area [%] | Area [mAU*min] | Rel. Area [%] | Area [mAU*min] | Rel. Area [%] | Area [mAU*min] | Rel. Area [%] | Content [mg/mL] |
| Ref. Lot | | 282.42 | 97.40 | 4.55 | 1.57 | 2.15 | 0.74 | 0.85 | 0.29 | |
| Formulation 7 | T0 | 184.4 | 95.1 | 163.8 | 1.6 | 72.8 | 1 | | | |
| Formulation 7 | T1 5° C. | 390.84 | 97.85 | 5.72 | 1.43 | 2.80 | 0.70 | 0.06 | 0.01 | |
| Formulation 7 | T1 40° C. | 379.81 | 96.74 | 7.04 | 1.79 | 5.77 | 1.47 | 0 | 0 | |
| Formulation 7 | T2 5° C. | 863.01 | 97.75 | 14.19 | 1.61 | 4.14 | 0.47 | 1.54 | 0.18 | 164.88 |
| Formulation 7 | T2 40° C. | 1085.91 | 95.22 | 29.59 | 2.60 | 23.25 | 2.04 | 1.69 | 0.15 | 207.47 |
| Formulation 8 | T0 | 184.6 | 94.9 | 165.9 | 2.1 | 72.7 | 0.8 | | | |
| Formulation 8 | T1 5° C. | 507.64 | 97.74 | 7.52 | 1.45 | 4.19 | 0.81 | 0.05 | 0.01 | |
| Formulation 8 | T1 40° C. | 461.44 | 96.98 | 8.05 | 1.69 | 6.19 | 1.30 | 0 | 0 | |
| Formulation 8 | T2 5° C. | 416.54 | 97.46 | 6.59 | 1.54 | 3.49 | 0.82 | 0.79 | 0.18 | 79.58 |
| Formulation 8 | T2 40° C. | 422.21 | 93.23 | 11.17 | 2.47 | 18.40 | 4.06 | 1.11 | 0.25 | 80.66 |
| Formulation 9 | T0 | 229.01 | 97.63 | 3.75 | 1.60 | 1.63 | 0.70 | 0.19 | 0.08 | 45.28 |
| Formulation 9 | T1 5° C. | 307.94 | 97.96 | 4.2 | 1.34 | 2.20 | 0.7 | 0 | 0 | |
| Formulation 9 | T1 40° C. | 319.10 | 97.54 | 5.24 | 1.60 | 2.59 | 0.79 | 0.23 | 0.07 | |
| Formulation 9 | T2 5° C. | 337.15 | 97.48 | 5.41 | 1.56 | 2.84 | 0.82 | 0.49 | 0.14 | 64.41 |
| Formulation 9 | T2 40° C. | 325.54 | 96.26 | 7.78 | 2.30 | 3.66 | 1.08 | 1.20 | 0.36 | 62.20 |
| Formulation 10 | T0 | 233.11 | 97.54 | 3.84 | 1.61 | 1.97 | 0.82 | 0.08 | 0.03 | 46.09 |
| Formulation 10 | T1 5° C. | 343.38 | 97.77 | 5.21 | 1.48 | 2.58 | 0.73 | 0.04 | 0.01 | |
| Formulation 10 | T1 40° C. | 329.56 | 97.21 | 5.06 | 1.49 | 4.29 | 1.26 | 0.13 | 0.04 | |
| Formulation 10 | T2 5° C. | 343.33 | 97.43 | 5.47 | 1.55 | 3.06 | 0.87 | 0.53 | 0.15 | 65.59 |
| Formulation 10 | T2 40° C. | 257.20 | 94.59 | 5.59 | 2.06 | 8.98 | 3.30 | 0.15 | 0.05 | 49.14 |

TABLE 15

SDS-PAGE data of Formulations 7 & 8 & 9 & 10

SDS-PAGE Analysis

| Sample Name | Time/Temp | ANTIBODY size [kDa] | ANTIBODY Rel. QTY [%] | Main 2.band size [kDa] | Main 2.band Rel. QTY [%] | Half molecules size [kDa] | Half molecules Rel. QTY [%] | Additional bands size [kDa] | Additional bands Rel. QTY [%] | comment |
|---|---|---|---|---|---|---|---|---|---|---|
| Ref. Lot | | 173.6 | 96.3 | 155.8 | 2.2 | 74 | 0.4 | | | |
| Formulation 7 | T0 | 184.4 | 95.1 | 163.8 | 1.6 | 72.8 | 1 | | | |
| Formulation 7 | T1 5° C. | 183.0 | 91.1 | 159.9 | 7.2 | 76.1 | 0.4 | | | |
| Formulation 7 | T1 40° C. | 182.2 | 83.1 | 158.4 | 13.8 | 74.0 | 0.4 | | | |
| Formulation 7 | T2 5° C. | 181.5 | 95.7 | 160.3 | 2.7 | 75.6 | 0.3 | | | |
| Formulation 7 | T2 40° C. | 173.0 | 84.6 | 151.1 | 10.3 | 73.9 | 0.7 | 12.1 | 0.9 | more LMWPs |
| Formulation 8 | T0 | 184.6 | 94.9 | 165.9 | 2.1 | 72.7 | 0.8 | | | |
| Formulation 8 | T1 5° C. | 180.1 | 86.2 | 158.3 | 11.4 | 73.9 | 0.4 | | | |
| Formulation 8 | T1 40° C. | 180.9 | 79.4 | 158.2 | 16.9 | 74.0 | 0.3 | | | |
| Formulation 8 | T2 5° C. | 175.1 | 95.2 | 154.9 | 3.1 | 74.4 | 0.3 | | | |
| Formulation 8 | T2 40° C. | 174.8 | 84.7 | 150.5 | 9.2 | 74.0 | 0.9 | 12.1 | 1.5 | more LMWPs |
| Formulation 9 | T0 | 187.7 | 95.5 | 163.1 | 1.1 | 72.9 | 0.9 | | | |
| Formulation 9 | T1 5° C. | 178.9 | 65.8 | 160.4 | 29.6 | 73.7 | 0.9 | | | |
| Formulation 9 | T1 40° C. | 184.7 | 82.9 | 160.3 | 14.8 | 74.4 | 0.3 | | | |
| Formulation 9 | T2 5° C. | 176.2 | 95.6 | 155.6 | 2.6 | 73.6 | 0.3 | | | |
| Formulation 9 | T2 40° C. | 174.3 | 91.5 | 153.9 | 3.1 | 73.1 | 0.3 | 12.1 | 0.2 | more LMWPs |
| Formulation 10 | T0 | 182.5 | 95.2 | 161.3 | 1.6 | 72.3 | 0.8 | | | |
| Formulation 10 | T1 5° C. | 184.5 | 68.4 | 156.4 | 26.6 | 75.1 | 0.3 | | | |
| Formulation 10 | T1 40° C. | 180.8 | 65.4 | 153.8 | 28.8 | 74.8 | 0.3 | | | |
| Formulation 10 | T2 5° C. | 188.7 | 88.6 | 165.0 | 9.6 | 73.5 | 0.2 | | | |
| Formulation 10 | T2 40° C. | 181.7 | 78.9 | 158.2 | 15.8 | 75.7 | 0.8 | 12.6 | 1.3 | more LMWPs |

Example 6

Development of High Antibody Concentration Formulation for Subcutaneous Administration Based on the successful results of the citrate-buffered formulations of Examples 2-5, a high-concentration (150 mg/ml) antibody formulation suitable for subcutaneous administration was developed. Formulation development was performed on the Lead LIGHT Antibody with the goal of developing a liquid dosage form with an acceptable shelf life when stored at +2 to +8° C. Preliminary stress studies showed the formation of subvisible and visible particles, high molecular weight species and more basic species. Therefore, these parameters were monitored during the screening of formulation candidates using visual assessment, dynamic light scattering, light obscuration, size exclusion chromatography, sodium dodocyl sulphate polyacrylamide gel electrophoresis, and weak cationic exchange chromatography. Different liquid formulations were used in the pre-formulation and formulation trials prior to selection of the clinical formulation. According to the findings, a formulation in 10 mM citrate buffer adjusted to pH 5.5 (Formulation 14) was selected for further development. The pH of the formulation is in the region of optimal physical and chemical stability of the drug substance and acceptable physiological tolerability (e.g., osmolarity).

As shown in Table 16, Formulation 14 is a solution for injection and is an aqueous, sterile, and clear solution containing the Lead LIGHT Antibody, sodium citrate dihydrate (buffering agent), polysorbate 20 (stabilizing agent), and mannitol (tonicity agent). Sodium hydroxide solution and hydrochloric acid were used to adjust the pH to 5.5.

All excipients were soluble and well tolerated pharmacopoeial standard excipients for parenterals and listed in Ph. Eur. and USP.

TABLE 16

| | Composition | | | |
|---|---|---|---|---|
| Components[a] | per mL (mg) | per vial (1.2 mL) (mg) | Function | Reference to standards[b] |
| Lead Antibody | 150.00 | 180.00 | Drug substance | In-house |
| Sodium citrate dehydrate | 2.94 | 3.53 | Buffering agent | Ph. Eur., USP |
| Mannitol | 40.00 | 48.00 | Tonicity agent | Ph. Eur., USP |
| Polysorbate 20 | 0.05 | 0.06 | Stabilizing agent | Ph. Eur., NF, JP |
| Hydrochloric acid, concentrated [Hydrochloric acid] | q.s pH 5.5 | q.s. pH 5.5 | Acidifying agent | Ph. Eur., NF |
| Sodium hydroxide | q.s.pH 5.5 | q.s. pH 5.5 | Alkalizing agent | Ph. Eur., NF |
| Water for injection | q.s. 1 mL | q.s. 1.2 mL | Solvent | Ph. Eur., USP |
| Nitrogen | Process aid for filtration | | | Ph. Eur., NF |

[a]Components are listed according to their pharmacopoeial names. If more than one monograph exists, other names are given in brackets, along with the compendial origin.
[b]Reference is made to the current edition of the Pharmacopoeia.

Example 7

Manufacturing Process for Subcutaneous Antibody Formulation

A GMP-compliant manufacturing process was developed for the subcutaneous, high-concentration antibody formulation (Formulation 14) of Example 6. The manufacturing procedure consisted of dissolving, pH adjustment, sterile filtration, filling, and packaging steps.

Drug substance (the Lead LIGHT Antibody) is provided in a liquid form in the formulation buffer (10 mM citrate buffer at pH 5.5). The excipients were all water-soluble and dissolved in the initial aqueous portion of the formulation buffer during manufacture. The bulk drug substance solution was further diluted with the same formulation buffer to reach the concentration of 150 mg/mL of Lead LIGHT Antibody. The bulk solution was well mixed to facilitate the dissolution process and to ensure homogeneity.

Sterilization by filtration was carried out (according to Ph. Eur. and USP) using bacteria retentive filters having a nominal pore size of 0.2 µm. An additional filtration procedure before "sterilization by filtration" was performed to ensure a low bioburden. Bioburden sampling was done before the pre-filtration step as well as the sterile filtration step.

Preparation and filling of the sterilized solution into the suitable containers was performed under aseptic conditions. This was in accordance with pharmacopoeial monographs and related guidelines, which required sterilization by filtration and subsequent aseptic processing. The equipment, which comes into contact with the product after the step "sterilization by filtration", was sterilized by heat or steam using a validated method (according to Ph. Eur./USP).

Vials were filled to about 1.2 mL to ensure an extractable volume of 1.0 mL. The 2 mL vials were made of clear, colorless type I glass, and closed with a stopper (fluoropolymer-coated bromobutyl) sealed with flip-off caps with a flange (polypropylene). The primary packaging materials met the requirements of the Ph. Eur. and USP. The suitability of the primary packaging materials was substantiated by the results of the stability tests. Incompatibilities with the primary packaging material used were not observed. Secondary packaging which provides protection of the product from light.

Compatibility with application syringes was assessed using 3 different syringe sizes and needles diameters (between 25 and 28 gauges) on the drug product solution. No differences in terms of product quality were obtained. Compatibility was proven for a time period of 8 hours.

Formulation 14 was made in 5 L batches, the composition of which is shown in Table 17. However, the batch size may be adjusted according to clinical requirements.

TABLE 17

Batch formula

| Components | Batch size 5 Liter[a] [g] |
|---|---|
| Lead Antibody [b] | 750.00 |
| Mannitol | 200.00 |
| Polysorbate 20 | 0.25 |
| Sodium citrate dihydrate | 14.71 |
| Hydrochloric acid, concentrated [c] | q.s. pH 5.5 |
| Sodium hydroxide [c] | q.s. pH 5.5 |
| Water for injection | Ad 5285.25 [d] |
| Nitrogen | Process aid for filtration |

[a] The vials were filled with a volume of 1.2 mL to ensure an extractable volume of 1.0 mL. A 6.0 L batch size therefore results in a theoretical yield of 5000 vials.
[b] For pH adjustment.
[c] This was calculated according to the density of the final drug product solution (1.05705 mg/mL)

Figure 9:
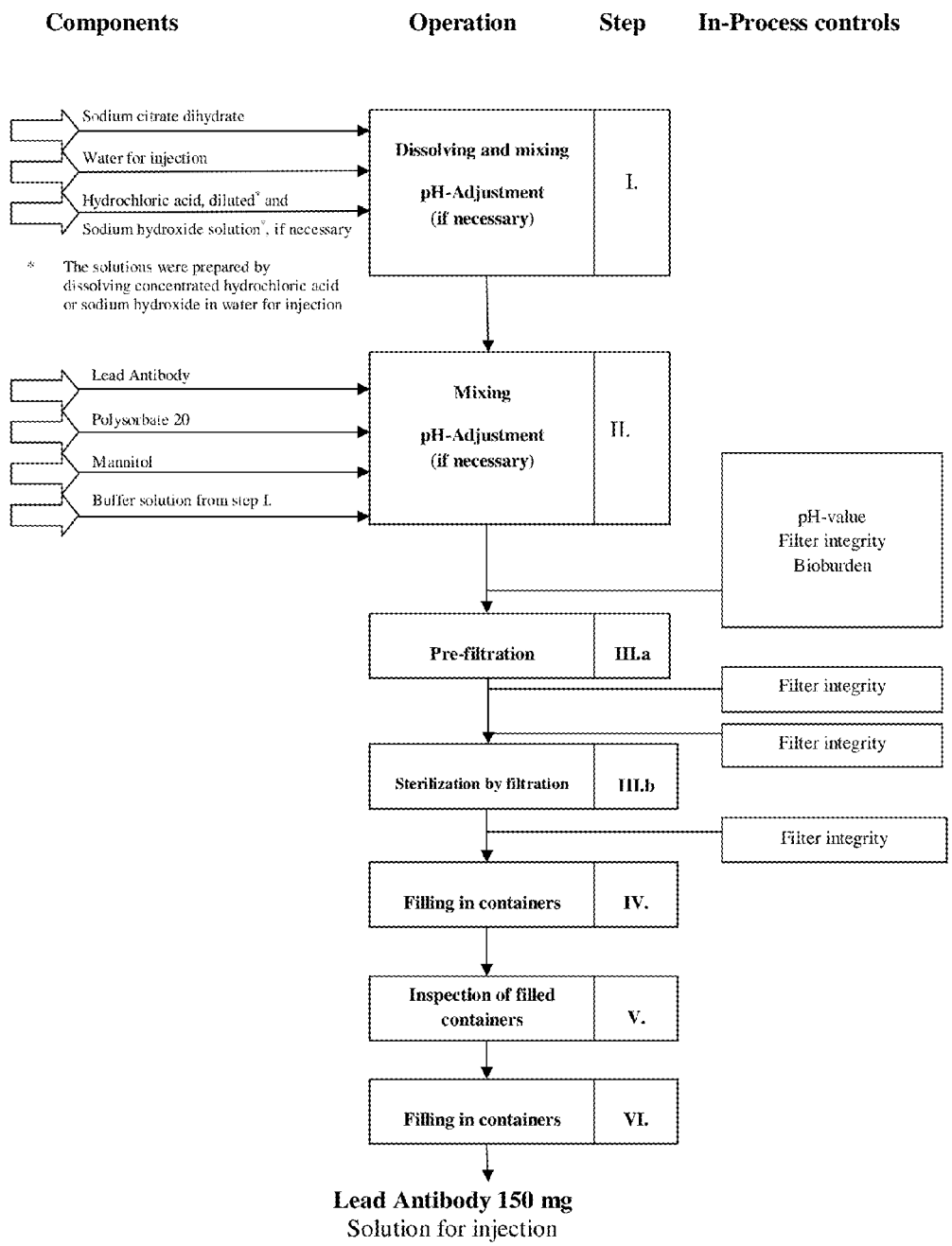
FIG. 9 is a flow diagram of the drug product manufacturing process for the high antibody concentration formulation.

The manufacturing process and process controls for Formulation 14 are shown in the flow diagram in FIG. 9. Batch manufacturing included the following steps:

I. Sodium citrate dihydrate was dissolved in water for injection while stirring in a vessel made of inert material (e.g., stainless steel or glass), until completely dissolved. The pH value was adjusted to 5.5 using hydrochloric acid, diluted (e.g., 0.1 M hydrochloric acid) and/or sodium hydroxide solution (e.g., 0.1 M sodium hydroxide), if necessary.

II. Lead Antibody, mannitol, and polysorbate 20 were diluted in the buffer solution from step 1 while stirring in a vessel made of inert material (e.g., stainless steel or glass) until completely dissolved. If necessary, the pH value was adjusted to 5.5 using hydrochloric acid, diluted (e.g., 1 M hydrochloric acid) or sodium hydroxide solution (e.g., 1 M sodium hydroxide). Buffer solution from step 1 (remainder) was added to adjust the final weight.

III. a) Pre-filtration:
Solution from step II was filtered under aseptic conditions using a sterilized, compatible membrane filter (e.g., polyether sulfone or polyvinylidene difluoride) having a nominal pore size of 0.2 µm.

b) Sterilization by filtration:
Solution from step III.a was sterilized by filtration under aseptic conditions into sterilized containers made out of inert material (e.g., stainless steel or glass) using a sterilized, compatible membrane filter (e.g., polyether sulfone or polyvinylidene difluoride) having a nominal pore size of 0.2 µm.

IV. Solution from step III.b was filled under aseptic conditions into sterilized vials, which were closed with stoppers and flip-off caps with a flange.

V. The containers from step IV were inspected for coarse contaminants, intact sealing, and visible particles.

VI. The inspected containers from step V were additionally packaged in suitable containers (e.g., cardboard boxes).

In addition, DLS was used to determine the hydrodynamic diameter of the antibody monomer and potential soluble aggregates. As shown in FIG. 10, aggregates were not seen in citrate buffer. However, as shown in FIGS. 7 & 8, aggregates were seen in PBS. Due to the higher concentration of antibody, an increase in ZAve to 28 nm was observed, compared to the sample in PBS.

Example 8

Stability Profile for Subcutaneous Antibody Formulation

The stability profile of the clinical batch (batch 2) of Example 7 was assessed for storage under long term and accelerated testing conditions according to ICH guidelines. Samples were packed and stored in 2 mL clear and colorless vials (glass type I) closed with stoppers (fluoropolymer-coated bromobutyl) and flip-off caps with a flange (polypropylene).

The following tests were performed during stability: appearance (clarity, color), assay (antigen ELISA, UV), purity (SEC, SDS-PAGE under reducing and non-reducing conditions), molecular integrity (SDS-PAGE under non-reducing conditions), charge heterogeneity (weak cation exchange chromatography, isoelectric focusing), pH, sterility, bacterial endotoxins, particulate matter (visible and subvisible particles), and closure integrity.

The samples were stored in inverted and upright positions. The results of the inverted storage were presented as the more stringent condition. Stability data at −20° C., +5° C. and +25° C. are presented in Tables 18-20, respectively. The investigations on physical, chemical, and biological properties of storage under long term testing conditions confirmed a good stability of the drug product at 5° C. (see Table 19). Under accelerated testing conditions (+25° C.), only a slight decrease in the purity was detected by size exclusion chromatography (see Table 20). Therefore, it was concluded that the drug product should be stored at +2° C. to +8° C. protected from light.

TABLE 18

Long term stability at −20° C. for drug product

| | | | | | | |
|---|---|---|---|---|---|---|
| Drug product: | Lead LIGHT Antibody solution for injection | | | Batch no.: | 11_021 | |
| Dosage strength: | 150 mg/mL | | | Formulation no.: | 14 | |
| Container/closure: | 2 mL glass vials | | | | | |
| Storage condition: | −20° C. ± 5° C. | | | | | |
| Storage orientation: | Upright | | | | | |

| | | | | Time | | | |
|---|---|---|---|---|---|---|---|
| Test item | Initial results | 1 month | 3 months | 6 months | 12 months | 18 months | 24 months |
| Appearance of solution | | | | | | | |
| Clarity | <I | III | II | >IV | IV | >IV | |
| Color | BY7 | BY7 | BY6 | BY6 | BY6 | BY7 | |
| Identification | | | | | | | |
| IEF | | | | | | | |
| Isoelectric pattern | Conforms | Conforms | Conforms | Conforms | Conforms | Conforms | |
| Assay | | | | | | | |
| Antigen-ELISA | | | | | | | |
| EC50 value (in comparison to reference | 76% | 110% | 76% | 103% | 96% | 105% | |
| Total protein content (UV) | 153 mg/mL | 148 mg/mL | 151 mg/mL | 151 mg/mL | 149 mg/mL | 156 mg/mL | |
| Purity | | | | | | | |
| HPLC (SEC) | | | | | | | |
| Monomer (% area) | 98.2% | 97.5% | 96.2% | 94.5% | 94.3% | 94.1% | |
| HMWPs (% area) | 1.3% | 2.3% | 3.7% | 5.4% | 5.5% | 5.5% | |
| LMWPs (% area) | 0.4% | 0.2% | 0.1% | 0.0% | 0.1% | 0.5% | |
| SDS-PAGE under non reducing conditions | | | | | | | |
| Half molecules | <1.0% | <1.0% | <1.0% | 2.7% | <1.0% | <5.0% | |
| SDS-PAGE under reducing conditions | | | | | | | |
| Relative purity | 98% | 100% | 100% | 100% | 96% | 100% | |
| Molecular integrity | | | | | | | |
| SDS-PAGE under non-reducing conditions | | | | | | | |
| Gel pattern | Conforms | Does not conform | Conforms | Conforms | Conforms | Conforms | |
| Charge heterogeneity | | | | | | | |
| HPLC (WCX) | | | | | | | |
| acidic | 40% | 36% | 44% | 42% | 43% | 41% | |
| neutral | 55% | 60% | 54% | 47% | 51% | 56% | |
| basic isoforms (% area) | 5% | 4% | 2% | 2% | 6% | 3% | |
| pH (potentiometry) | 5.5 | 5.5 | 5.5 | 5.5 | 5.5 | 5.5 | |
| Particulate matter (visible particles) | Complies | Complies | Complies | Complies | Complies | Complies | |
| Particulate matter (subvisible particles) | | Not tested | Not tested | Not tested | | Not tested | |
| Number of particles per vial ≥10 μm | 313 | | | | 33 | | |
| Number of particles per vial ≥25 μm | 10 | | | | 5 | | |
| Closure integrity | Complies | Not tested | Not tested | Not tested | Complies | Not tested | |
| Microbial contamination | | | | | | | |
| TAMC | <1 CFU/2 mL | Not tested | Not tested | Not tested | Not tested | Not tested | |
| TAnMC | <1 CFU/2 mL | Not tested | Not tested | Not tested | Not tested | Not tested | |

TABLE 19

Long term stability at +5° C. for drug product

| Drug product: | Lead LIGHT Antibody solution for injection | Batch no.: | 11_021 |
| Dosage strength: | 150 mg/mL | Formulation no.: | 14 |
| Container/closure: | 2 mL glass vials | | |
| Storage condition: | +5° C. ± 3° C. | | |
| Storage orientation: | Upright | | |

| | | | | Time | | | |
|---|---|---|---|---|---|---|---|
| Test item | Initial results | 1 month | 3 months | 6 months | 12 months | 18 months | 24 months |
| Appearance of solution | | | | | | | |
| Clarity | <I | <I | <I | <I | <IError! Reference source not found. | >IV | |
| Color | BY7 | BY7 | BY7 | BY7 | BY6 | BY7 | |
| Identification | | | | | | | |
| IEF | | | | | | | |
| Isoelectric pattern | Conforms | Conforms | Conforms | Conforms | Conforms | Conforms | |
| Assay | | | | | | | |
| Antigen-ELISA | | | | | | | |
| EC50 value (in comparison to reference | 76% | 119% | 83% | 107% | 96% | 115% | |
| Total protein content (UV) | 153 mg/mL | 150 mg/mL | 150 mg/mL | 151 mg/mL | 148 mg/mL | 155 mg/mL | |
| Purity | | | | | | | |
| HPLC (SEC) | | | | | | | |
| Monomer (% area) | 98.2% | 98.5% | 98.5% | 98.3% | 98.0% | 97.4% | |
| HMWPs (% area) | 1.3% | 1.4% | 1.5% | 1.7% | 1.9% | 2.0% | |
| LMWPs (% area) | 0.4% | 0.0% | 0.0% | 0.0% | 0.1% | 0.6% | |
| SDS-PAGE under non reducing conditions | | | | | | | |
| Half molecules | <1.0% | <1.0% | <1.0% | 1.8% | <1.0% | <1.0% | |
| SDS-PAGE under reducing conditions | | | | | | | |
| Relative purity | 98% | 100% | 100% | 100% | 96% | 100% | |
| Molecular integrity SDS-PAGE under non-reducing conditions | | | | | | | |
| Gel pattern | Conforms | Does not conform | Conforms | Conforms | Conforms | Conforms | |
| Charge heterogeneity HPLC (WCX) | | | | | | | |
| acidic | 40% | 36% | 44% | 42% | 43% | 39% | |
| neutral | 55% | 60% | 54% | 57% | 52% | 57% | |
| basic isoforms (% area) | 5% | 4% | 2% | 2% | 5% | 4% | |
| pH (potentiometry) | 5.5 | 5.5 | 5.5 | 5.5 | 5.5 | 5.5 | |
| Particulate matter (visible particles) | Complies | Complies | Complies | Complies | Complies | Complies | |
| Particulate matter (subvisible particles) | | Not tested | Not tested | Not tested | | Not tested | |
| Number of particles per vial ≥10 μm | 313 | | | | 35 | | |
| Number of particles per vial ≥25 μm | 10 | | | | 5 | | |
| Closure integrity | complies | Not tested | Not tested | Not tested | Complies | Complies | |
| Microbial contamination | | | | | | | |
| TAMC | <1 CFU/2 mL | Not tested | Not tested | Not tested | Not tested | Not tested | |
| TAnMC | <1 CFU/2 mL | Not tested | Not tested | Not tested | Not tested | Not tested | |

TABLE 20

Accelerated stability at +25° C. for drug product

| | | | | |
|---|---|---|---|---|
| Drug product: | Lead LIGHT Antibody solution for injection | | Batch no.: 11_021 | |
| Dosage strength: | 150 mg/mL | | Formulation no.: 14 | |
| Container/closure: | 2 mL glass vials | | | |
| Storage condition: | +25° C. ± 2° C./60% ± 5% RH | | | |
| Storage orientation: | Upright | | | |

| | Time | | | |
|---|---|---|---|---|
| Test Item | Initial results | 1 month | 3 months | 6 months |
| Appearance of solution | | | | |
| Clarity | <I | <I | <I | <I |
| Color | BY7 | BY7 | BY7 | BY7 |
| Identification | | | | |
| IEF Isoelectric pattern | Conforms | Conforms | Conforms | Conforms |
| Assay | | | | |
| Antigen-ELISA EC50 value (in comparison to reference | 76% | 108% | 96% | 111% |
| Total protein content (UV) | 153 mg/mL | 149 mg/mL | 150 mg/mL | 151 mg/mL |
| Purity HPLC (SEC) | | | | |
| Monomer (% area) | 98.2% | 98.2% | 97.7% | 96.8% |
| HMWPs (% area) | 1.3% | 1.7% | 2.2% | 3.1% |
| LMWPs (% area) | 0.4% | 0.1% | 0.1% | 0.1% |
| SDS-PAGE under non reducing conditions | <1.0% | <1.0% | <1.0% | <1.0% |
| Half molecules | 98% | 100% | 100% | 100% |
| SDS-PAGE under reducing conditions Relative purity | | | | |
| Molecular integrity | | | | |
| SDS-PAGE under non-reducing conditions Gel pattern | Conforms | Does not conform | Conforms | Conforms |
| Charge heterogeneity HPLC (WCX) | | | | |
| acidic | 40% | 36% | 44% | 41% |
| neutral | 55% | 59% | 53% | 56% |
| basic isoforms (% area) | 5% | 5% | 2% | 3% |
| pH (potentiometry) | 5.5 | 5.5 | 5.5 | 5.5 |
| Particulate matter (visible particles) | Complies | Complies | Complies | Complies |
| Particulate matter (subvisible particles) | | | | |
| Number of particles per vial ≥10 μm | 313 | Not tested | Not tested | 22 |
| Number of particles per vial ≥25 μm | 10 | | | 1 |
| Closure integrity | complies | Not tested | Not tested | Complies |
| Microbial contamination | | | | |
| TAMC | <1 CFU/2 mL | Not tested | Not tested | <1 CFU/2 mL |
| TAnMC | <1 CFU/2 mL | Not tested | Not tested | <1 CFU/2 mL |

Example 9

Development of Ultra-High Antibody Concentration Formulation for Subcutaneous Administration Based upon the successful results of the citrate-buffered formulations for antibody concentrations up to 150 mg/mL in Example 7, higher concentrated (up to 250 mg/ml) antibody formulations suitable for subcutaneous administration were developed.

Preliminary data showed that the formulation of antibody concentrations above 150 mg/mL may lead to higher viscosities affecting usage of the formulation.

TABLE 21

Ultra high concentrations with formulation 14

| Sample | Concentration [mg/mL] | Density [kg/m−3] | Viscosity [mPa] | DLS z-average [nm] | Size exclusion chromatography | | |
|---|---|---|---|---|---|---|---|
| | | | | | HMWPs | Monomer | LMWPs |
| Lead LIGHT Antibody_11_30A | 237 | 1.066 | 42.29 | 30 | 1.3 | 98.6 | 0.0 |
| Lead LIGHT Antibody_11_30B | 212 | 1.059 | 22.58 | 39 | 1.3 | 98.7 | 0.0 |
| Lead LIGHT Antibody_11_30C | 181 | 1.052 | 13.57 | 28 | 1.3 | 98.7 | 0.1 |
| Lead LIGHT Antibody_11_30D | 173 | 1.046 | 8.8 | 27 | 1.2 | 98.8 | 0.0 |
| Lead LIGHT Antibody_11_30E | 143 | 1.039 | 6.16 | 25 | 1.1 | 98.8 | 0.1 |

As can be seen in Table 21, the viscosity decreases with lower antibody concentrations, yet still being in an acceptable range at the higher concentration formulated with formulation 14. All other parameters seemed to be unaffected or just slightly affected by the ultra-high concentrations.

As shown in Table 22, the antibody concentrations did not affect the stability of the formulations, which was indicated by identical 1 month stability data at long term and stress conditions.

TABLE 22

1 month stability data of ultra high concentrated Lead Antibody formulations

| | Concentration [mg/mL] | HMWPs | Monomer | LMWPs |
|---|---|---|---|---|
| Lead LIGHT Antibody_11_30A 40° C. | 237 | 4.7 | 95.2 | 0.2 |
| Lead LIGHT Antibody_11_30B 40° C. | 212 | 4.4 | 95.4 | 0.2 |
| Lead LIGHT Antibody_11_30C 40° C. | 181 | 5.8 | 91.7 | 2.6 |
| Lead LIGHT Antibody_11_30D 40° C. | 173 | 3.9 | 96.0 | 0.2 |
| Lead LIGHT Antibody_11_30E 40° C. | 143 | 4.2 | 94.7 | 1.1 |
| Lead LIGHT Antibody_11_30A 5° C. | 237 | 1.4 | 98.6 | 0.0 |
| Lead LIGHT Antibody_11_30B 5° C. | 212 | 1.3 | 98.7 | 0.0 |
| Lead LIGHT Antibody_11_30C 5° C. | 181 | 1.3 | 98.7 | 0.0 |
| Lead LIGHT Antibody_11_30D 5° C. | 173 | 1.2 | 98.8 | 0.0 |
| Lead LIGHT Antibody_11_30E 5° C. | 143 | 1.1 | 98.9 | 0.0 |

Anti-CXCR5 (20 mg/mL) Pre-Formulation Studies

A humanized IgG4 anti-CXCR5 antibody comprising a heavy chain comprising the amino acid sequence of SEQ ID NO: 25 and a light chain comprising the amino acid sequence of SEQ ID NO: 26 (the "Lead CXCR5 Antibody") was used in Examples 10-12 in order to determine optimal formulation conditions for a 20 mg/mL formulation.

The Lead Antibody is a humanized monoclonal antibody (mAB) specific to human CXCR5, with an engineered IgG4 framework containing 2 amino acid substitutions aimed at reducing half-molecules (S241P) and effector functions (L248E). The Lead CXCR5 Antibody protein structure is comprised of two kappa light chains, each with a molecular weight of approximately 24 kDa, and two IgG4 heavy chains, each with a molecular weight of approximately 48 kDa linked through disulfide bridges. Each light chain consists of 219 amino acid residues, and each heavy chain consists of 437 amino acid residues.

The data in Examples 10-12 were collected during preformulation activities for the Lead CXCR5 Antibody and its drug product for intravenous and subcutaneous administration. The objective of the preformulation studies was to provide good stability of buffered Lead CXCR5 Antibody solutions with a target concentration of 20 mg/mL, with special emphasis on the aggregation behavior of the Lead CXCR5 Antibody and its tendency to form half-molecules, as the Lead Antibody is an IgG4 subclass antibody, which is prone to aggregation and the formation of particles.

Materials

Drug Substance (DS)

The Lead CXCR5 Antibody batch RSN0151 was formulated in PBS pH 7.2 with a concentration of 5.13 mg/mL.

Excipients

Table 23 shows excipients that were used during the preformulation studies.

TABLE 23

Excipients used during preformulation

| Excipients | Art. No./Charge | Supplier |
|---|---|---|
| Acetic acid | A002630 | MTP/VWR International SAS |
| Arginine-HCl | A1700 | AppliChem |
| Arginine | 1.01587 | Merck |
| Benzyl alcohol | 113594 | Industrial Affairs/Harrmann & Reimer |
| Citric acid | 100241 | Merck |
| Dextran 40 | CL-AO19A | Meito Sangyo |
| Glycine | 113560 | Industrial Affairs[1]/Tessenderlo Chemie. |
| HCl | 114027 | Industrial Affairs[1]/Merck |
| Histidine | 1.04352 | Merck |
| Potassium dihydrogen phosphate | 1.04871 | Merck |
| Lysine | 62840 | Fluka |
| Magnesium chloride | 814733 | Merck |
| Maltose | 105911 | Merck |
| Mannitol | A000780 | MTP/Roquette Freres |
| Sodium acetate | 1.06265 | Merck |
| Sodium chloride | 10158 | Industrial Affairs[1]/Riedel de Haen |
| Sodium hydroxide | 114076 | Industrial Affairs[1]/Merck |
| Sodium citrate | 114196 | Industrial Affairs[1]/Boehringer Ingelheim KG |
| Di-sodiumhydogen-phosphate anhydrous | 1.06586 | Merck |
| Polysorbate 20 | 139850 | Industrial Affairs[1]/Fluka |
| Succinat/Succinic acid | 14079 | Fluka |
| Sucrose | S3929 | Sigma-Aldrich |
| Trehalose-dihydrat | T9531 | Sigma-Aldrich |
| Trometamol | 114011 | Industrial Affairs/Merck |

Methods

The following methods were used to manufacture the experimental formulations and the formulations of the invention containing the Lead CXCR5 Antibody.

Manufacturing & Composition of Buffers

All buffers were manufactured by stirring constantly to dissolve the respective excipients. pH was adjusted using 0.1 M HCl or 0.1 M NaOH. The general concentration of all buffers was 10 mM.

Manufacturing & Composition of Excipient Stock Solutions

All stock solutions were manufactured by stirring constantly to dissolve the excipients. Concentrations were given as weight/weight (w/w).

UF/DF—Small Scale

UF/DF experiments were performed using Vivaspin units (Sartorius Stedim, Göttingen, Germany) with a Hydrosart membrane and a 30 kDa cut-off for removing phosphate buffer and replacing it with the appropriate buffers and to increase the concentration. These units were placed in a common laboratory centrifuge (Multifuge 3S, Haereus, Germany) and centrifuged at 2000 rpm (860 G, rotor radius 192 mm) at +5° C.

UF/DF—Larger Scale

UF/DF experiments were performed using Vivaflow units (Sartorius Stedim, Göttingen, Germany) with a Hydrosart membrane and a 30 kDa cut-off for removing phosphate buffer and replacing it with the appropriate buffers and to increase the concentration. The equipment was placed inside a clean-bench under aseptic conditions and the process was performed at room temperature.

Sterile Filtration of Samples

All samples, solutions, buffers, etc. were sterile filtered (0.22 µm) using a Sartopore-2 membrane. The samples were filtered into sterilized bottles or vials and closed under aseptic conditions inside a clean-bench to prevent microbiological contamination.

Mechanical Stress Test

Mechanical stress with an agitation speed of 350 rpm/min for 2.5 hours at room temperature was performed using a horizontal laboratory shaker with a 26 mm distance (shaker & incubation hood from Bailer Company). 2R vials were filled with 1 mL solution with a head space of about 2.5 cm³.

A mechanical stress test was planned and performed during the first preformulation studies. As the analytical results did not show any additional information compared to the thermal stress tests, during buffer selection or pH selection, this test was only used during surfactant selection.

Thermal Stress Test

Thermal stress was used as an accelerated stress test during all steps of the preformulation program. The samples were stored at +40° C. either for 24 h, 7 days, or 3 months, depending on the study.

Analytical Methods in Formulation Fill and Finish

The following analytical methods were used in the following examples.

Appearance

Appearance of the antibody solutions was checked visually and additionally documented by taking a picture with a camera.

pH

All pH measurements were performed using a pH-meter with a micro-electrode.

Concentration Using UV

The protein concentration of all antibody solutions was measured against buffer using a Nanodrop ND1000. Protein concentrations near or below 5 mg/mL were diluted 1:3, and higher protein concentrations near 20 mg/mL were diluted 1:20, before measuring the absorption at 215 nm and 280 nm.

Dynamic Light Scattering (DLS)

The hydrodynamic diameter of the molecule was measured using laser light scattering. The samples were sterile filtered prior to the analytics if turbidity was observed, thus only soluble aggregates could be detected.

Thioflavine-Ttest

Fluorescence measurements of some preformulation samples were carried out using a Tecan GENios Plus, XFLOUR4. The samples were stressed mechanically (4 h at +37° C., agitation speed 300 units/min and 26 mm distance in a shaker & incubator hood from Baler company). Thioflavin-T fluorescence spectra were measured at room temperature. 10 µl Thioflavin-T solution (10.1 mM in ultrapure water) was added to 1 ml of the formulations and gently mixed. The mixture was then dispensed into a black Eppendorf V-shaped cup, and then into a 96-well plate (100 µL per well).

The thioflavin-T test was used in the beginning of preformulation activities to detect insoluble aggregates. But, as these aggregates can be seen visually as a turbidity of the solution, this method was not used for the whole preformulation program.

Differential Scanning Calorimetry (DSC)

Aliquots of the preformulation samples were examined by DSC using a VPCapillary DSC from Microcal and scanned in the auto sampling instrument at 90° C./h with a filter time of 2 sec. 400 µl samples were placed into 96-well plates and analyzed for the unfolding temperature Tm.

Osmolarity

Osmolarity was measured using an automated Knaur Osmometer.

Density

Density of the formulations was measured using a falling sphere viscosimeter DMA4500 Anton Paar.

Analytical Methods in Bioanalytics FF

Size Exclusion Chromatography (SEC)

Oligomers/dimers of the antibodies were quantified by using size exclusion chromatography. The test was carried out by isocratic HPLC with a SUPERDEX 200 10/300 column.

SDS-PAGE, Reducing and Non-Reducing

Sodium dodecyl sulfate polyacrylamide gel electrophoresis (SDS-PAGE) was used to analyze the molecular integrity (e.g., half molecules) and appearance of degradation products. This electrophoresis analysis was performed with 15% homogenous gels under reducing and non-reducing conditions. The proteins were visualized with silver staining after electrophoresis separation.

WCX

Weak cationic exchange chromatography (WCX) was used to monitor the charge heterogeneity of the antibody. The percentage of basic, neutral, and acidic isoforms was reported. The test was carried out by discontinuous HPLC with a ProPac WCX10 column.

Antigen-ELISA

Antigen-ELISA was performed to determine the functionality of the antibody. The binding property to a 28mer peptide of the CXCR5 antigen was monitored in comparison to the current standard of the antibody. This potency was reported as the relative EC50.

Isoelectric Focusing (IEF)

IEF was performed.

Storage

All buffer solutions, excipient solutions, and samples were stored at +5° C., if not otherwise mentioned.

Summary of all Formulations Prepared & Analyzed

Table 24 below shows a summary of all of the formulations that were prepared and analyzed in Examples 10-12. Each of the formulations contained the Lead CXCR5 Antibody. PBS stands for phosphate buffered saline. PB stands for phosphate buffer. PS stands for polysorbate. LA stands for the Lead CXCR5 Antibody.

TABLE 24

Summary of all formulations prepared and analyzed

| Sample number | Buffer | pH |
|---|---|---|
| LA_09_05-1 | PBS 155 mM | 7.5 |
| LA_09_05-2 | PBS 155 mM | 7.0 |
| LA_09_05-3 | PBS 155 mM | 6.5 |
| LA_09_06-1 | PB 5 mM | 7.5 |
| LA_09_06-2 | PB 5 mM | 7.0 |
| LA_09_06-3 | PB 5 mM | 6.5 |
| LA_09_07-1 | PB 10 mM | 7.5 |
| LA_09_07-2 | PB 10 mM | 7.0 |
| LA_09_07-3 | PB 10 mM | 6.5 |
| LA_09_08-1 | Citrate 10 mM | 7.0 |
| LA_09_08-2 | Citrate 10 mM | 6.5 |
| LA_09_08-3 | Citrate 10 mM | 6.0 |
| LA_09_08-4 | Citrate 10 mM | 5.5 |
| LA_09_08-5 | Citrate 10 mM | 5.0 |
| LA_09_09-1 | Saline 150 mM | 6.0 |
| LA_09_10-1 | Acetate 10 mM | 5.5 |
| LA_09_10-2 | Acetate 10 mM | 5.0 |
| LA_09_11-1 | Succinate 10 mM | 6.0 |
| LA_09_11-2 | Succinate 10 mM | 5.5 |
| LA_09_11-3 | Succinate 10 mM | 5.0 |
| LA_09_12-1 | Histidine 10 mM | 6.5 |
| LA_09_12-2 | Histidine 10 mM | 6.0 |
| LA_09_12-3 | Histidine 10 mM | 5.5 |
| LA_09_13-1 | Glycine 10 mM | 8.0 |
| LA_09_13-2 | Glycine 10 mM | 7.0 |

TABLE 24-continued

Summary of all formulations prepared and analyzed

| Sample number | Buffer | pH |
|---|---|---|
| LA_09_14-1 | Arginine 10 mM | 8.0 |
| LA_09_14-2 | Arginine 10 mM | 6.0 |
| LA_09_15-1 | TRIS 10 mM | 8.5 |
| LA_09_15-2 | TRIS 10 mM | 7.5 |
| LA_09_16 | Citrate 10 mM | 6.0 |
| LA_09_16_1 | Citrate 10 mM/PS20 | 6.0 |
| LA_09_16_2 | Citrate 10 mM/PS80 | 6.0 |
| LA_09_16_3 | Citrate 10 mM/LutrolF68 | 6.0 |
| LA_09_16_4 | Citrate 10 mM/Cremophor | 6.0 |
| LA_09_16_5 | Citrate 10 mM/SolutolHS15 | 6.0 |
| LA_09_16_6 | Citrate 10 mM/SDS | 6.0 |
| LA_09_17 | Acetate 10 mM | 5.5 |
| LA_09_17_1 | Acetate 10 mM + PS20 | 5.5 |
| LA_09_17_2 | Acetate 10 mM + PS80 | 5.5 |
| LA_09_17_3 | Acetate 10 mM + Lutrol F68 | 5.5 |
| LA_09_17_4 | Acetate 10 mM + Cremophor R40 | 5.5 |
| LA_09_17_5 | Acetate 10 mM + Solutol HS15 | 5.5 |
| LA_09_17_6 | Acetate 10 mM + SDS | 5.5 |
| LA_09_18 | Succinate 10 mM | 5.0 |
| LA_09_18_1 | Succinate 10 mM + PS20 | 5.0 |
| LA_09_18_2 | Succinate 10 mM + PS80 | 5.0 |
| LA_09_18_3 | Succinate 10 mM + Lutrol F68 | 5.0 |
| LA_09_18_4 | Succinate 10 mM + Cremophor | 5.0 |
| LA_09_18_5 | Succinate 10 mM + Solutol HS15 | 5.0 |
| LA_09_19 | Histidine 10 mM | 5.5 |
| LA_09_19_1 | Histidine 10 mM + PS20 | 5.5 |
| LA_09_19_2 | Histidine 10 mM + PS80 | 5.5 |
| LA_09_19_3 | Histidine 10 mM + Lutrol F68 | 5.5 |
| LA_09_19_4 | Histidine 10 mM + Cremophor | 5.5 |
| LA_09_19_5 | Histidine 10 mM + Solutol HS15 | 5.5 |
| LA_09_20 | Arginine 10 mM | 6.0 |
| LA_09_20_1 | Arginine 10 mM + PS20 | 6.0 |
| LA_09_20_2 | Arginine 10 mM + PS80 | 6.0 |
| LA_09_20_3 | Arginine 10 mM + Lutrol F68 | 6.0 |
| LA_09_20_4 | Arginine 10 mM + Cremophor | 6.0 |
| LA_09_20_5 | Arginine 10 mM + Solutol HS15 | 6.0 |
| LA_09_21 | Histidine 10 mM + PS20 | 5.5 |
| LA_09_22 | PBS 155 mM | 7.2 |
| LA_09_22_1 | PBS 155 mM | 7.2 |
| LA_09_22_2 | PBS 155 mM + NaCl | 7.2 |
| LA_09_22_3 | PBS 155 mM + MgCl$_2$ | 7.2 |
| LA_09_22_4 | PBS 155 mM + CaCl$_2$ | 7.2 |
| LA_09_22_5 | PBS 155 mM + Mannitol | 7.2 |
| LA_09_22_6 | PBS 155 mM + Maltose | 7.2 |
| LA_09_22_7 | PBS 155 mM + Trehalose | 7.2 |
| LA_09_22_8 | PBS 155 mM + Sucrose | 7.2 |
| LA_09_22_9 | PBS 155 mM + Dextran40 | 7.2 |
| LA_09_22_10 | PBS 155 mM + Benzyl alcohol | 7.2 |
| LA_09_22_11 | PBS 155 mM + Arginine | 7.2 |
| LA_09_22_12 | PBS 155 mM + Lysine | 7.2 |
| LA_09_23 | Citrate 10 mM (=LA_09_16) | 6.0 |
| LA_09_23_1 | Citrate 10 mM | 6.0 |
| LA_09_23_2 | Citrate 10 mM + NaCl | 6.0 |
| LA_09_23_3 | Citrate 10 mM + MgCl$_2$ | 6.0 |
| LA_09_23_4 | Citrate 10 mM + Mannitol | 6.0 |
| LA_09_23_5 | Citrate 10 mM + Maltose | 6.0 |
| LA_09_23_6 | Citrate 10 mM + Trehalose | 6.0 |
| LA_09_23_7 | Citrate 10 mM + Sucrose | 6.0 |
| LA_09_23_8 | Citrate 10 mM + Benzyl alcohol | 6.0 |
| LA_09_23_9 | Citrate 10 mM + Arginine | 6.0 |
| LA_09_23_10 | Citrate 10 mM + Lysine | 6.0 |
| LA_09_24 | Acetate 10 mM (=LA_09_17) | 5.5 |
| LA_09_24_1 | Acetate 10 mM | 5.5 |
| LA_09_24_2 | Acetate 10 mM + NaCl | 5.5 |
| LA_09_24_3 | Acetate 10 mM + MgCl$_2$ | 5.5 |
| LA_09_24_4 | Acetate 10 mM + Mannitol | 5.5 |
| LA_09_24_5 | Acetate 10 mM + Maltose | 5.5 |
| LA_09_24_6 | Acetate 10 mM + Trehalose | 5.5 |
| LA_09_24_7 | Acetate 10 mM + Sucrose | 5.5 |
| LA_09_24_8 | Acetate 10 mM + Benzyl alcohol | 5.5 |
| LA_09_24_9 | Acetate 10 mM + Arginine | 5.5 |
| LA_09_24_10 | Acetate 10 mM + Lysine | 5.5 |
| LA_09_25 | Histidine 10 mM (=LA_09_19) | 5.5 |
| LA_09_25_1 | Histidine 10 mM + NaCl 50 mM | 5.5 |
| LA_09_25_2 | Histidine 10 mM + MgCl$_2$ 50 mM | 5.5 |
| LA_09_25_3 | Histidine 10 mM + Mannitol 5% | 5.5 |

TABLE 24-continued

Summary of all formulations prepared and analyzed

| Sample number | Buffer | pH |
|---|---|---|
| LA_09_25_4 | Histidine 10 mM + Maltose 10% | 5.5 |
| LA_09_26_1 | Histidine 10 mM + PS20 (=LA_09_21) | 5.5 |
| LA_09_26_2 | Histidine 10 mM + PS20 + NaCl 50 mM | 5.5 |
| LA_09_26_3 | Histidine 10 mM + PS20 + MgC$_{l2}$ 50 mM | 5.5 |
| LA_09_26_4 | Histidine + PS20 + 5% Mannitol | 5.5 |
| LA_09_26_5 | Histidine + PS20 + 10% Maltose | 5.5 |
| LA_09_26_6 | Histidine + PS20 + 6% Trehalose | 5.5 |
| LA_09_26_7 | Histidine + PS20 + 5% Sucrose | 5.5 |
| LA_09_26_8 | Histidine + PS20 + 9 mg Benzyl alcohol | 5.5 |
| LA_09_26_9 | Histidine + PS20 + 20 mM Arginine-HCl | 5.5 |
| LA_09_26_10 | Histidine + PS20 + 20 mM Lysine | 5.5 |
| LA_09_27 | Citrate 10 mM + PS20 | 6.0 |
| LA_09_27_A | Citrate 10 mM + PS20 Prototype formulation | 6.0 |
| LA_09_27_B | Citrate 10 mM + PS20 Prototype formulation | 6.0 |
| LA_09_27_C | Citrate 10 mM + PS20 Prototype formulation | 6.0 |
| LA_09_27_D | Citrate 10 mM + PS20 Prototype formulation | 6.0 |
| LA_09_28 | Acetate 10 mM + PS20 | 5.5 |
| LA_09_28_A | Acetate 10 mM + PS20 Prototype formulation | 5.5 |
| LA_09_28_B | Acetate 10 mM + PS20 Prototype formulation | 5.5 |
| LA_09_28_C | Acetate 10 mM + PS20 Prototype formulation | 5.5 |
| LA_09_28_D | Acetate 10 mM + PS20 Prototype formulation | 5.5 |
| LA_09_29 | Histidine 10 mM + PS20 | 5.0 |
| LA_09_29_A | Histidine 10 mM + PS20 Prototype formulation | 5.0 |
| LA_09_29_B | Histidine 10 mM + PS20 Prototype formulation | 5.0 |
| LA_09_29_C | Histidine 10 mM + PS20 Prototype formulation | 5.0 |
| LA_09_29_D | Histidine 10 mM + PS20 Prototype formulation | 5.0 |

Example 10

Phosphate Buffer Formulation

The following will give an overview on results of the characterization of the Lead CXCR5 Antibody drug substance in phosphate buffer.

IEF

The pI (isoelectric point) of the Lead CXCR5 Antibody was theoretically calculated as 7.6, and confirmed by denaturized isoelectric focusing (pI of 7.6-8.4). See FIG. 11.

SDS-PAGE

Figure 12:
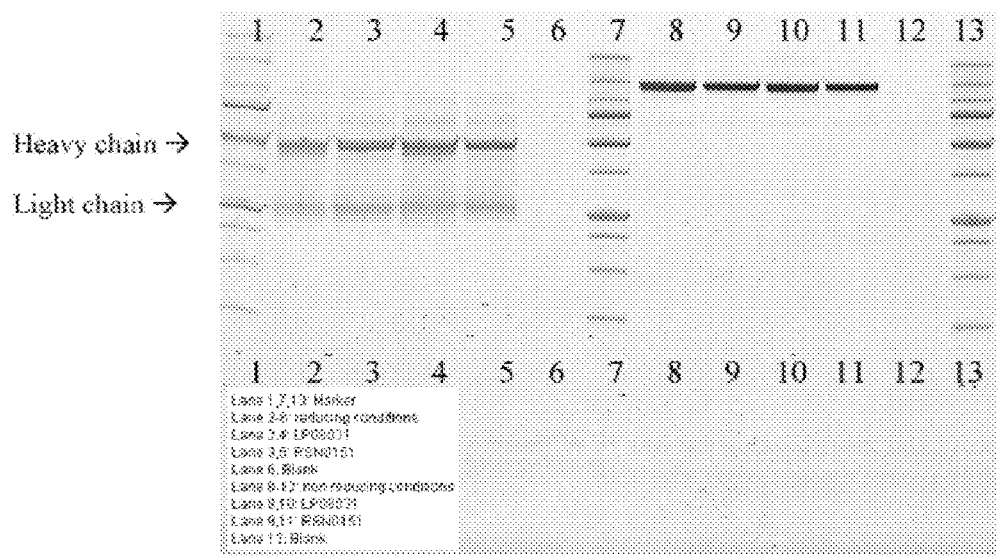
FIG. 12 is a picture of an SDS-PAGE gel that compared different drug substance batches under reducing and non-reducing conditions. The gel was also used to determine the molecular weight of the Lead CXCR5 Antibody, and the presence of any aggregates.

SDS-PAGE was used to determine the molecular weight of the antibody monomer, potential aggregates, or the presence of half-molecules. FIG. 12 showed an example of an SDS-PAGE gel to compare different drug substance batches under reducing and non-reducing conditions.

ELISA

Figure 13:
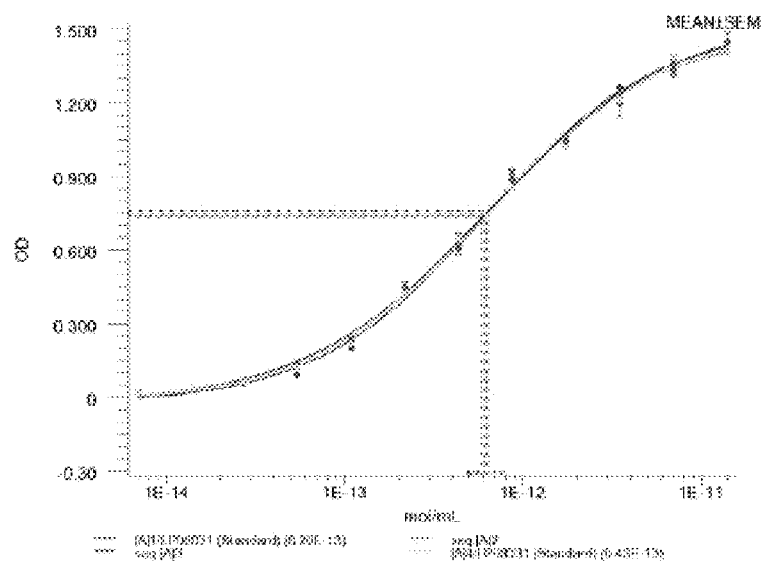
FIG. 13 is an ELISA graph that was used to determine antigen binding activity of the Lead CXCR5 Antibody to a 28mer peptide of the CXCR5 antigen.

FIG. 13 shows an example of an ELISA graph to determine antigen binding activity of the Lead Antibody.

SEC

Figure 14:
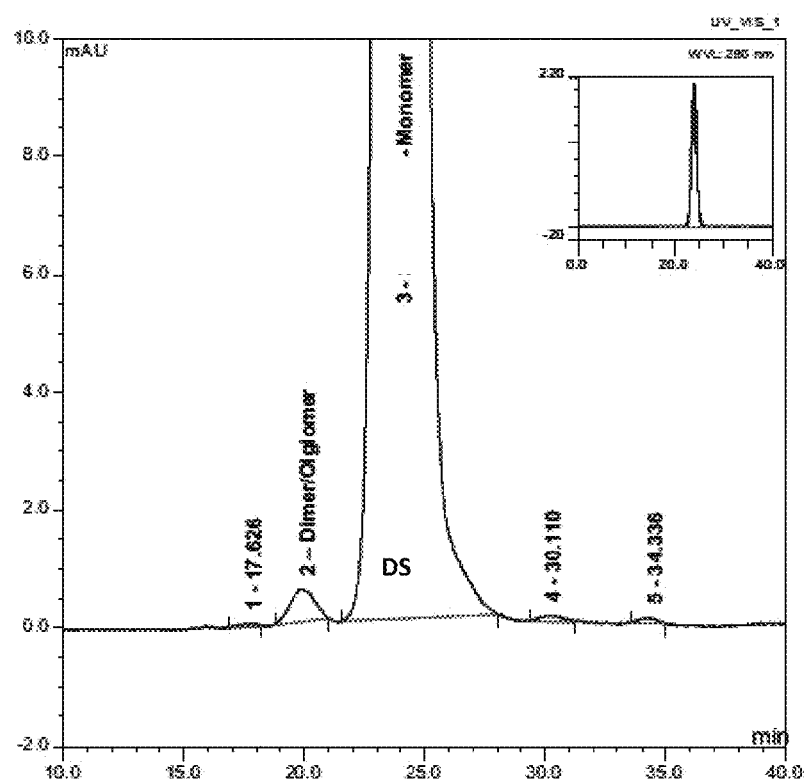
FIG. 14 is a SEC chromatogram of stressed Lead CXCR5 Antibody. SEC could detect high molecular weight proteins (HMWP), e.g., di-/oligomers or aggregates and low molecular weight proteins (LMWP) or degradation products. The Lead CXCR5 Antibody had a purity of 99% monomer content.

As shown in FIG. 14, size exclusion chromatography detected high molecular weight proteins (HMWP), e.g., di-/oligomers or aggregates and low molecular weight proteins (LMWPs) or degradation products. The Lead CXCR5 Antibody batch had a purity of 99% monomer content.

WCX

Figure 15:
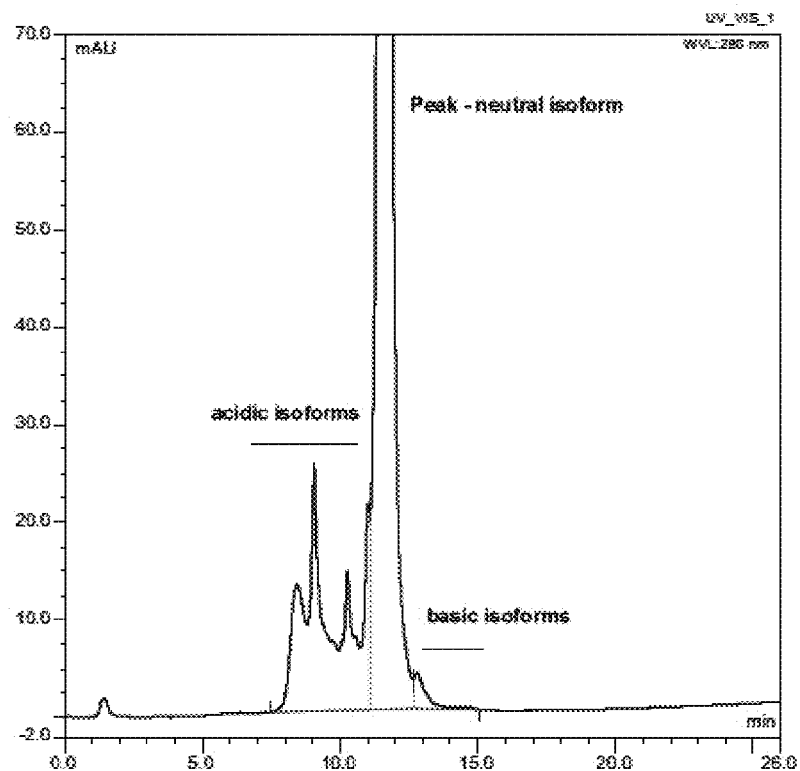
FIG. 15 is a WCX chromatogram that was used to determine acidic, neutral, and basic isoforms of the Lead CXCR5 Antibody. The Lead CXCR5 Antibody had a distribution of acidic/neutral/basic isoforms of 14/85/1%.

Weak cationic exchange chromatography for the Lead Antibody shows in FIG. 15, display charge heterogeneity. During stability studies, the arrangement of the acidic peaks changed and the percentage of basic isoforms increased. The Lead CXCR5 Antibody had a distribution of acidic/neutral/basic isoforms of 14/85/1%.

Dynamic Light Scattering

Figure 16:
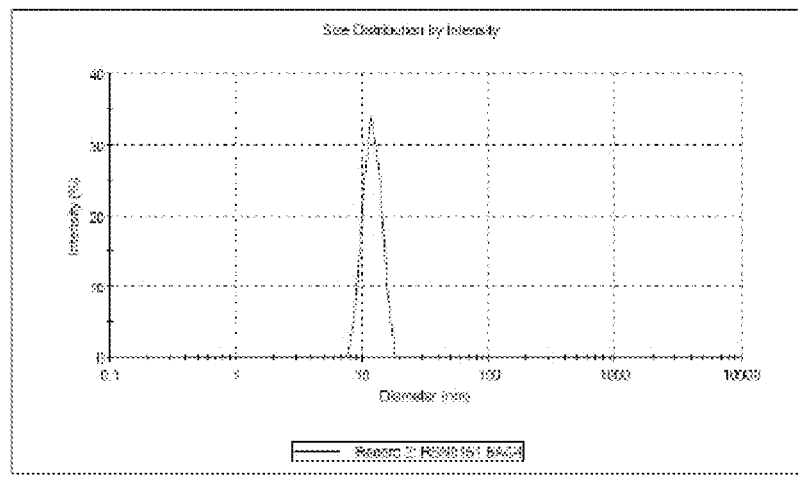
FIG. 16 is a DLS measurement that was used to determine the hydrodynamic diameter of the antibody monomer and potential soluble aggregates.

As shown in FIG. 16, DLS was used to determine the hydrodynamic diameter of the antibody monomer and potential soluble aggregates.

In conclusion, the Lead Antibody might be stable in PBS, but aggregate formation is easy to generate by shear forces or light stress.

In addition, the pH of PBS is close to the pI of the Lead CXCR5 Antibody. Therefore, the formulation should be formulated at least one pH step below the pI.

Table 25 shows 3 the results of a three month stability study for the Lead CXCR5 Antibody. The Lead Antibody was stored at different temperatures and analyzed after one and three months.

TABLE 25

Analytical results of a 3-month stability study of DS

| | | | | | 5° C. | | −20° C. | | 25° C. | |
|---|---|---|---|---|---|---|---|---|---|---|
| | Method | Test item | Spec for release | Release | 1 month | 3 months | 1 month | 3 months | 1 month | 3 months |
| Appearance | Color | | Monitoring | >B9, >BY7 | >B9, >BY7 | >B9, >BY7 | >B9, >BY7 | >B9, >BY7 | >B9, >BY7 | >B9, >BY7 |
| | Clarity | | Monitoring | <I | <I | <I | <I | <I | <I | <I |
| Identity | IEF | | Conform | 8.30-7.50* | 8.31-7.60 | 8.31-7.51 | 8.30-7.63 | 8.34-7.57 | 8.30-7.58 | 8.31-7.61 |
| Potency | UV | mg/mL | Monitoring | 5.13 | 5.26 | 5.18 | 5.14 | 5.16 | 5.20 | 5.11 |
| | SEC | Monomer (mg/mL) | Monitoring | 5.34 | 5.04 | 5.13 | 5.02 | 5.11 | 5.00 | 5.08 |
| | Ag-ELISA | EC50% | 50-200 | 100 | 83 | 112 | 132 | 93 | 106 | 108 |
| Purity | SDS-PAGE reduced | kD values gel pattern | Monitoring Monitoring | 46.8/26.1 does not conform | 47.4/25.5 No changes | 47.4/25.0 No changes | 46.8/25.2 No changes | 47.9/25.2 No changes | 46.5/25.7 No changes | 47.2/25.2 No changes |
| | SDS-PAGE non-reduced | kD values gel pattern Half-molecules | Monitoring Monitoring | 134.6 conforms <5% | 128.0 No changes <5% | 147.5 No changes <5% | 128.4 No changes <5% | 145.9 No changes <5% | 131.3 No changes <5% | 147.1 No changes <5% |
| | Western Blot reduced | gel pattern | | does not conform | No changes | No changes | No changes | No changes | No changes | Additional bands (155.0 kD, 134.4 kD) |

TABLE 25-continued

Analytical results of a 3-month stability study of DS

| | | | | | 5° C. | | −20° C. | | 25° C. | |
|---|---|---|---|---|---|---|---|---|---|---|
| | | Test | Spec for | | 1 | 3 | 1 | 3 | 1 | 3 |
| | Method | item | release | Release | month | months | month | months | month | months |
| | Western Blot non-reduced | gel pattern | | does not conform | No changes | No changes | No changes | No changes | No changes | Additional bands (117.2 kD, 33.0 kD) |
| | SDS-PAGE reduced silver | gel pattern | | does not conform | No changes | No changes | No changes | No changes | No changes | No changes |
| | SDS-PAGE non-reduced silver | gel pattern | | conforms | No changes | No changes | No changes | No changes | No changes | Additional band (122.5 kD) |
| | SEC | % Monomer | ≥90 | 99.8 | 99.8 | 99.7 | 99.7 | 99.7 | 99.5 | 99.4 |
| Charge hetero-geneity | WCX | (acidic/ neutral/ basic) (%) | | 13.9/ 84.9/1.2 | 13.2/ 86.2/0.6 | 13.1/ 86.1/0.8 | 13.1/ 86.1/0.9 | 13.3/ 85.5/1.2 | 13.0/ 85.8/1.3 | 12.6/ 85.2/2.2 |
| pH | pH | pH | 6.5-8.0 | 7.2 | 7.2 | 7.2 | 7.2 | 7.2 | 7.2 | 7.2 |

*Initially reported pH 8.61-7.66

The 3-month stability data with the Lead CXCR5 Antibody buffered in PBS indicated no relevant changes at +5° C. and −20° C. storage. After 3 months at accelerated conditions (+25° C.), significant changes could be observed. Additional bands, as analyzed by SDS-PAGE and Western-Blot analysis, showed an increase of basic- and decrease of acidic-isoforms, suggesting degradation products.

Example 11

Buffer and pH Optimization

PBS pH 7.2 showed aggregation and degradation after freeze/thaw cycles and after freezing storage. Thus, it was necessary to find another buffer and a better pH range. In addition, PBS is not suitable for freezing of the solutions, as a pH shift occurs.

30 different buffers with various pH and buffer systems were used to select the best pH range. These experiments were run in a very small scale, and analyzed intensively.
Best Buffer & pH Selection Screening—Small Scale (Yield 5 mL)

The analytical results are summarized in Table 39, Table 40, Table 41, and Table 42.

Figure 17:
FIG. 17 is a picture of the Lead CXCR5 Antibody in acetate buffer pH 5.0 (left) and pH 5.5 (right); each v. WFI (water for injection) and after thermal stress. This figure shows that acetate is a suitable buffer system.
Figure 18:
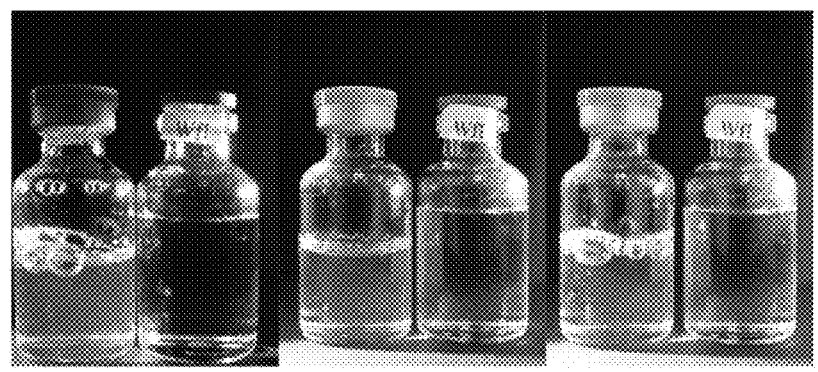
FIG. 18 is a picture of the Lead CXCR5 Antibody in histidine buffer pH 6.0 (left), pH 5.5 (middle), and pH 5.0 (right); each v. WFI (water for injection) and after thermal stress. This figure shows that histidine is a suitable buffer.
Figure 19:
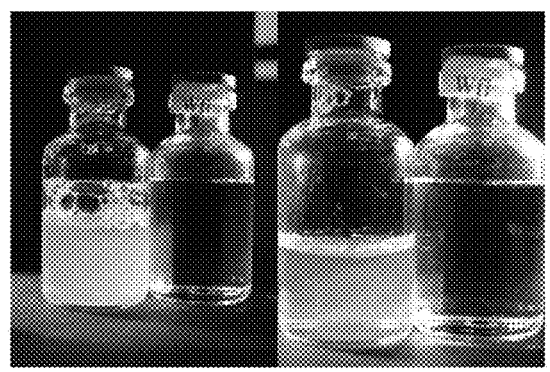
FIG. 19 is a picture of the Lead CXCR5 Antibody in TRIS buffer pH 7.5 after UF/DF (left) and after filtration (right); each v. WFI (water for injection) and after thermal stress. This figure shows that TRIS is an incompatible buffer system.

In FIG. 17 and FIG. 18, the appearance of two suitable buffer systems (acetate & histidine) after thermal stress are shown. pH 5.5 in acetate and pH 5.0 in histidine were chosen for further evaluation. By way of contrast, in FIG. 19, the appearance of an incompatible buffer system (TRIS buffer) is shown.

The following buffers were selected to test in larger UF/DF scale:
  Citrate 10 mM, pH 6
  Acetate 10 mM, pH 5.5
  Succinate 10 mM, pH 5
  Histidine 10 mM, pH 5
  Arginine 10 mM, pH 6
Best Buffer & pH Selection Screening—Large Scale (Yield ~20 g)

After the best buffers and pH could be selected, a larger quantity of Lead CXCR5 Antibody in each buffer system was prepared by using the Sartorius Vivaflow system. Each batch was analytically tested and the results are described below.

Citrate Buffer 10 mM, pH 6 (LA_09_016)

The UF/DF step worked well and only a slightly turbid solution was obtained; no difficulties during sterile filtration were encountered. No increase of hydrodynamic diameter, as analyzed by DLS, was seen.

Figure 20:
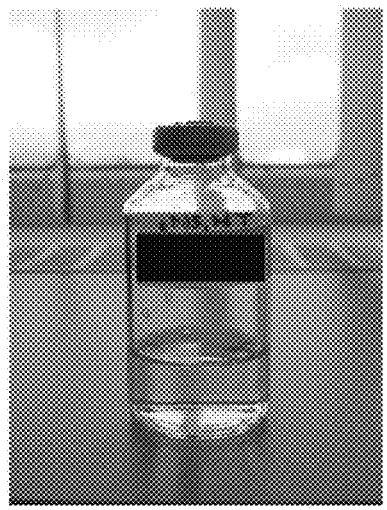
FIG. 20 is a picture of the Lead CXCR5 Antibody in citrate buffer pH 6.0 after UF/DF and filtration.

The analytical results indicated no increase in dimers, and no changes in basic or acidic isoforms compared to the Lead CXCR5 Antibody batch material. See Table 26 and FIG. 20.

TABLE 26

Analytical results of Lead Antibody in citrate buffer pH 6

| Sample | pH | Appearance | Conc. UV | DLS | Yield | Tm |
|---|---|---|---|---|---|---|
| LA_09_016 | 6.0 | Slightly turbid after UF/DF, Clear after filtration | 18.2 mg/mL | 12.73 nm | 20.8 g | 79.4° C. |

Acetate Buffer 10 mM, pH 5.5 (LA_09_017)

The UF/DF step worked well, but a turbid solution was obtained; filter blockage during sterile filtration.

Figure 21:
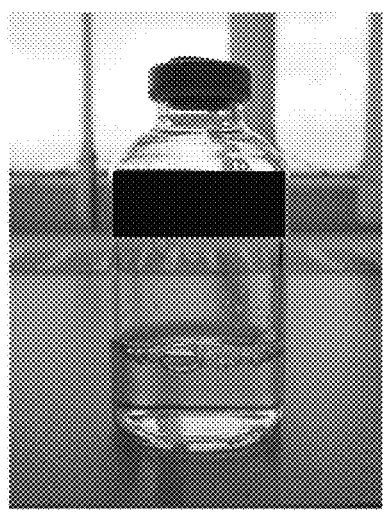
FIG. 21 is a picture of the Lead CXCR5 Antibody in acetate buffer pH 5.5 after UF/DF and filtration.

The analytical results indicated no increase in dimers, and no changes in basic or acidic isoforms compared to the Lead CXCR5 Antibody batch material. See Table 27 and FIG. 21.

TABLE 27

Analytical results of Lead Antibody in acetate buffer pH 5.5

| Sample | pH | Appearance | Conc. UV | DLS | Yield | Tm |
|---|---|---|---|---|---|---|
| LA_09_017 | 5.5 | Slightly turbid after UF/DF, Clear after filtration | 17.8 mg/mL | 12.22 nm | 20.4 g | 77.7° C. |

Succinate Buffer 10 mM, pH 5 (LA_09_018)

The sterile filtration after UF/DF was difficult to perform because of filter blockage. The yield of 12 g was very low.

Figure 22:
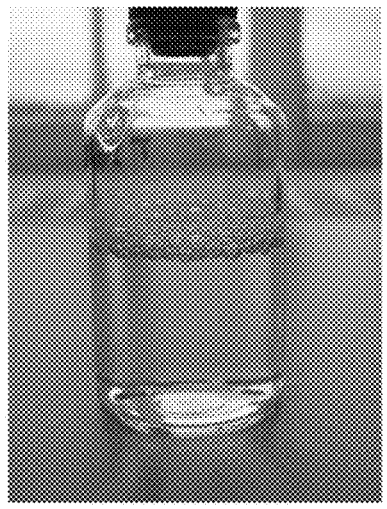
FIG. 22 is a picture of the Lead CXCR5 Antibody in succinate buffer pH 5.0 after UF/DF and filtration.

The analytical results indicated a slight decrease in dimers, and no changes in basic or acidic isoforms compared to the Lead CXCR5 Antibody batch material. After mechanical stress, the dimer concentration increased slightly, and the acidic isoforms peak in WCX decreased as the basic isoforms increased. See Table 28 and FIG. 22.

TABLE 28

Analytical results of Lead Antibody in succinate buffer pH 5

| Sample | pH | Appearance | Conc. UV | Yield | DLS | Tm |
|---|---|---|---|---|---|---|
| LA_09_018 | 4.9 | Slightly turbid after UF/DF, Clear after filtration | 22.4 mg/mL | 12 g | 12.82 nm | 73.3° C. |

Histidine Buffer 10 mM, pH 5 (LA_09_019)

The sterile filtration after UF/DF was very difficult to perform because of filter blockage. The yield of 10.5 g was very low.

Figure 23:
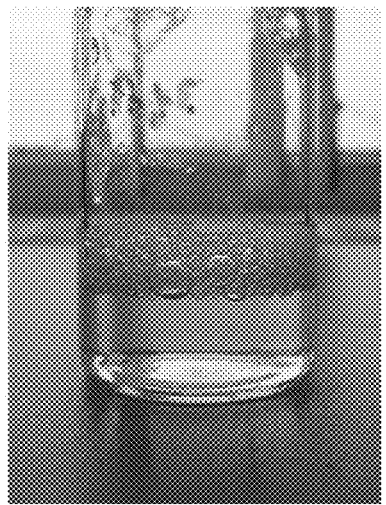
FIG. 23 is a picture of the Lead CXCR5 Antibody in histidine buffer pH 5.0 after UF/DF and filtration.

The analytical results indicated a slight decrease in dimers, and no changes in basic or acidic isoforms compared to the Lead CXCR5 Antibody batch material. After mechanical stress, the dimer concentration increased slightly and the acidic isoforms peak in WCX decreased as the basic isoforms increased. See Table 29 and FIG. 23.

TABLE 29

Analytical results of Lead Antibody in histidine buffer pH 5

| Sample | pH | Appearance | Conc. UV | Yield | DLS | Tm |
|---|---|---|---|---|---|---|
| LA_09_019 | 5.4 | Slightly turbid after UF/DF, Clear after filtration | 23.4 mg/mL | 10.5 g | 11.32 nm | nd |

Arginine Buffer 10 mM, pH 6 (LA_09_020)

The sterile filtration after UF/DF was very difficult to perform. DLS showed a brought peak with a hydrodynamic diameter of 21.08 nm, which might indicate dimer formation.

Figure 24:
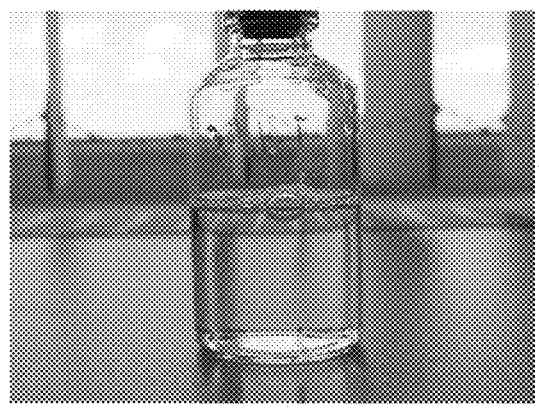
FIG. 24 is a picture of the Lead CXCR5 Antibody in arginine buffer pH 6.0 after UF/DF and filtration.

The analytical results indicated a slight increase in dimers from 0.29% in the Lead CXCR5 Antibody batch to 0.49% in arginine. After mechanical stress, 0.61% dimers were found and an increase in basic isoforms in WCX was detected. See Table 30 and FIG. 24.

TABLE 30

Analytical results of Lead Antibody in arginine buffer pH 5

| Sample | pH | Appearance | Conc. UV | Yield | DLS | Tm |
|---|---|---|---|---|---|---|
| LA_09_020 | 6.2 | Slightly turbid after UF/DF, Clear after filtration | 22.5 mg/mL | 15.3 g | 21.08 nm | nd |

In conclusion, three of the five batches are compatible with Lead CXCR5 Antibody in 20 mg/ml concentration:
Citrate pH 6.0
Acetate pH 5.5
Histidine pH 5.0
These batches were characterized in terms compatibility and stability more in detail.

Example 12

Compatibility with Excipients

All the above mentioned batches were used for compatibility studies with surfactants. Compatibility studies were performed with Lead CXCR5 Antibody and four selected buffers. Succinate pH 5.0 and arginine pH 6.0 were not tested with excipients anymore, as these buffers were not compatible with the Lead CXCR5 Antibody. Excipients were classified as follows:
Surfactants
Sugars
Salts
Others (amino acids, preservative)
Mechanical stress (agitator speed 350/min, 2.5 h, room temperature) was applied to test the effect of surfactants, and thermal stress (+40° C., one week) was used to test all other excipients.
Surfactants Orientating studies on selection of type of surfactants (LA_08_001) and surfactant concentration (LA_09_003; 0.01%, 0.05%, and 0.1%) indicated that a concentration of 0.01% was sufficient to prevent visible aggregates. The following surfactants were not suitable for the Lead CXCR5 Antibody: PVP K12 and K17, as both showed turbidity before mechanical stress was applied. Additionally, it was shown that ionic surfactants such as sodium dodecyl sulfate were not compatible with Lead CXCR5 Antibody protein solutions.

Figure 25:
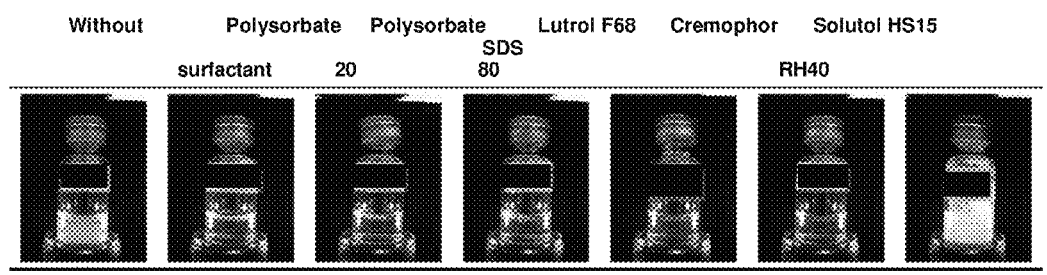
FIG. 25 is a picture of the appearance of Lead CXCR5 Antibody LA_09_016 solutions with different surfactants (without surfactant, polysorbate 20, polysorbate 80, Lutrol F68, Cremophor RH40, Solutol HS15, and SDS) after mechanical stress (350 rpm, 2.5 h, RT).

As an example, FIG. 25 shows the appearance of different citrate buffered solution with various surfactants after mechanical stress, and in comparison to a solution without any surfactant. Analytical results are collected in Table 43 and Table 44.

Other Excipients

After thermal stress of +40° C. for one week and analytical determination, a selection of compatible excipients with Lead CXCR5 Antibody in different buffer systems could be given.

Some excipients could not be tested in all four buffer systems, as there was only little sample volume available.

After reviewing all analytical data, the excipients in Table 31 were identified to be compatible with the Lead CXCR5 Antibody. These excipients did not show a significant increase in dimers, HMWPs or basic isoforms analyzed by SEC and WCX.

All hydrodynamic diameter measurements were indicating a sharp monomer peak and the Tm of the suitable excipients was not decreasing compared to Lead CXCR5 Antibody in the respective buffer system. All analytical data were summarized in Table 45, Table 46, Table 47 and Table 48.

TABLE 31

Compatibility of all tested excipients in the different buffer systems

| | PBS pH 7.2 | Citrate pH 6.0 | Acetate pH 5.5 | Histidine pH 5.0 |
|---|---|---|---|---|
| NaCl | X | X | X | |
| MgCl$_2$ | X | X | X | X |
| CaCl$_2$ | X | Nd | Nd | Nd |
| Mannitol | | X | X | X |
| Maltose | | | | |
| Trehalose | | X | X | Nd |
| Sucrose | X | X | X | Nd |
| Dextran | | Nd | Nd | Nd |
| Benzyl alcohol | | | | Nd |
| Arginine-HCl | X | X | X | Nd |
| Lysine | | | X | Nd |

In conclusion, compatibility studies with surfactants show clearly that polysorbate 20 is suited for all selected buffers in combination with the Lead CXCR5 Antibody at 20 mg/mL. The surfactant prevents particle formation during mechanical stress. Nearly all other surfactants led to an increase of HMWPs.

The following excipients were selected to formulate the different prototype formulations: NaCl, Trehalose (sucrose is more or less comparable to trehalose in terms of stability), and Arginine-HCl.

3-Months Prototype Stability Study

To support the formulation development of the Lead CXCR5 Antibody, twelve different prototype formulations were manufactured and put on stability at different conditions (−20° C., +5° C. and +40° C.) for three months.

Three different buffer systems were selected based on the before described buffer, pH and excipients screening.

Citrate pH 6.0 (formulation number LA_09_027), acetate pH 5.5 (LA_09_028), and histidine pH 5.0 (LA_09_029) were used as 10 mM buffer solutions with 20 mg/mL Lead Antibody and four different excipient combinations (Table 32).

These four excipients showed promising results after the excipient screening. NaCl was selected to adjust the osmolarity, trehalose was chosen for tonicity adjustment and to have a sugar for a lyophilization option, if needed. Additionally trehalose can stabilize the antibody, and arginine-HCl was selected as a stabilizer as well. Polysorbate 20 was found to be helpful to prevent aggregation during mechanical stress.

The following paragraphs show selected data that were compiled during the stability study to select the best buffer system and the best excipients for formulation development. In Table 33 all storage conditions, time points and analytical methods were collected.

Unfortunately, the 3 month stability data of the Lead CXCR5 Antibody in PBS buffer was not comparable to the prototype stability due to batch differences and due to different accelerated conditions.

Size Exclusion Chromatography (SEC)

Figure 26:
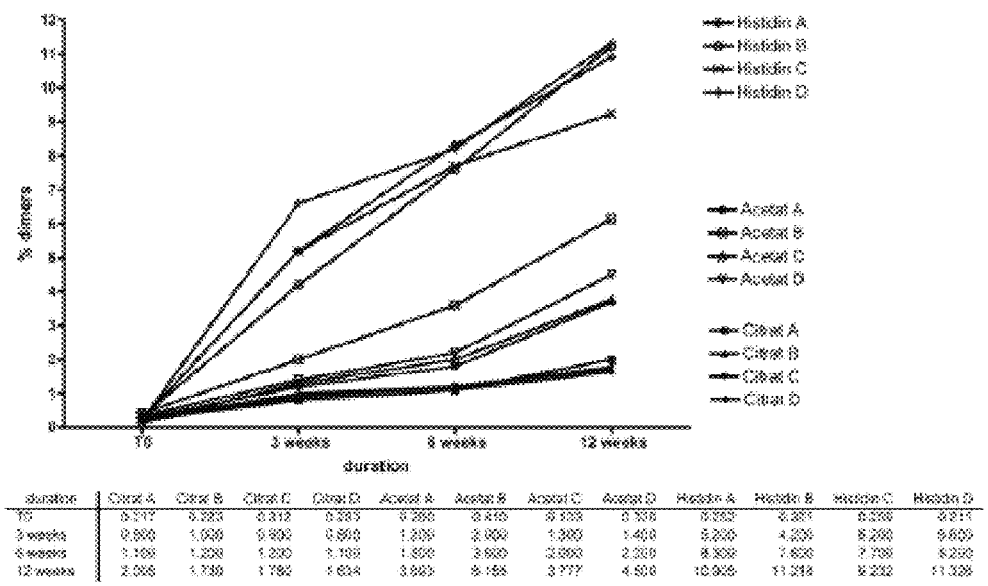
FIG. 26 is a graph that shows an increase of dimers under accelerated conditions, as analyzed by SEC. An increase of dimer formation up to 10% after three months of storage in all four histidine formulation can be seen. Acetate formulations showed an increase of dimer content up to 6%. In all four citrate formulations, the dimer concentration was below 2%, even after three months at +40° C.

In FIG. 26, an increase of dimer formation up to 10% after three months of storage in all four histidine formulations can be clearly seen. Acetate formulations showed an increase of dimer content up to 6%. In all four citrate formulations, the dimer concentration was below 2%, even after three months at +40° C.

Weak Cationic Exchange Chromatography (WCX)

As the determination of neutral, basic, and acidic isoforms is a good indicator for the stability of different formulations, theses methods were used to amend the SEC data.

Figure 27:
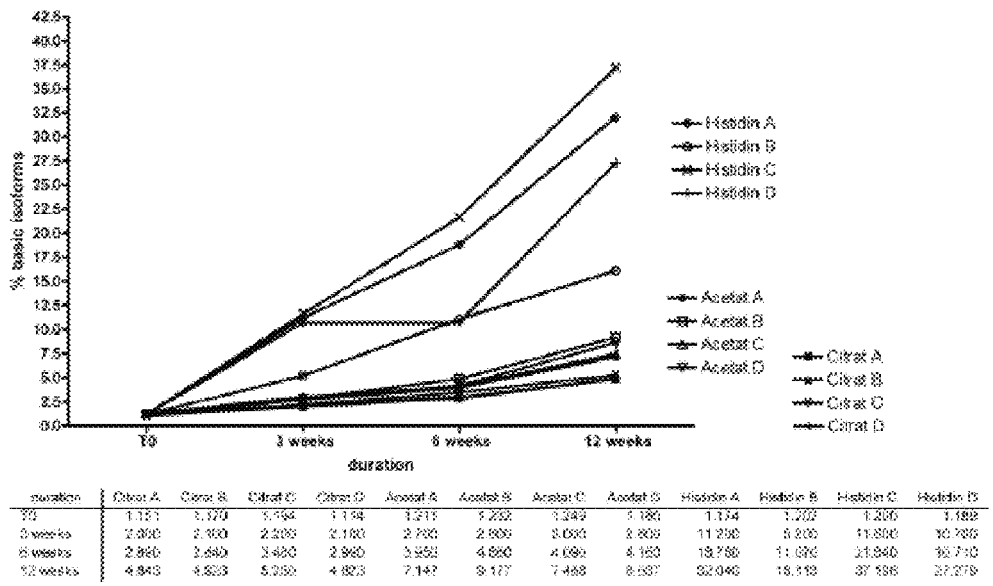
FIG. 27 is a graph showing an increase of basic isoforms under accelerated conditions, as analyzed by WCX. Histidine is worse for Lead CXCR5 Antibody stability under accelerated conditions. A slight increase of basic isoforms can be noticed for all four acetate formulations. Interestingly, it was not possible to discriminate between the four citrate formulations.
Figure 28:
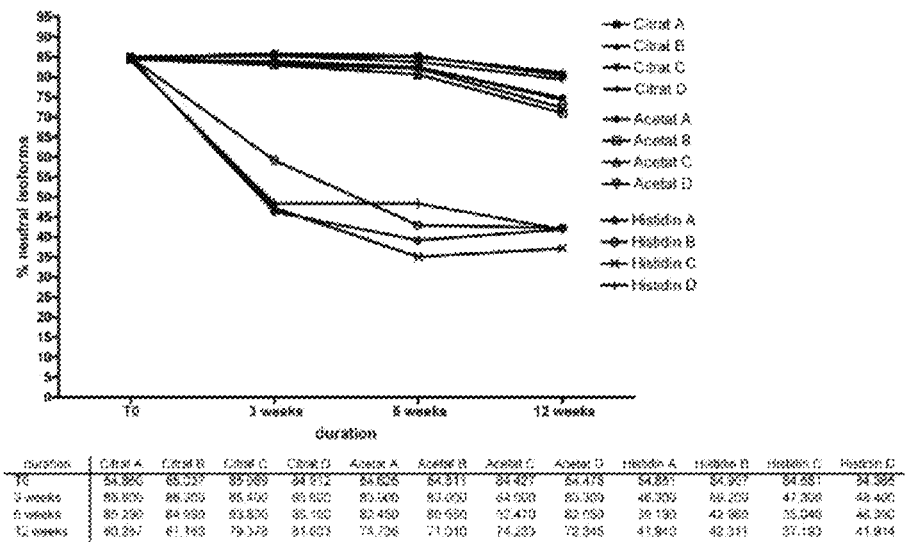
FIG. 28 is a graph showing a decrease of neutral isoforms under accelerated conditions, as analyzed by WCX. This figure shows a strong decrease in neutral isoforms for the histidine formulations. A slight decrease was seen in acetate. Citrate was affected the least.

In FIG. 27 it can be seen again that histidine is worse for the Lead CXCR5 Antibody stability under accelerated conditions. A slight increase of basic isoforms can be noticed for all four acetate formulations, but interestingly for citrate formulations, discrimination between the four formulations is not possible here. In addition, FIG. 28 shows a strong decrease in neutral isoforms for the histidine formulations, and a slight decrease in acetate. Again, the Lead CXCR5 Antibody in citrate is affected the least.

SDS-Page

The results of SDS-PAGE measurements can be found in the result tables in the appendix. See Tables 36-60.

Unfolding Temperature (Tm)

The unfolding temperature can be used to predict the stability of different formulations and was measured here with the Microcal equipment. The higher the Tm, the more promising the formulations were. Precision of the Tm measurements were +/−0.4° C.

Between citrate and acetate formulations, nearly no differences between Tm at T0 were noticed. In addition, formulations A, B, and D did have a slightly higher Tm, compared to C. The formulations A, B, and D all contain trehalose.

Histidine formulations did have a significantly lower Tm in all cases.

TABLE 32

Compositions of four different formulation options

| Formulation | NaCl | α,α-Trehalose* H$_2$O | Arginine | Polysorbate 20 |
|---|---|---|---|---|
| A | 3 mg | 25 mg | 20 mM | 10 mg |
| B |  | 50 mg |  | 10 mg |
| C | 6 mg |  | 20 mM | 10 mg |
| D |  | 50 mg | 20 mM | 10 mg |

TABLE 33

Storage conditions and time points for the analytical testing

| Storage conditions | T0 | T 21 days | T 6 weeks | T 3 months |
|---|---|---|---|---|
| −80° C. | SEC, WCX, SDS-PAGE, ELISA, Tm, pH, DLS, UV, Appearance, HIAC, Osmolarity |  | SEC, WCX, SDS-PAGE*, Tm, pH, DLS, UV |  |
| −20° C. |  | SEC, WCX, SDS-PAGE*, Tm, pH, DLS, UV | SEC, WCX, SDS-PAGE*, Tm, pH, DLS, UV | SEC, WCX, SDS-PAGE*, Tm, pH, DLS UV, Appearance |
| +5° C. |  | SEC, WCX, SDS-PAGE*, Tm, pH, DLS, UV, HIAC | SEC, WCX SDS-PAGE, Tm, pH, DLS, UV | SEC, WCX, SDS-PAGE*, Tm, pH, DLS, UV, Appearance |
| +40° C. |  | SEC, WCX, SDS-PAGE*, Tm, pH, DLS, UV | SEC, WCX, SDS-PAGE*, Tm, pH, DLS, UV | SEC, WCX, SDS-PAGE*, Tm, pH, DLS, UV |

*if reasonable

TABLE 34

Unfolding temperatures at T$_0$

| Formulation | LA_09_027 | LA_09_028 | LA_09_29 |
|---|---|---|---|
| A | 81.4° C. | 81.1° C. | 79.4° C. |
| B | 81.5° C. | 81.6° C. | 81.0° C. |
| C | 80.7° C. | 80.5° C. | 78.9° C. |
| D | 81.6° C. | 81.7° C. | 80.7° C. | pH

As the pH is of major interest and importance for the stability of an antibody solution, the pH was monitored. The following figures show the delta pH between T0, T1, T2, and T3 at accelerated storage conditions.

Figure 29:
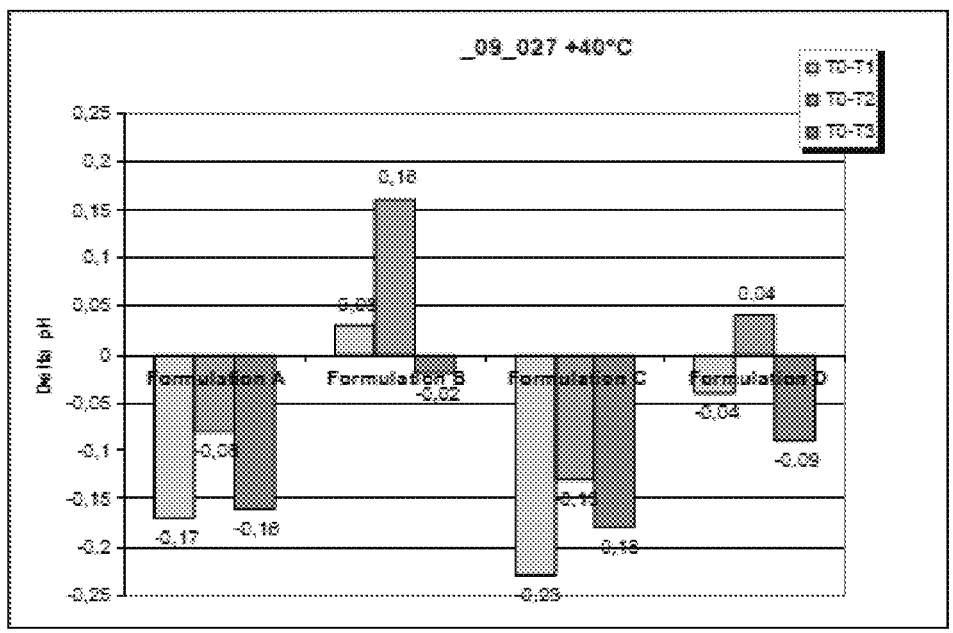
FIG. 29 shows the delta pH of all four formulations (A-D) in citrate buffer at accelerated conditions. The most pH stabilizing formulations are the citrate buffered, and especially formulation B and D.
Figure 30:
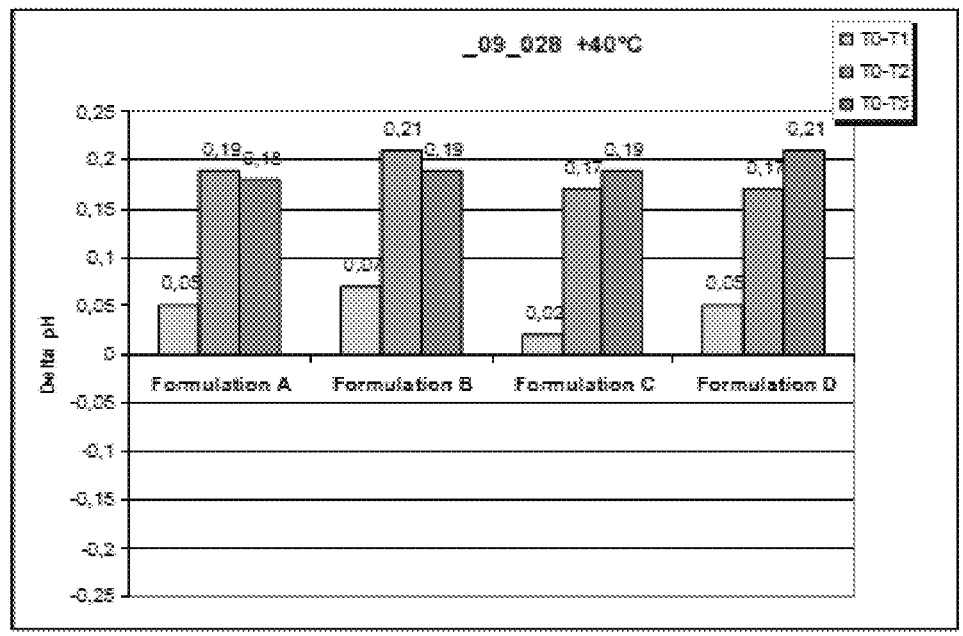
FIG. 30 shows the delta pH of all four formulations (A-D) in acetate buffer at accelerated conditions. In acetate buffered solutions of the Lead CXCR5 Antibody, the pH was shifted towards higher value.
Figure 31:
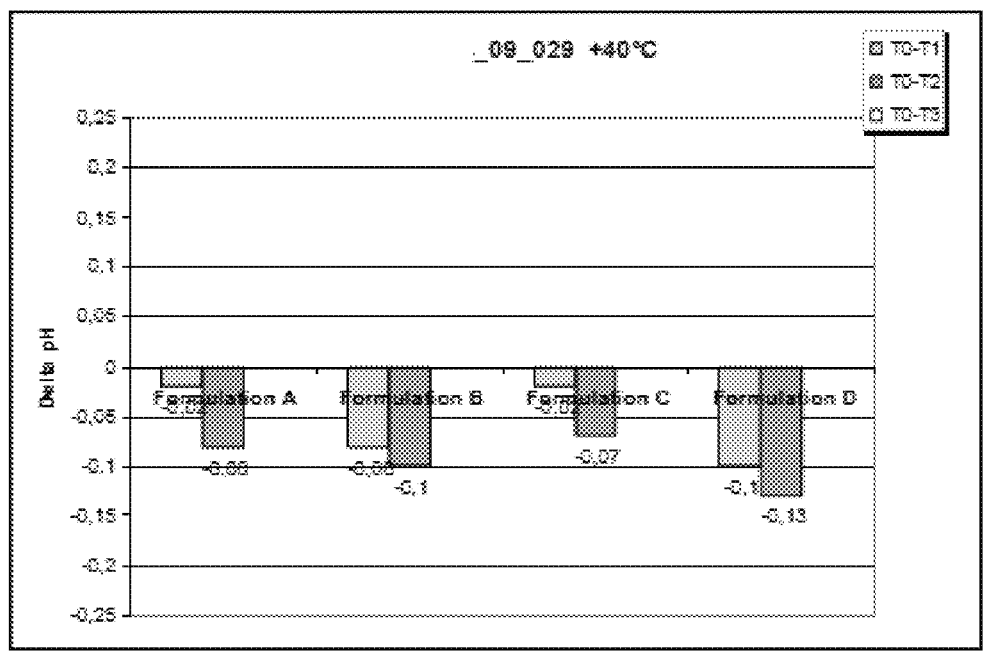
FIG. 31 shows the delta pH of all four formulations (A-D) in histidine buffer at accelerated conditions. In histidine buffered solutions of the Lead CXCR5 Antibody, the pH was slightly decreasing.

The most pH stabilizing formulations are the citrate buffered, and especially formulations B and D (FIG. 29). In acetate buffered solutions of Lead CXCR5 Antibody, the pH was shifted towards higher values (FIG. 30). In histidine buffered solutions, the pH was slightly decreasing (FIG. 31).

DLS

The hydrodynamic diameter of the monomer and potential soluble aggregates were measured using dynamic light scattering.

Only after storage under accelerated conditions (+40° C.), soluble aggregates <200 nm could be seen. These aggregates mainly occurred in histidine buffered formulation LA_09_029 A, C, D after 3 weeks of storage.

Figure 32:
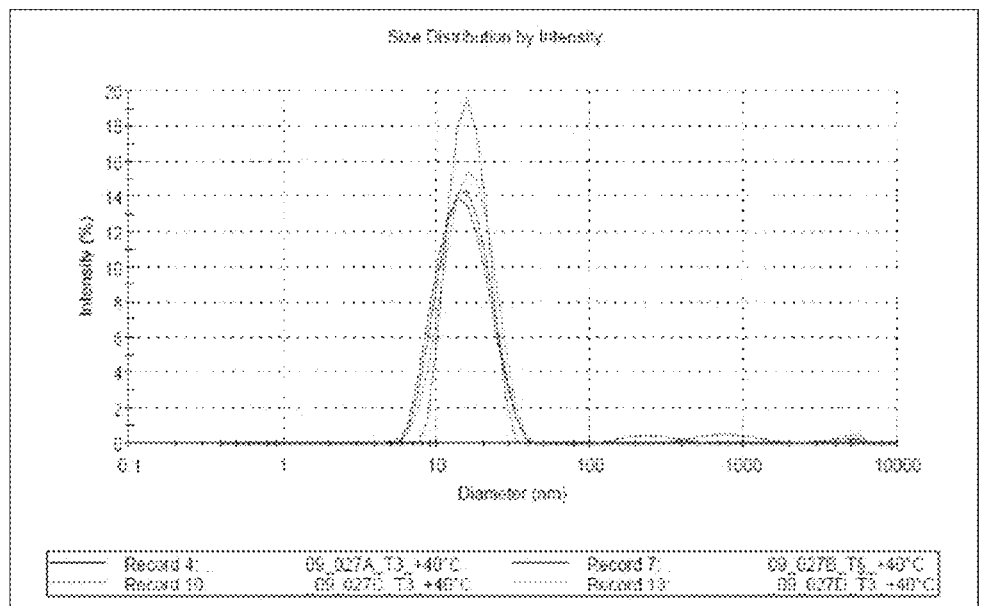
FIG. 32 is a graph showing the hydrodynamic diameter of CXCR5 LA_09_027 A-D after 3 months storage at 40° C. Citrate buffered formulations showed only slight aggregates after three weeks in formulation C, and after six weeks of storage in formulation A. Some aggregates could be detected after three months in formulation B as well. But, compared to acetate buffered formulations, the amount was very little.

Citrate buffered formulations showed only slightly aggregates (FIG. 32) after three weeks in formulation C, and after six weeks of storage in formulation A. Some aggregates could be detected after three months in formulation B as well. But, compared to acetate buffered formulations, the amount was very little.

Figure 33:
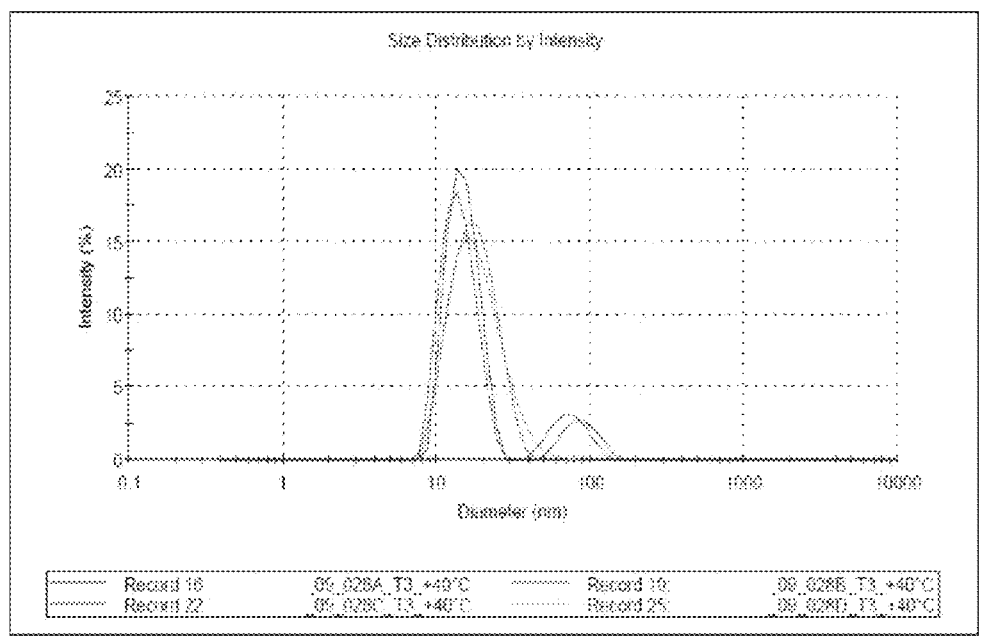
FIG. 33 is a graph showing the hydrodynamic diameter of CXCR5 LA_09_028 A-D after 3 months storage at 40° C. The acetate buffered formulation C showed some aggregates <200 nm after three weeks. Formulation A showed some aggregates after three months.

Acetate buffered formulation LA_09_028 C showed some aggregates <200 nm after three weeks, and after three months as well in formulation A. See FIG. 33.

UV

By monitoring the protein concentration by UV measurements, no significant differences between all time points, samples, and formulations were noticeable. As the sample volume was very little, the concentration was measured with a Nanodrop equipment. The results did vary +/−5%. For detailed information, see Tables Tables 49-60.

Appearance

After the three month storage period, all samples remained clear and colorless without any turbidity, even in histidine. This observation indicates as well, that all measured aggregates in DLS were soluble. Insoluble and sub visible aggregates could be detected by light blockage measurement by HIAC.

HIAC

Sub visible particles were detected at T0 and after three weeks of storage at +5° C. The formation of particles was mainly observed in acetate buffer. Interestingly, histidine showed good results for all four different formulations. In citrate formulations A, B, and C are good as well. As the level of particles >10 µm and >25 µm and the values in all formulations are far below the limits defined in Ph. Eur. and USP, particle formation is of no concern.

Osmolarity

The quantification of the excipients to adjust the osmolarity were done prior the manufacturing of the samples by calculation, as no samples volume was available for orientating experiments. Therefore, the osmolarity was lower then it should be (ideally between 280 and 320 mOsmol/kg)

Table 35. Further studies for better adjustment will be done during formulation optimization studies.

TABLE 35

Osmolarity at T0 for all prototype formulations.

| Formulation | LA_09_027 | LA_09_028 | LA_09_29 |
|---|---|---|---|
| A | 241 | 221 | 220 |
| B | 181 | 160 | 165 |
| C | 238 | 220 | 220 |
| D | 214 | 192 | 197 |

Conclusion

In conclusion, citrate buffer, acetate buffer, and histidine buffer showed no changes after storage at +5° C. and −20° C., and only a minor increase in degradation products was seen with acetate-buffer after 3 months.

The storage of Lead CXCR5 Antibody under accelerated conditions led to significant changes of the DS. While minor changes in citrate buffer were observed, acetate buffer showed a significant increase of degradation- and aggregation products and a decrease of neutral isoforms in acidic- or basic isoforms.

A tremendous effect on the Lead CXCR5 Antibody was observed under accelerated conditions (up to 29.6% high molecular weight proteins and up to 8.2% di-/oligomer and up to 1.3% low molecular weight proteins). Also, cationic exchange chromatography revealed a decrease of the neutral isoforms to 50%.

The target concentration of 20 mg/mL could be achieved with all tested buffers, e.g. citrate, acetate, and histidine.

The pH range of a stable DP could be defined as pH 5-6.5.

Two scale-up steps (4 mL/E 100 mL-1000 mL UF/DF) with three selected buffers were successfully performed.

The reduction of aggregate formation with 0.01% polysorbate 20 in all selected buffers after mechanical stress (agitator speed 350/min, 2.5 h, RT) was evaluated and analytically confirmed.

The absence or decrease of HMWPs could be observed, thus increasing filterability (0.22 µm) by adding 0.01% polysorbate 20 could be achieved.

The amount of dimers/oligomers was highly dependent on buffer and pH and was analyzed by using SEC, SDS-PAGE and DLS.

Characterization of Drug Substance

The Lead CXCR5 Antibody molecule is very stable in terms of degradation or half molecules formation, but it turned out during preformulation activities, that Lead CXCR5 Antibody dissolved in PBS at pH 7.2 does have an aggregation tendency. Therefore, this buffer is not suitable for long term stability. The formation of visible and sub-visible particles during storage or freeze/thaw cycles should be monitored carefully during formulation development and stability studies.

Best Buffer & pH Selection

After the best buffer and pH selection, citrate buffer 10 mM at pH 6.0 was identified to be suitable for 20 mg/mL Lead CXCR5 Antibody solutions. 10 mM histidine buffer pH 5 or 10 mM acetate buffer pH 5.5 could serve as backup options.

Compatibility Study with Excipients

The following excipients are recommended for prototype formulations:

Polysorbate 20
Trehalose/sucrose
NaCl
Arginine-HCl

The following excipients are not recommended for development:
Benzyl alcohol
Maltose
Mannitol
Dextran
Lysin-HCl Prototype Formulation 3-Months Stability Study Excellent stability of 20 mg/mL Lead CXCR5 Antibody in citrate buffer pH 6.0, acetate buffer pH 5.5, and histidine buffer pH 5.0 was seen at +5° C. and −20° C. after three months of storage. A slight degradation at +40° C. (<5% reduction of monomer content) was observed with citrate buffer, while acetate buffer showed low, but significant—and histidine buffer strong artefact increases.

All tested formulations showed significant reduction of particle formation during storage compared to the generic discovery formulation in PBS pH 7.2.

Thus, the recommendation of this preformulation study is to use 10 mM citrate buffer pH 6 for DS and DP of Lead CXCR5 Antibody. A sterile filtered buffered solution with 20 mg/mL Lead CXCR5 Antibody, and stability increasing excipients should be feasible with a storage recommendation at +5° C. in vials.

For tonicity adjustment trehalose and NaCl could be used and polysorbate 20 should be used to prevent the formation of aggregates.

The feasibility of UF/DF experiments to either change the buffer system and/or to increase the mAB concentration from 5 mg/mL to 20 mg/mL could be shown in different scales.

TABLE 36

Explanation of data assessment
Lead CXCR5 Antibody Preformulation Data Assessment

| | Process | | | | | T0 | | |
| --- | --- | --- | --- | --- | --- | --- | --- | --- |
| Assessment | Processability | Duration | Apperance | | | Ranking personal | | |
| in principle | small scale | small scale | clearity | particle | pH | assessment | DLS | UV |
| good | good | good | clear | no | ok | 0 | no aggregates no subvisible aggregates observed in DLS measurements | |
| | easy to handle, viscosity ok | <10 h @ +5° C. for 4 ml | no turbidity observed | no visible particles | if pH differes <0.3 from basic value in row C | not acceptable for further studies | | |
| medium | | | clear-turbid no clear assessment applicable | | | 0.5 not totally clear, if acceptable or not | | basic value measured at T0 |
| bad | bad | bad | turbid | yes | not ok | 1 | aggregates subvisible particles observed in DSL (in 0.22 μm filtered sample) | |
| | highly viscous, difficult to handle | >10 h @ +5° C. for 4 ml | strong turbidity observed | visible particles observed | if pH differes >0.31 from basic value in row C | buffer can be recommended for further studies | | |

| | | after 1 week at +40° C. | | | | | |
| --- | --- | --- | --- | --- | --- | --- | --- |
| Assessment | | Apperance | | | Ranking personal | | |
| in principle | clearity | particle | pH | | assessment | DLS | UV |
| good | clear | no | ok | | 0 | no aggregates no subvisible aggregates observed in DLS measurements | ok |
| | no turbidity observed | no visible particles | if pH differes <0.3 from basic value in row C | | not acceptable for further studies | | if value after thermal stress differs from basic value in row K <10% |
| medium | clear-turbid no clear assessment applicable | | | | 0.5 not totally clear, if acceptable or not | | |
| bad | turbid | yes | not ok | | 1 | aggregates subvisible particles | not ok |

TABLE 36-continued

Explanation of data assessment
Lead CXCR5 Antibody Preformulation Data Assessment

| strong turbidity observed | visible particles observed | if pH differes >0.31 from basic value in row C | buffer can be recommended for further studies | observed in DSL (in 0.22 µm filtered sample) | if value after thermal stress differs from basic value in row K <10% |
|---|---|---|---|---|---|

TABLE 37

Results of preliminary packaging material testing (data assessment)

| Buffer | Formulationnumber | Packaging material | Stress | pH | PSD DLS [nm] | UV [mg/mL] | ASD SEC Monomer [%] | Dimer/Oligomer [%] | Elisa EC 50% | EC50 | slope | |
|---|---|---|---|---|---|---|---|---|---|---|---|---|
| PBS 155 mM | LA_09_004_1 Standard: RSN0151 | Clear glas type I | 24 h +40° C. | 7.1 | 11.4 | 4.8 | 99.793 99.780 | 0.207 0.22 | 131.1 100 | 5.18E−13 3.95E−13 | 0.98 1.18 | 1.12 1.12 |
| | LA_09_004_2 Standard: RSN0151 | Amber glass type II | 24 h +40° C. | 7.1 | 10.5 | 4.6 | 99.793 99.780 | 0.207 0.22 | 90.1 100 | 3.56E−13 3.95E−13 | 1.16 1.08 | 1.12 1.12 |
| | LA_09_004_3 Standard: RSN0151 | Polyethylen-high density | 24 h +40° C. | 7.1 | 11.1 | 5.3 | 99.767 99.780 | 0.233 0.22 | 157 100 | 6.20E−13 3.95E−13 | 1.06 1 | |
| | LA_09_004_4 Standard: RSN0151 | Polyethylen-Low density | 24 h +40° C. | 7.1 | 11.0 | 4.4 | 99.722 99.780 | 0.278 0.22 | 104.3 100 | 4.12E−13 3.95E−13 | | |
| | LA_09_004_5 Standard: RSN0151 | Polypropylen | 24 h +40° C. | 7.1 | 11.2 | 5.1 | 99.781 99.780 | 0.219 0.22 | 106.9 100 | 5.11E−13 4.78E−13 | | |

TABLE 38

Results of preliminary various stress tests (data assessment)

| Buffer | Formulationnumber | Stress | Temperature | Appearance | pH | PSD DLS [nm] | UV [mg/mL] | ASD SEC Monomer [%] | Dimer/Oligomer [%] | Elisa EC 50% | EC50 | slope |
|---|---|---|---|---|---|---|---|---|---|---|---|---|
| PBS 155 mM | LA_09_004_6 Standard: RSN0151 | Clear glas type I + V2A piece | 24 h | Clear | 7.1 | 11.9 | 4.9 | 99.551 99.780 | 0.391 0.22 | 80.8 100 | 3.86E−13 4.78E−13 | 1.15 1 |
| | LA_09_004_7 Standard: RSN0151 | Clear glas type I + 1 h purged with N2 | 24 h | Turbid | 7.1 | 11.2 | 4.6 | 99.727 99.780 | 0.273 0.22 | 89.3 100 | 4.27E−13 4.78E−13 | 1.04 1 |
| | LA_09_004_8 Standard: RSN0151 | Clear glas type I + 1 h purged with air | 24 h | Turbid | 7.0 | 11.0 | 4.4 | 99.791 99.780 | 0.265 0.22 | 84.3 100 | 4.03E−13 4.78E−13 | 1.05 1 |
| | LA 09_004_9 Standard: RSN0151 | Clear glas type I + light stress | 24 h | Turbid | 7.1 | 10.1 | 4.7 | 99.662 99.780 | 0.338 0.22 | 72.3 100 | 3.55E−13 4.91E−13 | 1.06 1.15 |
| | LA_09_004_10 Standard: RSN0151 | Clear glass type I as T0 | 24 h | Clear | 7.1 | 11.1 | 4.3 | 99.773 99.780 | 0.227 0.22 | 62.3 100 | 3.06E−13 4.91E−13 | 1.19 1.15 |

TABLE 39

Results of small scale buffer selection (data assessment)
Lead CXCR5 Antibody Preformulation Data Assessment

| Formulation number | Buffer | pH | Process Processability small scale | Duration small scale | T0 Apperance clarity | particle | pH | Ranking |
|---|---|---|---|---|---|---|---|---|
| LA_09_05-1 | PBS 155 mM | 7.50 | good | good | clear-turbid | yes | 7.5 | 0 |
| LA_09_05-2 | PBS 155 mM | 7.00 | good | good | clear-turbid | yes | 7 | 0.5 |
| LA_09_05-3 | PBS 155 mM | 6.50 | good | good | clear-turbid | yes | 6.6 | 1 |
| LA_09_06-1 | PB 5 mM | 7.50 | bad | bad | turbid | yes | 7.4 | 0 |
| LA_09_06-2 | PB 5 mM | 7.00 | bad | bad | turbid | yes | 7 | 0 |
| LA_09_06-3 | PB 5 mM | 6.50 | bad | bad | turbid | yes | 6.6 | 0 |
| LA_09_07-1 | PB 10 mM | 7.50 | bad | bad | turbid | yes | 7.5 | 0 |

TABLE 39-continued

Results of small scale buffer selection (data assessment)
Lead CXCR5 Antibody Preformulation Data Assessment

| | | | | | | | | |
|---|---|---|---|---|---|---|---|---|
| LA_09_07-2 | PB 10 mM | 7.00 | bad | bad | turbid | yes | 7 | 0 |
| LA_09_07-3 | PB 10 mM | 6.50 | bad | bad | turbid | yes | 6.6 | 0 |
| LA_09_08-1 | Citrate 10 mM | 7.00 | good | good | clear | no | 7 | 1 |
| LA_09_08-2 | Citrate 10 mM | 6.50 | good | good | clear | no | 8.5 | 1 |
| LA_09_08-3 | Citrate 10 mM | 6.00 | good | good | clear | no | 6 | 1 |
| LA_09_08-4 | Citrate 10 mM | 5.50 | good | good | clear | no | 5.5 | 1 |
| LA_09_08-5 | Citrate 10 mM | 5.00 | good | good | clear | no | 5 | 1 |
| LA_09_09-1 | Saline 150 mM | 6.00 | good | good | clear-turbid | yes | 7 | 0 |
| LA_09_10-1 | Acetate 10 mM | 5.50 | good | good | clear | yes | 5.8 | 0.5 |
| LA_09_10-2 | Acetate 10 mM | 5.00 | good | good | clear-turbid | yes | 5.2 | 0 |
| LA_09_11-1 | Succinate 10 mM | 6.00 | bad | good | clear-turbid | yes | 6.1 | 1 |
| LA_09_11-2 | Succinate 10 mM | 5.50 | good | good | clear-turbid | yes | 5.7 | 0.5 |
| LA_09_11-3 | Succinate 10 mM | 5.00 | good | good | clear-turbid | yes | 6.1 | 0 |
| LA_09_12-1 | Histidine 10 mM | 6.5 | good | good | clear-turbid | yes | 6.6 | 0.5 |
| LA_09_12-2 | Histidine 10 mM | 6 | good | good | clear-turbid | no | 6.1 | 1 |
| LA_09_12-3 | Histidine 10 mM | 5.5 | good | good | clear-turbid | yes | 5.1 | 0 |
| LA_09_13-1 | Glycine 10 mM | 8 | bad | bad | turbid | yes | 0 | 0 |
| LA_09_13-2 | Glycine 10 mM | 7 | good | good | clear-turbid | yes | 6.91 | 0 |
| LA_09_14-1 | Arginine 10 mM | 8 | bad | bad | turbid | yes | 7.7 | 0 |
| LA_09_14-2 | Arginine 10 mM | 6 | good | good | clear | yes | 6.4 | 0.5 |
| LA_09_15-1 | TRIS 10 mM | 8.5 | bad | bad | turbid | yes | 3.4 | 0 |
| LA_09_15-2 | TRIS 10 mM | 7.5 | bad | bad | turbid | yes | 7.5 | 0 |

| Formulation | T0 | | Apperance | | | | after 1 week at +40° C. | |
|---|---|---|---|---|---|---|---|---|
| number | DLS | UV | clearity | particle | pH | Ranking | DLS | UV |
| LA_09_05-1 | no aggregate | 23.39 | clear | no | 7.39 | 1 | no aggregate | 18 |
| LA_09_05-2 | no aggregate | 22.63 | clear | yes | 6.99 | 0 | no aggregate | 21.71 |
| LA_09_05-3 | no aggregate | 22.73 | clear | yes | 6.64 | 0.5 | no aggregate | 23.77 |
| LA_09_06-1 | no aggregate | 13.44 | turbid | yes | 7.45 | 0 | no aggregate | 12.72 |
| LA_09_06-2 | no aggregate | 18.34 | turbid | no | 7 | 0.5 | no aggregate | 16.94 |
| LA_09_06-3 | no aggregate | 20.75 | turbid | no | 6.5 | 0.5 | no aggregate | 20.4 |
| LA_09_07-1 | no aggregate | 18.12 | clear | no | 7.43 | 1 | no aggregate | 16.24 |
| LA_09_07-2 | no aggregate | 16.97 | clear-turbid | no | 7 | 0 | no aggregate | 17.42 |
| LA_09_07-3 | no aggregate | 20.73 | clear-turbid | yes | 6.5 | 0 | no aggregate | 18.88 |
| LA_09_08-1 | no aggregate | 19.69 | clear | no | 7.4 | 1 | no aggregate | 23 |
| LA_09_08-2 | no aggregate | 23.77 | clear | no | 6.8 | 1 | no aggregate | 24.55 |
| LA_09_08-3 | no aggregate | 21.93 | clear | no | 6.1 | 1 | no aggregate | 22.58 |
| LA_09_08-4 | no aggregate | 23.67 | clear | no | 5.6 | 1 | no aggregate | 24.6 |
| LA_09_08-5 | no aggregate | 22.97 | clear | no | 5.1 | 1 | aggregate | 23.42 |
| LA_09_09-1 | no aggregate | 24.13 | clear | no | 6.8 | 1 | no aggregate | 22.48 |
| LA_09_10-1 | no aggregate | 24.86 | clear | no | 5.8 | 1 | no aggregate | 24.32 |
| LA_09_10-2 | no aggregate | 24.99 | clear | yes | 5.2 | 0.5 | no aggregate | 22.45 |
| LA_09_11-1 | no aggregate | 23.99 | clear | no | 6.2 | 0.5 | no aggregate | 26.13 |
| LA_09_11-2 | no aggregate | 24.54 | clear | no | 5.6 | 0.5 | no aggregate | 23.33 |
| LA_09_11-3 | no aggregate | 24.22 | clear | no | 5.2 | 1 | no aggregate | 26.1 |
| LA_09_12-1 | no aggregate | 19.75 | clear-turbid | yes | 6.57 | 1 | no aggregate | 19.38 |
| LA_09_12-2 | no aggregate | 20.95 | clear-turbid | no | 6.09 | 0.5 | no aggregate | 20.74 |
| LA_09_12-3 | no aggregate | 21.37 | clear-turbid | no | 5.56 | 0 | no aggregate | 21.98 |
| LA_09_13-1 | aggregate | 0 | turbid | yes | 0 | 0 | aggregate | 0 |
| LA_09_13-2 | aggregate | 21.19 | clear-turbid | yes | 7.09 | 0 | aggregate | 20.4 |
| LA_09_14-1 | no aggregate | 10.06 | turbid | yes | 7.6 | 0 | no aggregate | 9.6 |
| LA_09_14-2 | no aggregate | 21.17 | turbid | yes | 6.4 | 0.5 | no aggregate | 21.5 |
| LA_09_15-1 | aggregate | 6.37 | clear | no | 6.5 | 0.5 | no aggregate | 6.12 |
| LA_09_15-2 | aggregate | 14.28 | turbid | yes | 7.5 | 0 | no aggregate | 13.26 |

TABLE 40

Results of small scale buffer selection, T0 (data assessment)
Lead CXCR5 Antibody Preformulation Data Assessment

| | | | T0 | | | | | | | | | | |
|---|---|---|---|---|---|---|---|---|---|---|---|---|---|
| | | | SEC | | | | | WCX | | | SDS-PAGE red. | | SDS-PAGE non-red. |
| Formulation number | Buffer | pH | Monomer [%] | Dimer/ Oligomer [%] | EC50 % | Elisa EC50 | slope | % acic | % neutral | % basic | HC [kDa] | LC [kDa] | main band |
| LA_09_05-1 | PBS 155 mM | 7.50 | 99.543 | 0.457 | 81 | 4.00E-13 | 0.96 | 13.4 | 85.6 | 1.1 | 49.81 | 25.79 | 141.88 |
| LA_09_05-2 | PBS 155 mM | 7.00 | 99.546 | 0.452 | 74 | 3.82E-13 | 1.01 | 13.6 | 85.4 | 1 | 50.81 | 26.37 | 136.83 |
| LA_09_05-3 | PBS 155 mM | 6.50 | 99.582 | 0.416 | 139 | 1.43E-12 | 0.72 | 13.3 | 85.6 | 1.1 | 50.91 | 26.87 | 136.69 |
| LA_09_06-1 | PB 5 mM | 7.50 | 99.437 | 0.563 | 176 | 1.81E-12 | 0.78 | 12 | 86.5 | 1.5 | 47.62 | 25.94 | 161.36 |
| LA_09_06-2 | PB 5 mM | 7.00 | 99.194 | 0.606 | 68 | 9.48E-13 | 0.76 | 14 | 84.6 | 1.4 | 48.06 | 25.19 | 168.27 |
| LA_09_06-3 | PB 5 mM | 6.50 | 99.266 | 0.714 | 109.63 | 8.54E-13 | 1.12 | 14.2 | 84.4 | 1.3 | 49.79 | 26.56 | 157.05 |
| LA_09_07-1 | PB 10 mM | 7.50 | 98.676 | 1.124 | 117 | 1.44E-12 | 0.81 | 14.2 | 83.7 | 2.1 | 52.1 | 25.31 | 148.91 |
| LA_09_07-2 | PB 10 mM | 7.00 | 98.670 | 1.130 | 144.66 | 1.49E-12 | 0.87 | 13.9 | 84.2 | 1.9 | 50.16 | 25.81 | 140.47 |
| LA_09_07-3 | PB 10 mM | 6.50 | 99.342 | 0.658 | 105 | 1.29E-12 | 0.73 | 13.9 | 85.1 | 1 | 50.34 | 25.61 | 131.66 |
| LA_09_08-1 | Citrate 10 mM | 7.00 | 99.394 | 0.606 | 59.85 | 7.90E-13 | 0.90 | 12.6 | 86.0 | 1.1 | 49.5 | 26.1 | 157.3 |
| LA_09_08-2 | Citrate 10 mM | 6.50 | 99.596 | 0.404 | 59 | 1.26E-12 | 0.53 | 12.7 | 85.6 | 1.4 | 49.7 | 26.4 | 147.0 |
| LA_09_08-3 | Citrate 10 mM | 6.00 | 99.681 | 0.339 | 52 | 1.10E-12 | 0.50 | 12.7 | 86.0 | 1.2 | 50.9 | 26.8 | 144.5 |
| LA_09_08-4 | Citrate 10 mM | 5.50 | 99.766 | 0.234 | 112 | 8.83E-13 | 1.01 | 12.8 | 88.1 | 1.1 | 49.1 | 26.0 | 147.9 |
| LA_09_08-5 | Citrate 10 mM | 5.00 | 99.830 | 0.17 | 79 | 1.46E-12 | 0.66 | 12.7 | 86.1 | 1.2 | 49.77 | 26.18 | 143.43 |
| LA_09_09-1 | Saline 150 mM | 6.00 | 99.232 | 0.768 | 96.18 | 1.51E-12 | 0.71 | 13.4 | 84.9 | 1.6 | 50 | 26.26 | 128.56 |
| LA_09_10-1 | Acetate 10 mM | 5.50 | 99.507 | 0.493 | 180.25 | 2.83E-12 | 0.55 | 13.5 | 85.2 | 1.3 | 49.46 | 25.31 | 126.83 |
| LA_09_10-2 | Acetate 10 mM | 5.00 | 99.622 | 0.378 | 146.86 | 9.81E-13 | 0.77 | 13.4 | 85.2 | 1.4 | 50.35 | 26.61 | 127.54 |
| LA_09_11-1 | Succinate 10 mM | 6.00 | 99.447 | 0.553 | 112.43 | 7.51E-13 | 0.81 | 13.0 | 85.7 | 1.3 | 49.45 | 25.17 | 165.19 |
| LA_09_11-2 | Succinate 10 mM | 5.50 | 99.582 | 0.418 | | | | 13.0 | 85.8 | 1.3 | 50.3 | 25.44 | 155.06 |
| LA_09_11-3 | Succinate 10 mM | 5.00 | 99.703 | 0.297 | 124 | 1.81E-12 | 0.72 | 12.9 | 85.8 | 1.2 | 50.15 | 25.51 | 150.47 |
| LA_09_12-1 | Histidine 10 mM | 6.5 | 99.547 | 0.453 | 110 | 1.60E-12 | 0.60 | 13.3 | 86 | 0.7 | 47.7 | 24.5 | 157.44 |
| LA_09_12-2 | Histidine 10 mM | 6 | 99.630 | 0.37 | 184 | 2.68E-12 | 0.55 | 13.1 | 86.2 | 0.6 | 47.77 | 24.7 | 157.86 |
| LA_09_12-3 | Histidine 10 mM | 5.5 | 99.683 | 0.317 | 57 | 1.71E-12 | 0.71 | 13.2 | 86.1 | 0.7 | 47.41 | 25 | 156.38 |
| LA_09_13-1 | Glycine 10 mM | 8 | n/a | | | | | | | | | | |
| LA_09_13-2 | Glycine 10 mM | 7 | 99.176 | 0.324 | 127 | 3.81E-12 | 0.57 | 13.6 | 85.5 | 0.8 | 48.74 | 25.04 | 163.07 |
| LA_09_14-1 | Arginine 10 mM | 8 | 99.705 | 0.295 | 121 | 2.10E-12 | 0.71 | 15.9 | 83.6 | 0.5 | 49 | 25.22 | 157.49 |
| LA_09_14-2 | Arginine 10 mM | 6 | 99.582 | 0.438 | 114 | 1.97E-12 | 0.66 | 13.1 | 88.3 | 0.6 | 49.43 | 25.96 | 147.5 |
| LA_09_15-1 | TRIS 10 mM | 8.5 | 99.226 | 0.774 | 118 | 2.05E-12 | 0.71 | 25.5 | 74.1 | 0.4 | 50.06 | 25.8 | 147.5 |
| LA_09_15-2 | TRIS 10 mM | 7.5 | 99.294 | 0.706 | 104 | 1.64E-i2 | 0.71 | 13 | 88.1 | 0.8 | 48.75 | 25.41 | 159.79 |

Buffers selected for larger scale testing

TABLE 41

Results of small scale buffer selection, T one week +40° C. (ASD data assessment)
Lead CXCR5 Antibody Preformulation Data Assessment

| | | | after 1 week at +40° C. | | | | | |
|---|---|---|---|---|---|---|---|---|
| | | | SEC | | | | Elisa | |
| Formulation number | Buffer | pH | Monomer [%] | Dimer/ Oligomer [%] | HMW [%] | EC50 % | EC50 | slope |
| LA_09_05-1 | PBS 155 mM | 7.50 | 98.897 | 1.103 | | 52 | 2.67E-13 | 1.11 |
| LA_09_05-2 | PBS 155 mM | 7.00 | 99.279 | 0.721 | | 97 | 9.96E-13 | 0.86 |
| LA_09_05-3 | PBS 155 mM | 6.50 | 99.233 | 0.767 | | 115 | 1.18E-12 | 0.84 |
| LA_09_06-1 | PB 5 mM | 7.50 | 98.770 | 1.23 | | 141 | 1.96E-12 | 0.88 |
| LA_09_06-2 | PB 5 mM | 7.00 | 98.673 | 1.327 | | 68 | 9.49E-13 | 0.81 |
| LA_09_06-3 | PB 5 mM | 6.50 | 98.644 | 1.356 | | 77 | 1.07E-12 | 0.75 |
| LA_09_07-1 | PB 10 mM | 7.50 | 98.307 | 1.679 | 0.014 | 68 | 8.40E-13 | 0.81 |
| LA_09_07-2 | PB 10 mM | 7.00 | 98.612 | 1.388 | | 109 | 1.34E-12 | 0.68 |
| LA_09_07-3 | PB 10 mM | 6.50 | 98.909 | 1.091 | | 78.79 | 1.04E-12 | 0.78 |
| LA_09_08-1 | Citrate 10 mM | 7.00 | 99.214 | 0.786 | | 111 | 1.36E-12 | 0.72 |
| LA_09_08-2 | Citrate 10 mM | 6.50 | 99.588 | 0.404 | | 46 | 9.79E-13 | 0.60 |
| LA_09_08-3 | Citrate 10 mM | 6.00 | 99.661 | 0.338 | | 98 | 7.77E-13 | 1.01 |
| LA_09_08-4 | Citrate 10 mM | 5.50 | 99.766 | 0.234 | | | | 0.84 |
| LA_09_08-5 | Citrate 10 mM | 5.00 | 99.772 | 0.228 | | 75 | 1.38E-12 | 0.82 |
| LA_09_09-1 | Saline 150 mM | 6.00 | 98.962 | 1.038 | | 80.89 | 1.27E-12 | 0.59 |
| LA_09_10-1 | Acetate 10 mM | 5.50 | 99.106 | 0.834 | | 94.9 | 1.49E-12 | 0.55 |
| LA_09_10-2 | Acetate 10 mM | 5.00 | 99.463 | 0.537 | | 101.5 | 6.78E-13 | 0.79 |
| LA_09_11-1 | Succinate 10 mM | 6.00 | 99.145 | 0.855 | | 125.90 | 8.41E-13 | 0.74 |
| LA_09_11-2 | Succinate 10 mM | 5.50 | 99.410 | 0.590 | | | | |
| LA_09_11-3 | Succinate 10 mM | 5.00 | 99.521 | 0.479 | | 157 | 2.29E-12 | 0.64 |

TABLE 41-continued

Results of small scale buffer selection, T one week +40° C. (ASD data assessment)
Lead CXCR5 Antibody Preformulation Data Assessment

| LA_09_12-1 | Histidine 10 mM | 6.5 | 99.300 | 0.700 | 175 | 2.55E-12 | 0.57 |
| LA_09_12-2 | Histidine 10 mM | 6 | 99.508 | 0.492 | 77 | 2.32E-12 | 0.65 |
| LA_09_12-3 | Histidine 10 mM | 5.5 | 99.567 | 0.333 | 81 | 2.45E-12 | 0.64 |
| LA_09_13-1 | Glycine 10 mM | 8 | | | | | |
| LA_09_13-2 | Glycine 10 mM | 7 | 98.446 | 1.554 | 65 | 1.95E-12 | 0.70 |
| LA_09_14-1 | Arginine 10 mM | 8 | 99.247 | 0.783 | 88 | 1.53E-12 | 0.80 |
| LA_09_14-2 | Arginine 10 mM | 6 | 99.277 | 0.723 | 99 | 1.72E-12 | 0.76 |
| LA_09_15-1 | TRIS 10 mM | 8.5 | 98.456 | 1.644 | 237 | 3.72E-12 | 0.84 |
| LA_09_15-2 | TRIS 10 mM | 7.5 | 98.998 | 1.002 | 184 | 2.89E-12 | 0.69 |

| | after 1 week at +40° C. | | | | | | |
|---|---|---|---|---|---|---|---|
| | WCX | | | SDS-PAGE red. | | SDS-PAGE non-red. | |
| Formulation number | % acic | % neutral | % basic | HC [kDa] | LC [kDa] | main band | comment |
| LA_09_05-1 | 14.8 | 83.5 | 1.7 | 50.25 | 26.07 | 142.27 | usatzbande in:61.02 kD |
| LA_09_05-2 | 13.4 | 85.2 | 1.4 | 51.14 | 26.27 | 135.83 | |
| LA_09_05-3 | 13.3 | 85.3 | 1.4 | 49.79 | 25.9 | 141 | Zusatzbande in:59.27 |
| LA_09_06-1 | 15.3 | 82.6 | 2 | 46.92 | 26.73 | 166.69 | |
| LA_09_06-2 | 11.7 | 86.1 | 2.2 | 49 | 26.11 | 159.55 | |
| LA_09_06-3 | 13.9 | 84.1 | 2 | 49.35 | 26.15 | 164.49 | |
| LA_09_07-1 | 15.1 | 82.2 | 2.6 | 50.18 | 25.41 | 137.71 | |
| LA_09_07-2 | 14.8 | 88.2 | 2 | 49.89 | 25.52 | 131.79 | |
| LA_09_07-3 | 14.1 | 84 | 1.9 | 51.63 | 26.2 | 139.92 | |
| LA_09_08-1 | 10.500 | 88.000 | 1.5 | 50.060 | 26.830 | 153.790 | |
| LA_09_08-2 | 12.700 | 85.800 | 1.4 | 49.690 | 26.390 | 146.970 | |
| LA_09_08-3 | 12.700 | 86.000 | 1.2 | 50.880 | 26.780 | 144.500 | |
| LA_09_08-4 | 12.5 | 86.1 | 1.4 | 49.23 | 25.9 | 144.79 | Zusatzbande in 152 62 kDa |
| LA_09_08-5 | 12.7 | 86 | 1.3 | 49.05 | 25.84 | 144.336 | |
| LA_09_09-1 | 13 | 85.1 | 1.3 | 49.33 | 25.23 | 127.67 | |
| LA_09_10-1 | 13.5 | 84.7 | 1.9 | 50.17 | 26.14 | 126.06 | |
| LA_09_10-2 | 13.4 | 84.8 | 1.8 | 49.86 | 26.18 | 128.96 | |
| LA_09_11-1 | 12.7 | 85.6 | 1.7 | 49.95 | 49.4 | 163.2 | |
| LA_09_11-2 | 12.6 | 85.7 | 1.6 | 49.84 | 25.23 | 161.74 | |
| LA_09_11-3 | 12.8 | 85.6 | 1.6 | 49.72 | 25.01 | | Im Vergleich zum Standard weist die |
| LA_09_12-1 | 13.4 | 85.7 | 0.9 | 47.73 | 24.7 | 158.71 | |
| LA_09_12-2 | 12.6 | 86.9 | 0.5 | 48.03 | 24.9 | 159.02 | |
| LA_09_12-3 | 13.1 | 88.2 | 0.8 | 47.67 | 24.69 | 153.93 | |
| LA_09_13-1 | | | | | | | |
| LA_09_13-2 | 13.4 | 85.1 | 1.3 | 49.02 | 25.27 | 160.97 | |
| LA_09_14-1 | 14.1 | 84.6 | 1.3 | 49.13 | 25.52 | 154.37 | |
| LA_09_14-2 | 12.9 | 88.3 | 0.8 | 49.57 | 25.56 | 149.34 | |
| LA_09_15-1 | 23.8 | 73.9 | 2.3 | 49.37 | 25.05 | 150.98 | |
| LA_09_15-2 | 13.7 | 85 | 1.3 | 49.25 | 25.14 | 158.5 | |

Buffers selected for larger scale testing

TABLE 42

Results of small scale buffer selection, after mechanical stress (data assessment)
Lead CXCR5 Antibody Preformulation Data Assessment

| | | | after mechanical stress 350 rpm, 2.5 h | | | | | | | | | | | |
|---|---|---|---|---|---|---|---|---|---|---|---|---|---|---|
| | | | SEC | | | | | WCX | | | SDS-PAGE red. | | SDS-PAGE non-red. | |
| Formulation number | Buffer | pH | Mono-mer [%] | mer/Oligo-mer | HMW [%] | Elisa EC50 % | EC50 | slope | % acic | % neu-tral | % basic | HC [kDa] | LC [kDa] | main band | com-ment |
| LA_09_05-1 | PBS 155 mM | 7.50 | 99.263 | 0.658 | 0.080 | 71 | 3.64E-13 | 0.9 | 10.2 | 88.6 | 1.2 | 51.01 | 26.64 | 144.8 | |
| LA_09_05-2 | PBS 155 mM | 7.00 | 98.753 | 0.650 | 0.597 | 50 | 2.58E-13 | 1.02 | 10.1 | 88.6 | 1.3 | 51.38 | 26.94 | 138.72 | bande in 59 |
| LA_09_05-3 | PBS 155 mM | 6.50 | 98.923 | 0.527 | 0.551 | 79.3 | 9.12E-13 | 0.77 | 11.6 | 87.4 | 1.2 | 50.4 | 26.17 | 135.68 | |
| LA_09_06-1 | PB 5 mM | 7.50 | 99.677 | 0.423 | | 111 | 1.54E-12 | 0.79 | 17.1 | 82 | 0.9 | 47.57 | 25.79 | 163.25 | |
| LA_09_06-2 | PB 5 mM | 7.00 | 99.084 | 0.916 | | 110.14 | 8.58E-13 | 0.89 | 11.2 | 87.6 | 1.2 | 47.36 | 24.75 | 166.93 | |
| LA_09_06-3 | PB 5 mM | 6.50 | 99.202 | 0.798 | | 150 | 1.23E-12 | 0.94 | 13.6 | 86.2 | 1.3 | 50.68 | 26.88 | 168.84 | |
| LA_09_07-1 | PB 10 mM | 7.50 | 98.909 | 1.091 | | 60.85 | 4.99E-13 | 0.87 | 12.9 | 86.3 | 1.8 | 50.47 | 26.26 | 147.83 | |
| LA_09_07-2 | PB 10 mM | 7.00 | 99.053 | 0.947 | | 61.36 | 6.32E-13 | 0.92 | 14.8 | 83.6 | 1.6 | 52.27 | 26.31 | 136.88 | |
| LA_09_07-3 | PB 10 mM | 6.50 | 99.272 | 0.728 | | 89.39 | 1.18E-12 | 0.94 | 13.6 | 86.4 | 1 | 50.05 | 25.62 | 131.53 | |

TABLE 42-continued

Results of small scale buffer selection, after mechanical stress (data assessment)
Lead CXCR5 Antibody Preformulation Data Assessment

| | | | after mechanical stress 350 rpm, 2.5 h | | | | | | | | | | | |
|---|---|---|---|---|---|---|---|---|---|---|---|---|---|---|
| | | | SEC | | | | | WCX | | | SDS-PAGE red. | | SDS-PAGE non-red. | |
| Formulation number | Buffer | pH | Monomer [%] | Oligomer | mer/HMW [%] | EC50 % | Elisa EC50 | slope | % acic | % neutral | % basic | HC [kDa] | LC [kDa] | main band | comment |
| LA_09_08-1 | Citrate 10 mM | 7.00 | 99.138 | 0.838 | 0.024 | 100.76 | 1.33E−12 | 0.74 | 10.5 | 88.0 | 1.5 | 50.06 | 26.83 | 153.79 | |
| LA_09_08-2 | Citrate 10 mM | 6.50 | 99.517 | 0.468 | 0.015 | 41 | 8.61E−13 | 0.51 | 10.6 | 88.2 | 1.2 | 50.82 | 26.79 | 143.82 | |
| LA_09_08-3 | Citrate 10 mM | 6.00 | 99.608 | 0.334 | 0.058 | 136 | 1.07E−12 | 0.85 | 10.3 | 88.4 | 1.3 | 49.57 | 25.38 | 145.79 | |
| LA_09_08-4 | Citrate 10 mM | 5.50 | 98.317 | 0.328 | 0.345 | 79 | 1.46E−12 | 0.73 | 10.1 | 88.6 | 1.4 | 49.29 | 25.88 | 144.93 | |
| LA_09_08-5 | Citrate 10 mM | 5.00 | 99.299 | 0.269 | 1.433 | 99 | 1.84E−12 | 0.71 | 10.1 | 83.4 | 1.5 | 49.31 | 26.02 | 143.32 | |
| LA_09_09-1 | Saline 150 mM | 6.00 | | | | | N/A | | | | | | | | |
| LA_09_10-1 | Acetate 10 mM | 5.50 | | | | | | | | | | | | | |
| LA_09_10-2 | Acetate 10 mM | 5.00 | | | | | | | | | | | | | |
| LA_09_11-1 | Succinate 10 mM | 6.00 | | | | | | | | | | | | | |
| LA_09_11-2 | Succinate 10 mM | 5.50 | | | | | | | | | | | | | |
| LA_09_11-3 | Succinate 10 mM | 5.00 | | | | | | | | | | | | | |
| LA_09_12-1 | Histidine 10 mM | 6.5 | | | | | | | | | | | | | |
| LA_09_12-2 | Histidine 10 mM | 6 | | | | | | | | | | | | | |
| LA_09_12-3 | Histidine 10 mM | 5.5 | | | | | | | | | | | | | |
| LA_09_13-1 | Glycine 10 mM | 8 | | | | | | | | | | | | | |
| LA_09_13-2 | Glycine 10 mM | 7 | | | | | | | | | | | | | |
| LA_09_14-1 | Arginine 10 mM | 8 | | | | | | | | | | | | | |
| LA_09_14-2 | Arginine 10 mM | 6 | | | | | | | | | | | | | |
| LA_09_15-1 | TRIS 10 mM | 8.5 | | | | | | | | | | | | | |
| LA_09_15-2 | TRIS 10 mM | 7.5 | | | | | | | | | | | | | |

Buffers selected for larger scale testing

TABLE 43

Results - Surfactant selection data assessment
Lead CXCR5 Antibody Assessment - Surfactant data

| | Formulation number | Mechanical Stress 350 rpm 2.5 h | Surfactant | pH | Tm [° C.] | pH | PSD DLS [nm] | UV [mg/mL] | Appearance |
|---|---|---|---|---|---|---|---|---|---|
| Citrate 10 mM | LA_09_16 | no | non | | 79.4 | 6.0 | 12.7 | 18.2 | Clear |
| | LA_09_16 | yes | non | | nd | 6.1 | N/A | 18.1 | Turbid |
| | LA_09_16-1 | yes | Polysorbate 20 | | 79.1 | 6.1 | 12.2 | 17.1 | Clear |
| | LA_09_16-2 | yes | Polysorbate 80 | | 78.6 | 6.1 | 12.5 | 18.6 | Clear |
| | LA_09_16-3 | yes | Lutrol F68 | 6.0 | 78.6 | 6.1 | 12.7 | 18.5 | Clear |
| | LA_09_16-4 | yes | Cremophor RH40 | | 78.6 | 6.1 | 13.0 | 17.7 | Clear |
| | LA_09_16-5 | yes | Solutol HS15 | | 78.4 | 6.1 | 12.8 | 19.2 | Clear |
| | LA_09_16_6 | N/A | SDS | | nd | 6.1 | N/A | N/A | Turbid |
| Acetate 10 mM | LA_09_17 | no | non | | 77.7 | 5.5 | 12.2 | 17.8 | Clear |
| | LA_09_17 | yes | non | | nd | 5.6 | 13.4 | 13.2 | Turbid |
| | LA_09_17-1 | yes | Polysorbate 20 | | 77.4 | 5.5 | 12.5 | 17.7 | Clear |
| | LA_09_17-2 | yes | Polysorbate 80 | 5.5 | 76.4 | 5.6 | 12.8 | 17.8 | Clear |
| | LA_09_17-3 | yes | Lutrol F68 | | 76.7 | 5.5 | 12.5 | 18.0 | Clear |
| | LA_09_17-4 | yes | Cremophor RH40 | | 76.7 | 5.5 | 13.3 | 17.7 | Clear |
| | LA_09_17-5 | yes | Solutol HS15 | | 76.4 | 5.5 | 12.9 | 17.7 | Clear |
| | LA_09_17_6 | yes | SDS | | nd | 5.6 | N/A | N/A | Turbid |

TABLE 43-continued

Results - Surfactant selection data assessment
Lead CXCR5 Antibody Assessment - Surfactant data

| | | | | | | | | | |
|---|---|---|---|---|---|---|---|---|---|
| Succinate 10 mM | LA_09_18 | no | non | | 73.3 | 4.9 | 12.8 | 20.1 | Clear |
| | LA_09_18 | yes | non | | nd | 5.0 | 13.0 | 20.8 | Clear |
| | LA_09_18-1 | yes | Polysorbate 20 | | 72.9 | 5.0 | 12.6 | 20.4 | Clear |
| | LA_09_18-2 | yes | Polysorbate 80 | 5.0 | 72.6 | 5.0 | 12.7 | 20.1 | Clear |
| | LA_09_18-3 | yes | Lutrol F68 | | 72.6 | 5.0 | 12.7 | 21.0 | Clear |
| | LA_09_18-4 | yes | Cremophor RH40 | | 72.4 | 5.0 | 12.9 | 21.1 | Clear |
| | LA_09_18-5 | yes | Solutol HS15 | | nd | 5.0 | 12.6 | 20.4 | Clear |

| | | ASD | | | | | | | |
|---|---|---|---|---|---|---|---|---|---|
| | | SEC | | | WCX | | | | SDS-PAGE |
| | Formulation | Monomer | Dimer/Oligomer | HMW | % | % | % | | non- |
| | number | [%] | [%] | [%] | acic | neutral | basic | Comment | main band | comment |
| Citrate 10 mM | LA_09_16 | 99.74 | 0.260 | | 12.79 | 86.98 | 1.28 | | 153.79 | |
| | | 99.74 | 0.260 | | 13.43 | 85.41 | 1.16 | | 146.19 | |
| | LA_09_16 | | | | N/A | | | | | |
| | LA_09_16-1 | 99.72 | 0.280 | | 12.28 | 85.92 | 1.28 | | 151.33 | |
| | | 99.74 | 0.260 | | 13.43 | 85.41 | 1.16 | | 146.19 | |
| | LA_09_16-2 | 99.71 | 0.290 | | 12.71 | 86.04 | 1.26 | | 149.35 | |
| | | 99.74 | 0.260 | | 13.43 | 85.41 | 1.16 | | 146.19 | |
| | LA_09_16-3 | 99.73 | 0.270 | | 13.13 | 85.6 | 1.27 | | 147.77 | |
| | | 99.74 | 0.260 | | 13.43 | 85.41 | 1.16 | | 146.19 | |
| | LA_09_16-4 | 98.52 | 0.440 | 1.04 | 11.37 | 86.86 | 1.19 | 1. saurer P | 149.68 | |
| | | 99.74 | 0.260 | | 13.43 | 85.41 | 1.16 | | 146.19 | |
| | LA_09_16-5 | 99.1 | 0.560 | 0.56 | 12.92 | 88.52 | 1.28 | 1. saurer P | 151.82 | |
| | | 99.74 | 0.260 | | 13.43 | 85.41 | 1.16 | | 146.19 | |
| | LA_09_16_6 | | | | N/A | | | | | |
| Acetate 10 mM | LA_09_17 | 99.74 | 0.260 | | 12.92 | 89.98 | 1.11 | | 173.63 | |
| | | 99.75 | 0.250 | | 13.42 | 85.43 | 1.14 | | 169.47 | |
| | LA_09_17 | | | | N/A | | | | | |
| | LA_09_17-1 | 99.74 | 0.280 | | 12.88 | 86.02 | 1.12 | | 175.92 | |
| | | 99.75 | 0.250 | | 13.42 | 85.43 | 1.14 | | 169.47 | |
| | LA_09_17-2 | 99.52 | 0.369 | 0.1 | 12.76 | 89.03 | 1.21 | | 178.34 | |
| | | 99.75 | 0.250 | | 13.42 | 85.43 | 1.14 | | 169.47 | |
| | LA_09_17-3 | 98.76 | 0.240 | | 12 | 85.86 | 1.14 | | 176.33 | |
| | | 99.75 | 0.250 | | 13.42 | 85.43 | 1.14 | | 169.47 | |
| | LA_09_17-4 | 97.23 | 0.830 | 1.95 | 11.51 | 87.18 | 1.31 | k im saure | 174.25 | |
| | | 99.75 | 0.250 | | 13.42 | 85.43 | 1.14 | | 169.47 | |
| | LA_09_17-5 | 98.54 | 0.450 | 1.01 | 12.28 | 89.67 | 1.1 | k im saure | 169.78 | |
| | | 99.75 | 0.250 | | 13.42 | 85.43 | 1.14 | | 169.47 | |
| | LA_09_17_6 | | | | N/A | | | | | |
| Succinate 10 mM | LA_09_18 | 98.76 | 0.240 | | 13.318 | 85.425 | 1.258 | | 159.8 | |
| | | 99.71 | 0.290 | | 13.8 | 85.06 | 1.13 | | 160.51 | |
| | LA_09_18 | 99.7 | 0.300 | | 12.189 | 86.388 | 1.423 | rer Peak k | 155.65 | |
| | | 99.71 | 0.290 | | 13.8 | 85.06 | 1.13 | | 160.51 | |
| | LA_09_18-1 | | | | N/A | | | | | |
| | LA_09_18-2 | | | | | | | | | |
| | LA_09_18-3 | | | | | | | | | |
| | LA_09_18-4 | | | | | | | | | |
| | LA_09_18-5 | | | | | | | | | |

TABLE 44

Results - Surfactant selection data assessment

| | | | | | | | | | | |
|---|---|---|---|---|---|---|---|---|---|---|
| Histidin 10 mM | LA_09_19 | | non | | | nd nd | N/A | 11.3 | 23.1 | Clear Turbid | 99.76 |
| | LA_09_19 | no | non | | | nd nd | 5.4 | | | | 99.7 |
| | | yes | | | | | | 21.9 | 23.4 | Clear Clear | 97.98 |
| | LA_09_19-1 | | Polysorbate 20 | | | nd | 5.3 | | | | 99.7 |
| | | yes | | | | | | 21.0 | 21.1 | Turbid | |
| | LA_09_19-2 | | Polysorbate 80 | | | | | | | | 99.3 |
| | | yes | | | 5.0 | | 5.3 | 21.0 | 21.0 | | 99.7 |
| | LA_09_19-3 | yes | Lutrol F68 | | | | 5.3 | 21.0 | 21.3 | | 99.53 |
| | | | | | | | | | | | 99.7 |

TABLE 44-continued

Results - Surfactant selection data assessment

| | | | | | | | | | | | |
|---|---|---|---|---|---|---|---|---|---|---|---|
| | LA_09_19-4 | yes | Cremophor RH40 | | nd | 5.3 | N/A | 20.1 | Clear | 98.37 | |
| | | | | | | | | | | 99.7 | |
| | LA_09_19-5 | yes | Solutol HS15 | | nd | 5.3 | 21.5 | 21.2 | Clear | 99.14 | |
| | | | | | | | | | | 99.7 | |
| Arginine | LA_09_20 | no | non | | nd | | 20.2 | | Clear | 99.61 | |
| 10 mM | | | | | | | | | | 99.71 | |
| | LA_09_20-1 | yes | non | | nd | 6.2 | N/A | 22.5 | Turbid | 99.29 | |
| | | | | | | | | | | 99.71 | |
| | LA_09_20-2 | yes | Polysorbate 20 | | 71.8 | 6.2 | 11.9 | 22.64 | Clear | N/A | |
| | LA_09_20-3 | yes | Polysorbate 80 | 6.0 | nd | 6.2 | 12.22 | 22.16 | Clear | | |
| | LA_09_20-4 | yes | Lutrol F68 | | nd | 6.2 | 12.34 | 22.79 | Turbid | | |
| | LA_09_20-5 | yes | Cremophor RH40 | | nd | 6.2 | 13.2 | 22.36 | Clear | | |
| | LA_09_20-1 | yes | Solutol HS15 | | nd | 6.2 | N/A | 22.04 | Turbid | | |
| Histidin | LA_09_19 | 0.240 | | 13.967 | 84.657 | 1.457 | | | 157.26 | | |
| 10 mM | | | | 13.662 | 85.263 | 1.173 | | | 160.51 | | |
| | LA_09_19 | 0.300 | 1.6 | 12.237 | 86.306 | 1.257 | rer Peak k | | 162.08 | Zusatzba de | |
| | | 0.420 | | 13.662 | 85.263 | 1.173 | | | 160.51 | | |
| | LA_09_19-1 | 0.300 | | 12.756 | 84.86 | 1.384 | | | 159.2 | | |
| | | | | 13.662 | 85.263 | 1.173 | | | 160.51 | | |
| | LA_09_19-2 | 0.320 | 0.13 | 12.516 | 84.949 | 1.535 | | | 161.06 | | |
| | | 0.300 | | 13.662 | 85.263 | 1.173 | | | 160.51 | Zusatzba de | |
| | LA_09_19-3 | 0.350 | 1.23 | 12.182 | 86.561 | 1.257 | rer Peak k | | 163.05 | | |
| | | 0.300 | | 13.662 | 85.263 | 1.173 | | | 160.51 | | |
| | LA_09_19-4 | 0.850 | 1.96 | 10.437 | 87.667 | 1.906 | rer Peak k | | 168.73 | Zusatzba de | |
| | | 0.300 | | 13.662 | 85.263 | 1.173 | | | 160.51 | | |
| | LA_09_19-5 | 0.330 | 0.52 | 12.561 | 85.891 | 1.548 | rer Peak k | | 160.22 | | |
| | | 0.300 | | 13.662 | 85.263 | 1.173 | | | 160.51 | | |
| Arginine | LA_09_20 | 0.490 | | 13.31 | 85.224 | 1.267 | | | 157.89 | | |
| 10 mM | | 0.290 | | 13.8 | 85.06 | 1.13 | | | 155.98 | | |
| | LA_09_20-1 | 0.610 | 3.1 | 12.32 | 88.015 | 1.636 | | | 152.77 | Zusatzba den: 300 | |
| | | 0.290 | | 13.8 | 85.06 | 1.13 | | | 155.98 | | |
| | LA_09_20-2 | | | | | N/A | | | | | |
| | LA_09_20-3 | | | | | | | | | | |
| | LA_09_20-4 | | | | | | | | | | |
| | LA_09_20-5 | | | | | | | | | | |
| | LA_09_20-1 | | | | | | | | | | |

N/A, samples were not tested analytically, as too little sample volume was available.

Excipients and Lead CXCR5 Antibody (LA_09_022)

TABLE 45

Results - compatibility of Lead Antibody with excipients
Lead CXCR5 Antibody Assessment - Compatibility

| Thermal | | | | pH | PSD Tm [° C.] | pH | DLS [nm] | UV [mg/mL] | Appearance | SEC Monomer [%] | Dimer/Oligimer [%] | HMW [%] |
|---|---|---|---|---|---|---|---|---|---|---|---|---|
| RSNO151 | LA_09_22 | no | non | | 80.3 | 6.0 | 12.7 | 18.2 | Clear | 99.689 | 0.314 | |
| 155 mM | Standard: RSN0151 | | | | | | | | | 99.707 | 0.293 | |
| PBS | LA_09_22_1 | yes | non | | | 6.1 | N/A | 18.1 | Turbid | 99.388 | 0.542 | |
| | Standard: RSN0151 | | | | | | | | | 99.707 | 0.293 | |
| | LA_09_22_2 | yes | NaCl | | 80.3 | 6.1 | 12.2 | 17.1 | Clear | 99.538 | 0.4 | |
| | Standard: RSN0151 | | | | | | | | | 99.707 | 0.293 | |
| | LA_09_22_3 | yes | MgCl2 | | nd | 6.1 | 12.5 | 18.6 | Clear | 99.697 | 0.303 | |
| | Standard: RSN0151 | | | | | | | | | 99.707 | 0.293 | |
| | LA_09_22_4 | yes | CaCl2 | | 78.2 | 6.1 | 12.7 | 18.5 | Clear | 99.656 | 0.132 | |
| | Standard: RSN0151 | | | | | | | | | 99.707 | 0.293 | |
| | LA_09_22_5 | yes | Mannitol | | nd | 6.1 | 13.0 | 17.7 | Clear | 89.488 | 0.499 | 0.013 |
| | Standard: RSN0151 | | | | | | | | | 99.707 | 0.293 | |
| | LA_09_22_6 | yes | Maltose | | nd | 6.1 | 12.8 | 19.2 | Clear | 98.324 | 1.676 | |
| | Standard: RSN0151 | | | | | | | | | 99.707 | 0.293 | |
| | LA_09_22_7 | yes | Trehalose | | 80.8 | 6.1 | N/A | N/A | Turbid | 98.507 | 0.389 | |
| | standard: RSN0151 | | | | | | | | | 99.366 | 0.343 | |
| | LA_09_22_8 | yes | Sucrose | | 80.5 | 5.5 | 12.2 | 17.8 | Clear | 99.307 | 0.535 | |
| | Standard: RSN0151 | | | | | | | | | 99.366 | 0.343 | |
| | LA_09_22_9 | yes | Dextran 40 | | 79.3 | 5.6 | 13.4 | 13.2 | Turbid | 99.821 | 1.545 | |
| | Standard: RSN0151 | | | | | | | | | 99.366 | 0.343 | |

TABLE 45-continued

Results - compatibility of Lead Antibody with excipients
Lead CXCR5 Antibody Assessment - Compatibility

| | | | | | | | | | |
|---|---|---|---|---|---|---|---|---|---|
| LA_09_22_10 | yes | Benzylalkohol | 75.8 | 5.5 | 12.5 | 17.7 | Clear | 99.821 | 1.027 |
| Standard: RSN0151 | | | | | | | | 99.366 | 0.343 |
| LA_09_22_11 | yes | Arginine-HCl | 80.0 | 5.6 | 12.8 | 17.8 | Clear | 99.622 | 0.331 |
| Standard: RSN0151 | | | | | | | | 99.366 | 0.343 |
| LA_09_22_12 | yes | Lysin | 80.9 | 5.5 | 12.5 | 18.0 | Clear | 99.047 | 0.701 |
| Standard: RSN0151 | | | | | | | | 99.366 | 0.343 |

| | | | WCX | | | SDS-PAGE non-red. | |
|---|---|---|---|---|---|---|---|
| | Thermal | | % acic | % neutral | % basic Comment | Main band | comment |
| | RSN0151 | LA_09_22 | 14.323 | 84.306 | 1.373 | 155.76 | |
| | 155 mM PBS | Standard: RSN0151 | 13.867 | 85.032 | 1.102 | 155.98 | |
| | | LA_09_22_1 | 13.878 | 84.289 | 1.833 | 142.95 | |
| | | Standard: RSN0151 | 13.867 | 85.032 | 1.102 | 154.13 | |
| | | LA_09_22_2 | 13.606 | 84.404 | 1.790 | 147.97 | |
| | | Standard: RSN0151 | 13.867 | 85.032 | 1.102 | 154.13 | |
| | | LA_09_22_3 | 13.353 | 81.235 | 1.412 | 149.38 | |
| | | Standard: RSN0151 | 13.867 | 85.032 | 1.102 | 154.13 | |
| | | LA_09_22_4 | 14.887 | 83.908 | 1.296 | 148.81 | |
| | | Standard: RSN0151 | 13.867 | 85.032 | 1.102 | 154.13 | |
| | | LA_09_22_5 | 15.757 | 82.849 | 1.824 | 150.42 | |
| | | Standard: RSN0151 | 13.867 | 85.032 | 1.102 | 154.13 | |
| | | LA_09_22_6 | 34.894 | 62.913 | 2.191 | 152.49 | 271.47 kDa Bandesta |
| | | Standard: RSN0151 | 13.867 | 85.032 | 1.102 | 154.13 | |
| | | LA_09_22_7 | 17.291 | 81.167 | 1.552 | 154.74 | |
| | | standard: RSN0151 | 14.019 | 84.575 | 1.407 | 154.13 | |
| | | LA_09_22_8 | 15.184 | 83.506 | 1.508 | 158.76 | |
| | | Standard: RSN0151 | 14.019 | 84.575 | 1.407 | 154.13 | |
| | | LA_09_22_9 | 20.308 | 77.996 | 1.596 | 166.61 | |
| | | Standard: RSN0151 | 14.019 | 84.575 | 1.407 | 154.13 | |
| | | LA_09_22_10 | 14.005 | 83.508 | 2.17 | 168.13 | |
| | | Standard: RSN0151 | 14.019 | 84.575 | 1.407 | 154.13 | |
| | | LA_09_22_11 | 15.262 | 83.116 | 1.621 | 169.77 | |
| | | Standard: RSN0151 | 14.019 | 84.575 | 1.407 | 154.13 | |
| | | LA_09_22_12 | 19.042 | 83.104 | 17.854 | 169.9 | Adation bands main ca/ |
| | | Standard: RSN0151 | 14.019 | 84.575 | 1.407 | 15.413 | |

Excipients and Acetate Buffered (LA_09_024)

TABLE 46

Results - compatibility of Lead Antibody in acetate buffer with excipients
Lead CXCR5 Antibody Assessment - Compatibility in citrate buffer

| | | | | | | | ASD | | | | | |
|---|---|---|---|---|---|---|---|---|---|---|---|---|
| | | | | | | | | SEC | | | | SDS-PAGE |
| | | | | | PSD | pH | | | Dimer/ | | | |
| | | | | | | | UV | Mono- | Oligomer | WCX | | non-red |
| | | Thermal | Excipient | pH | Tm [°C.] | DLS [nm] | [mg/mL] | mer [%] | [% HMW [%]] | % Acid | % neutral | % basic | Main band |
| RSN0151 155 mMpBS | LA_09_23 | No | Non | | 81.5 | 12.6 | 18.6 | 99.596 | 0.404 | 13.307 | 85.310 | 1.383 | 155.59 |
| | Standard: RSN0151 | | | | | | | | | 14.058 | 84.609 | 1.333 | 146.11 |
| | LA_09_23_1 | Yes | Non | | | 12.4 | 18.7 | 99.491 | 0.509 | 12.807 | 85.597 | 1.596 | 151.85 |
| | Standard: RSN0151 | | | | | | | 99.686 | 0.314 | 14.058 | 84.609 | 1.333 | 146.11 |
| | LA_09_23_2 | Yes | NaCl | | 81.7 | 12.2 | 21.8 | 99.498 | 0.502 | 12.805 | 85.641 | 1.554 | 145.12 |
| | Standard: RSN0151 | | | | | | | 99.686 | 0.314 | 14.058 | 84.609 | 1.333 | 146.11 |
| | LA_09_23_3 | Yes | MgCl2 | | 77.2 | 12.3 | 14.7 | 99.538 | 0.462 | 12.799 | 85.692 | 1.509 | 151.67 |
| | Standard: RSN0151 | | | | | | | 99.686 | 0.314 | 14.058 | 84.609 | 1.333 | 146.11 |
| | LA_09_23_4 | Yes | Mannitol | | 82.1 | 13.5 | 23.3 | 99.533 | 0.467 | 12.703 | 85.802 | 1.495 | 147.96 |
| | Standard: RSN0151 | | | | | | | 99.686 | 0.314 | 14.058 | 84.609 | 1.333 | 146.11 |

TABLE 46-continued

Results - compatibility of Lead Antibody in acetate buffer with excipients
Lead CXCR5 Antibody Assessment - Compatibility in citrate buffer

| | | | | | | | ASD | | | | | SDS-PAGE |
| --- | --- | --- | --- | --- | --- | --- | --- | --- | --- | --- | --- | --- |
| | | | | | | | SEC | | WCX | | | non-red |
| | | | | PSD pH | | | Dimer/ | | | | | |
| | Thermal | Excipient | pH | Tm [° C.] | DLS [nm] | UV [mg/mL] | Monomer [%] | Oligomer [% HMW [%]] | % Acid | % neutral | % basic | Main band |
| LA_09_23_5 | | | | | | | 98.899 | 0.677 | 16.363 | 82.106 | 1.631 | 155.02 |
| Standard: RSN0151 | | | | | | | 99.686 | 0.314 | 14.058 | 84.609 | 1.333 | 146.11 |
| LA_09_23_6 | Yes | Trehalose | | 82.1 | 13.9 | 17.6 | 99.656 | 0.344 | 12.693 | 85.843 | 1.465 | 151.43 |
| Standard: RSN0151 | | | | | | | 99.686 | 0.314 | 14.058 | 84.609 | 1.333 | 146.11 |
| LA_09_23_7 | Yes | Sucrose | | 81.9 | 13.5 | 17.5 | 99.594 | 0.406 | 12.758 | 85.754 | 1.487 | 152.67 |
| Standard: RSN0151 | | | | | | | 99.686 | 0.314 | 14.058 | 84.609 | 1.333 | 146.11 |
| LA_09_23_8 | Yes | Benzyl-alkohol | | 77.1 | 13.9 | 20.5 | 97.744 | 0.507 1.322 | 11.591 | 87.216 | 1.192 | 145.93 |
| Standard: RSN0151 | | | | | | | 99.686 | 0.314 | 14.058 | 84.609 | 1.333 | 146.11 |
| LA 09_23_9 | Yes | Arginine-HCl | | 80.7 | 14.7 | 17.6 | 99.327 | 0.412 | 13.047 | 85.843 | 1.500 | 146.01 |
| Standard: RSN0151 | | | | | | | 99.686 | 0.314 | 14.058 | 84.609 | 1.333 | 146.11 |
| LA_09_23_10 | Yes | Lysin | | nd | 12.0 | 16.7 | 98.849 | 0.969 | 13.642 | 80.767 | 5.591 | 144.05 |
| Standard: RSN0151 | | | | | | | 99.686 | 0.314 | 14.058 | 84.609 | 1.333 | 146.11 |

Excipients and Acetate Buffered (LA_09_024)

TABLE 47

Results - compatibility with excipients and Lead Antibody in acetate buffer
Lead CXCR5 Antibody Assessment - Compatibility in acetate buffer - data

| | | | | | | | | ASD | | | | | |
| --- | --- | --- | --- | --- | --- | --- | --- | --- | --- | --- | --- | --- | --- |
| | | | | | | | SEC | | WCX | | | SDS-PAGE | |
| | | | | PSD pH | | | | Dimer/ | | | % | non-red | |
| | | | | | | UV | Mono- | Oligomer | | | basic | | |
| | | Thermal | Excipient | pH | Tm [° C.] | DLS [nm] | [mg/mL] | mer [%] | [% HMW [%]] | % Acid | % neutral | Comment | Main band | comment |
| RSN0151 155 mMpBS | LA_09_24 | No | Non | | 81.8 | | 12.2 | 99.603 | 0.397 | 13.408 | 85.225 | 1.368 | 173.63 | |
| | Standard: RSN0151 | | | | | | | 99.628 | 0.309 | 14.230 | 84.407 | 1.363 | 169.47 | |
| | LA 09_24_1 | Yes | Non | | nd | | 12.5 | 99.405 | 0.595 | 13.368 | 85.052 | 1.580 | 149.18 | |
| | Standard: R5N0151 | | | | | | | 99.628 | 0.309 | 14.230 | 84.407 | 1.363 | 151.63 | |
| | LA_09_24_2 | Yes | NaCl | | 81.3 | | 12.3 | 99.479 | 0.521 | 13.507 | 84.895 | 1.598 | 156.31 | |
| | Standard: RSN0151 | | | | | | | 99.628 | 0.309 | 14.230 | 84.407 | 1.363 | 151.63 | |
| | LA 09_24_3 | Yes | MgCl2 | | 81.0 | | 12.3 | 99.517 | 0.483 | 13.470 | 84.915 | 1.615 | 142.23 | |
| | Standard: RSN0151 | | | | | | | 99.628 | 0.309 | 14.230 | 84.407 | 1.363 | 151.63 | |
| | LA_09_24_4 | Yes | Mannitol | | 82.5 | | 14.2 | 99.546 | 0.431 0.023 | 13.557 | 84.965 | 1.478 | 155.69 | |
| | Standard: RSN0151 | | | | | | | 99.628 | 0.309 | 14.230 | 84.407 | 1.363 | 151.63 | |
| | LA_09_24_5 | Yes | | | | | | 98.647 | 0.539 0.029 | 16.304 | 82.016 | 1.680 | 156.15 | |
| | Standard: RSN0151 | | | | | | | 99.628 | 0.309 | 14.230 | 84.407 | 1.363 | 151.63 | |
| | LA09_24_6 | Yes | Trehalose | | 82.5 | | 14.0 | 99.522 | 0.478 | 13.558 | 84.905 | 1.537 | 146.61 | |
| | Standard: RSN0151 | | | | | | | 99.628 | 0.309 | 14.230 | 84.407 | 1.363 | 151.63 | |
| | LA_09_24_7 | Yes | Sucrose | | 82.3 | | 14.0 | 99.542 | 0.458 | 13.587 | 84.923 | 1.490 | 149.12 | |
| | Standard: RSN0151 | | | | | | | 99.628 | 0.309 | 14.230 | 84.407 | 1.363 | 151.63 | |
| | LA_09_24_8 | Yes | Benzyl-alkohol | | 78.0 | | 13.2 | 98.272 | 0.67 0.745 | 12.739 | 85.960 | 1.301 | 152.48 | |
| | Standard: RSN0151 | | | | | | | 99.628 | 0.309 | 14.230 | 84.407 | 1.363 | 151.63 | |

TABLE 47-continued

Results - compatibility with excipients and Lead Antibody in acetate buffer
Lead CXCR5 Antibody Assessment - Compatibility in acetate buffer - data

| | Thermal | Excipient | pH | PSD Tm [° C.] | pH DLS [nm] | UV [mg/mL] | SEC Monomer [%] | Dimer/Oligomer [% HMW [%]] | ASD WCX % Acid | % neutral | % basic Comment | SDS-PAGE non-red Main band | comment |
|---|---|---|---|---|---|---|---|---|---|---|---|---|---|
| LA_09_24_9 Standard: RSN0151 | Yes | Arginine-HCl | | 81.5 | | 12.2 | 99.226 99.628 | 0.439 0.309 | 13.412 14.230 | 84.978 84.407 | 1.611 1.363 | 152.88 151.63 | |
| LA 09_24_10 Standard: R5N0151 | Yes | Lysin | | 81.2 | | 12.3 | 99.134 99.628 | 0.692 0.309 | 13.546 14.230 | 84.814 84.407 | 1.636 1.363 | 153.32 151.63 | |

Excipients and Histidine Buffered (LA_09_025)

TABLE 48

Results - compatibility with excipients and Lead Antibody in histidine buffer
Lead CXCR5 Antibody Assessment - Compatibility in Histidine buffer - data

| Buffer | Formulation Number | Thermal stress | Excipient | pH | PSD Tm [° C.] | pH | DL8 [nm] | UV [mg/mL] | SEC Monomer [%] | Dimer/Oligomer [% HMW [%]] | WCX % Acid | % neutral | % basic | SDS-PAGE non-red Main band | Comment |
|---|---|---|---|---|---|---|---|---|---|---|---|---|---|---|---|
| Histidine 10 mM | SAR113244_09_25 (-SAR11324409-019) Standard: RSN0151 | No | non | | | Not tested | 11.3 | 23.1 | 22.76 22.7 | 0.240 0.300 | 13.287 13.882 | 84.557 85.283 | 1.457 1.173 | 157.28 150.51 | |
| | SAR113244_09_25_1 Standard: RSN0151 | Yes | NaCl | | 78.8 | | 25.8 | 23.8 | 25.784 22.458 | 0.5 0.317 | 13.687 14.121 | 84.223 84.602 | 1.320 1.277 | 158.38 154.13 | |
| | SAR1I3244_09_25_2 Standard: RSN0151 | Yes | MgCl2 | 5.5 | nd | | 12.8 | 21.5 | 22.558 22.458 | 0.442 0.317 | 13.880 14.121 | 84.783 84.602 | 1.557 1.277 | 153.77 154.13 | |
| | SAR113244_09_25_3 Standard: RSN0151 | Yes | Mannitol | | 82.3 | | 13.1 | 22.1 | 22.582 22.458 | 0.411 0.317 | 13.704 14.121 | 85.008 84.602 | 1.282 1.277 | 158.28 154.13 | |
| | SARI 1324409254 Standard: R5N0151 | Yes | Maltose | | 80.8 | | 15.5 | 21.5 | 22.257 22.458 | 0.475 0.317 | 16.228 14.121 | 82.223 84.602 | 1.478 1.277 | 155.32 154.13 | |

TABLE 49

Results - Prototype formulation LA_09_27A

| Buffer | Formulation number | Time point | Storage condition | °C. | Tm [°C] | pH | DLS [nm] | UV [mg/mL] | Mono-mer [%] | Dimer/Oligomer [%] | SEC HMW [%] | NP [%] | % acid | WCX % neutral | % basic | Com-ment | SDA-PAGE non-red main band | com-ment | EC50% | Elisa EC50 | slope |
|---|---|---|---|---|---|---|---|---|---|---|---|---|---|---|---|---|---|---|---|---|---|
| Citrate 10 mM, 3 mg/ml NaCl 25 mg/mL Trehalose, 20 mM Arginine-HCl, 0.01% Polysorbate 20 | LA_A_09_27A | T0 | N/A | | 81.6 | N/A | 12.2 | 20.0 | 99.712 | 0.217 | | | 13.988 | 84.86 | 1.151 | | 118.94 | | 112 | 2.09E+12 | 0.53 |
| | Standard: RSN0151 | | | | | | | | 99.691 | 0.309 | | | 13.759 | 85.041 | 1.2 | | 122.88 | | 100 | 1.86E+12 | 0.56 |
| | LA_A_09_27A | T: 3 weeks | +5° C. | | 81.4 | 5.8 | 12.2 | 19.7 | 99.670 | 0.309 | | 0.021 | 14.143 | 84.561 | 1.297 | | | | | | |
| | Standard: RSN0151 | | | | | | | | 99.463 | 0.563 | | | 14.000 | 84.450 | 1.551 | | | N/A | | | |
| | LA_A_09_27A | T: 3 weeks | -20° C. | | 81.6 | 5.8 | 12.2 | 20.1 | 99.649 | 0.318 | | 0.33 | 14.382 | 84.423 | 1.195 | | N/A | | 112 | 2.09E+12 | 0.53 |
| | Standard: RSN0151 | | | | | | | | 99.463 | 0.563 | | | 14.000 | 84.450 | 1.551 | | | | 100 | 1.86E+12 | 0.56 |
| | LA_A_09_27A | T: 3 weeks | +40° C. | | 81.6 | 5.8 | 13.4 | 19.3 | 97.322 | 0.807 | 1.324 | 0.547 | 12.133 | 85.819 | 2.048 | | | | | | |
| | Standard: RSN0151 | | | | | | | | 99.463 | 0.563 | | | 14.000 | 84.450 | 1.551 | | | | | | |
| | LA_A_09_27A | T: 6 weeks | +5° C. | | 81.6 | 5.9 | 12.3 | 24.8 | 99.673 | 0.327 | | | 13.798 | 85.176 | 1.026 | | | | | | |
| | Standard: RSN0151 | | | | | | | | 99.460 | 0.54 | | | 14.054 | 84.285 | 1.662 | | | | | | |
| | LA_A_09_27A | T: 6 weeks | -20° C. | 6.0 | 81.4 | 5.9 | 12.2 | 24.9 | 99.670 | 0.33 | | | 13.756 | 85.192 | 1.052 | | | | | | |
| | Standard: RSN0151 | | | | | | | | 99.460 | 0.54 | | | 14.054 | 84.285 | 1.662 | | | | | | |
| | LA_A_09_27A | T: 6 weeks | +40° C. | | 81.4 | 5.9 | 13.8 + A | 25.9 | 96.290 | 1.06 | 1.919 | 0.731 | 11.826 | 85.289 | 2.886 | | | | | | |
| | Standard: RSN0151 | | | | | | | | 99.460 | 0.54 | | | 14.054 | 84.285 | 1.662 | | | N/A | | | |
| | LA_A_09_27A | T: 6 weeks | -80° C. | | N/A | 5.9 | 12.2 | 24.7 | 99.667 | 0.333 | | | 13.298 | 85.669 | 1.033 | | | | | | |
| | Standard: RSN0151 | | | | | | | | 99.460 | 0.54 | | | 14.054 | 84.285 | 1.662 | | | | | | |
| | LA_A_09_27A | T: 3 weeks | +5° C. | | 81.7 | 5.8 | 12.2 | 19.9 | 99.582 | 0.418 | | | 14.528 | 83.929 | 1.543 | | | | | | |
| | Standard: RSN0151 | | | | | | | | 99.427 | 0.573 | | | 14.413 | 84.08 | 1.507 | | | | | | |
| | LA_A_09_27A | T: 3 weeks | -20° C. | | 81.7 | 5.8 | 12.4 | 20.4 | 99.684 | 0.316 | | | 14.936 | 83.655 | 1.409 | | | | | | |
| | Standard: RSN0151 | | | | | | | | 99.427 | 0.573 | | | 14.413 | 84.08 | 1.507 | | | | | | |
| | LA_A_09_27A | T: 3 weeks | +40° C. | | 81.6 | 5.8 | 14.66 + A | 20.3 | 94.276 | 2.005 | 2.599 | | 14.871 | 80.287 | 4.843 | | | | | | |
| | | | | | | | | | 99.427 | 0.573 | | | 14.413 | 84.08 | 1.507 | | | | | | |

TABLE 50

Results - Prototype formulation La_09_027B

| Buffer | Formulation number | Time point | Storage condition | Tm pH [° C.] | PSD pH | PSD DLS [nm] | UV [mg/mL] | SEC Mono-mer [%] | SEC Dimer/Oligomer [%] | SEC HMW [%] | SEC NP [%] | ASD WCX % acid | ASD WCX % neutral | ASD WCX % basic | ASD WCX Com-ment | SDS-PAGE non-red. main band | SDS-PAGE non-red. com ment | EC50% | Elisa EC50 | slope |
|---|---|---|---|---|---|---|---|---|---|---|---|---|---|---|---|---|---|---|---|---|
| Citrate 10 mM, 50 mg Trehalose, 0.01% Polysorbate 20 | LA_09_27B Standard: RSN0151 | T0 | N/A | 81.5 | N/A | 13.6 | 20.9 | 99.688 99.691 | 0.312 0.309 | | | 13.723 13.759 | 85.064 85.041 | 2.194 1.2 | | 117.40 122.68 | | 104 100 | 1.90E+12 1.86E+12 | 0.62 0.56 |
| | LA_09_27B Standard: RSN0151 | T: 3 weeks | '+5 °C. | | 6.1 | 13.6 | 20.5 | 99.321 99.463 | 0.384 0.563 | | 0.295 | 13.911 14.000 | 84.772 84.450 | 1.317 1.551 | | | | | | |
| | LA_09_27B Standard: RSN0151 | T: 3 weeks | '−20° C. | | 6.0 | 13.6 | 19.7 | 99.626 99.463 | 0.374 0.563 | | | 14.14 14.000 | 84.541 84.450 | 1.318 1.551 | | | | | | |
| | LA_09_27B Standard: RSN0151 | T: 3 weeks | '+40° C. | | 6.0 | 14.4 | 19.9 | 96.851 99.463 | 0.934 0.563 | 1.7 | 0.515 | 12.455 14.000 | 85.392 84.450 | 2.153 1.551 | | | | N/A | | |
| | LA_09_27B Standard: RSN0151 | T: 6 weeks | '+5° C. | | 6.1 | 13.6 | 25.6 | 99.612 99.460 | 0.388 0.54 | | | 13.747 14.054 | 84.96 84.285 | 1.273 1.662 | | | | | | |
| | LA_09_27B Standard: RSN0151 | T: 6 weeks | '−20° C. | N/A | 6.1 | 13.6 | 25.0 | 99.628 99.460 | 0.372 0.54 | | | 13.835 14.054 | 84.901 84.285 | 1.264 1.662 | | | | | | |
| | LA_09_27B Standard: RSN0151 | T: 6 weeks | '+40° C. | | 6.2 | 14.9 | 24.9 | 95.806 | 1.283 | 2.182 | 0.729 | 12.665 | 83.832 | 3.483 | | 2.18.32 189.54 | 90.28.14 kD | | N/A | |
| | Standard: RSN0151 | | | | | | | 99.460 | 0.54 | | | 14.054 | 84.265 | 1.662 | | | | | | |
| | LA_09_27B Standard: RSN0151 | T: 6 weeks | '−80° C. | | 6.1 | 13.7 | 25.0 | 99.460 | 0.54 | | | 13.882 14.054 | 84.783 84.265 | 1.336 1.662 | | | | | | |
| | LA_09_27B Standard: RSN0151 | T: 3 weeks | '+5° C. | | 6.1 | 13.7 | 20.8 | 99.636 99.427 | 0.349 0.573 | | | 14.63 14.413 | 83.796 84.06 | 1.571 1.507 | | | | | | |
| | LA_09_27B Standard: RSN0151 | T: 3 weeks | '−20° C. | | 6.1 | 13.6 | 19.9 | 99.621 99.427 | 0.379 0.573 | | | 15.128 14.413 | 83.406 84.06 | 1.466 1.507 | | | | | | |
| | LA_09_27B Standard: RSN0151 | T: 3 weeks | '+40° C. | | 6.0 | 15.56 + A | 19.4 | 94.631 | 1.783 | 2.567 | | 15.373 | 79.378 | 5.25 | | | | N/A | | |
| | Standard: RSN0151 | | | | | | | 99.427 | 0.573 | | | 14.413 | 84.06 | 1.507 | | | | | | |

TABLE 51

Results - Prototype formulation LA_09_027C

| Buffer | Formulation number | Time point | Storage condition | Tm [° C.] | pH | PSD DLS [nm] | UV [mg/mL] | SEC Mono-mer [%] | Dimer/Oligomer [%] | HMW [%] | NP [%] | ASD WCX % acid | % neutral | % basic | Com-ment | SDS-PAGE non-red. main band | comment | EC50% | Elisa EC50 | slope |
|---|---|---|---|---|---|---|---|---|---|---|---|---|---|---|---|---|---|---|---|---|
| Citrate 10 mM, 6 mg NaCl, 0.01% Polysorbate 20 | LA_09_27C | T0 | N/A | 80.7 | N/A | 11.6 | 19.921.1 | 99.688 | 0.312 | | | 13.723 | 85.084 | 1.194 | | 117.40 | | 104 | 1.93E+12 | 0.62 |
| | Standard: RSN0151 | | | | | | | 99.691 | 0.309 | | | 13.759 | 85.041 | 1.2 | | 122.88 | | 100 | 1.86E+12 | 0.56 |
| | LA_09_27C | T: 3 weeks | '+5° C. | 80.9 | 5.8 | 11.6 | 20.620.4 | 99.321 | 0.384 | | 0.295 | 13.911 | 84.772 | 1.317 | | | | | | |
| | Standard: RSN0151 | | | | | | | 99.463 | 0.563 | | | 14.000 | 84.450 | 1.551 | | | | | | |
| | LA_09_27C | T: 3 weeks | '−20° C. | 80.7 | 5.8 | 11.6 | 25.425.4 | 99.626 | 0.374 | | | 14.14 | 84.541 | 1.318 | | | | | | |
| | Standard: RSN0151 | | | | | | | 99.463 | 0.563 | | | 14.000 | 84.450 | 1.551 | | | | | | |
| | LA_09_27C | T: 3 weeks | '+40° C. | 80.4 | 5.8 | 12.98 + A | 5.325.7 | 96.851 | 0.934 | 1.7 | 0.515 | 12.455 | 85.392 | 2.153 | | | | N/A | | |
| | Standard: RSN0151 | | | | | | | 99.463 | 0.563 | | | 14.000 | 84.450 | 1.551 | | | | | | |
| | LA_09_27C | T: 6 weeks | '+5° C. | 80.7 | 5.9 | 11.6 | 21.420.9 | 99.612 | 0.388 | | | 13.747 | 84.98 | 1.273 | | | | | | |
| | Standard: RSN0151 | | | | | | | 99.460 | 0.54 | | | 14.054 | 84.285 | 1.662 | | | | | | |
| | LA_09_27C | T: 6 weeks | '−20° C. | 80.9 | 6.0 | 11.5 | 21.4 | 99.626 | 0.372 | | | 13.835 | 84.901 | 1.264 | | | | | | |
| | Standard: RSN0151 | | | | | | | 99.460 | 0.54 | | | 14.054 | 84.285 | 1.662 | | | | | | |
| | LA_09_27C | T: 6 weeks | '+40° C. | 80.7 | 5.9 | 13.77 + A | | 95.806 | 1.283 | 2.182 | 0.729 | 12.685 | 83.832 | 3.483 | | 218.32 | 90.28.14 kD | | | |
| | Standard: RSN0151 | | | | | | | 99.460 | 0.54 | | | 14.054 | 84.285 | 1.662 | | 189.54 | | | | |
| | LA_09_27C | T: 6 weeks | '−80° C. | N/A | 5.8 | 18.7 | | | | | | 13.882 | 84.783 | 1.336 | | | | | | |
| | Standard: RSN0151 | | | | | | | | | | | 14.054 | 84.285 | 1.662 | | | | | | |
| | LA_09_27C | T: 3 weeks | '+5° C. | 80.9 | 5.8 | 11.6 | | 99.636 | 0.349 | | | 14.63 | 83.798 | 1.571 | | | | | | |
| | Standard: RSN0151 | | | | | | | 99.427 | 0.573 | | | 14.413 | 84.08 | 1.507 | | | | | | |
| | LA_09_27C | T: 3 weeks | '−20° C. | 81.2 | 5.8 | 11.7 | | 99.621 | 0.379 | | | 15.128 | 83.406 | 1.466 | | | | N/A | | |
| | Standard: RSN0151 | | | | | | | 99.427 | 0.573 | | | 14.413 | 84.08 | 1.507 | | | | | | |
| | LA_09_27C | T: 3 weeks | '+40° C. | 80.9 | 5.8 | 14.28 + A | | 94.631 | 1.783 | 2.567 | | 15.373 | 79.378 | 5.25 | | | | | | |
| | Standard: RSN0151 | | | | | | | 99.427 | 0.573 | | | 14.413 | 84.08 | 1.507 | | | | | | |

TABLE 52

Results - Prototype formulation LA 09 027D

| Buffer | Formulation number | Storage Time point | Storage condition | pH | Tm [° C.] | PSD pH | PSD DLS [nm] | UV [mg/mL] | SEC Monomer [%] | SEC Dimer/Oligomer [%] | SEC HMW [%] | SEC NP [%] | WCX % acid | WCX % neutral | WCX % basic | Com-ment | SDS-PAGE non-red. main band | SDS-PAGE non-red. comment | EC50% | Elisa EC50 | slope |
|---|---|---|---|---|---|---|---|---|---|---|---|---|---|---|---|---|---|---|---|---|---|
| Citrate 10 mM, 50 mg Trehalose, 20 mM Arginine-HCl, 0.01% Polysorbate 20 | LA_09_27D | T0 | N/A | | 81.6 | N/A | 13.3 | 19.8 | 99.579 | 0.283 | | | 13.974 | 84.912 | 1.114 | | 117.29 | | 94 | 1.75E+12 | 0.61 |
| | Standard: RSN0151 | | | | | | | | 99.691 | 0.309 | | | 13.759 | 85.041 | 1.2 | | 122.88 | | 100 | 1.86E+12 | 0.56 |
| | LA_09_27D | T: 3 weeks | '+5° C. | | 81.4 | 6.0 | 13.1 | 19.5 | 99.676 | 0.313 | | 0.011 | 13.825 | 84.918 | 1.256 | | | | | | |
| | Standard: RSN0151 | | | | | | | | 99.463 | 0.563 | | | 14.000 | 84.450 | 1.551 | | | | | | |
| | LA_09_27D | T: 3 weeks | '-20° C. | | 81.4 | 5.8 | 13.2 | 20.4 | 99.638 | 0.338 | | 0.024 | 14.028 | 84.745 | 1.227 | | | | N/A | | |
| | Standard: RSN0151 | | | | | | | | 99.463 | 0.563 | | | 14.000 | 84.450 | 1.551 | | | | | | |
| | LA_09_27D | T: 3 weeks | '+40° C. | | 81.4 | 6.0 | 13.9 | 19.6 | 97.653 | 0.809 | 0.946 | 0.592 | 12.315 | 85.553 | 2.131 | | | | | | |
| | Standard: RSN0151 | | | | | | | | 99.463 | 0.563 | | | 14.000 | 84.450 | 1.551 | | | | | | |
| | LA_09_27D | T: 6 weeks | '+5° C. | | 80.9 | 6.0 | 13.1 | 24.4 | 99.660 | 0.34 | | | 13.475 | 85.337 | 1.188 | | | | | | |
| | Standard: RSN0151 | | | | | | | | 99.460 | 0.54 | | | 14.054 | 84.285 | 1.662 | | | | | | |
| | LA_09_27D | T: 6 weeks | '-20° C. | 6.0 | 80.6 | 6.0 | 13.2 | 24.2 | 99.648 | 0.352 | | | 13.445 | 85.502 | 1.053 | | | | | | |
| | Standard: RSN0151 | | | | | | | | 99.460 | 0.54 | | | 14.054 | 84.285 | 1.662 | | | | | | |
| | LA_09_27D | T: 6 weeks | '+40° C. | | 80.9 | 6.0 | 14.5 | 24.8 | 96.544 | 1.056 | 1.637 | 0.763 | 11.916 | 85.099 | 2.985 | | 192.29 | 90.14 kDa | | | |
| | Standard: RSN0151 | | | | | | | | 99.460 | 0.54 | | | 14.054 | 84.285 | 1.662 | | 189.54 | | | N/A | |
| | LA_09_27D | T: 6 weeks | '-80° C. | | N/A | 6.0 | 13.2 | 24.5 | 99.664 | 0.336 | | | 13.485 | 85.357 | 1.159 | | | | | | |
| | Standard: RSN0151 | | | | | | | | 99.460 | 0.54 | | | 14.054 | 84.285 | 1.662 | | | | | | |
| | LA_09_27D | T: 3 weeks | '+5° C. | | 82.1 | 5.9 | 13.1 | 20.4 | 99.636 | 0.341 | | | 14.09 | 84.529 | 1.38 | | | | | | |
| | Standard: RSN0151 | | | | | | | | 99.427 | 0.573 | | | 14.413 | 84.08 | 1.507 | | | | | | |
| | LA_09_27D | T: 3 weeks | '-20° C. | | 82.1 | 5.9 | 13.2 | 19.8 | 99.655 | 0.334 | | | 14.521 | 84.08 | 1.398 | | | | N/A | | |
| | Standard: RSN0151 | | | | | | | | 99.427 | 0.573 | | | 14.413 | 84.08 | 1.507 | | | | | | |
| | LA_09_27D | T: 3 weeks | '+40° C. | | 81.9 | 5.9 | 15.2 | 20.4 | 94.413 | 1.634 | 2.446 | 1.12 | 14.173 | 81.003 | 4.823 | | | | | | |
| | Standard: RSN0151 | | | | | | | | 99.427 | 0.573 | | | 14.413 | 84.08 | 1.507 | | | | | | |

TABLE 53

Results - Prototype formulation LA_09_028A

| Buffer | Formulation number | Time point | Storage condition | pH | Tm [° C.] | pH | PSD DLS [nm] | UV [mg/mL] | SEC Mono-mer [%] | SEC Dimer/Oligomer [%] | SEC HMW [%] | SEC NP [%] | WCX % acid | WCX % neutral | WCX % basic | ASD Comment | SDS-PAGE non-red. main band | SDS-PAGE comment | EC50% | Elisa EC50 | slope |
|---|---|---|---|---|---|---|---|---|---|---|---|---|---|---|---|---|---|---|---|---|---|
| Acetate 10 mM, 3 mg/mL NaCl, 25 mg/mL Trehalose, 20 mM Arginine-HCl, = 0.01% Polysorbate 20 | LA_09_28A Standard: RSN0151 | T0 | N/A | | 81.1 | N/A | 12.9 | 17.4 | 99.503 99.691 | 0.26 0.309 | | | 14.153 13.772 | 84.626 85.204 | 1.221 1.204 | | 118.94 122.88 | | 112 100 | 2.09E+12 1.86E+12 | 0.53 0.56 |
| | LA_09_28A Standard: RSN0151 | T: 3 weeks | +5° C. | | 81.1 | 5.6 | 12.6 | 16.1 | 99.650 99.481 | 0.35 0.519 | | | 14.036 14.278 | 84.717 84.346 | 1.247 1.377 | | N/A | | N/A | | |
| | LA_09_28A Standard: RSN0151 | T: 3 weeks | -20° C. | | 81.1 | 5.6 | 12.5 | 15.7 | 99.639 99.481 | 0.315 0.519 | | 0.046 | 13.99 14.278 | 84.778 84.346 | 1.231 1.377 | | N/A | | 112 100 | 2.09E+12 1.86E+12 | 0.53 0.56 |
| | LA_09_28A Standard: RSN0151 | T: 3 weeks | +40° C. | | 81.1 | 5.6 | 13.9 | 15.6 | 96.870 99.481 | 1.168 0.519 | 1.484 | 0.478 | 13.418 14.278 | 83.852 84.346 | 2.730 1.377 | | | | N/A | | |
| | LA_09_28A Standard: RSN0151 | T: 6 weeks | +5° C. | | 81.1 | 5.6 | 12.6 | 16.4 | 99.634 99.460 | 0.366 0.545 | | | 13.803 13.864 | 84.981 85.048 | 1.216 1.088 | | | | | | |
| | LA_09_28A Standard: RSN0151 | T: 6 weeks | -20° C. | 5.5 | 81.1 | 5.6 | 12.7 | 16.6 | 99.650 99.460 | 0.35 0.545 | | | 13.844 13.864 | 84.952 85.048 | 1.205 1.088 | | | | | | |
| | LA_09_28A Standard: RSN0151 | T: 6 weeks | +40° C. | | N/A | 5.7 | 14.7 | 16.5 | 94.853 | 1.837 | 2.189 | 1.121 | 13.596 | 82.452 | 3.952 | | 195.57 | 66.28.14 kDa | | | |
| | Standard: RSN0151 | | | | | | | | 99.460 | 0.545 | | | 13.864 | 85.048 | 1.088 | | 189.54 | | N/A | N/A | |
| | LA_09_28A Standard: RSN0151 | T: 6 weeks | -80° C. | | N/A | 5.6 | 12.8 | 16.6 | 99.628 99.460 | 0.372 0.545 | | | | 85.048 | 1.088 | | | | | | |
| | LA_09_28A Standard: RSN0151 | T: 3 weeks | +5° C. | | 81.1 | 5.7 | 12.5 | 16.6 | 99.564 99.421 | 0.415 0.579 | | | 13.864 14.363 14.618 | 83.628 83.409 | 2.009 1.973 | | | | | | |
| | LA_09_28A Standard: RSN0151 | T: 3 weeks | -20° C. | | 81.3 | 5.7 | 12.7 | 16.4 | 99.594 99.421 | 0.88 0.579 | | | 14.314 14.618 | 83.738 83.409 | 1.948 1.973 | | | | N/A | | |
| | LA_09_28A | T: 3 weeks | +40° C. | | 80.7 | 5.7 | 15.86 + A | 16.5 | 91.596 | 3.693 | 2.839 | 1.872 | 18.117 | 74.736 | 7.147 | | | | | | |
| | | | | | | | | | 99.421 | 0.579 | | | 14.618 | 83.409 | 1.973 | | | | | | |

TABLE 54

Results - Prototype formulation LA_09_028B

| Buffer | Formulation number | Time point | Storage condition | pH | Tm [° C.] | PSD pH | DLS [nm] | UV [mg/mL] | SEC Mono-mer [%] | SEC Dimer/Oligomer [%] | SEC HMW [%] | SEC NP [%] | ASD WCX % acid | ASD WCX % neutral | ASD WCX % basic | Com-ment | SDS-PAGE non-red. main band | SDS-PAGE non-red. comment | EC50% | Elisa EC50 | slope |
|---|---|---|---|---|---|---|---|---|---|---|---|---|---|---|---|---|---|---|---|---|---|
| Acetate 10 mM, Trehalose, 50 mg 0.01% Polysor-bate 20 | LA_09_28B Standard: RSN0151 | T0 | N/A | | 81.6 | N/A | 14.4 | 17.1 | 99.590 99.691 | 0.41 0.309 | | | 14.257 13.772 | 84.511 85.024 | 1.232 1.204 | | 118.94 122.88 | | 112 100 | 2.09E+12 1.86E+12 | 0.53 0.56 |
| | LA_09_28B Standard: RSN0151 | T: 3 weeks | '+5° C. | 5.6 | 81.6 | 5.6 | 14.2 | 16.3 | 99.476 99.481 | 0.476 0.519 | | 0.048 | 14.56 14.278 | 84.112 84.346 | 1.328 1.377 | | | | N/A | | |
| | LA_09_28B Standard: RSN0151 | T: 3 weeks | '-20° C. | 5.7 | 81.6 | 5.7 | 14.2 | 16.2 | 99.411 99.481 | 0.497 0.519 | | 0.092 | 14.174 14.278 | 84.403 84.346 | 1.423 1.377 | | N/A | | 112 100 | 2.09E+12 1.86E+12 | 0.53 0.56 |
| | LA_09_28B Standard: RSN0151 | T: 3 weeks | '+40° C. | 5.6 | 81.6 | 5.6 | 14.8 | 16.2 | 97.322 99.481 | 2.039 0.519 | | 0.639 | 14.243 14.278 | 82.977 84.346 | 2.76 1.377 | | | | | | |
| | LA_09_28B Standard: RSN0151 | T: 6 weeks | '+5° C. | 5.7 | 81.6 | 5.7 | 14.3 | 16.7 | 99.510 99.460 | 0.49 0.545 | | | 13.844 13.864 | 84.829 85.048 | 1.327 1.088 | | | | N/A | | |
| | LA_09_28B Standard: RSN0151 | T: 6 weeks | '-20° C. | 5.5 | 81.6 | 5.7 | 14.6 | 17.4 | 99.530 99.460 | 0.47 0.545 | | | 13.755 13.864 | 84.943 85.048 | 1.302 1.088 | | | | | | |
| | LA_09_28B Standard: RSN0151 | T: 6 weeks | '+40° C. | 5.7 | 81.6 | 5.7 | 15.4 | 16.7 | 94.607 99.460 | 3.574 0.545 | 0.776 | 1.043 | 14.485 13.864 | 80.651 85.048 | 4.864 1.088 | | 203.14 189.54 | 66.28.14 kDa | | N/A | |
| | LA_09_28B Standard: RSN0151 | T: 6 weeks | '-80° C. | 5.7 | N/A | 5.7 | 14.5 | 17.2 | 99.536 99.460 | 0.464 0.545 | | | 13.98 13.864 | 84.747 85.048 | 1.273 1.088 | | | | | | |
| | LA_09_28B Standard: RSN0151 | T: 3 weeks | '+5° C. | 5.7 | 82.1 | 5.7 | 14.04 | 16.9 | 99.446 99.421 | 0.554 0.579 | | | 14.511 14.618 | 83.408 83.409 | 2.081 1.973 | | | | | | |
| | LA_09_28B Standard: RSN0151 | T: 3 weeks | '-20° C. | 5.7 | 81.9 | 5.7 | 14.1 | 16.8 | 99.548 99.421 | 0.452 0.579 | | | 15.255 14.618 | 82.643 83.409 | 2.103 1.973 | | | | N/A | | |
| | LA_09_28B Standard: RSN0151 | T: 3 weeks | '+40° C. | 5.7 | 81.9 | 5.7 | 16.3 | 16.8 | 90.598 99.421 | 6.155 0.579 | 1.864 | 1.383 | 19.813 14.618 | 71.010 83.409 | 9.177 1.973 | | | | | | |

TABLE 55

Results - Prototype formulation LA_09_028C

| Buffer | Formulation number | Storage | | Tm | | PSD | | UV | SEC | | | | | WCX | | | ASD Comment | SDS-PAGE non-red. | | EC50% | Elisa | | |
|---|---|---|---|---|---|---|---|---|---|---|---|---|---|---|---|---|---|---|---|---|---|---|---|
| | | Time point | condition | [° C.] | pH | DLS [nm] | | [mg/mL] | Monomer [%] | Dimer/Oligomer [%] | HMW [%] | | NP [%] | % acid | % neutral | % basic | | main band | comment | | EC50 | slope |
| Acetate 10 mM, 6 mg NaCl, 0.01% Polysorbate 20 | LA_09_28C Standard: RSN0151 | T0 | N/A | 80.5 | N/A | 11.9 | | 18.0 | 99.561 99.691 | 0.439 0.309 | | | | 14.329 13.772 | 84.427 85.024 | 1.244 1.204 | | 130.69 122.88 | 142 100 | | 1.52E+12 1.07E+12 | 0.87 0.81 |
| | LA_09_28C Standard: RSN0151 | T: 3 weeks | '+5° C. | 80.5 | 5.6 | 11.9 | | 17.1 | 99.560 99.481 | 0.44 0.519 | | | | 14.581 14.278 | 84.001 84.346 | 1.418 1.377 | | | | | | |
| | LA_09_28C Standard: RSN0151 | T: 3 weeks | '−20° C. | 80.7 | 5.6 | 11.8 | | 16.3 | 99.611 99.481 | 0.389 0.519 | | | | 14.478 14.278 | 84.192 84.346 | 1.330 1.377 | | | | N/A | | |
| | LA_09_28C Standard: RSN0151 | T: 3 weeks | '+40° C. | 80.7 | 5.5 | 13.48 + A | | 16.4 | 95.969 | 1.283 | 1.917 | | 0.831 | 12.989 | 83.971 | 3.04 | | | | | | |
| | Standard: RSN0151 | | | | | | | | 99.461 | 0.519 | | | | 14.278 | 84.346 | 1.377 | | | | | | |
| | LA_09_28C Standard: RSN0151 | T: 6 weeks | '+5° C. | 80.5 | 5.6 | 12.1 | | 17.7 | 99.586 99.460 | 0.414 0.545 | | | | 13.913 13.864 | 84.88 85.048 | 1.207 1.088 | | | | | | |
| | LA_09_28C Standard: RSN0151 | T: 6 weeks | '−20° C. | 80.7 | 5.6 | 12.1 | | 17.6 | 99.584 99.460 | 0.416 0.545 | | | | 13.975 13.864 | 84.693 85.048 | 1.332 1.088 | | | | | | |
| | LA_09_28C | T: 6 weeks | '+40° C. | 80.5 | 5.7 | 14.34 + A | | 17.2 | 84.811 | 1.975 | 2.38 | | 0.834 | 13.449 | 82.466 | 4.085 | | 204.41 189.54 | 66.28.14 kDa | N/A | N/A | |
| | Standard: RSN0151 | | | | | | | | 99.460 | 0.545 | | | | 13.864 | 85.048 | 1.088 | | | | | | |
| | LA_09_28C Standard: RSN0151 | T: 6 weeks | '−80° C. | N/A | 5.6 | 12.1 | | 16.1 | 99.524 99.460 | 0.476 0.545 | | | | 13.949 13.864 | 84.815 85.048 | 1.235 1.088 | | | | | | |
| | LA_09_28C Standard: RSN0151 | T: 3 weeks | '+5° C. | 80.5 | 5.660 | 11.64 | | 17.2 | 99.522 99.421 | 0.478 0.579 | | | | 14.849 14.618 | 83.298 83.409 | 1.853 1.973 | | | | | | |
| | LA_09_28C Standard: RSN0151 | T: 3 weeks | '−20° C. | 80.5 | 5.6 | 11.7 | | 17.2 | 99.565 99.421 | 0.435 0.579 | | | | 14.827 14.618 | 82.896 83.409 | 2.277 1.973 | | | | N/A | | |
| | LA_09_28C | T: 3 weeks | '+40° C. | 80.5 | 5.7 | 15.17 + A | | 17.2 | 91.992 | 3.777 | 2.953 | | 1.278 | 18.279 | 74.233 | 7.488 | | | | | | |
| | | | | | | | | | 99.421 | 0.579 | | | | 14.616 | 83.409 | 1.973 | | | | | | |

TABLE 56

Results - Prototype formulation LA_09_028D

| Buffer | Formulation number | Time point | Storage condition | pH | Tm [°C] | PSD pH | PSD DLS [nm] | UV [mg/mL] | SEC Mono-mer [%] | SEC Dimer/Oligomer [%] | SEC HMW [%] | SEC NP [%] | WCX % acid | WCX % neutral | WCX % basic | ASD Com-ment | SDS-PAGE non-red. main band | SDS-PAGE non-red. comment | ECS0% | Elisa EC50 | slope |
|---|---|---|---|---|---|---|---|---|---|---|---|---|---|---|---|---|---|---|---|---|---|
| Acetate 10 mM, 50 mg Trehalose, 20 mM Arginine-HCl, 0.01% Polysorbate 20 | LA_09_28D Standard: RSN0151 | T0 | N/A | | 81.7 | N/A | 14.3 | 16.2 | 99.231 99.691 | 0.336 0.309 | | | 14.336 13.772 | 84.478 85.024 | 1.186 1.204 | | 131.16 122.88 | | 91 100 | 9.75E+13 1.07E+12 | 0.60 0.81 |
| | LA_09_28D Standard: RSN0151 | T: 3 weeks | +5° C. | | 81.7 | 5.6 | 14.1 | 15.9 | 99.608 99.481 | 0.353 0.519 | | 0.039 | 14.309 14.278 | 84.351 84.346 | 1.34 1.377 | | | | | | |
| | LA_09_28D Standard: RSN0151 | T: 3 weeks | −20° C. | | 81.5 | 5.6 | 14.1 | 15.5 | 99.558 99.481 | 0.395 0.519 | | 0.047 | 14.048 14.278 | 84.700 84.346 | 1.252 1.377 | | | | N/A | | |
| | LA_09_28D Standard: RSN0151 | T: 3 weeks | +40° C. | | 81.7 | 5.6 | 14.8 | 15.7 | 96.904 99.481 | 1.403 0.519 | 0.957 | 0.736 | 13.872 14.278 | 83.307 84.346 | 2.821 1.377 | | | | | | |
| | LA_09_28D Standard: RSN0151 | T: 6 weeks | +5° C. | | 81.5 | 5.6 | 14.3 | 16.5 | 99.600 99.460 | 0.4 0.545 | | | 13.931 13.864 | 84.894 85.048 | 1.175 1.088 | | | | | | |
| | LA_09_28D Standard: RSN0151 | T: 6 weeks | −20° C. | 5.5 | 81.5 | 5.6 | 14.4 | 16.5 | 99.633 99.460 | 0.367 0.545 | | | 13.683 13.864 | 85.139 85.049 | 1.179 1.088 | | | | | | |
| | LA_09_28D Standard: RSN0151 | T: 6 weeks | +40° C. | | 81.8 | 5.7 | 16.0 | 16.4 | 95.087 99.460 | 2.24 0.545 | 1.578 | 1.095 | 13.794 13.864 | 82.051 85.048 | 4.155 1.088 | | 203.72 189.54 | 66.28.14 kDa | | N/A | |
| | LA_09_28D Standard: RSN0151 | T: 6 weeks | −80° C. | | N/A | 5.6 | 14.4 | 15.5 | 99.616 99.460 | 0.384 0.545 | | | 13.795 13.864 | 84.882 85.048 | 1.323 1.088 | | | | | | |
| | LA_09_28D Standard: RSN0151 | T: 3 weeks | +5° C. | | 81.8 | 5.7 | 13.8 | 16.3 | 99.562 99.421 | 0.416 0.579 | | | 14.089 14.616 | 83.957 83.409 | 1.954 1.973 | | | | | | |
| | LA_09_28D Standard: RSN0151 | T: 3 weeks | −20° C. | | 81.7 | 5.7 | 14.1 | 15.8 | 99.578 99.421 | 0.380 0.579 | | | 14.488 14.618 | 83.570 83.409 | 1.942 1.973 | | | | N/A | | |
| | LA_09_28D Standard: RSN0151 | T: 3 weeks | +40° C. | | 81.5 | 5.7 | 16.9 | 16.4 | 90.910 99.421 | 4.506 0.579 | 2.69 | 1.894 | 19.018 14.618 | 72.345 83.409 | 8.637 1.973 | | | | | | |

TABLE 57

Results - Prototype formulation LA_09_029A

| Buffer | Formulation number | Storage Time point | Storage condition | Tm [°C] | pH | PSD DLS [nm] | UV [mg/mL] | SEC Mono-mer [%] | SEC Dimer/Oligomer [%] | SEC HMW [%] | SEC NP [%] | ASD WCX % acid | ASD WCX % neutral | ASD WCX % basic | ASD WCX Com-ment | SDS-PAGE non-red. main band | SDS-PAGE non-red. com-ment | EC50% | Elisa EC50 | slope |
|---|---|---|---|---|---|---|---|---|---|---|---|---|---|---|---|---|---|---|---|---|
| Histidine 10 mM, 3 mg/mL NaCl, 25 mg/mL Trehalose, 20 mM Arginine-HCl, 0.01% Polysorbate | LA_09_29A Standard: RSN0151 | T0 | N/A | 79.4 | N/A | 12.5 | 20.3 | 99.748 99.691 | 0.252 0.309 | | | 13.946 13.755 | 84.881 85.045 | 1.174 1.2 | | 123.08 122.88 | | 174 100 | 1.71E+12 9.84E+13 | 0.77 0.64 |
| | LA_09_29A Standard: RSN0151 | T: 3 weeks | +5° C. | 79.7 | 5.1 | 12.5 | 18.1 | 99.690 99.504 | 0.31 0.496 | | | 14.304 | 84.620 | 1.077 | | | | | | |
| | LA_09_29A Standard: RSN0151 | T: 3 weeks | -20° C. | 79.3 | 5.2 | 12.5 | 17.9 | 99.625 99.504 | 0.338 0.496 | | 0.037 | 14.252 | 84.531 | 1.217 | | | | | | |
| | LA_09_29A Standard: RSN0151 | T: 3 weeks | +40° C. | 78.4 | 5.0 | 19.43 + A | 18.6 | 85.224 99.504 | 5.159 0.496 | 9.048 | 0.569 | | 50.132 | 7.197 | | | | N/A | | |
| | LA_09_29A Standard: RSN0151 | T: 6 weeks | +5° C. | 78.3 | 5.1 | 12.3 | 18.9 | 99.664 99.461 | 0.336 0.539 | | | 13.962 13.982 | 84.777 84.916 | 1.261 1.102 | | | | | | |
| | LA_09_29A Standard: RSN0151 | T: 6 weeks | -20° C. | 78.9 | 5.1 | 29.13 + A | 18.7 | 99.683 99.461 | 0.317 0.539 | | | 16.596 13.982 | 85.342 84.916 | 1.061 1.102 | | | | | | |
| | LA_09_29A Standard: RSN0151 | T: 6 weeks | +40° C. | 75.8 | 4.9 | 12.5 | 17.9 | 67.866 99.461 | 8.317 0.539 | 22.58 | 1.237 | 42.029 13.982 | 39.19 84.916 | 18.78 1.102 | | 205.8 189.54 | 90.14 kDa | | N/A | |
| | LA_09_29A Standard: RSN0151 | T: 6 weeks | -80° C. | N/A | 5.2 | | 19.3 | 99.666 99.461 | 0.334 0.539 | | | 13.621 13.982 | 85.201 84.916 | 1.177 1.102 | | | | | | |
| | LA_09_29A Standard: RSN0151 | T: 3 weeks | +5° C. | 79.2 | | | | 99.642 99.424 | 0.358 0.576 | | | 14.401 14.922 | 83.691 83.041 | 1.908 2.037 | | | | | | |
| | LA_09_29A Standard: RSN0151 | T: 3 weeks | -20° C. | 79.2 | | N/A | | 99.684 99.424 | 0.316 0.576 | | | 14.169 14.922 | 83.583 83.041 | 2.228 2.037 | | | | N/A | | |
| | LA_09_29A Standard: RSN0151 | T: 3 weeks | +40° C. | 77.3 | | | | 46.856 99.424 | 10.905 0.576 | 39.135 | 3.104 | 26.766 14.922 | 41.194 83.041 | 32.04 2.037 | | | | | | |

TABLE 58

Results - Prototype formulation LA_09_029B

| Buffer | Formulation number | Time point | Storage condition | pH | Tm [° C.] | PSD DLS [nm] | UV [mg/mL] | SEC Mono-mer [%] | SEC Dimer/Oligomer [%] | SEC HMW [%] | SEC NP [%] | WCX % acid | WCX % neutral | WCX % basic | ASD Com-ment | SDS-PAGE non-red. main band | SDS-PAGE non-red. com-ment | EC50% | Elisa EC50 | slope |
|---|---|---|---|---|---|---|---|---|---|---|---|---|---|---|---|---|---|---|---|---|
| Histidine 10 mM, 50 mg Trehalose, 0.01% Polysorbate 20 | LA_09_27B Standard: RSN0151 | T0 | N/A | N/A | 81.0 | 10.7 | 20.2 | 99.679 99.691 | 0.321 0.309 | | | 13.891 13.755 | 84.907 85.045 | 1.202 1.2 | | 122.26 122.88 | 118 100 | | 1.16E+12 9.84E+13 | 0.73 0.64 |
| | LA_09_27B Standard: RSN0151 | T: 3 weeks | '+5° C. | 5.0 | 81.3 | 10.5 | 19.3 | 99.622 99.504 | 0.351 0.496 | | | 14.145 14.208 | 84.674 84.672 | 1.182 1.22 | | | | | | |
| | LA_09_27B Standard: RSN0151 | T: 3 weeks | '-20° C. | 5.1 | N/A | 10.4 | 17.6 | 99.623 99.504 | 0.342 0.496 | | | 14.369 14.208 | 84.470 84.672 | 1.162 1.22 | | | | N/A | | |
| | LA_09_27B Standard: RSN0151 | T: 3 weeks | '+40° C. | 4.9 | N/A | 11.2 | 18.2 | 93.016 99.504 | 4.186 0.496 | 2.446 | 0.368 | 35.561 14.208 | 59.191 84.672 | 5.247 1.22 | | | | | | |
| | LA_09_27B Standard: RSN0151 | T: 6 weeks | '+5° C. | 5.1 | 81.0 | 10.4 | 19.9 | 99.613 99.461 | 0.387 0.539 | | | 13.622 13.982 | 85.381 84.916 | 0.988 1.102 | | | | | | |
| | LA_09_27B Standard: RSN0151 | T: 6 weeks | '-20° C. | 5.0 5.1 | | 10.4 | 19.2 | 99.653 99.461 | 0.347 0.539 | | | 13.758 13.982 | 85.184 84.916 | 1.058 1.102 | | | | | | |
| | LA_09_27B Standard: RSN0151 | T: 6 weeks | '+40° C. | 4.9 | | 11.98 + A | 19.4 | 85.502 | 7.644 | 6.093 | 0.761 | 45.968 | 42.961 | 11.071 | | 200.33 189.54 | 90.14 kDa | | N/A | |
| | | | | | | | | 99.461 | 0.539 | | | 13.982 | 84.916 | 1.102 | | | | | | |
| | LA_09_27B Standard: RSN0151 | T: 6 weeks | '-80° C. | 5.1 | | 10.3 | 19.0 | 99.654 99.461 | 0.346 0.539 | | | 13.454 13.982 | 83.382 84.916 | 1.164 1.102 | | | | | | |
| | LA_09_27B Standard: RSN0151 | T: 3 weeks | '+5° C. | | N/A | | | 99.603 99.424 | 0.397 0.576 | | | 14.238 14.922 | 63.852 83.041 | 1.910 2.037 | | | | | | |
| | LA_09_27B Standard: RSN0151 | T: 3 weeks | '-20° C. | | | N/A | | 99.650 99.424 | 0.350 0.576 | | | 14.108 14.922 | 83.764 83.041 | 2.128 2.037 | | | | N/A | | |
| | LA_09_27B Standard: RSN0151 | T: 3 weeks | '+40° C. | | | | | 67.612 99.424 | 11.218 0.576 | 18.161 | 3.009 | 41.575 14.922 | 42.311 83.041 | 16.113 2.037 | | | | | | |

TABLE 59

Results - Prototype formulation LA_09_029C

| Buffer | Formulation number | Time point | Storage condition | Tm [° C.] | pH | PSD DLS [nm] | UV [mg/mL] | SEC Mono-mer [%] | Dimer/Oligomer [%] | HMW [%] | NP [%] | ASD % acid | WCX % neutral | % basic | Com-ment | SDS-PAGE non-red. main band | com-ment | Elisa EC50% | EC50 | slope |
|---|---|---|---|---|---|---|---|---|---|---|---|---|---|---|---|---|---|---|---|---|
| Histidine 10 mM, 6 mg NaCl, 0.01% Polysorbate 20 | LA_09_29C Standard: RSN0151 | T0 | N/A | 78.9 | N/A | 11.9 | 19.4 | 99.741 99.691 | 0.259 0.309 | | | 14.119 13.755 | 84.681 85.045 | 1.2 1.2 | | 122.43 122.88 | | | | |
| | LA_09_29C Standard: RSN0151 | T: 3 weeks | '+5° C. | 79.0 | 5.1 | 11.9 | 19.0 | 99.643 99.504 | 0.357 0.496 | | | 14.046 14.208 | 84.796 84.672 | 1.158 1.22 | | | | | | |
| | LA_09_29C Standard: RSN0151 | T: 3 weeks | '-20° C. | 78.4 | 5.2 | 12.0 | 18.6 | 99.674 99.504 | 0.326 0.496 | | | 14.171 14.208 | 84.753 84.672 | 1.076 1.22 | | | | N/A | | |
| | LA_09_29C Standard: RSN0151 | T: 3 weeks | '+40° C. | 77.4 | 5.0 | 19.67 + A | 18.7 | 84.940 99.504 | 5.173 0.496 | 9.325 | 0.562 | 41.068 14.208 | 47.301 84.672 | 11.631 1.22 | | | | | | |
| | LA_09_29C Standard: RSN0151 | T: 6 weeks | '+5° C. | 78.1 | 5.2 | 11.8 | 19.7 | 99.627 99.461 | 0.373 0.539 | | | 13.871 13.982 | 84.916 84.916 | 1.213 1.102 | | | | | | |
| | LA_09_29C Standard: RSN0151 | T: 6 weeks | '-20° C. | 77.8 | 5.2 | 12.0 | 20.8 | 99.661 99.461 | 0.339 0.539 | | | 13.764 13.982 | 85.153 84.916 | 1.083 1.102 | | | | | | |
| | LA_09_29C Standard: RSN0151 | T: 6 weeks | '+40° C. | 76.6 | 4.9 | 34.92 + A | 19.2 | 61.267 99.461 | 7.789 0.539 | 29.686 | 1.359 | 43.326 13.982 | 35.038 84.916 | 21.636 1.102 | | 199.58 189.54 | 90.14 | | N/A | |
| | LA_09_29C Standard: RSN0151 | T: 6 weeks | '-80° C. | N/A | 5.2 | 11.9 | 19.9 | 99.663 99.461 | 0.337 0.539 | | | 13.521 13.982 | 85.426 84.916 | 1.053 1.102 | | | | | | |
| | LA_09_29C Standard: RSN0151 | T: 3 weeks | '+5° C. | 78.4 | | | | 99.594 99.424 | 0.406 0.576 | | | 14.244 14.922 | 83.772 83.041 | 1.984 2.037 | | | | | | |
| | LA_09_29C Standard: RSN0151 | T: 3 weeks | '-20° C. | 78.5 | | N/A | | 99.680 99.424 | 0.32 0.576 | | | 14.199 14.922 | 83.824 83.041 | 1.977 2.037 | | | | N/A | | |
| | LA_09_29C | T: 3 weeks | '+40° C. | 76.6 | | | | 36.901 99.424 | 9.237 0.576 | 50.322 | 3.54 | 25.609 14.922 | 37.193 83.041 | 37.198 2.037 | | | | | | |

TABLE 60

Results - Prototype formulation LA_09_029D

| Buffer | Formulation number | Storage Time point | Storage Condition | Tm [° C.] | pH | PSD DLS [nm] | UV [mg/mL] | SEC Mono-mer [%] | SEC Dimer/ Oligomer [%] | SEC HMW [%] | SEC NP [%] | ASD WCX % acid | ASD WCX % neutral | ASD WCX % basic | ASD Com-ment | SDS-PAGE non-red. main band | SDS-PAGE non-red. com-ment | Elisa EC50% | Elisa EC50 | slope |
|---|---|---|---|---|---|---|---|---|---|---|---|---|---|---|---|---|---|---|---|---|
| Histidine 10 mM, 50 mg Trehalose, 20 mM Arginine-HCl, 0.01% Polysor-bate 20 | LA_09_29D Standard: RSN0151 | T0 | N/A | 80.7 | N/A | 13.1 | 19.4 | 99.789 99.691 | 0.211 0.309 | | | 14.446 13.755 | 84.366 85.045 | 1.189 1.2 | | 124.60 122.88 | 169 100 | | 1.66E+12 9.84E+13 | 0.66 0.64 |
| | LA_09_29D Standard: RSN0151 | T: 3 weeks | '+5° C. | 80.3 | 5.1 | 12.6 | 17.8 | 99.670 99.504 | 0.33 0.496 | | | 14.168 14.208 | 84.691 84.672 | 1.141 1.22 | | | | | | |
| | LA_09_29D Standard: RSN0151 | T: 3 weeks | '−20° C. | 75.5 | 5.1 | 12.8 | 17.1 | 99.663 99.504 | 0.337 0.496 | | | 14.366 14.208 | 84.473 84.672 | 1.161 1.22 | | | | | | |
| | LA_09_29D Standard: RSN0151 | T: 3 weeks | '+40° C. | 78.6 | 4.9 | 15.99 + A | 17.2 | 87.165 99.504 | 6.561 0.496 | 6.721 | 0.553 | 40.897 14.208 | 48.391 84.672 | 10.712 1.22 | | | | N/A | | |
| | LA_09_29D Standard: RSN0151 | T: 6 weeks | '+5° C. | 80.0 | 5.1 | 12.6 | 18.7 | 99.655 99.461 | 0.345 0.539 | | | 13.796 13.982 | 84.86 84.916 | 1.344 1.102 | | | | | | |
| | LA_09_29D Standard: RSN0151 | T: 6 weeks | '−20° C. | 72.1 | 5.1 | 12.6 | 18.9 | 99.687 99.461 | 0.313 0.539 | | | 13.806 13.982 | 84.995 84.916 | 1.2 1.102 | | | | | | |
| | LA_09_29D Standard: RSN0151 | T: 6 weeks | '+40° C. | 72.7 | 4.9 | 20.47 + A | 17.9 | 76.511.000 99.461 | 8.167 0.539 | 14.268 | 1.054 | 44.302 13.982 | 41.575 84.916 | 14.124 1.102 | | 198.81 189.54 | 90.14 kDa | | N/A | |
| | Standard: RSN0151 | T: 6 weeks | '−80° C. | N/A | 5.1 | 12.5 | 18.5 | 99.680 99.461 | 0.32 0.539 | | | 13.995 13.982 | 84.985 84.916 | 1.020 1.102 | | | | | | |
| | LA_09_29D Standard: RSN0151 | T: 3 weeks | '+5° C. | 80.0 | | | | 99.632 99.424 | 0.368 0.576 | | | 14.623 14.922 | 83.446 83.041 | 1.931 2.037 | | | | | | |
| | LA_09_29D Standard: RSN0151 | T: 3 weeks | '−20° C. | 80.0 | | N/A | | 99.677 99.424 | 0.323 0.576 | | | 14.150 14.922 | 83.575 83.041 | 2.276 2.037 | | | | N/A | | |
| | LA_09_29D Standard: RSN0151 | T: 3 weeks | '+40° C. | 78.0 | | | | 56.365 99.424 | 11.328 0.576 | 29.509 | 2.8 | 30.807 14.922 | 41.914 83.041 | 27.279 2.037 | | | | | | |

Anti-CXCR5 (20 mg/mL) Formulation Studies

The data in Examples 13-16 were collected during formulation studies for the Lead CXCR5 Antibody and its drug product for intravenous and subcutaneous administration. The objective of the formulation studies was to provide a stable, clear or slightly opalescent, and colorless or slightly yellow, visual particle-free Lead CXCR5 Antibody solution for injection for phase I.

Materials

Drug Substance (DS)

Two drug substance batches were used for these formulation studies. One was formulated in phosphate buffered saline (PBS) and the other was formulated in citrate buffer. See Table 61.

TABLE 61

Available drug substance batches

| Batch no. | Amount | Lead Ab concentration | Buffer | pH-value [—] |
|---|---|---|---|---|
| RSN0151 | 10 g | 5.0 mg/mL | 155 mM PBS | 7.2 |
| SCB0001 | 20 g | 20.30 mg/mL | 10 mM Citrate | 6.0 |

Excipients

Table 62 shows excipients that were used during the formulation studies.

TABLE 62

Excipients

| Excipient | Material no. | Supplier |
|---|---|---|
| Arginine | 1.01587 | Merck |
| Citric acid | 100241 | Merck |
| Histidine | 1.04352 | Merck |
| Hydrochloric acid | 114027 | H600 |
| Saccharose | S3929 | Sigma-Aldrich |
| Sodium acetate | 1.06265 | Merck |
| Sodium chloride | 10158 | H600 |
| Sodium citrate | 114196 | H600 |
| Sodium hydroxide | 114076 | H600 |
| Polysorbate 20 | 139850 | H600 |
| α,α-Trehalose | T9531 | Sigma-Aldrich |

Methods

Sample Preparation

Ultrafiltration/Diafiltration was performed on a small scale using VivaSpin devices with a Hydrosart membrane and a 30 kDa cut-off. RSN material was concentrated from 5 mg/mL to 20 mg/mL, and phosphate (PBS) buffer was exchanged to either 10 mM citrate buffer pH 6.0, acetate buffer pH 5.5, or histidine buffer pH 5.0. The VivaSpin units were placed at room temperature (RT) in a common laboratory centrifuge and centrifuged with 2000 rpm. The solution was filtered over a 0.2 μm Minisart before analytical testing. All samples were stored between +2° and +8° C., tightly closed, and protected from light, until analytical testing at T0 and after one week thermal stress at +40° C. or after mechanical stress for 2.5 hours, 300 rpm at RT (only for evaluation of polysorbate 20 concentration).

Analytical Methods

The following techniques were used for sample analysis:

TABLE 63

Analytical techniques used

| Technique (Company) | Parameter to investigate |
|---|---|
| Organoleptic (—) | Appearance |
| Nephelometer (Hach Lange) | Turbidity |
| pH-meter (WTW) | pH-value |
| UV (Perkin Elmer) | Concentration of mAB |
| Densimeter (Paar) | Density |
| Osmometer (Knauer) | Osmolality |
| Viscosimeter (Paar) | Viscosity |
| Dynamic Light Scattering (Malvern) | Hydrodynamic diameter |
| SEC (N/A) | Mono-/Di-/Oligomer and High Molecular Weight Protein (HMWP)/ Low Molecular Weight (LMW) content |
| WCX(N/A) | Isoforms (acid/basic/neutral) |
| ELISA*(N/A) | Potency (Binding) |
| SDS-Page (red.)** (N/A) | HC/LC, mAB-fragments |
| SDS-Page (non-red.)** (N/A) | Aggregation and degradation products |
| HIAC*(N/A) | Particulate matter |

*Some samples will be analyzed.
**SDS-Page will be performed in case SEC shows unusual results.

Example 13

Additional pH Optimization

Preformulation studies identified 10 mM citrate buffer at pH 6.0 as the best buffer with less Lead CXCR5 Antibody aggregation tendency. To obtain a pH-profile in citrate buffer, stepwise pH-dependent stability from pH 5.0 to 7.0 was evaluated. Due to limited drug substance availability, in-depth pH-screening was performed only with 10 mM citrate buffer. Samples were taken at T0 and after one week thermal stress at +40° C. See Tables 64-68.

TABLE 64

Overview of samples

| Batch no. | Target pH-value (—) | Measured pH-value (—) |
|---|---|---|
| LA_09_030 | 5.0 | 5.1 |
| LA_09_031 | 5.3 | 5.4 |
| LA_09_032 | 5.5 | 5.6 |
| LA_09_033 | 5.7 | 5.8 |
| LA_09_034 | 6.0 | 6.1 |
| LA_09_035 | 6.3 | 6.4 |
| LA_09_036 | 6.5 | 6.6 |
| LA_09_037 | 6.7 | 6.8 |
| LA_09_038 | 7.0 | 7.1 |

TABLE 65 results T0

| Batch no. | Appearance | Measured pH-value (—) | mAB conc. (mg/mL) | Hydrodynamic diameter (nm) |
|---|---|---|---|---|
| LA_09_030 | Clear | 5.1 | 23.35 | 15.42 + aggr. |
| LA_09_031 | Clear | 5.4 | 21.95 | 12.85 |
| LA_09_032 | Clear | 5.6 | 23.00 | 12.98 |
| LA_09_033 | Clear | 5.8 | 21.21 | 12.99 |
| LA_09_034 | Clear | 6.1 | 22.77 | 12.83 |
| LA_09_035 | Clear | 6.4 | 23.87 | 13.22 |
| LA_09_036 | Clear | 6.6 | 23.74 | 13.04 |
| LA_09_037 | Clear | 6.8 | 22.85 | 13.00 |
| LA_09_038 | Clear | 7.1 | 21.96 | 13.32 |

TABLE 66 results T1 week +40° C.

| Batch no. | Appearance | Measured pH value (—) | mAB conc. [mg/mL] | Hydrodynamic diameter (nm) |
|---|---|---|---|---|
| LA_09_030 | Clear | 5.2 | 15.62* | 15.27 + aggr. |
| LA_09_031 | Clear | 5.5 | 21.91 | 16.74 + aggr. |
| LA_09_032 | Clear | 5.6 | 24.32 | 13.59 |
| LA_09_033 | Clear | 5.8 | 24.74 | 13.83 |
| LA_09_034 | Clear | 6.1 | 24.18 | 13.25 |
| LA_09_035 | Clear | 6.5 | N/A | 13.41 |
| LA_09_036 | Clear | 6.6 | 23.03 | 13.37 |
| LA_09_037 | Clear | 6.9 | 22.68 | 13.24 |
| LA_09_038 | Clear | 7.2 | 23.33 | 14.40 |

*Unusual result due to dilution mistake

TABLE 67

ASD results T0

| Batch no. | % Monomer | % Di-/Oligomer | % HMWP | % | % | % | % basic |
|---|---|---|---|---|---|---|---|
| LA_09_030 | 99.63 | 0.37 | — | — | 13.60 | 85.18 | 1.22 |
| LA_09_031 | 99.57 | 0.43 | — | — | 13.52 | 85.24 | 1.24 |
| LA_09_032 | 99.48 | 0.52 | — | — | 13.71 | 85.04 | 1.25 |
| LA_09_033 | 99.51 | 0.49 | — | — | 13.99 | 84.61 | 1.40 |
| LA_09_034 | 99.41 | 0.59 | — | — | 13.62 | 85.17 | 1.21 |
| LA_09_035 | 99.24 | 0.76 | — | — | 13.72 | 84.64 | 1.64 |
| LA_09_036 | 98.72 | 1.28 | — | — | 13.72 | 84.45 | 1.83 |
| LA_09_037 | 98.95 | 1.05 | — | — | 13.60 | 84.73 | 1.67 |
| LA_09_038 | 98.58 | 1.42 | — | — | 13.84 | 84.13 | 2.03 |

TABLE 68 results T1 week +40° C.

| Batch no. | % Monomer | % Di-/Oligomer | % HMWP | % LMW | % acidic | % neutral | % basic |
|---|---|---|---|---|---|---|---|
| LA_09_030 | 95.19 | 0.97 | 3.29 | 0.55 | 11.90 | 83.92 | 4.18 |
| LA_09_031 | 96.47 | 0.89 | 2.14 | 0.50 | 12.19 | 84.70 | 3.11 |
| LA_09_032 | 96.82 | 0.92 | 1.69 | 0.57 | 12.14 | 85.48 | 2.38 |
| LA_09_033 | 97.13 | 0.94 | 1.48 | 0.45 | 12.41 | 85.04 | 2.55 |
| LA_09_034 | 97.73 | 0.97 | 0.82 | 0.48 | 12.35 | 85.69 | 1.96 |
| LA_09_035 | 97.58 | 1.12 | 0.89 | 0.41 | 11.93 | 85.74 | 2.33 |
| LA_09_036 | 97.47 | 1.32 | 0.86 | 0.35 | 12.01 | 85.46 | 2.53 |
| LA_09_037 | 97.35 | 1.41 | 0.87 | 0.37 | 12.08 | 85.28 | 2.64 |
| LA_09_038 | 96.97 | 1.62 | 0.97 | 0.44 | 11.65 | 85.10 | 3.25 |

In conclusion, the data confirm the results already generated during preformulation studies: increasing the pH causes the monomer content to decrease and dimer rate to increase. Samples at +40° C. showed with lower pH-value decrease in HMWs up to pH 6.0 and then increase up to pH 5.0.

Example 14

Additional Buffer Optimization

Next, citrate, acetate, and histidine (as back-up buffer) buffers were screened at 5/10/25/50 mM at the selected pH-values. See Tables 69-83.

TABLE 69

Overview on samples - Citrate buffer pH 6.0

| Batch no. | Citrate buffer conc. [mM] |
|---|---|
| LA_09_040 | 5 |
| LA_09_034 | 10 |
| LA_09_041 | 25 |
| LA_09_042 | 50 |

TABLE 70 results after T0

| Batch no. | Appearance | Measured pH value (—) | mAB conc. [mg/mL] | Hydrodynamic diameter (nm) |
|---|---|---|---|---|
| LA_09_040 | Clear | 6.1 | 20.05 | 13.47 |
| LA_09_034 | Clear | 6.1 | 22.77 | 12.83 |
| LA_09_041 | Clear | 6.2 | 20.48 | 11.91 |
| LA_09_042 | Clear | 6.1 | 22.19 | 11.87 |

TABLE 71 results after T1 week +40° C.

| Batch no. | Appearance | Measured pH value (—) | mAB conc. [mg/mL] | Hydrodynamic diameter (nm) |
|---|---|---|---|---|
| LA_09_040 | Clear | 6.3 | 21.62 | 13.78 |
| LA_09_034 | Clear | 6.1 | 24.18 | 13.25 |

TABLE 71-continued results after T1 week +40° C.

| Batch no. | Appearance | Measured pH value (—) | mAB conc. [mg/mL] | Hydrodynamic diameter (nm) |
|---|---|---|---|---|
| LA_09_041 | Clear | 6.2 | 18.37 | 12.50 |
| LA_09_042 | Clear | 6.2 | 20.59 | 12.07 |

TABLE 72 results T0

| Batch no. | % Monomer | % Di-/Oligomer (RRT 0.84) | % HMWP (RRT 0.68) | % | % | % | % basic |
|---|---|---|---|---|---|---|---|
| LA_09_040 | 99.49 | 0.51 | — | — | 13.19 | 85.81 | 1.00 |
| LA_09_034 | 99.41 | 0.59 | — | — | 13.62 | 85.17 | 1.21 |
| LA_09_041 | 99.55 | 0.42 | 0.03 | — | 13.24 | 85.67 | 1.09 |
| LA_09_042 | 99.60 | 0.39 | 0.01 | — | 13.41 | 85.48 | 1.11 |

TABLE 73 results after thermal stress 1 week/+40° C.

| Batch no. | % Monomer | % Di-/Oligomer (RRT 0.84) | % HMWP (RRT 0.68) | % | % | % | % basic |
|---|---|---|---|---|---|---|---|
| LA_09_040 | 98.58 | 0.86 | 0.17 | 0.39 | 12.52 | 85.95 | 1.53 |
| LA_09_034 | 97.73 | 0.97 | 0.82 | 0.48 | 12.35 | 85.69 | 1.96 |
| LA_09_041 | 98.81 | 0.65 | 0.21 | 0.33 | 12.54 | 86.07 | 1.38 |
| LA_09_042 | 98.87 | 0.59 | 0.14 | 0.40 | 12.45 | 86.10 | 1.45 |

TABLE 74

Overview on samples - Histidine buffer pH 5.0

| Batch no. | Histidine buffer conc. [mM] |
|---|---|
| LA_09_043 | 5 |
| LA_09_044 | 10 |
| LA_09_045 | 25 |
| LA_09_046 | 50 |

TABLE 75 results after T0

| Batch no. | Appearance | Measured pH value (—) | mAB conc. [mg/mL] | Hydrodynamic diameter (nm) |
|---|---|---|---|---|
| LA_09_043 | Clear | 5.5 | 21.89 | 8.40 + aggr. |
| LA_09_044 | Clear | N/A | 6.95* | 11.34 |
| LA_09_045 | Clear | 5.2 | 21.78 | 11.86 + aggr. |
| LA_09_046 | Clear | 5.1 | 20.04 | 11.86 |

*Low data due to sample dilution mistake

TABLE 76 results after T1 week +40° C.

| Batch no. | Appearance | Measured pH value (—) | mAB conc. [mg/mL] | Hydrodynamic diameter |
|---|---|---|---|---|
| LA_09_043 | Clear | 5.5 | 21.34 | 8.81 |
| LA_09_044 | Clear | 5.5 | 24.18 | 13.25 |
| LA_09_045 | Clear | 5.2 | 23.62 | 11.88 |
| LA_09_046 | Clear | 5.1 | 21.41 | 12.50 + aggr. |

TABLE 77

ASD results T0

| Batch no. | % | % Di- | % HMWP | % | % acidic | % | % basic |
|---|---|---|---|---|---|---|---|
| LA_09_043 | 99.55 | 0.45 | — | — | 13.69 | 85.16 | 1.15 |
| LA_09_044* | N/A | N/A | N/A | N/A | N/A | N/A | N/A |
| LA_09_045 | 99.68 | 0.32 | — | — | 13.73 | 85.00 | 1.27 |
| LA_09_046 | 99.70 | 0.30 | — | — | 13.43 | 85.49 | 1.08 |

*not analyzed due to dilution mistake

TABLE 78 results after thermal stress 1 week/+40° C.

| Batch no. | % | % Di- | % HMWP | % | % acidic | % | % basic |
|---|---|---|---|---|---|---|---|
| LA_09_043 | 98.72 | 0.82 | — | 0.46 | 13.63 | 84.60 | 1.75 |
| LA_09_044* | N/A | N/A | N/A | N/A | N/A | N/A | N/A |
| LA_09_045 | 98.30 | 0.80 | 0.44 | 0.56 | 12.79 | 85.19 | 2.02 |
| LA_09_046 | 97.79 | 0.68 | 1.07 | 0.46 | 12.61 | 84.75 | 2.64 |

*not analyzed due to dilution mistake

TABLE 79

Overview of samples - Acetate buffer pH 5.5

| Batch no. | Acetate buffer conc. [mM] |
|---|---|
| LA113244_09_053 | 5 |
| LA113244_09_054 | 10 |
| LA113244_09_055 | 25 |
| LA113244_09_056 | 50 |

TABLE 80 results after T0

| Batch no. | Appearance | Measured pH value (—) | mAB conc. [mg/mL] | Hydrodynamic diameter |
|---|---|---|---|---|
| LA_09_053 | Clear | 5.88 | 25.41 | 10.44 |
| LA_09_054 | Clear | 5.68 | 21.91 | 13.21 + aggr. |
| LA_09_055 | Clear | 5.56 | 21.53 | 14.06 |
| LA_09_056 | Clear | 5.56 | 22.08 | 13.54 |

TABLE 81 results after T0

| Batch no. | Appearance | Measured pH value (—) | mAB conc. [mg/mL] | Hydrodynamic diameter |
|---|---|---|---|---|
| LA_09_053 | Clear | 5.88 | 26.43 | 11.48 |
| LA_09_054 | Clear | 5.69 | 23.40 | 13.44 |

TABLE 81-continued results after T0

| Batch no. | Appearance | Measured pH value (—) | mAB conc. [mg/mL] | Hydrodynamic diameter |
|---|---|---|---|---|
| LA_09_055 | Clear | 5.61 | 21.53 | 14.46 |
| LA_09_056 | Clear | 5.56 | 21.68 | 13.71 |

TABLE 82 results T0

| Batch no. | % | % Di- | % HMWP | % | % acidic | % | % basic |
|---|---|---|---|---|---|---|---|
| LA_09_053 | 98.89 | 0.99 | 0.02 | 0.10 | 14.44 | 83.67 | 1.89 |
| LA_09_054 | 98.84 | 1.09 | 0.07 | — | 11.30 | 86.80 | 1.90 |
| LA_09_055 | 98.91 | 0.99 | 0.07 | 0.03 | 11.30 | 86.77 | 1.93 |
| LA_09_056 | 98.97 | 0.87 | 0.10 | 0.06 | 11.27 | 86.90 | 1.83 |

TABLE 83 results after thermal stress 1 week/+40° C.

| Batch no. | % Monomer | % Di-/Oligomer (RRT 0.84) | % HMWP (RRT 0.68) | % | % acidic | % | % basic |
|---|---|---|---|---|---|---|---|
| LA_09_053 | 97.68 | 1.96 | 0.04 | 0.32 | 14.53 | 81.50 | 3.91 |
| LA_09_054 | 97.83 | 1.99 | 0.09 | 0.09 | 11.13 | 85.79 | 3.08 |
| LA_09_055 | 97.88 | 2.00 | 0.09 | 0.09 | 11.09 | 85.76 | 3.15 |
| LA_09_056 | 98.10 | 1.22 | 0.59 | 0.09 | 10.92 | 86.24 | 2.74 |

In conclusion, the data confirm the results generated during the preformulation studies. Using citrate as the buffer agent, the monomer content is slightly higher than with acetate buffer and histidine buffer. With histidine, high aggregation behavior is observable, even at T0, leading to difficulties in analytical sample preparation. A significant difference between the tested buffer concentrations cannot be measured, so all three buffers citrate, histidine, and acetate will be used with a concentration of 10 mM.

Example 15

Additional Surfactant Optimization

Based on preformulation trials, the addition of non-ionic surfactant polysorbate 20 (0.01%) showed beneficial effects on stability, so further evaluation of its concentration was performed by adding the following polysorbate 20 concentrations to the respective buffers: 0.0025%/0.005%/0.01%/0.02%. See Tables 84-93.

TABLE 84

Overview of samples in acetate buffer

| | Polysorbate 20 concentration | |
|---|---|---|
| Batch no. | in [mg/mL] | as percent[%] |
| LA_09_058 | 0.2 | 0.02 |
| LA_09_059 | 0.1 | 0.01 |
| LA_09_060 | 0.05 | 0.005 |
| LA_09_061 | 0.025 | 0.0025 |

TABLE 85 results after T0

| Batch no. | Appearance | Measured pH value (—) | mAB conc. [mg/mL] | Hydrodynamic diameter (nm) |
|---|---|---|---|---|
| LA_09_058 | Clear | 5.61 | 23.71 | 12.50 |
| LA_09_059 | Clear | 5.64 | 22.76 | 12.94 |
| LA_09_060 | Clear | 5.63 | 23.89 | 12.83 |
| LA_09_061 | Clear | 5.64 | 25.79 | 12.88 |

TABLE 86 results after mechanical stress 300 rpm/150 min

| Batch no. | Appearance | Measured pH value (—) | mAB conc. [mg/mL] | Hydrodynamic diameter (nm) |
|---|---|---|---|---|
| LA_09_058 | Clear | 5.61 | 22.82 | 12.48 |
| LA_09_059 | Clear | 5.67 | 22.47 | 12.73 |
| LA_09_060 | Clear | 5.55 | 22.90 | 12.59 |
| LA_09_061 | Clear | 5.65 | 25.19 | 12.76 |

TABLE 87 results T0

| Batch no. | % | % Di- | % HMWP | % | % acidic | % | % basic |
|---|---|---|---|---|---|---|---|
| LA_09_058 | 99.17 | 0.80 | 0.03 | — | 11.25 | 86.94 | 1.81 |
| LA_09_059 | 99.16 | 0.81 | 0.03 | — | 11.27 | 86.94 | 1.79 |
| LA_09_060 | 99.17 | 0.81 | 0.03 | — | 11.44 | 86.80 | 1.76 |
| LA_09_061 | 99.13 | 0.84 | 0.03 | — | 11.31 | 86.91 | 1.78 |

TABLE 88 results after mechanical stress 300 rpm/150 min

| Batch no. | % Monomer | % Di-/Oligomer (RRT 0.84) | % HMWP (RRT 0.68) | % | % acidic | % | % basic |
|---|---|---|---|---|---|---|---|
| LA_09_058 | 99.16 | 0.81 | 0.03 | — | 11.27 | 86.95 | 1.78 |
| LA_09_059 | 99.16 | 0.82 | 0.02 | — | 11.24 | 86.91 | 1.85 |
| LA_09_060 | 99.17 | 0.81 | 0.03 | — | 11.46 | 86.77 | 1.77 |
| LA_09_061 | 99.16 | 0.81 | 0.02 | | 11.22 | 86.97 | 1.79 |

TABLE 89

Overview of samples in citrate buffer

| | Polysorbate 20 concentration | |
|---|---|---|
| Batch no. | in (mg/mL) | as percent (%) |
| LA_09_062 | 0.2 | 0.02 |
| LA_09_063 | 0.1 | 0.01 |
| LA_09_064 | 0.05 | 0.005 |
| LA_09_065 | 0.025 | 0.0025 |

TABLE 90 results after T0

| Batch no. | Appearance | Measured pH value (—) | mAB conc. (mg/mL) | Hydrodynamic diameter (nm) |
|---|---|---|---|---|
| LA_09_062 | Clear | 6.05 | 23.72 | 12.67 |
| LA_09_063 | Clear | 6.03 | 25.18 | 12.73 |
| LA_09_064 | Clear | 6.04 | 23.85 | 12.47 |
| LA_09_065 | Clear | 6.04 | 22.65 | 12.46 |

TABLE 91 results after T1 week +40° C.

| Batch no. | Appearance | Measured pH value (—) | mAB conc. [mg/mL] | Hydrodynamic diameter (nm) |
|---|---|---|---|---|
| LA_09_062 | Clear | 6.07 | 23.44 | 12.99 |
| LA_09_063 | Clear | 6.03 | 24.39 | 12.59 |
| LA_09_064 | Clear | 6.04 | 23.93 | 12.39 |
| LA_09_065 | Clear | 6.04 | 22.27 | 12.37 |

TABLE 92 results T0

| Batch no. | % Monomer | % Di-/Oligomer | % HMWP | % acidic | % | % basic |
|---|---|---|---|---|---|---|
| LA_09_062 | 99.25 | 0.70 | 0.05 | — | 11.33 | 86.24 | 2.43 |
| LA_09_063 | 99.28 | 0.68 | 0.04 | — | 11.00 | 86.36 | 2.64 |
| LA_09_064 | 99.23 | 0.74 | 0.03 | — | 10.93 | 86.45 | 2.62 |
| LA_09_065 | 99.28 | 0.69 | 0.03 | — | 10.97 | 86.25 | 2.77 |

TABLE 93 results after mechanical stress 300 rpm/150 min

| Batch no. | % Monomer | % Di-/Oligomer | % HMWP | % acidic | % | % basic |
|---|---|---|---|---|---|---|
| LA_09_062 | 99.27 | 0.69 | 0.04 | — | 11.25 | 86.27 | 2.48 |
| LA_09_063 | 99.32 | 0.65 | 0.03 | — | 10.87 | 86.59 | 2.54 |
| LA_09_064 | 99.19 | 0.78 | 0.03 | — | 10.91 | 86.56 | 2.53 |
| LA_09_065 | 99.16 | 0.80 | 0.04 | — | 10.79 | 86.51 | 2.70 |

In conclusion, no significant differences in samples containing acetate or citrate buffer with various polysorbate concentration were measurable. To ensure mAb prevention against mechanical stress over a longer period of time than tested for 150 min, the polysorbate concentration was set to 0.2 mg/mL. This amount was also proposed based on preformulation studies.

Example 16

Additional Isotonicity Optimization

During preformulation studies, NaCl, Trehalose, and Arginine-HCl were identified as additives for isotonicity and stability purposes. Arginine-HCl was then dropped due to less mAb stability effects. Depending on buffer concentration and pH-value, isotonant/stabilizer amount is adapted to achieve osmolality of at least 240 mOsmol/kg according to Ph.Eur.

The use of trehalose was challenged as it is not a compendial excipient and is high priced. During preformulation studies, sucrose (saccharose) caused slightly more aggregation, but was not followed-up and verified in further studies. Therefore, a new short-term stability study over four weeks was designed, including trehalose as well as saccharose in both 10 mM citrate and acetate buffer with storage temperatures at +5°, +25°, and +40° C. See Tables 94-102.

Fine-tuning of osmolality of at least 240 mOsmol/kg was performed with NaCl.

TABLE 94

Overview of samples

| Batch no. | Buffer | Target pH-value [—] | Polysorbate 20 | NaCl | Stabilizing agent |
|---|---|---|---|---|---|
| LA_09_051A | 10 mM Citrate | 6.0 | 0.2 mg/mL | 2 mg/mL | Sucrose 60 mg/mL |
| LA_09_051B | 10 mM Citrate | 6.0 | 0.2 mg/mL | 2 mg/mL | Trehalose 60 mg/mL |
| LA_09_052A | 10 mM Citrate | 5.5 | 0.2 mg/mL | 2 mg/mL | Sucrose 60 mg/mL |
| LA_09_052B | 10 mM Citrate | 5.5 | 0.2 mg/mL | 2 mg/mL | Trehalose 60 mg/mL |

TABLE 95 results T0

| Batch no. | Appearance | Measured pH value (—) | mAB-conc. (mg/mL) | Osmolality (mOsmol/kg) |
|---|---|---|---|---|
| LA_09_051A | Clear | 5.89 | 21.46 | 289 |
| LA_09_051B | Clear | 5.94 | 21.46 | 268 |
| LA_09_052A | Clear | 5.82 | 22.07 | 273 |
| LA_09_052B | Clear | 5.80 | 22.07 | 256 |

TABLE 96 results T 4 weeks, +5° C.

| Batch no. | Measured pH-value (—) | mAB-conc. (mg/mL) | Hydrodynamic diameter (nm) |
|---|---|---|---|
| LA_09_051A | 6.02 | 21.81 | 13.58 |
| LA_09_051B | 5.95 | 22.10 | 13.35 |
| LA_09_052A | 5.86 | 21.70 | 15.12 |
| LA_09_052B | N/A | N/A | N/A |

TABLE 97 results T 4 weeks, +25° C.

| Batch no. | Measured pH-value | mAB-conc. (mg/mL) | Hydrodynamic diameter (nm) |
|---|---|---|---|
| LA_09_051A | 6.06 | 22.30 | 13.57 |
| LA_09_051B | 6.02 | 22.09 | 13.41 |
| LA_09_052A | 5.91 | 21.98 | 15.14 |
| LA_09_052B | N/A | N/A | N/A |

TABLE 98 results T 4 weeks, +40° C.

| Batch no. | Measured pH-value | mAB-conc. (mg/mL) | Hydrodynamic diameter (nm) |
|---|---|---|---|
| LA_09_051A | 6.04 | 22.21 | 14.73 |
| LA_09_051B | 5.95 | 21.86 | 14.11 |
| LA_09_052A | 5.91 | 22.23 | 16.37 |
| LA_09_052B | 5.89 | 22.84 | 16.02 |

TABLE 99 results T0

| Batch no. | % | % Di- | % | % | % | mAB-conc. (mg/mL) |
|---|---|---|---|---|---|---|
| LA_09_051A | 99.53 | 0.47 | 13.78 | 83.85 | 2.37 | 23.45 |
| LA_09_051B | 99.54 | 0.46 | 13.73 | 84.83 | 1.94 | 22.91 |
| LA_09_052A | 99.44 | 0.56 | 13.83 | 83.99 | 2.18 | 22.54 |
| LA_09_052B | 99.44 | 0.56 | 14.39 | 83.38 | 2.23 | 23.19 |

TABLE 100 results after thermal stress 4 weeks/+5° C.

| Batch no. | % | % Di- (RRT 0.84) | % HMWP (RRT 0.68) | % | % | % | % | mAB-conc. (mg/mL) |
|---|---|---|---|---|---|---|---|---|
| LA_09_05 1A | 99.21 | 0.38 | — | 0.41 | 11.34 | 87.11 | 1.55 | 24.24 |
| LA_09_05 1B | 98.97 | 0.46 | — | 0.57 | 11.26 | 87.17 | 1.58 | 23.71 |
| LA_09_05 2A | 98.81 | 0.54 | — | 0.65 | 11.47 | 86.86 | 1.67 | 22.63 |
| LA_09_05 2B | 99.00 | 0.55 | — | 0.45 | 11.46 | 86.90 | 1.64 | 23.17 |

TABLE 101 results after thermal stress 4 weeks/+25° C.

| Batch no. | % | % Di- | % | % LMW | % | % | % | mAB-conc. (mg/mL) |
|---|---|---|---|---|---|---|---|---|
| LA_09_051A | 98.87 | 0.46 | — | 0.67 | 11.01 | 87.31 | 1.69 | 26.16 |
| LA_09_051B | 98.72 | 0.53 | — | 0.75 | 11.02 | 87.29 | 1.70 | 23.63 |
| LA_09_052A | 98.25 | 0.83 | — | 0.92 | 11.69 | 86.35 | 1.96 | 24.27 |
| LA_09_052B | 98.52 | 0.74 | — | 0.74 | 11.46 | 86.62 | 1.92 | 23.52 |

TABLE 102 results after thermal stress 4 weeks/+40° C.

| Batch no. | % | % Di- | % | % LMW | % | % | % | mAB-conc. (mg/mL) |
|---|---|---|---|---|---|---|---|---|
| LA_09_051A | 96.84 | 0.95 | 1.06 | 1.15 | 10.16 | 87.05 | 2.79 | 25.04 |
| LA_09_051B | 96.96 | 0.97 | 1.01 | 1.06 | 10.01 | 87.05 | 2.83 | 23.60 |
| LA_09_052A | 96.00 | 1.63 | 1.17 | 1.20 | 11.32 | 84.89 | 3.79 | 24.11 |
| LA_09_052B | 96.23 | 1.49 | 1.21 | 1.07 | 11.01 | 85.30 | 3.69 | 24.29 |

In conclusion, no significant differences between citrate and acetate buffer were measured, and no difference at accelerated conditions between trehalose and saccharose was visible. Citrate buffer with saccharose was selected for further studies.

Determination of DP Manufacturing Process Parameters

DS batch in citrate buffer was used to determine manufacturing process parameters. Preformulation studies indicated that the DS was not that susceptible to oxidation, and that light protection or nitrogen overlay or purging during manufacturing was required. Standard glass equipment as well as silicone tubings (SaniTech65) were used.

Adding Order

Experiments evaluating the adding order of the excipients were limited due to the small dilution volume of DS.

The DS was weighed in a glass bottle, polysorbate 20 as first excipient, saccharose as the second excipient, and NaCl as third excipient were added and rinsed with citrate buffer 10 mM pH 6.0 to dilute the content of DS to 20 mg/mL.

Stirring Speed and Time

Stirring speed was set at 100 rpm to reduce mechanical stress for the DS. Due to the fact that all excipients were well water-soluble, stirring time was set to 5 minutes.

Monitoring Parameters and IPCs

Monitoring parameters such as appearance, turbidity, density, and viscosity, and IPCs such as pH-value and osmolality were routinely checked during sample manufacturing according to the following Table 103:

TABLE 103

| | Before Filtration | After Filtration | After Filling |
|---|---|---|---|
| Appearance | colorless to slightly yellow | colorless to slightly yellow | colorless to slightly yellow |
| Density | 1.006 mg/mL | Not measured | Not measured |
| Turbidity | Clear | Clear | Clear |
| Viscosity | Not measured | Not measured | <5 mPa s |

TABLE 103-continued

|  | Before Filtration | After Filtration | After Filling |
|---|---|---|---|
| pH-value | 6.0 ± 0.2 (20-25° C.) | 6.0 ± 0.2 (20-25° C.) | Not measured |
| Osmolality | 290 ± 40 mOsmol/kg | 290 ± 40 mOsmol/kg | Not measured |

No issues were observed during manufacturing. The limits for osmolality were set-up based on measured data.

Filtration Process

According to preformulation studies, polyethersulfone was a suitable membrane for sterile filtration (Sartorius, 0.22 μm). No potential pH-shifts after filtration could be observed, as filtration rate and time showed standard values for filtration of an aqueous solution. Filter integrity testing was routinely performed without any issues.

Filling Process

Standard dosing equipment made of stainless steel, such as the filling pump and filling needle were investigated. Also, duration and filling speed was monitored. Extractable volume of filled DP was determined. An overfilling of 0.2 mL was required to ensure an extractable volume of 1.5 mL.

Material Compatibility

All preformulation and formulation studies were performed in glass as standard manufacturing equipment, which is also the recommendation for equipment to be used for GMP manufacturing.

Cleaning Agents

Cleaning of manufacturing equipment was performed according to the respective SOPs using the dishwasher with standard cleaning agent Neodisher®. A manual pre-cleaning with water for injection was routinely done before. No harmful effects of cleaning agents were observed.

Summary of Additional Formulation Studies for Lead CXCR5 Antibody (20 mg/mL)

For selection of phase I Lead CXCR5 Antibody DP formulation, citrate 10 mM at pH 6.0 was selected as the buffer over histidine and acetate. The pH-value of the solution was set at 6.0, as increasing or decreasing the pH-value means a reduction in monomer content. The buffer concentration was set at a medium concentration of 10 mM, although there was no significant difference between concentrations of 5-50 mM.

Polysorbate 20 was chosen as the surfactant with 0.2 mg/mL (0.02%), sufficient to stabilize the DS against mechanical stress.

Sucrose (saccharose) was selected as the stabilizer against thermal stress in favour of trehalose. The concentration of saccharose was set at 60 mg/mL (6%).

NaCl will be used as the isotonant agent in a concentration of 2.0 mg/mL (0.2%) in order to achieve an osmolality of DP of about 300 mOsmol/kg.

Anti-CXCR5 (100 mg/mL) Formulation Studies

The data in Examples 17-21 were collected during formulation studies for the Lead CXCR5 Antibody and its drug product for intravenous and subcutaneous administration. The objective of the formulation studies was to provide a stable, clear or slightly opalescent, and colorless or slightly yellow, visual particle-free Lead CXCR5 Antibody solution for injection for phase I.

Methods

Sample Preparation

UF/DF was performed on a small scale using VivaSpin devices with a Hydrosart membrane and a 30 kDa cut-off. RSN material was concentrated from ca. 20 mg/mL to 100 mg/mL. All solutions were already in the final formulation buffer (10 mM citrate buffer at pH 6.0).

The VivaSpin units were placed at RT in a common laboratory centrifuge and centrifuged at 2000 rpm. Solution was filtered over 0.2 μm Minisart before analytical testing.

All samples were stored between +2° and +8° C., tightly closed and protected from light, until analytical testing at T0 and after one week thermal stress at +40° C. or after mechanical stress.

Analytical Methods

The following techniques were used for sample analysis:

TABLE 104

Analytical techniques used

| Technique | Parameter to investigate |
|---|---|
| Organoleptic | Appearance |
| Nephelometer | Turbidity |
| pH-meter | pH-value |
| UV | mAB-concentration |
| Densimeter | Density |
| Osmometer | Osmolality |
| Viscosimeter | Viscosity |
| DLS | Hydrodynamic diameter |
| DSC* | Unfolding temperature |
| SEC | Mono-/Di-/Oligomer/HMW content |
| WCX | Isoforms (acid/basic/neutral) |
| ELISA* | Potency (Binding) |
| SDS-Page (red.)** | HC/LC, mAB-fragments |
| SDS-Page (non-red.)** | Aggregation and degradation products |
| HIAC* | Subvisible particles |

*Some samples will be analyzed.
**SDS-Page will be performed in case SEC shows unusual results.

Example 17

Excipient Screening

Preformulation studies identified 10 mM citrate buffer at pH 6.0 as the best buffer with less Lead CXCR5 Antibody aggregation tendency. In previous studies at 20 mg/mL, a formulation containing 10 mM citrate buffer, 60 mg/mL (6%) sucrose, 2 mg/mL (0.2%) NaCl, and 0.2 mg/mL (0.02%) Polysorbate 20 was selected. Those excipients plus some alternatives were tested to confirm the suitability of the selected formulation at a higher concentration (100 mg/mL).

Different formulations were stressed thermally at 40° C. for 7 days and mechanically at 100 rpm for 5 hrs. Additionaly, the unfolding temperature for the different formulations were screened at 100 mg/mL using DSC (Differential scanning calorimetry).

The following excipients were tested:

Sucrose→60 mg/mL

Trehalose→60 mg/mL

Arginine→30 mg/mL

Lysine→30 mg/mL

Glycine→30 mg/mL

NaCl or Mannitol was added as an isotonant. No salts were needed for viscosity reduction (around 2.1 cP).

The results of T0 and T7 days are shown in Table 105.

stress. Arginine showed a better effect than Glycine. Both amino acids were considered for the final design of experiment in order to choose the best excipient combination.

TABLE 105

Excipients screening

| T | Formulation composition (mg/mL) | Nr. | SEC | | Isoforms by WCX | | | Activity | SDS-Page |
| | | | HMW [%] | Mono. [%] | acidic [%] | neutral [%] | basic [%] | rel. potency [%] | non-reducing conditions |
|---|---|---|---|---|---|---|---|---|---|
| T zero | Sucrose (60) + NaCl (2) | 72_A1 | 2.7 | 97.0 | 11.7 | 84.2 | 4.0 | 165 | comparable to reference |
| | Sucrose (60) + Mannitol (15) | 72_A2 | 2.8 | 97.1 | 11.9 | 84.4 | 3.7 | 205 | comparable to reference |
| | Trehalose (60) + NaCl (2) | 72_B1 | 2.8 | 97.0 | 11.7 | 84.8 | 3.6 | 110 | comparable to reference |
| | Trehalose (60) + Mannitol (15) | 72_B2 | 2.8 | 97.0 | 11.8 | 84.2 | 4.0 | 156 | comparable to reference |
| | Arginine (30) | 72_C1 | 2.5 | 97.2 | 11.9 | 84.3 | 3.8 | 160 | comparable to reference |
| | Arginine (20) + NaCl (2) | 72_C2 | 2.6 | 97.2 | 11.8 | 84.6 | 3.6 | 144 | comparable to reference |
| | Arginine (20) + Mannitol (15) | 72_C3 | 2.6 | 97.2 | 12.2 | 83.8 | 3.9 | 117 | comparable to reference |
| | Lysine (30) + NaCl (2) | 72_D1 | 2.6 | 97.1 | 12.7 | 82.1 | 5.3 | 130 | comparable to reference |
| | Lysine (30) + Mannitol (15) | 72_D21 | 2.6 | 97.1 | 12.6 | 82.2 | 5.3 | 88 | comparable to reference |
| | Glycine (20) | 72_E1 | 2.7 | 97.1 | 12.4 | 83.5 | 4.1 | 170 | comparable to reference |
| | Glycine (20) + NaCl (2) | 72_E2 | 2.7 | 97.1 | 12.4 | 83.5 | 4.1 | 174 | comparable to reference |
| | Glycine (20) + Mannitol (15) | 72_E3 | 2.7 | 97.0 | 12.7 | 83.3 | 4.1 | 111 | comparable to reference |
| T 7 days at 40° C. | Sucrose (60) + NaCl (2) | 72_A1 | 3.5 | 96.3 | 11.4 | 84.4 | 4.2 | 188 | comparable to reference |
| | Sucrose (60) + Mannitol (15) | 72_A2 | 3.5 | 96.3 | 11.3 | 84.6 | 4.2 | 243 | comparable to reference |
| | Trehalose (60) + NaCl (2) | 72_B1 | 3.4 | 96.4 | 11.5 | 84.4 | 4.1 | 191 | comparable to reference |
| | Trehalose (60) + Mannitol (15) | 72_B2 | 3.5 | 96.3 | 11.4 | 84.3 | 4.3 | 266 | comparable to reference |
| | Arginine (30) | 72_C1 | 3.6 | 96.1 | 11.2 | 84.9 | 4.0 | 143 | comparable to reference |
| | Arginine (20) + NaCl (2) | 72_C2 | 3.4 | 96.4 | 11.6 | 84.5 | 3.9 | 164 | comparable to reference |
| | Arginine (20) + Mannitol (15) | 72_C3 | 3.3 | 96.4 | 11.3 | 85.3 | 3.4 | not tested | comparable to reference |
| | Lysine (30) + NaCl (2) | 72_D1 | 6.5 | 93.1 | 30.9 | 48.0 | 21.1 | 264 | comparable to reference |
| | Lysine (30) + Mannitol (15) | 72_D21 | 5.9 | 93.7 | 31.2 | 47.9 | 20.9 | 297 | comparable to reference |
| | Glycine (20) | 72_E1 | 3.2 | 96.6 | 11.3 | 84.4 | 4.3 | 180 | comparable to reference |
| | Glycine (20) + NaCl (2) | 72_E2 | 3.3 | 96.4 | 11.6 | 84.4 | 4.0 | not tested | comparable to reference |
| | Glycine (20) + Mannitol (15) | 72_E3 | 3.2 | 96.6 | 11.2 | 84.6 | 4.2 | not tested | comparable to reference |

Thermal Stress

None of the samples showed turbidity before or after stress.

Lysine showed: a pH shift to 9.8, a very high tendency to aggregate, a very high increase in acidic and basic isoforms, and high molecular weight bands in SDS-PAGE. As a result, it was excluded from further consideration.

Formulations with mannitol showed bad binding in an ELISA assay after stress. As a result, NaCl is the favored isotonant.

Sucrose showed slightly better chemical stability than trehalose, but additional bands were seen in SDS-PAGE after stress (for both).

Arginine (especially in the presence of NaCl) and glycine had a similar SEC profile, but no additional bands were seen in SDS-PAGE after stress.

Protein Associated Formation Measured by Dynamic Light Scattering (DLS)

Figure 34:
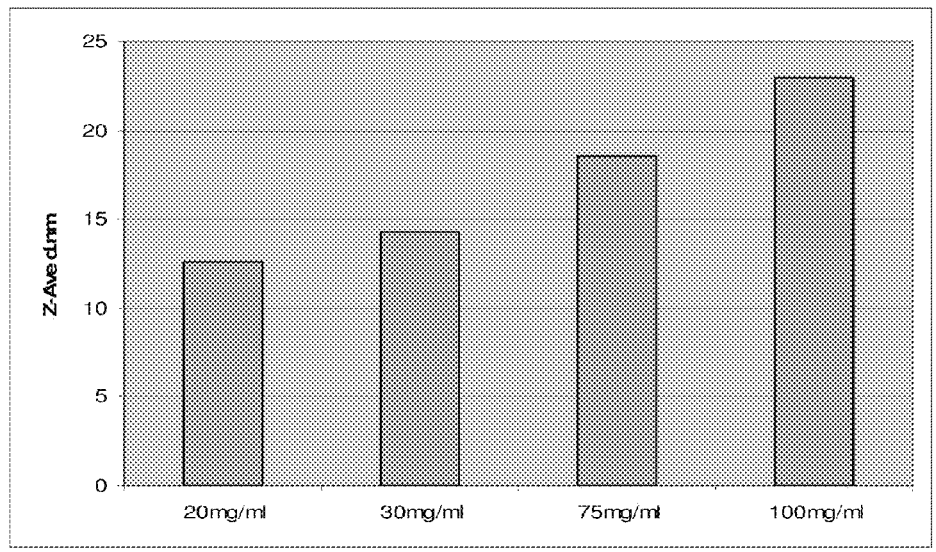
FIG. 34 is a chart showing the effect of increasing Lead CXCR5 Antibody concentration on the Z-average. The Lead CXCR5 Antibody showed a significant increase in the hydrodynamic diameter (Z-Average) by increasing the concentration of the antibody.

Lead CXCR5 Antibody showed a significant increase in the hydrodynamic diameter (Z-Average) by increasing the concentration (FIG. 34). This behavior was fully reversible upon dilution. For further investigation of this effect, the different Lead CXCR5 Antibody concentrations were measured by analytical ultra centrifugation (AUC) and aggregation was excluded. The conclusion of the AUC study was that this behavior was due to the formation of protein associates.

Figure 35:
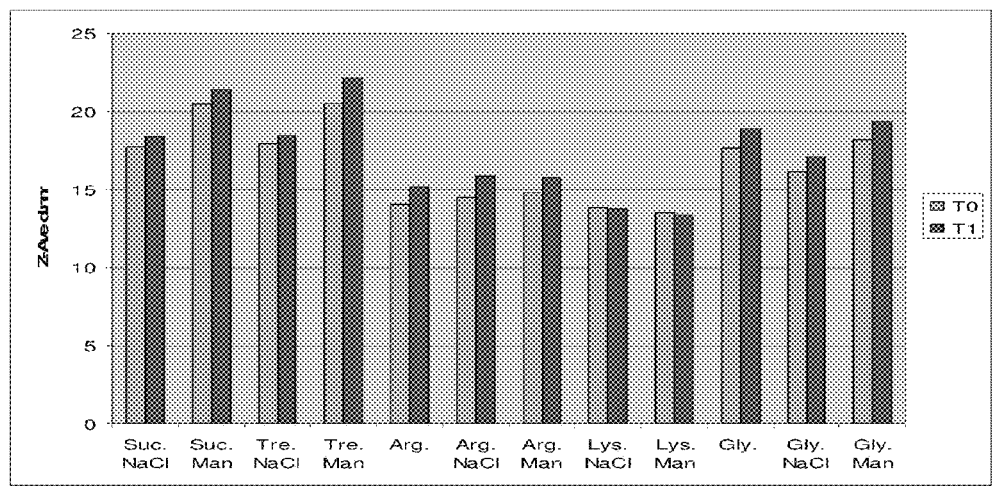
FIG. 35 is a chart showing the effect of different stabilizers (excipients) on the Z-Average at 100 mg/mL of Lead CXCR5 Antibody after thermal stress. Z-Average was measured before and after thermal stress. The stabilizing effect was similar to all tested excipients, but the increase in Z-average was generally reduced by using amino acids as stabilizers (arginine, lysine, or glycine). Lysine was excluded due to a higher content of aggregates after stress. Arginine showed a better effect than glycine.

The effect of the above listed excipient on this behavior was studied and the results are shown in FIG. 35. The Z-Average was measure before and after thermal stress. The stabilizing effect was similar to all tested recipients, but the increase in Z-average was generally reduced by using amino acids as stabilizers (Arginine, Lysine or Glycine). Lysine was excluded due to higher content of aggregates after Mechanical Stress Lysine formulations were excluded as well as all formulations containing mannitol. SEC data showed no effect of the stress on the tested samples. See Table 106.

TABLE 106

Mechanical stress

| Formulation | | SEC before mechanical stress | | SEC after mechanical stress | |
| composition (mg/mL) | Formulation No. | HMW [%] | monomer [%] | HMW [%] | monomer [%] |
|---|---|---|---|---|---|
| Sucrose (60) + NaCl (2) | 080_A | 2.6 | 97.3 | 2.7 | 97.2 |
| Trehalose (60) + NaCl (2) | 080_B | 2.7 | 97.2 | 2.6 | 97.3 |
| Arginine (30) | 080_C1 | 2.5 | 97.5 | 2.3 | 97.6 |
| Arginine (20) + NaCl (2) | 080_C2 | 2.5 | 97.4 | 2.5 | 97.4 |
| Glycine (20) | 080_D1 | 2.5 | 97.5 | 2.4 | 97.5 |
| Glycine (20) + NaCl (2) | 080_D2 | 2.5 | 97.5 | 2.4 | 97.5 |

Figure 36:
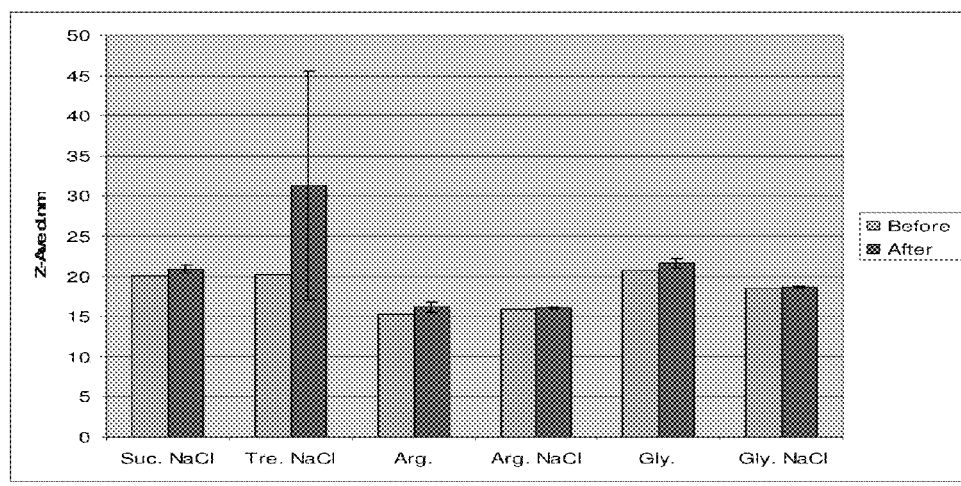
FIG. 36 is a chart showing the effect of different stabilizers on the Z-Average at 100 mg/mL Lead CXCR5 Antibody after mechanical stress. Z-Average was measured before and after mechanical stress. The same reduction in Z-average was noticed in the presence of amino acids. Sucrose had a better protective effect than trehalose against mechanical stress. Arginine and glycine performed better in combination with NaCl.

The same reduction in Z-average was noticed in the presence of amino acids. Sucrose had a better protective effect than trehalose against mechanical stress. Arginine and glycine performed better in combination with NaCl. See FIG. 36.

Differential Scanning Calorimetry (DSC) Screening

A screening study to determine the unfolding temperature of Lead CXCR5 Antibody was performed using Differential scanning calorimetry (DSC). Sucrose, trehalose, argenine, and glycine were screened.

The Tm results are listed in Table 107.

TABLE 107

Effect of different excipients on the Tm values of Lead CXCR5 Antibody. All formulations were in 10 mM citrate buffer at pH 6

| Excipient screened | Tm1 | Tm2 | Tm3 |
|---|---|---|---|
| Sucrose + NaCl | 65.3 | 73.6 | 83.8 |
| Trehalose + NaCl | 65.5 | 73.9 | 83.9 |
| Arginine | 63.8 | 72.2 | 82.6 |
| Arginine + NaCl | 64.3 | 72.8 | 82.6 |
| Glycine | 64.8 | 74.1 | 84.2 |
| Glycine + NaCl | 64.9 | 73.6 | 83.8 |

Based on Tm1, sucrose and trehalose showed the highest values. Arginine performed better in combination with NaCl.

In conclusion, the data collected suggests that the final Lead CXCR5 Antibody 100 mg/ml formulation would contain a combination of a sugar (in some embodiments, sucrose) and an amino acid (in some embodiments, arginine or glycine) in the presence of NaCl as the isotonant.

Example 18

Surfactant Screening

Polysorbate as a stabilizer was evaluated for protection of Lead CXCR5 Antibody against both thermal and mechanical stresses.

Polysorbate 20 and 80 were tested in two different concentrations: 0.1 and 0.2 mg/ml.

Thermal Stress

DLS showed no effect by the addition of Polysorbate after thermal stress. The formation of HMWs and fragments after 7 days storage at 40° C. was noticed in all samples, as detected by SEC. No additional bands in SDS-PAGE were detected. Slight changes were seen after thermal stress, but no differences between PS20 and PS80, as well as between the 2 concentrations, were seen (data not shown).

Mechanical Stress

DLS showed no changes after mechanical stress. Polysorbate 20 showed no aggregations after mechanical stress. Polysorbate 80 showed aggregates formation after mechanical stress. No additional bands in SDS-PAGE (data not shown) were seen.

In conclusion, Polysorbate 20 was the desired surfactant due to superiority in mechanical stabilization of the Lead CXCR5 Antibody.

Example 19

Prototype Formulation Pre-Selection Using DSC

Based on the excipient screening and the surfactant screening studies, 12 different excipient combinations were suggested (see Tables 108 and 109))

The unfolding temperature for all formulations was determined using DSC and the resulting Tms, as well as the osmolality for each formulation, are listed in Tables 108 and 109.

TABLE 108

Excipient combinations for prototype formulations (Arginine) pre-selection study using DSC. Tm values and osmolality are listed as well

| | Composition mg/mL | | | | DSC | | | Osmo. |
|---|---|---|---|---|---|---|---|---|
| Formulation | Sucrose | Arginine | NaCl | PS 20 | Tm1 | Tm2 | Tm3 | (mosmol/kg) |
| LA_10_087_A | 60 | 20 | 2 | 0.1 | 65.2 | 73.3 | 83.2 | 495 |
| LA_10_087_C | 60 | 20 | 2 | 0.2 | 65.1 | 73.0 | 83.2 | 486 |
| LA_10_087_E | 30 | 10 | 2 | 0.1 | 64.5 | 72.8 | 83.0 | 304 |
| LA_10_087_G | 30 | 10 | 2 | 0.2 | 64.4 | 72.7 | 83.0 | 304 |
| LA_10_087_L | 45 | 10 | 2 | 0.1 | 64.7 | 73 | 83.2 | 349 |
| LA_10_087_M | 45 | 10 | 2 | 0.2 | 64.6 | 72.8 | 83.1 | 357 |

TABLE 109

Excipient combinations for prototype formulations (glycine) pre-selection study using DSC. Tm values and osmolality are listed as well

| | Composition mg/mL | | | | DSC | | | Osmo. |
|---|---|---|---|---|---|---|---|---|
| Formulation | Sucrose | Glycine | NaCl | PS 20 | Tm1 | Tm2 | Tm3 | (mosmol/kg) |
| LA_10_087_B | 60 | 15 | 2 | 0.1 | 66.2 | 74.1 | 84.3 | 539 |
| LA_10_087_D | 60 | 15 | 2 | 0.2 | 65.8 | 74.1 | 84.3 | 533 |
| LA_10_087_F | 30 | 7.5 | 2 | 0.1 | 65.0 | 73.3 | 83.5 | 330 |
| LA_10_087_H | 30 | 7.5 | 2 | 0.2 | 64.8 | 73.1 | 83.4 | 320 |
| LA_10_090_A | 45 | 7.5 | 2 | 0.1 | 65.3 | 73.7 | 83.6 | 408 |
| LA_10_090_B | 45 | 7.5 | 2 | 0.2 | 65.3 | 73.7 | 83.9 | 391 |

The formulations didn't show great differences in Tm, but the osmolality varied a lot. The pre-selection of the prototype formulations were made based on Tm and osmolality. Accordingly, in each excipient group (arginine and glycine), the highest Tm was selected (regardless of the osmolality). In addition, the highest Tm in the isotonic region was also selected.

Example 20

Prototype Expolatory Stability Study

The above prototype selection resulted in 4 prototype formulations, which are listed in Table 110. Those formulations were tested for mechanical stress (100 rpm for 5 hours), 5 freeze/thaw cycles and isothermal stress at 5, 20, and 40° C.

TABLE 110

Prototype formulations for the 100 mg/mL Lead CXCR5 Antibody formulation

| Formulation | Composition | | | | | |
|---|---|---|---|---|---|---|
| | Sucrose | Arginine | Glycine | NaCl | PS 20 | Osmo. (mosmol/kg) |
| LA_10_102_A | 60 | 20 | | 2 | 0.1 | 518 |
| LA_10_102_B | 45 | 10 | | 2 | 0.1 | 374 |
| LA_10_102_C | 60 | | 15 | 2 | 0.1 | 550 |
| LA_10_102_D | 30 | | 7.5 | 2 | 0.1 | 325 |

Mechanical Stability

Figure 37:
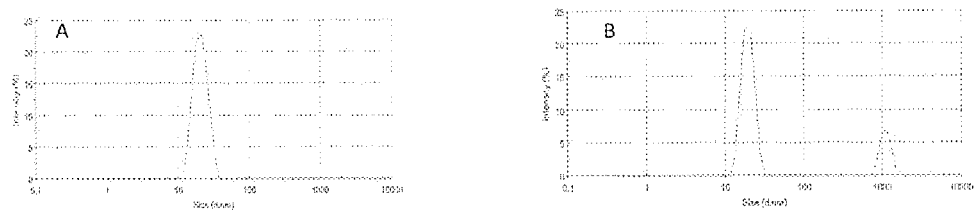
FIG. 37 is a set of graphs showing particle size distribution, as measured by DLS, of Lead CXCR5 Antibody formulated in 10 mM citrate buffer at pH 6 before mechanical stress (A) and after mechanical stress (B). A higher molecular weight species was measured by DLS after mechanical stress of DS.
Figure 38:
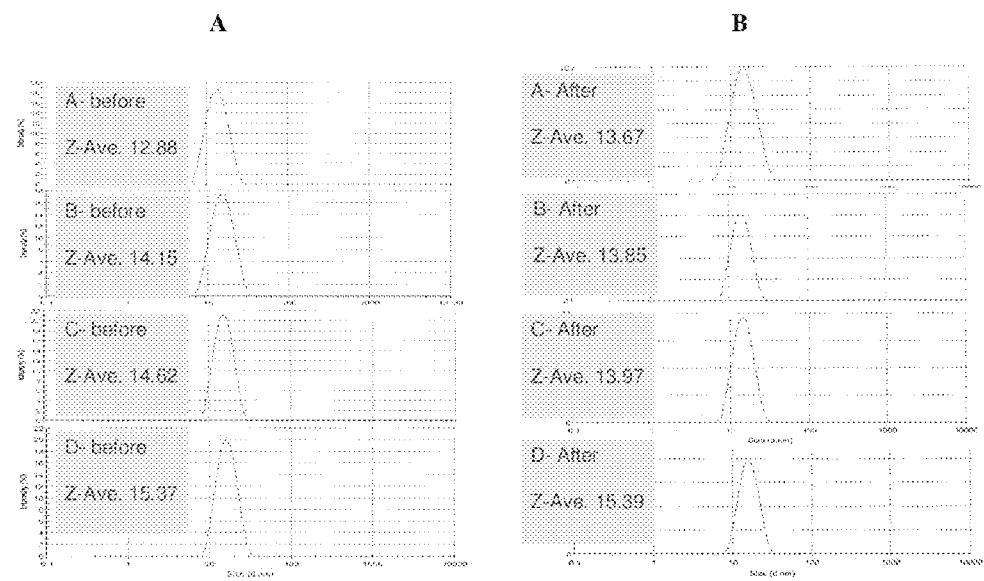
FIG. 38 is a set of graphs showing particle size distribution, as measured by DLS, of Lead CXCR5 Antibody drug product prototype formulations (A-D; Table 110) before (A) and after (B) mechanical stress.

Lead CXCR5 Antibody in 10 mM citrate buffer at pH 6, without addition of any excipients (DS formulation), was also stressed in parallel with the prototype formulations. A higher molecular weight species was measured by DLS after mechanical stress of DS (FIG. 37), stress where no changes have been seen in all tested formulations after mechanical stress. The formation of aggregates after mechanical stress was measured using size exclusion chromatography (SEC) and the results are shown in Table 111. In general, the 4 formulations were equally stable to mechanical stress except formulation A, where more HMWs were found by SEC after mechanical stress. See FIG. 38.

TABLE 111

Size exclusion chromatography (SEC) results of the prototype formulations before and after mechanical stress SEC

| | For_A % Mon. | For_B % Mon. | For_C % Mon. | For_D % Mon. |
|---|---|---|---|---|
| | | −20° C. | | |
| Before | 99.6 | 99.5 | 99.5 | 99.5 |
| After | 98.1 | 99.5 | 99.3 | 99.4 |

Freeze/Thaw Stability

No significant differences were detected, either on DS or DP, after 5 freeze/thawing cycles. Therefore, there should be no instability issues by freezing and thawing (data are not shown).

Exploratory Prototype Stability Study

The prototype formulations were stored at −20, 5, 20, and 40° C. They were analyzed at the start of the study, after 1 month, after 3 months, and after 6 months. The formulations were selected based on the 3 months results (Tables 112-114). The results showed that formulation B performed the best with regard to SEC, WCX, and sub-visible particles, especially at 40° C.

TABLE 112

Size exclusion chromatography (SEC) results of the prototype formulations after 3 months SEC

| | For_A % Mon. | For_B % Mon. | For_C % Mon. | For_D % Mon. |
|---|---|---|---|---|
| | | −20° C. | | |
| T0 | 99.6 | 99.5 | 99.5 | 99.5 |
| T1 month | N/A | N/A | N/A | N/A |
| T3 months | 99.1 | 99.1 | 99 | 99.5 |
| | | 5° C. | | |
| T0 | 99.6 | 99.5 | 99.5 | 99.5 |
| T1 month | 99.3 | 99.4 | 99.5 | 99.5 |
| T3 months | 99 | 99.4 | 98.8 | 99.4 |
| | | 20° C. | | |
| T0 | 99.6 | 99.5 | 99.5 | 99.5 |
| T1 month | 99.5 | 99.5 | 99.4 | 99.4 |
| T3 months | 99 | 98.9 | 98.6 | 99.1 |
| | | 40° C. | | |
| T0 | 99.6 | 99.5 | 99.5 | 99.5 |
| T1 month | 96.9 | 96.7 | 96.5 | 96.3 |
| T3 months | 91.5 | 91.6 | 89.5 | 90.2 |

TABLE 113

Weak Cationic exchange chromatography (WCX) results of the prototype formulations after 3 months WCX

| | For_A % Basic | For_B % Basic | For_C % Basic | For_D % Basic |
|---|---|---|---|---|
| | | −20° C. | | |
| T0 | 2 | 2.2 | 2.1 | 2.2 |
| T1 month | N/A | N/A | N/A | N/A |
| T3 months | 1.5 | 1.6 | 1.6 | 1.6 |
| | | 5° C. | | |
| T0 | 2 | 2.2 | 2.1 | 2.2 |
| T1 month | 1.1 | 1.2 | 1.2 | 1.3 |
| T3 months | 1.5 | 1.6 | 1.7 | 1.6 |
| | | 20° C. | | |
| T0 | 2 | 2.2 | 2.1 | 2.2 |
| T1 month | 1.3 | 1.3 | 1.4 | 1.3 |
| T3 months | 1.7 | 1.9 | 2 | 2 |
| | | 40° C. | | |
| T0 | 2 | 2.2 | 2.1 | 2.2 |
| T1 month | 2.2 | 2.2 | 2.7 | 2.5 |
| T3 months | 6.5 | 5.1 | 8.6 | 8.2 |

TABLE 114

Sub-visible particles measured by Light blockage at T zero and after 3 months (5° C.)

| | For_A | | For_B | | For_C | | For_D | |
|---|---|---|---|---|---|---|---|---|
| | >10 μm | >25 μm | >10 μm | >25 μm | >10 μm | >25 μm | >10 μm | >25 μm |
| T0 | 4 | 3 | 4 | 4 | 5 | 4 | 4 | 3 |
| T2 | 8 | 1 | 5 | 1 | 34 | 14 | 6 | 2 |

In conclusion, the studies showed better results for the formulation LA_10_102_B. This formulated had a concentration of 100 mg/mL Lead CXCR5 Antibody in 10 mM citrate buffer at pH 6 and contained the following excipients:

| | |
|---|---|
| Sucrose | 45 mg/mL (4.5%); |
| Arginine | 10 mg/mL (1%); |
| NaCl | 2 mg/mL (0.2%); and |
| Polysorbate 20 | 0.1 mg/mL (0.01%). |

Example 21

Supporting Stability Data for the 100 mg/mL Formulation

Additional stability studies were done on the 100 mg/mL Lead CXCR5 Antibody formulation identified in Example 20. The additional studies were performed at −20, 5, and 25° C. The results are shown in Tables 115-117.

TABLE 115

Stability Data for 100 mg/mL Lead CXCR5 Antibody formulation at −20° C.

| | | | | |
|---|---|---|---|---|
| Drug product: | Lead CXCR5 Antibody-solution for injection | | Batch no.: | 11_106/LST0008 |
| Dosage strength: | 100 mg/mL | | Manufacturer batch no.: | 11_106 |
| Storage condition: | −20° C. ± 5° C. | | | |
| Storage orientation: | Inverted | | | |

| | Time | | | | | | | |
|---|---|---|---|---|---|---|---|---|
| Test item | Initial results | 1 month | 3 months | 6 months | 9 months | 12 months | 18 months | 24 months |
| Appearance of solution | | | | | | | | |
| Clarity | I | <I | <I | <I | II | <IV (20 NTU) | <IV (19 NTU) | |
| Color | Y7 | Y7 | Y7 | Y7 | Y7 | Y6 | Y6 | |
| Assay | | | | | | | | |
| Potency (Antigen ELISA) $EC_{50}$ value (in comparison to reference) | 75% | 107% | 84% | 96% | 101% | 96% | 127% | |
| Total protein content (UV) | 103 mg/mL | 101 mg/mL | 101 mg/mL | 101 mg/mL | 102 mg/mL | 101 mg/mL | 102 mg/mL | |
| Molecular integrity | | | | | | | | |
| SDS-PAGE under non-reducing conditions (Band pattern) | Conforms to reference | Conforms to reference | Conforms to reference | Conforms to reference | Conforms to reference | Conforms to reference | Conforms to reference | |
| Purity | | | | | | | | |
| HPLC (SEC) Monomer (% area) | 99.1% | 99.0% | 99.0% | 98.8% | 98.9% | 98.8% | 98.9% | |
| High molecular weight proteins (% area) | 0.8% | 0.8% | 0.8% | 0.8% | 0.8% | 0.8% | 0.8% | |
| SDS-PAGE under non-reducing conditions Half molecules (%) | <1.0% | <1.0% | <1.0% | <1.0% | <1.0% | <1.0% | <1.0% | |
| SDS-PAGE under reducing conditions Relative purity (%) | 99% | 97% | 99% | 97% | 99% | 98% | 97% | |
| Charge heterogeneity | | | | | | | | |
| HPLC (weak cation exchange) Isoforms (acidic/neutral/basic) (% area) | 4%/94%/2% | 4%/94%/2% | 4%/94%/2% | 4%/94%/2% | 4%/94%/2% | 4%/94%/2% | 4%/95%/2% | |

TABLE 115-continued

Stability Data for 100 mg/mL Lead CXCR5 Antibody formulation at −20° C.

Drug product: Lead CXCR5 Antibody-solution for injection
Batch no.: 11_106/LST0008
Dosage strength: 100 mg/mL
Manufacturer batch no.: 11_106
Storage condition: −20° C. ± 5° C.
Storage orientation: Inverted

| Test item | Initial results | 1 month | 3 months | 6 months | 9 months | 12 months | 18 months | 24 months |
|---|---|---|---|---|---|---|---|---|
| IEF | Conforms to reference | Conforms to reference | Conforms to reference | Conforms to reference | Conforms to reference | Conforms to reference | Conforms to reference | |
| pH (potentiometry) | 5.9 | 5.8 | 6.0 | 5.9 | 5.9 | 5.9 | 5.9 | |
| Particulate matter (visible particles) | Practically free from particles | Complies | Complies | Complies | Complies | Complies | Complies | |
| Particulate matter (subvisible particles) | | | | | | | | |
| Number of particles per vial ≥10 μm | 2 | | | | | 7 | | |
| Number of particles per vial ≥25 μm | 0 | | | | | 1 | | |
| Microbial contamination | <1 cfu/2 mL | | | | | | | |
| Closure integrity | No trace of coloration visible | | | | | No trace of coloration visible | | |
| Dynamic light scattering | z-average: 8.1 r · nm Pdl: 0.05 | z-average: 8.0 r · nm Pdl: 0.05 | z-average: 8.0 r · nm Pdl: 0.05 | z-average: 8.1 r · nm Pdl: 0.05 | z-average: 8.1 r · nm Pdl: 0.05 | z-average: 8.1 r · nm Pdl: 0.07 | z-average: 8.1 r · nm Pdl: 0.05 | |

TABLE 116

Stability Data for 100 mg/mL Lead CXCR5 Antibody formulation at 5° C.

Drug product: Lead CXCR5 Antibody - solution for injection
Batch no.: 11_106/LST0008
Dosage strength: 100 mg/mL
Manufacturer batch no.: 11/106
Storage condition: +5° C. ± 3° C.
Storage orientation: Inverted

| Test item | Initial results | 1 month | 3 months | 6 months | 9 months | 12 months | 15 months | 18 months | 24 months |
|---|---|---|---|---|---|---|---|---|---|
| Appearance of solution | | | | | | | | | |
| Clarity | I | <I | <I | <I | I | <IV (22 NTU) | <IV (22 NTU) | <IV (21 NTU) | |
| Color | Y7 | Y7 | Y7 | Y7 | Y7 | Y6 | Y6 | Y6 | |
| Assay | | | | | | | | | |
| Potency (Antigen ELISA) $EC_{50}$ value (in comparison to reference) | 75% | 105% | 95% | 97% | 92% | 93% | 114% | 119% | |
| Total protein content (UV) | 103 mg/mL | 101 mg/mL | 102 mg/mL | 101 mg/mL | 102 mg/mL | 102 mg/mL | 101 mg/mL | 102 mg/mL | |

TABLE 116-continued

Stability Data for 100 mg/mL Lead CXCR5 Antibody formulation at 5° C.

| Drug product: | Lead CXCR5 Antibody - solution for injection | Batch no.: | 11_106/ LST0008 |
|---|---|---|---|
| Dosage strength: | 100 mg/mL | Manufacturer batch no.: | 11/106 |
| Storage condition: | +5° C. ± 3° C. | | |
| Storage orientation: | Inverted | | |

| Test item | Initial results | 1 month | 3 months | 6 months | 9 months | 12 months | 15 months | 18 months | 24 months |
|---|---|---|---|---|---|---|---|---|---|
| Molecular integrity | | | | | | | | | |
| SDS-PAGE under non-reducing conditions (Band pattern) | Conforms to reference | Conforms to reference | Conforms to reference | Conforms to reference | Conforms to reference | Conforms to reference | Conforms to reference | Conforms to reference | |
| Purity | | | | | | | | | |
| HPLC (SEC) | | | | | | | | | |
| Monomer (% area) | 99.1% | 99.0% | 99.1% | 98.8% | 98.8% | 98.7% | 98.9% | 98.8% | |
| High molecular weight proteins (% area) | 0.8% | 0.7% | 0.7% | 0.7% | 0.8% | 0.8% | 0.9% | 0.9% | |
| SDS-PAGE under non-reducing conditions Half molecules (%) | <1.0% | <1.0% | <1.0% | <1.0% | <1.0% | <1.0% | <1.0% | <1.0% | |
| SDS-PAGE under reducing conditions Relative purity (%) | 99% | 98% | 99% | 95% | 99% | 97% | 99% | 98% | |
| Charge heterogeneity | | | | | | | | | |
| HPLC (weak cation exchange) Isoforms (acidic/neutral/basic) (% area) | 4%/94%/2% | 4%/94%/2% | 3%/94%/2% | 4%/94%/2% | 4%/94%/2% | 4%/94%/2% | 4%/94%/2% | 4%/94%/2% | |
| IEF | Conforms to reference | Conforms to reference | Conforms to reference | Conforms to reference | Conforms to reference | Conforms to reference | Conforms to reference | Conforms to reference | |
| pH (potentiometry) | 5.9 | 5.9 | 6.0 | 5.9 | 5.9 | 5.9 | 5.9 | 5.9 | |
| Particulate matter (visible particles) | Complies | Complies | Complies | Complies | Complies | Complies | Complies | Complies | |
| Particulate matter (subvisible particles) | | | | | | | | | |
| Number of particles per vial ≥10 μm | 2 | | | | | 14 | 2 | 16 | |
| Number of particles per vial ≥25 μm | 0 | | | | | 2 | 0 | 0 | |
| Microbial contamination | <1 cfu/2 mL | | | | | | | | |
| Closure integrity | No trace of coloration visible | | | | | No trace of coloration visible | | | |
| Dynamic light scattering | z-average: 8.1 r · nm PdI: 0.05 | z-average: 8.0 r · nm PdI: 0.05 | z-average: 7.9 r · nm PdI: 0.04 | z-average: 8.0 r · nm PdI: 0.04 | z-average: 8.1 r · nm PdI: 0.06 | z-average: 8.1 r · nm PdI: 0.06 | z-average: 8.0 r · nm PdI: 0.05 | z-average: 8.1 r · nm PdI: 0.05 | |

TABLE 117

Stability Data for 100 mg/mL Lead CXCR5 Antibody formulation at 25° C.

Drug product: Lead CXCR5 Antibody-solution for injection
Dosage strength: 100 mg/mL
Storage condition: +25° C. ± 2° C./60% ± 5% RH
Storage orientation: Inverted
Batch no.: 11_106/LST0008
Manufacturer 11_106 batch no.:

| Test item | Initial results | 1 month | 3 months | 6 months |
|---|---|---|---|---|
| Appearance of solution | | | | |
| Clarity | I | <I | <I | <I |
| Color | Y7 | Y7 | Y7 | Y7 |
| Assay | | | | |
| Potency (Antigen ELISA) $EC_{50}$ value (in comparison to reference) | 75% | 121% | 96% | 104% |
| Total protein content (UV) | 103 mg/mL | 101 mg/mL | 102 mg/mL | 102 mg/mL |
| Molecular integrity | | | | |
| SDS-PAGE under non-reducing conditions (Band pattern) | Conforms to reference | Conforms to reference | Conforms to reference | Conforms to reference |
| Purity | | | | |
| HPLC (SEC) | | | | |
| Monomer (% area) | 99.1% | 98.9% | 98.8% | 98.2% |
| High molecular weight proteins (% area) | 0.8% | 0.8% | 1.0% | 1.2% |
| SDS-PAGE under non-reducing conditions Half molecules (%) | <1.0% | <1.0% | <1.0% | <1.0% |
| SDS-PAGE under reducing conditions Relative purity (%) | 99% | 96% | 99% | 96% |
| Charge heterogeneity | | | | |
| HPLC (weak cation exchange) Isoforms (acidic/neutral/basic) (% area) | 4%/94%/2% | 4%/94%/2% | 4%/94%/3% | 4%/93%/3% |
| IEF | Conforms to reference | Conforms to reference | Conforms to reference | Conforms to reference |
| pH (potentiometry) | 5.9 | 5.9 | 6.0 | 6.1 |
| Particulate matter (visible particles) | Complies | Complies | Complies | Complies |
| Particulate matter (subvisible particles) | | | | |
| Number of particles per vial ≥10 μm | 2 | | | 17 |
| Number of particles per vial ≥25 μm | 0 | | | 1 |
| Microbial contamination | <1 cfu/2 mL | | | <1 cfu/2 mL |
| Closure integrity | No trace of coloration visible | | | No trace of coloration visible |
| Dynamic light scattering | z-average: 8.1 r · nm; PdI: 0.05 | z-average: 8.0 r · nm PdI: 0.05 | z-average: 8.1 r · nm PdI: 0.05 | z-average: 8.1 r · nm PdI: 0.06 |

What is claimed is:

1. An antibody formulation comprising:
   a) about 20 mg/mL of a humanized IgG4 anti-CXCR5 (C-X-C chemokine receptor type 5) antibody comprising a heavy chain variable region comprising complementary determining regions (CDRs) comprising the amino acid sequences of SEQ ID NOS: 15, 16, and 17, and a light chain variable region comprising CDRs comprising the amino acid sequences of SEQ ID NOS: 18, 19, and 20;
   b) about 10 mM citrate buffer;
   c) about 0.02% polysorbate 20;
   d) about 6% sucrose; and
   e) about 0.2% sodium chloride;
   wherein the pH of the formulation is at or below the lower of about pH 6.0 and the pI of the binding agent.

2. An antibody formulation comprising:
   a) about 100 mg/mL of a humanized IgG4 anti-CXCR5 (C-X-C chemokine receptor type 5) antibody comprising a heavy chain variable region comprising complementary determining regions (CDRs) comprising the amino acid sequences of SEQ ID NOS: 15, 16, and 17, and a light chain variable region comprising CDRs comprising the amino acid sequences of SEQ ID NOS: 18, 19, and 20;
   b) about 10 mM citrate buffer;
   c) about 0.01% polysorbate 20;
   d) about 4.5% sucrose;
   e) about 0.2% sodium chloride; and
   f) about 1% arginine;
   wherein the pH of the formulation is at or below the lower of about pH 6.0 and the pI of the binding agent.

3. An antibody formulation comprising:
   a) about 5 mg/mL to about 280 mg/mL of a humanized IgG4 anti-CXCR5 (C-X-C chemokine receptor type 5) antibody comprising a heavy chain variable region comprising complementary determining regions (CDRs) comprising the amino acid sequences of SEQ ID NOS: 15, 16, and 17, and a light chain variable region comprising CDRs comprising the amino acid sequences of SEQ ID NOS: 18, 19, and 20;
   b) about 10 mM citrate buffer;
   c) about 0.01% polysorbate 20;
   d) about 4.5% sucrose;
   e) about 0.2% sodium chloride; and
   f) about 1% arginine;
   wherein the pH of the formulation is at or below the lower of about pH 6.0 and the pI of the binding agent.

4. The formulation of claim 3, wherein the formulation is a liquid formulation.

5. The formulation of claim 3, wherein the formulation is a lyophilized formulation.

6. The formulation of claim 3, wherein 5% or less of the binding agent in the formulation forms aggregates.

7. The formulation of claim 3, wherein a monomer of the antibody has a purity of about 90%.

8. The formulation of claim 3, wherein the antibody has a biological activity of at least about 90% of the biological activity exhibited at the time the formulation was prepared, as determined in an antigen binding assay.

9. The formulation of claim 3, wherein the humanized IgG4 anti-CXCR5 (C-X-C chemokine receptor type 5) antibody is present in an amount of from about 5 to about 25 mg/mL, from about 26 to about 50 mg/mL, from about 51 to about 75 mg/mL, from about 76 to about 100 mg/mL, from about 101 to about 125 mg/mL, from about 126 to about 150 mg/mL, from about 151 to about 175 mg/mL, from about 176 to about 200 mg/mL, from about 201 mg/mL to about 225 mg/mL, from about 226 mg/mL to about 250 mg/mL, or from about 251 to about 280 mg/mL.

10. A kit comprising a container comprising: 1) the formulation of claim 3, and 2) a label or instructions for the administration and use of the formulation.

11. A pre-filled device or pre-filled container comprising the formulation of claim 3.

12. The pre-filled device of claim 11, wherein the pre-filled device comprises a pre-filled syringe or a pre-filled autoinjector.

13. The pre-filled container of claim 11, wherein the pre-filled container comprises a sealed ampoule, a vial, a bottle, a test tube, a cartouche, or a sachet.

* * * * *